(12) United States Patent
Bredesen et al.

(10) Patent No.: US 6,235,872 B1
(45) Date of Patent: May 22, 2001

(54) PROAPOPTOTIC PEPTIDES DEPENDENCE POLYPEPTIDES AND METHODS OF USE

(75) Inventors: Dale E. Bredesen, Rancho Santa Fe; Shahrooz Rabizadeh, Del Mar, both of CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 09/041,886

(22) Filed: Mar. 12, 1998

(51) Int. Cl.[7] ........................... C07K 7/00; C07K 14/435; C07K 19/00
(52) U.S. Cl. ........................ 530/300; 530/326; 530/327; 530/328; 530/350; 514/2; 514/13; 514/14; 514/15
(58) Field of Search .................................. 514/2, 13, 14, 514/15; 530/300, 326, 327, 328, 350; 435/375, 377

(56) References Cited

U.S. PATENT DOCUMENTS 5,849,995 * 12/1998 Hayden .................................... 800/2

FOREIGN PATENT DOCUMENTS

| 02069665A | * | 3/1990 | (JP) . |
| WO 91/07423 | * | 5/1991 | (WO) . |
| WO 95/01437 | * | 1/1995 | (WO) . |
| WO 96/25941 | * | 8/1996 | (WO) . |
| WO 97/17443 | * | 5/1997 | (WO) . |

OTHER PUBLICATIONS

Ambrose et al., "Structure and expression of the Huntington's disease gene: evidence against simple inactivation due to an expanded CAG repeat" *Somat. Cell. Mol. Genet.* 20:27–38 (1994).
Banfi et al., "Identification and characterization of the gene causing type 1 spinocerebellar ataxia" *Nat. Genet.* 7:513–519 (1994).
Banfi et al., "Mapping and cloning of the critical region for the spinocerebellar ataxia type 1 gene (SCA1) in a yeast artificial chromosome contig spanning 1.2 Mb" *Genomics* 18:627–635 (1993).
Bingham et al., "Stability of an expanded trinucleotide repeat in the androgen receptor gene in transgenic mice" *Nat. Genet.* 9:191–196 (1995).
Brando et al., "Analysis of the DRPLA triplet repeat in brain tissue and leukocytes from schizophrenics" *Psych. Genetics* 6:1–5 (1996).
Chang et al., "Structural analysis of complementary DNA and amino acid sequences of human and rat androgen receptors" *Proc. Natl. Acad. Sci USA* 85:7211–7215 (1988).
Cooper et al., "Cloning of the mouse homologue of the deleted in colorectal cancer gene (mDCC) and its expression in the developing mouse embryo" *Oncogene* 11:2243–2254 (1995).

Ekstrand et al., "DCC expression is altered by multiple mechanisms in brain tumours" *Oncogene* 11:2393–2402 (1995).
Ellerby et al., "Establishment of a cell–free system of neuronal apoptosis: comparison of premitochondrial, mitochondrial, and postmitochondrial phases" *J. Neurosci.* 17:6165–6178 (1997).
Goldberg et al., "Cleavage of Huntington by apopain, a proapoptotic cysteine protease, is modulated by the polyglutamine tract" *Nat. Genet.* 13:442–449 (1996).
Greene et al., "Sequence and expression of human estrogen receptor complementary DNA" *Science* 231:1150–1154 (1986).
Hedrick et al., "The DCC gene product in cellular differentiation and colorectal tumorigenesis" *Genes Dev.* 8:1174–1183 (1994).
Imbert et al., "Cloning of the gene for spinocerebellar ataxia 2 reveals a locus with high sensitivity to expanded CAG/glutamine repeats." *Nat. Genet.* 14:285–291 (1996).
Johnson et al., "Expression and structure of the human NGF receptor" *Cell* 47:545–554 (1986).
Kane et al., "Expression of bcl–2 inhibits necrotic neural cell death" *J. Neurosci. Res.* 40:269–275 (1995).
Kawaguchi et al., "CAG expansions in a novel gene for machado–joseph disease at chromosome 14q32.1" *Nat. Genet.* 8:221–228 (1994).
Koide et al., "Unstable expansion of CAG repeat in hereditary dentatorubral–pallidoluysian atrophy (DRPLA)" *Nat. Genet.* 6:9–13 (1994).
La Spada et al., "Androgen receptor gene mutations in X–linked spinal and bulbar muscular atrophy" *Nature* 352:77–79 (1991).
Macdonald et al., "A novel gene containing a trinucleotide repeat that is expanded and unstable on huntington's disease chromosomes" *Cell* 72:971–983 (1993).
Matsuyama et al., "Molecular features of the CAG repeats of spinocerebellar ataxia 6 (SCA6)" *Hum. Molec. Gen.* 6:1283–1287 (1997).

(List continued on next page.)

Primary Examiner—David Saunders
Assistant Examiner—Mary Beth Tung
(74) Attorney, Agent, or Firm—Campbell Flores

(57) ABSTRACT

The present invention provides substantially pure proapoptotic dependence peptides. The peptides consist substantially of the sequence of an active dependence domain selected from the group of dependence polypeptides consisting of p75[NTR], androgen receptor, DCC, huntingtin polypeptide, Machado-Joseph disease gene product, SCA1, SCA2, SCA6 and atrophin-1 polypeptide. Substantially pure proapoptotic dependence peptides include SATLDALLAALRRI (SEQ ID NO:3), Q14 (SEQ ID NO:7), SATLDALLAALGGI (SEQ ID NO:4), SATLDALLAALRGI (SEQ ID NO:5), SATLQALLAALRRI (SEQ ID NO:6), tat-GG-SATLDALLAALRRI (SEQ ID NO:37) and tat-GG-Q14 (SEQ ID NO:36).

23 Claims, 4 Drawing Sheets

OTHER PUBLICATIONS

Onodera et al., "Molecular Cloning of a full–length cDNA for dentatorubral–pallidoluysian atrophy and regional expressions of the expanded alleles in the CNS" *Am. J. Hum. Genet.* 57:1050–1060 (1995).

Orr et al., "Expansion of an unstable trinucleotide CAG repeat in spinocerebellar ataxia type 1" *Nat. Genet.* 4:221–226 (1993).

Petronilli et al., "The voltage sensor of the mitochondrial permeability transition pore is tuned by the oxidation–reduction state of vicinal thiols" *J. Biol. Chem.* 269:16638–16642 (1994).

Pfeiffer et al., "The peptide mastoparan is a potent facilitator of the mitochondrial permeability transition" *J. Biol. Chem.* 270:4923–4932 (1995).

Rabizadeh et al., "Induction of apoptosis by the low–affinity NGF receptor" *Science* 261:345–348 (1993).

Riess et al., "SCA6 is caused by moderate CAG expansion in the $\alpha_{1A}$ –voltage–dependent calcium channel gene" *Hum. Molec. Gen.* 6:1289–1293 (1997).

Rovelli et al., "Chimeric tumor necrosis factor–TrkA receptors reveal that ligand–dependent activation of the TrkA tyrosine kinase is sufficient for differentiation and survival of PC12 cells" *Proc. Natl. Acad. Sci. USA* 90:8717–8721 (1993).

Sanpei et al., "Identification of the spinocerebellar ataxia type 2 gene using a direct identification of repeat expansion and cloning technique, Direct" *Nat. Genet.* 14:277–284 (1996).

Stamenkovic et al., "A B–lymphocyte activation molecule related to the nerve growth factor receptor and induced by cytokines in carcinomas" *EMBO J.* 8:1403–1410 (1989).

Trottier et al., "Cellular localization of the Huntington's disease protein and discrimination of the normal and mutated form" *Nat. Genet.* 10:104–110 (1995).

Zhuchenko et al., "Autosomal dominant cerebellar ataxia (SCA6) associated with small polyglutamine expansions in the $\alpha_{1A}$ –voltage–dependent calcium channel" *Nat. Genet.*, 15:62–69 (1997).

Hileman et al., "A cytoplasmic peptide of the neurotrophin receptor p75NTR: induction of apoptosis and NMR determined helical conformation," *FEBS Letters*, 415:145–154 (1997).

Bredesen et al., "p75$^{NTR}$ and apoptosis: Trk–dependent and Trk–independent effects," *Trends Neruosci.* 20:287–290 (1997).

Burgess et al., Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine, J of Cell Bio. 111:2129–21, Aug. 1990.*

Lazar et al, Transforming Growth Factor alpha: Mutation of Aspartic Acid 47 and Leucine 48 Result in Different Biological Activities, Molecular and Cellular Biology 8:1247–1252, Mar. 1988.*

Tao et al., Role of Carbohydrate in the Structure and Effector Functions Mediated by the Human IgG Constant Region, The Journal of Immunology, 143:2595–2601, Sep. 1989.*

Bowie et al, Deciphering the Message in Protein Sequences: Tolerance to Amino Acid Substitutions, Science, 247:1306–1310, Mar. 1990.*

* cited by examiner

PROAPOPTOTIC PEPTIDES DEPENDENCE POLYPEPTIDES AND METHODS OF USE

This invention was made with government support under grant number CA69381 awarded by the National Institutes of Health. The United States Government has certain rights in this invention.

BACKGROUND OF THE INVENTION

This invention relates to negative signal transduction and cell death signaling and, more specifically to the particular amino acid sequences and structures which directly mediate cell death through negative signaling.

Apoptosis is a normal physiological process of cell death that plays a critical role in the regulation of tissue homeostasis by ensuring that the rate of new cell accumulation produced by cell division is offset by a commensurate rate of cell loss due to death. It has now become clear that disturbances in apoptosis, also referred to as physiological cell death or programmed cell death, that prevent or delay normal cell turnover can be just as important to the pathogenesis of diseases as are known abnormalities in the regulation of proliferation and the cell cycle. Like cell division, which is controlled through complex interactions between cell cycle regulatory proteins, apoptosis is similarly regulated under normal circumstances by the interaction of gene products that either induce or inhibit cell death.

The stimuli which regulate the function of these apoptotic gene products include both extracellular and intracellular signals. Either the presence or the removal of a particular stimulus can be sufficient to evoke a positive or negative apoptotic signal. For example, physiological stimuli that prevent or inhibit apoptosis include, for example, growth factors, extracellular matrix, CD40 ligand, viral gene products, zinc, estrogen and androgens. In contrast, stimuli which promote apoptosis include growth factors such as tumor necrosis factor (TNF), Fas, and transforming growth factor $\beta$ (TGF$\beta$), growth factor withdrawal, loss of extracellular matrix attachment, intracellular calcium and glucocorticoids, for example. Other stimuli, including those of environmental and pathogenetic origins, also exist which can either induce or inhibit programmed cell death. Although apoptosis is mediated by diverse signals and complex interactions of cellular gene products, the results of these interactions is thought to feed into a cell death pathway that is evolutionarily conserved between humans, other mammals and invertebrates.

Several gene products which modulate the apoptotic process have now been identified. These gene products include cell survival polypeptides such as Bcl-2, cell death polypeptides such as Bax, and cysteine aspartate proteases (caspases). The interaction and regulation of these gene products with cell surface or cytoplasmic receptors which transduce cell survival or death signals from outside the cell is as yet fairly uncharacterized. Additionally, it is unclear as to how many other genes exist which participate in apoptosis or what role they may play in the programmed cell death pathway. Finally, it also is unclear what the physiological control mechanisms are which regulate programmed cell death or how the cell death pathways interact with other physiological processes within the organism.

Thus, there exists a need for the elucidation of cell death pathways and the identification of novel molecular components which mediate apoptosis. Such molecular components can be used for the treatment or diagnosis of cell death mediated diseases. The present invention satisfies this need and provides related advantages as well.

SUMMARY OF THE INVENTION

The present invention provides substantially pure proapoptotic dependence peptides. The peptides consist substantially of the sequence of an active dependence domain selected from the group of dependence polypeptides consisting of p75$^{NTR}$, androgen receptor, DCC, huntingtin polypeptide, Machado-Joseph disease gene product, SCA1, SCA2, SCA6 and atrophin-1 polypeptide. Substantially pure proapoptotic dependence peptides include SATLDAL-LAALRRI (SEQ ID NO:3), Q14 (SEQ ID NO:7), SATLDALLAALGGI (SEQ ID NO:4), SATLDALLAAL-RGI (SEQ ID NO:5), SATLQALLAALRRI (SEQ ID NO:6), tat-GG-SATLDALLAALRRI (SEQ ID NO:37) and tat-GG-Q14 (SEQ ID NO:36). The invention also provide a method of increasing cell survival. The method consists of inhibiting the function of an active proapoptotic dependence domain. A method of increasing cell survival consisting of preventing or reducing the rate of formation of an active proapoptotic dependence domain is also provided. The invention further provides a method of identifying compounds which prevent or inhibit apoptosis. The method consists essentially of administering a test compound to a cell undergoing dependence domain mediated apoptosis, and determining whether the compound increases cell survival. A method of reducing the severity of a proapoptotic dependence domain mediated pathological condition is also provided. The method consists of inhibiting the function of an active dependence domain. Additionally provided is a method of reducing the severity of a pathological condition mediated by unregulated cell growth. The method consists of cytoplasmically administering a proapoptotic dependence peptide.

DETAILED DESCRIPTION OF THE INVENTION

Figure 1:
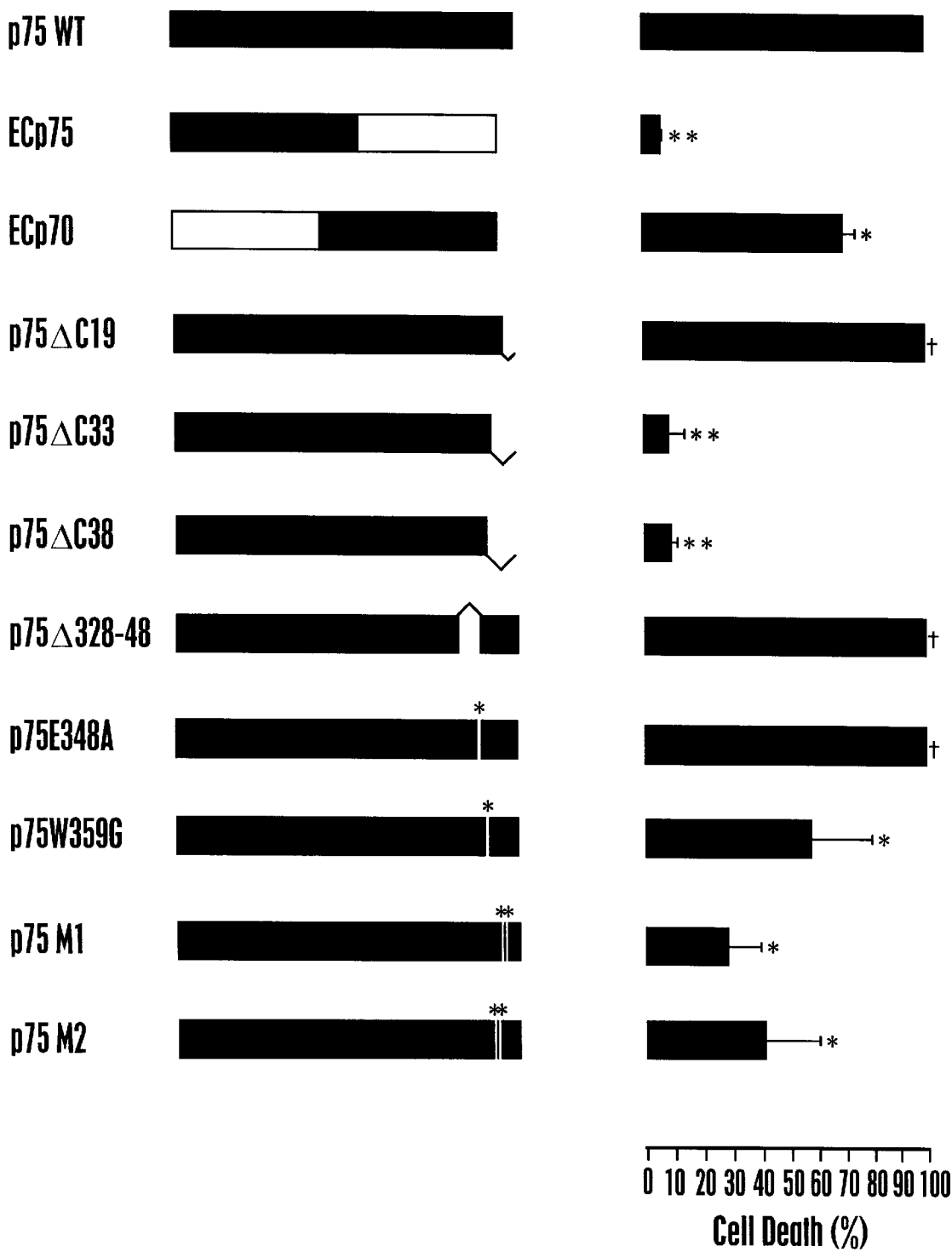
FIG. 1 shows the ability of p75$^{NTR}$, p75$^{NTR}$ variants and p75$^{NTR}$/TNFR I chimeras to stimulate apoptosis.

This invention is directed to proapoptotic peptides, which are capable of inducing cell death, and methods of using proapoptotic peptides. The proapoptotic peptides, also termed proapoptotic dependence peptides, are generally derived from negative signaling polypeptides or other molecules participating in cell death. Negative signaling polypeptides induce cell death when these polypeptides fail to interact with their respective ligands or are otherwise activated by some form of structural alteration. The proapoptotic dependence peptides of the invention are advantageous in that they can directly mediate cellular apoptosis. Thus, the peptides are useful for the treatment of various pathological conditions characterized by unregulated cell growth or survival such as cancer, autoimmune and fibrotic disorders. Moreover, proapoptotic dependence peptides derived from negative signaling polypeptides are advantageous in that they can be used for the identification of compounds which inhibit cell death mediated by negative signaling polypeptides.

In one embodiment, the invention is directed to a proapoptotic dependence peptide derived from or modeled after the dependence polypeptide p75$^{NTR}$ (SEQ ID NO:2). The neurotrophin receptor, or p75$^{NTR}$, is a negative signaling polypeptide that mediates apoptosis, neuronal atrophy and decreased neurite outgrowth in the absence of bound neurotrophin. The presence of the neurotrophin receptor p75$^{NTR}$ therefore creates a state of dependence on neurotrophin for the survival of neuronal cells. It is a region of the cytoplasmic domain of p75$^{NTR}$, the proapoptotic dependence domain, that directly induces apoptosis in the absence of neurotrophin. The region within the cytoplasmic domain which confers this dependent state and exhibits proapoptotic activity is a region of about fourteen amino acid residues having the sequence SATLDALLAALRRI (SEQ ID NO:3).

In another embodiment, the invention is directed to proapoptotic dependence peptides derived from or modeled after other dependence polypeptides such as the androgen receptor (SEQ ID NO:11), the Machado-Joseph disease polypeptide (SEQ ID NO:13), the huntingtin polypeptide (SEQ ID NO:15), and the SCA1 (SEQ ID NO:17), SCA2 (SEQ ID NO:19), SCA6 (SEQ ID NO:21) and atrophin-1 (DRPLA; SEQ ID NO:23) polypeptides. These dependence polypeptides contain a polyglutamine sequence of variable length that when synthesized as a peptide exhibits proapoptotic activity that directly induces programmed cell death when introduced or expressed intracellularly. The region of the dependence polypeptide that confers this dependent state and exhibits proapoptotic activity is a polyglutamine region of about fourteen amino acids having the sequence QQQQQQQQQQQQQQ (SEQ ID NO:7). The invention is also directed to proapoptotic dependence peptides in which the polyglutamine sequence region is between about 6 to 100 amino acid residues, sometimes about 200 amino acid residues, generally about 14 to 40 amino acids.

As used herein, the term "proapoptotic" refers to a peptide that is capable in itself of inducing apoptosis or programmed cell death when expressed or introduced intracellularly. The induction of apoptosis by proapoptotic peptides does not depend upon normal physiological stimuli such as the absence of growth or survival factors, or the presence of cell death stimuli. Although proapoptotic dependence peptides function in the absence of physiological stimuli, these peptides can additionally increase the rate or extent of apoptosis when expressed or introduced into a cell which has been induced to undergo apoptosis by such physiological stimuli. Proapoptotic dependence peptides can also induce apoptosis at different rates, and at different points of the cell cycle, depending on the nature of the peptide and the cells in which the dependence peptide is expressed.

As used herein, the term "dependence domain" when used in reference to a dependence polypeptide is intended to mean the portion or domain of a dependence polypeptide which can be induced to stimulate apoptosis. Dependence domains can exist in a range of apoptotically active states or be in an inactive state in the dependence polypeptide. To stimulate apoptosis, a dependence domain is induced to the apoptotically active state and, once induced, the dependence domain can directly stimulate apoptosis. A dependence domain can be induced to an apoptotically active state by a conformational change of a dependence polypeptide or a structural change mediated by altered or induced processing of the dependence polypeptide. A dependence domain therefore requires the induction of a conformational or structural change within the larger dependence polypeptide to enable its interaction with a component of the cellular apoptotic machinery to stimulate apoptosis.

Conformational or structural changes can occur, for example, by the removal of a growth or survival factor from a dependence polypeptide which functions as a receptor for the growth or survival factor. In this situation removal of the growth factor ligand activates the dependence domain. Alternatively, addition of a ligand to a dependence polypeptide can induce a conformational or structural change which activates the dependence domain. Likewise, a dependence polypeptide other than a cell surface receptor, for example an intracellular protein, can undergo a conformational or structural change induced by binding to a ligand or dissociation from a ligand.

A conformational or structural change also can be induced by processing of the dependence polypeptide. For example, proteolytic cleavage of the dependence polypeptide in vivo can liberate an apoptotically active dependence domain that is accessible to the cellular apoptotic machinery. Alternatively, cleavage of an apoptotically active dependence polypeptide can inactivate the proapoptotic activity of the dependence domain.

A dependence domain also can be activated by association with another molecule, such as an effector molecule that induces a conformational or structural change upon a dependence domain. For example, a ligand other than a receptor agonist can bind to the dependence polypeptide and induce a conformational or structural change that activates the proapoptotic activity of the dependence domain. A conformational or structural change also can be induced by an effector molecule that, for example, phosphorylates the dependence polypeptide.

Specific examples of dependence domains include, for example, regions within the cytoplasmic domain of receptors which negatively signal cell death such as p75$^{NTR}$ (neurotrophin receptor; SEQ ID NO:2), DCC (deleted in colonic carcinoma; SEQ ID NO:25) and CD40 (SEQ ID NO:27). A dependence domain of p75$^{NTR}$ contains, for example, the sequence SATLDALLAALRRI (SEQ ID NO:3). Other examples of dependence domains include the polyglutamine regions of the androgen receptor (SEQ ID NO:11), the Machado-Joseph polypeptide (SEQ ID NO:13), the huntingtin polypeptide (SEQ ID NO:15), the atrophin-1 polypeptide (SEQ ID NO:23), and the SCAL (SEQ ID NO:17), SCA2 (SEQ ID NO:19) and SCA6 (SEQ ID NO:21) polypeptides. Dependence domains are known to exist in other dependence polypeptides, and can be identified by those skilled in the art using the methods described herein. The size of the dependence domain can vary as they are contained within the parent dependence polypeptide. Such size differences are to be included within the meaning of the term so long as the dependence domain retains the ability to be induced to an apoptotically active state.

As used herein, the term "active" or "apoptotically active" when used to describe the state of a dependence domain is intended to mean that the domain exhibits a conformation or structure which can directly induce or stimulate apoptosis. It is the occurrence of a conformational or structural change within a dependence polypeptide which yields an active dependence domain capable of stimulating apoptosis. For example, when used in reference to a dependence polypeptide which is a receptor for a cell survival or growth factor, such as p75$^{NTR}$, DCC or the estrogen receptor, the dependence domain of the receptor is active when the factor is removed from the receptor. In the particular example of p75$^{NTR}$, removal of a dependence domain from a larger inhibitory context, for example, from an inactive dependence polypeptide, similarly yields an active dependence domain that is capable of directly stimulating apoptosis. Additional examples of active dependence domains are regions of the cytoplasmic domains of unliganded receptors such as p75$^{NTR}$, DCC and CD40, an N-terminal apopain cleavage fragment of the huntingtin polypeptide (SEQ ID NOS:28–31), a polyglutamine region containing between about 10 to 25 glutamine residues (Q10; SEQ ID NO:8 and Q25; SEQ ID NO:9, for example) that is a cleavage product of unliganded androgen receptor, and the polyglutamine regions from the Machado-Joseph, SCA1, SCA2, SCA6 and atrophin-1 polypeptides. Other examples of active dependence domains exist as well and are known or can be identified by those skilled in the art.

As used herein, the term "dependence peptide" when used in reference to a proapoptotic peptide is intended to mean a peptide having substantially the same amino acid sequence, or functional equivalent or fragment thereof, as a dependence domain. A proapoptotic dependence peptide can directly stimulate apoptosis when expressed or introduced into a cell. A proapoptotic dependence peptide is therefore a constitutively active dependence domain, or functional fragment thereof, whose proapoptotic activity is independent of a conformational or structural change. Dependence peptides can be as large or larger than the entire dependence domain or as small as 10 amino acids or less. Where the natural dependence polypeptide is known to be processed by a protease such as a caspase, the dependence peptide can be less than the naturally occurring processed polypeptide. A specific example of a proapoptotic dependence peptide is that derived from a dependence domain of p75$^{NTR}$ having the sequence SATLDALLAALRRI (SEQ ID NO:3). Another example is the polyglutamine peptide Q14 (SEQ ID NO:7) derived from a dependence domain of the androgen receptor, the Machado-Joseph polypeptide, the huntingtin polypeptide and the SCA1, SCA2 and atrophin-1 polypeptides. Additional examples include modified forms of a p75$^{NTR}$ derived dependence peptide which have the sequences SATLDALLAALGGI (SEQ ID NO:4), SATLDALLAALRGI (SEQ ID NO:5) and SATLQALLAALRRI (SEQ ID NO:6). Thus, proapoptotic dependence peptides of the invention are substantially pure proapoptotic peptides that are derived from or include dependence domains. It is intended that various lengths of polyglutamine-containing proapoptotic dependence peptides derived from or modeled after dependence polypeptides are within the scope of the invention.

As used herein, the term "functional equivalent" is intended to mean a peptide that has proapoptotic activity and is modeled after or derived from a dependence peptide. Peptides modeled after or derived from dependence peptides refers to an amino acid sequence or chemical structure that is deduced or produced from the amino acid or encoding nucleotide sequence of the dependence peptide. Functionally equivalent dependence peptides can be identified as those that stimulate apoptosis when introduced or expressed in cells. Specific examples of such functionally equivalent dependence peptides are described further below in Example III. A functionally equivalent dependence peptide can have a relatively high or low apoptotic activity and can be essentially any sequence modeled after or derived from a dependence peptide so long as it induces apoptosis in one or more cell types.

Functionally equivalent dependence peptides include those substituted at the level of the primary sequence, for example amino acid substitutions that include natural and nonnatural amino acids, such as penicillamine, and their derivatives or analogs, or those modified at the level of secondary structure, for example changes in cyclization mediated by disulfide bond formation. A functionally equivalent dependence peptide can be artificial, for example it can be engineered or be a chimera, or naturally occurring, for example it can be obtained from a dependence domain or fragment thereof, or be a peptidomimetic. Furthermore, a functional equivalent can be phosphorylated or otherwise modified by the addition of lipid and carbohydrate chains. Such substitutions and modifications of the proapoptotic dependence peptide are to be included within the meaning of the term so long as the peptide stimulates apoptosis in one or more cell types.

A "contingency peptide" as used herein, is intended to refer to a particular type of dependence peptide which corresponds substantially to the sequence of a natural in vivo proteolytic cleavage product or otherwise processed peptide or polypeptide that exhibits proapoptotic activity. Specific examples of contingency peptides include, for example, an amino-terminal apopain cleavage fragment of the huntingtin polypeptide (SEQ ID NOS:28–31) and the amino-terminal cleavage product of an unliganded androgen receptor (SEQ ID NO:32). It is noted that alternative cleavages can form different contingency peptides derived from the same dependence polypeptide.

As the term proapoptotic dependence peptide is used in reference to the compositions of the invention, the definition of this term is intended to exclude those isolated naturally occurring peptides that are known to possess inherent proapoptotic activity in the native peptide. Specific examples of known isolated naturally occurring proapoptotic peptides are the wasp venom peptide toxin mastoparan and the β-amyloid peptide. The definition however explicitly does not exclude the use of any of such compositions in the methods of the invention.

As used herein, terms which reference specific dependence polypeptides, unless stated to the contrary, are intended to maintain the meaning of these terms as they are commonly referred to in the art. Moreover, the nucleotide and amino acid sequences of each of these polypeptides are similarly intended to be substantially that which is known in the art. For example, the nucleotide and predicted amino acid sequence of the following dependence polypeptides can be found published in, for example, p75$^{NTR}$ (SEQ ID NO:1 and SEQ ID NO:2; Johnson et al. *Cell* 47:545–554 (1986)), DCC (SEQ ID NO:24 and SEQ ID NO:25; Hedrick et al. *Genes Dev.* 8:1174–1183 (1994)), androgen receptor (SEQ ID NO:10 and SEQ ID NO:11; Chang et al. *Proc. Natl Acad. Sci USA* 85:7211–7215 (1988)), estrogen receptor (SEQ ID NO:34 and SEQ ID NO:35; Greene et al. *Science* 231:1150–1154 (1986)), huntingtin (SEQ ID NO:14 and SEQ ID NO:15; Trottier et al. *Nat. Genet.* 10:104–110 (1995)); Ambrose et al. *Somat. Cell. Mol. Genet.* 20:27–38 (1994)), CD40 (SEQ ID NO:26 and SEQ ID NO:27; Stamenkovic et al. *EMBO J.* 8:1403–1410 (1989)), SCA1 (SEQ ID NO:16 and SEQ ID NO:17; Banfi et al. *Nat. Genet.* 7:513–519 (1994)), SCA2 (SEQ ID NO:18 and SEQ ID NO:19; Sanpei et al. *Nat. Genet.* 14:277–291 (1996)), SCA6 (SEQ ID NO:20 and SEQ ID NO:21; Zhuchenko et al. *Nat. Genet.* 15:62–69 (1997)), atrophin-1 (SEQ ID NO:22 and SEQ ID NO:23; Onodera et al. *Am. J. Hum. Genet.* 57:1050–1060 (1995)) and Machado-Joseph disease (SEQ ID NO:12 and SEQ ID NO:13; Kawaguchi et al. *Nat. Genet.* 8:221–228 (1994)). The sequences of the dependence polypeptides listed above are of human origin, however, it is noted that the sequences of the dependence polypeptides from other species are known and are intended to be included within the meaning of the term as used herein. Likewise, other dependence polypeptides are known or can be identified by those skilled in the art and are intended to be included within the meaning of the term as used herein.

As used herein, the term "peptide" when used in reference to the proapoptotic molecules of the invention is intended to mean any string of two or more amino acids covalently joined through a peptide bond. The proapoptotic peptides of the invention are generally less than about 250 residues, preferably the proapoptotic peptides are less than about 100 amino acids, and more preferably the proapoptotic peptides are between about 5 and 50 amino acids in length. Specific dependence peptides exemplified herein have sizes of 14 amino acid residues. The peptides can be obtained by biochemical, recombinant or synthetic means known to those skilled in the art. The term similarly includes natural and nonnatural amino acids as well as functionally alternative forms such as derivatives, analogs and mimetics thereof so long as the peptide or alternate form maintains its activity to directly stimulate apoptosis. The synthesis, testing and function of such amino acid derivatives, analogs and mimetics is well known to those skilled in the art.

As used herein, the term "heterologous functional domain" is intended to mean a non-proapoptotic domain that imparts a second function onto the proapoptotic peptides of the invention. For example, a heterologous functional domain can impart targeting capabilities or facilitate cell entry, enhance apoptosis, or modulate the proapoptotic activity of the dependence peptide. Heterologous functional domains can consist of peptide and polypeptide domains as well as other domains consisting of small organic and inorganic molecules, nucleic acids, carbohydrates, lipids and combinations thereof. Heterologous functional domains also can include chemical moieties such as a drug. Specific examples of heterologous functional domains include ligands to cell surface proteins or domains that otherwise facilitate cell entry which therefore function to target the proapoptotic peptides to specific cells and tissues. The HIV tat protein is such a heterologous functional domain which facilitates cellular entry. Heterologous functional domains also include, for example, cytotoxic and cytostatic chemical moieties that enhance apoptosis, or those that regulate activity, for example, modular derepressible motifs such as the glucocorticoid receptor hormone binding domain. Additional examples of heterologous functional domains are known to those skilled in the art and are intended to be included within the meaning of the term so long as they impart a second function onto the proapoptotic peptides of the invention.

As used herein, the term "ligand" is intended to mean a molecule or molecules that selectively interacts with another molecule. A ligand can consist of virtually any chemical structure and have any biological function so long as its interaction with another molecule is selective. Examples include, but are not limited to, a hormone receptor interacting with its hormone ligand, an enzyme interacting with a substrate, any protein-protein interaction such as an antibody interacting with an antigen, or a protein-lipid or protein-DNA interaction.

The invention provides a substantially pure proapoptotic dependence peptide. The peptide consists essentially of the sequence of an active dependence domain selected from the group of dependence polypeptides consisting of $p75^{NTR}$, androgen receptor, huntingtin polypeptide, Machado-Joseph polypeptide, SCA1, SCA2, SCA6 and atrophin-1 (DRPLA) polypeptide. Also provided are substantially pure proapoptotic dependence peptides consisting substantially of the amino acid sequence SATLDALLAALRRI (SEQ ID NO:3), SATLDALLAALGGI (SEQ ID NO:4), SATLDALLAALRGI (SEQ ID NO:5) and SATLQALLAALRRI (SEQ ID NO:6), or functional equivalents thereof. A proapoptotic dependence peptide comprising a polyglutamine region or functional equivalent thereof is also provided.

The cell surface neurotrophin receptor $p75^{NTR}$ (SEQ ID NO:2) is a negative cell signaling polypeptide that can be induced to stimulate apoptosis. For example, in the presence of bound neurotrophin or other ligand agonist, $p75^{NTR}$ is apoptotically inactive whereas in the absence of neurotrophin, unliganded $p75^{NTR}$ stimulates cellular apoptosis. Apoptosis is therefore mediated by a conformational or structural modulation of $p75^{NTR}$ induced by ligand release. The conformational or structural modulation of $p75^{NTR}$ can be inhibited by dimerization or multimerization with a different protein indicating that a monomeric form of $p75^{NTR}$ iS the active form which can stimulate apoptosis.

A region of the cytoplasmic domain of $p75^{NTR}$ that can mediate proapoptotic activity is included in an about fourteen amino acid region having substantially the sequence SATLDALLAALRRI (SEQ ID NO:3). When expressed or introduced into a cell, a peptide consisting essentially of the sequence SATLDALLAALRRI or functional equivalent thereof directly stimulates apoptosis. Thus, a region of $p75^{NTR}$ which contains this sequence is a dependence domain and a peptide containing the sequence SATLDALLAALRRI is a proapoptotic dependence peptide. This proapoptotic sequence is conserved across species and the identical sequence is found to be expressed in the human and rat $p75^{NTR}$ cytoplasmic domains. The proapoptotic peptide SATLDALLAALRRI further exhibits an α-helical secondary structure.

The cell surface DCC gene product (SEQ ID NO:25) also is a negative cell signaling polypeptide that can be induced to stimulate apoptosis. For example, in the presence of netrin or other ligand agonist, DCC is apoptotically inactive. The removal of netrin induces a conformational or structural change of the DCC receptor which results in a concomitant stimulation of apoptosis. A region of the amino-terminus of DCC (SEQ ID NO:33), which in intact cells is intracellular, can mediate proapoptotic activity of this dependence polypeptide.

The intracellular androgen receptor, or AR (SEQ ID NO:11), is another dependence polypeptide that can stimulate apoptosis. Apoptosis can be stimulated by the AR in response to a cell death signal. The apoptotic signal results in the induction of a structural or conformational change in the androgen receptor which stimulates the cell death pathway. One structural or conformational change that occurs in the AR is a proteolytic cleavage which liberates a contingency peptide of about 154 amino acids (SEQ ID NO:32). It is this contingency peptide that is capable of stimulating apoptosis.

In the above specific example, the contingency peptide released by caspase-3 mediated cleavage contains a dependence domain consisting of a polyglutamine containing sequence. A peptide containing this domain is capable of directly stimulating apoptosis. The size of the polyglutamine domain ranges from about 11 to 66 amino acids and a peptide of about 14 polyglutamine amino acids when synthesized and introduced into cells (Q14; SEQ ID NO:7) also can induce apoptosis. This Q14 peptide or other polyglutamine-containing peptides modeled after the AR dependence domain exhibits proapoptotic activity and is therefore a proapoptotic dependence peptide.

Similarly, the cytoplasmic huntingtin polypeptide (SEQ ID NO:15) is another dependence polypeptide that can be induced to stimulate apoptosis. Apoptosis can be stimulated by the huntingtin polypeptide in response to a cell death signal. As with the AR, the apoptotic signal induces a conformational or structural change in the huntingtin polypeptide which activates the cell death pathway. A particular type of structural or conformational change that occurs is a proteolytic cleavage which liberates a contingency peptide and thereby stimulates apoptosis. Apopain-mediated cleavage is one protease which can release an about 80 kDa contingency peptide which corresponds to an amino terminal peptide fragment of the huntingtin dependence polypeptide. The cleavage can occur at any of a cluster of four DXXD (SEQ ID NO:68) apopain cleavage-recognition motifs that are present in the huntingtin polypeptide. These motifs include DSVD, DEED, DLND and DGTD (SEQ ID NOS:69–72, respectively) and can be found at residues 510–513, 527–530, 549–552 and 586–589, respectively. (Goldberg et al. *Nat. Genet.* 13:442–449 (1996)).

The 80 kDa contingency peptide derived from the huntingtin polypeptide includes a polyglutamine containing dependence domain. The number of polyglutamine residues within this domain can vary and generally ranges from 7 to 28 amino acids in length but can exceed 36 amino acids in length. A peptide modeled after or derived from the polyglutamine-containing dependence domain of the huntingtin polypeptide exhibits substantially the same proapoptotic activity as the active dependence domain. Additionally, a peptide having a polyglutamine sequence of any of the sizes exhibited by the huntingtin polypeptide also exhibits substantially the same proapoptotic activity as the active dependence domain. Therefore, a peptide containing a polyglutamine region of huntingtin is one proapoptotic dependence peptide provided by the invention.

The intracellular Machado-Joseph polypeptide (SEQ ID NO:13) is another dependence polypeptide that can be induced into an active proapoptotic state through a conformational or structural change within a dependence domain. As with the AR and the huntingtin polypeptide, the dependence domain within the polypeptide is a polyglutamine-containing region. This region is the carboxy-terminal region of the Machado-Joseph protein and contains from about 13 to 36 or up to about 68 to 79 glutamine amino acids. Peptides containing this polyglutamine region sequence function as proapoptotic dependence peptides. Moreover, peptides consisting of polyglutamine residues within any of these ranges exhibit proapoptotic activity. Therefore, a peptide modeled after or derived from the dependence domain or the polyglutamine containing region of this domain is another proapoptotic dependence peptide provided by the invention.

Other dependence polypeptides which contain dependence domains that can be induced into an active state also are known to exist. These other polypeptides include, for example, the polypeptides encoded by the SCA1, SCA2, SCA6, atrophin-1 and CD40 genes. In particular, the SCA1, SCA2, SCA6 and atrophin-1 polypeptides include at least a polyglutamine-containing dependence domain similar to that previously described. A peptide modeled after or derived from the polyglutamine-containing dependence domain from any of these gene products induces apoptosis and is therefore a proapoptotic dependence peptide. A peptide containing a polyglutamine sequence within any of these polypeptides will similarly induce apoptosis and is therefore a proapoptotic dependence peptide. Thus, the invention provides proapoptotic dependence peptides selected from the group of dependence polypeptides SCA1, SCA2, SCA6 and atrophin-1.

The invention further provides proapoptotic dependence peptides consisting of a polyglutamine sequence. The polyglutamine sequence can be a variety of lengths so long as the peptide maintains its activity to induce apoptosis. The lengths of such polyglutamine containing dependence peptides can be from about 6 to 100 amino acid residues, sometimes up to about 250 amino acids. Preferably the length is about 10 to 100 amino acids, more preferably about 14 to 40 amino acids. Therefore, the invention provides dependence peptides of less than or equal to 40 amino acid residues.

Specific examples of dependence peptides that are derived from or modeled after dependence peptides are SATLDAL-LAALRRI (SEQ ID NO:3), SATLDALLAALGGI (SEQ ID NO:4), SATLDALLAALRGI (SEQ ID NO:5) and SATLQALLAALRRI (SEQ ID NO:6). These peptides were identified by generating variants of the p75$^{NTR}$ dependence peptide SATLDALLAALRRI and then testing for those which exhibit apoptotic activity.

Proapoptotic dependence peptides can be derived from or modeled after dependence domains. Dependence domains can exhibit a low- or non-apoptotic activity or alternatively, exhibit a moderate or high activity depending on the amino acid sequence of the domain and its conformational or structural state. In contrast, the activity of proapoptotic dependence peptides is independent of changes in conformation or structure and are therefore in a constitutively active state.

Factors that contribute to conformational and structural changes resulting in a dependence domain having more or less apoptotic activity can include, for example, the degree of ligand association. Specifically, in the case of a negative signaling molecule, a high affinity ligand can associate with a dependence polypeptide for a longer period of time than a low affinity ligand. This association can result in a dependence domain that is in an apoptotically active state for a comparatively longer period of time which prolongs the accessibility of the active dependence domain to the apoptotic machinery thereby enhancing apoptosis. In a cell, the apoptotic activity of the dependence domain and therefore the induction of apoptosis also can be affected by the degree of ligand association with a dependence polypeptide that is intracellular.

A dependence polypeptide also can exhibit different apoptotically active conformations and therefore different apoptotic activities by binding to a different ligand. For example, ligands with a similar affinity can bind to different sites on a dependence polypeptide and induce a conformational change that is specific for that site. The site of ligand binding on a dependence polypeptide therefore determines a level of apoptotic activity of a dependence domain. Multiple ligand-binding sites of a dependence polypeptide can result in a dependence domain that is capable of having a broad range of apoptotic activity.

Alternatively, a single binding site on a dependence polypeptide can bind to different ligands having different structures. The structure of a ligand also can control a conformation of a dependence polypeptide thereby determining the apoptotic activity of a dependence domain. Thus, the structure of a cell death or survival signal, such as a ligand, received by a dependence polypeptide can modulate its conformational state and therefore the proapoptotic activity of the dependence domain. In contrast, a contingency peptide of defined length produced by a structural change will likely contain a dependence domain that exhibits only a few variations in conformation that affect its apoptotic activity.

Another way in which the activity of a dependence domain can vary or be modulated is through the reversal of the conformational change associated with dependence polypeptide activation. Such a reversal can occur by, for example, the removal of ligand or addition of an antagonist. However, the ability to prevent or reverse the apoptotic activity of the dependence domain and therefore apoptosis after formation of an active dependence domain will be affected by the type of change required for dependence domain activation as described below.

In a cell, the level of apoptotic activity exhibited by a dependence domain is determined by, in part, the amount of a proapoptotic dependence domain that accumulates. The amount of active dependence domain that is needed for the stimulation of apoptosis in cells can be as few as a single proapoptotic dependence domain molecule or significantly more, for example, 10,000 molecules or greater. The amount needed to stimulate apoptosis can be highly variable among cell types and is largely determined by the apoptotic machinery within a particular cell and the interaction or regulation of the proapoptotic dependence domain with that apoptotic machinery.

Dependence polypeptides can be identified by a variety of methods known to those skilled in the art. Briefly, all that is required is to test for the induction of apoptosis following a conformational or structural change in a polypeptide that is mediated by a stimulus. Alternatively, those skilled in the art know or can determine if a particular stimulus induces programmed cell death and such stimuli can then be tested for the induction of a conformational or structural change in the polypeptide. Selection of the particular stimulus and corresponding polypeptide can be made by those skilled in the art based on current knowledge and accepted interpretations of experimental results known in the art. Proapoptotic polypeptides that undergo a structural or conformational change are potential candidates for the dependence polypeptides of the invention. Dependence polypeptides are identified as those polypeptides which yield proapoptotic peptides.

Selection of a polypeptide or stimulus to assess can be made by, for example, choosing molecules which are involved in programmed cell death or play a role in cell proliferation, differentiation, survival or growth. For example, receptors for cell regulatory factors can be tested for a change in conformation or structure of a domain and a concomitant induction of apoptosis in the presence or absence of ligand. Similarly, cytoplasmic or nuclear proteins can also be tested for a change in conformation or structure of a domain with a concomitant induction of apoptosis in the presence or absence of a stimulus. A specific example of such a cytoplasmic protein is where the stimulus is a growth factor. Other potential cellular dependence polypeptides include, for example, steroid hormone receptors, signal transduction molecules such as JAK, JNK and STAT, SH2 and SH3 containing proteins and a variety of transcription factors. Such molecules can all be tested in the presence or absence of a ligand or stimulus to determine the induction of a conformational or structural change which mediates apoptosis. A variety of methods exist for determining conformational or structural changes and the concomitant induction of apoptosis. For example, a selected molecule can be introduced or expressed in a cellular background which enables the determination of the functional properties of the polypeptide, ligand or stimulus. Using cell regulatory factor receptors as a specific example, such polypeptides can be expressed in apoptotically competent cells which normally do not express the receptors or in which the endogenous receptor can be selectively inhibited.

Cells that express or that are made to express, a candidate cell regulatory factor can then be tested for apoptosis in the presence or absence of the particular cell regulatory factor. Induction of apoptosis mediated through a change in conformation or structure of the receptor identifies that polypeptide as a potential candidate for a dependence polypeptide. Synthesis and testing for apoptotic activity of peptide fragments corresponding to different portions of the dependence polypeptide will confirm or refute that the potential candidate is a dependence polypeptide.

Alternatively, dependence polypeptides can be identified by first selecting ligands or polypeptides that are known or predicted to play a role in cell growth, proliferation, differentiation or survival. Such ligands or polypeptides can be tested for their ability to induce a conformational or structural change in a cognate binding partner which can then mediate apoptosis.

The identification of a cognate binding partner can be performed using methods well known to those skilled in the art. Such methods include, for example, affinity and immunoaffinity selection using ligands, antibodies and anti-idiotype antibodies, for example. Chromatography, affinity precipitation such as immunoaffinity precipitation, solid phase blotting procedures and panning methods are applicable for the identification of ligand or polypeptide binding partners. Numerous formats of such methods are known to those skilled in the art and can be used or modified according to the need and the particular type of binding partner to be identified. Additionally, biochemical purification methods and cloning procedures such as expression cloning with the ligand or polypeptide labeled so as to allow detection of binding interactions. Alternatively, the binding partner can be determined by selection of cells from an expression library for survival or death in the presence or absence of the ligand or polypeptide.

Dependence polypeptides also can be identified by hybridization techniques using nucleic acid probes that encode a polyglutamine containing sequence or other sequences such as SATLDALLAALRRI (SEQ ID NO:3), SATLDALLAALGGI (SEQ ID NO:4), SATLDALLAAL-RGI (SEQ ID NO:5) or SATLQALLAALRRI (SEQ ID NO:6) to screen a nucleic acid library. Probes derived from or modeled after nucleotide or amino acid sequences from other dependence domains or proapoptotic peptides can similarly be used to screen libraries for the identification of dependence polypeptides. Additionally, such nucleotide sequences can be used to search for similar or related sequences in EST and other databases.

Dependence polypeptides also can be identified by having regions of amino acid sequence homology to known dependence domains. For example, polypeptides having a polyglutamine region equal to or greater than an about 6 amino acid residue sequence can be selected and tested for dependence polypeptide function. Similarly, polypeptides identified as having a region of homology to the SATLDAL-LAALRRI (SEQ ID NO:3) dependence domain or modified forms of a dependence domain, SATLDALLAALGGI (SEQ ID NO:4), SATLDALLAALRGI (SEQ ID NO:5) or SATLQALLAALRRI (SEQ ID NO:6) can be dependence polypeptides. These and other methods are well known to those skilled in the art and can be used to identify dependence polypeptides.

Conformational or structural changes can also be determined by a variety of methods known to those skilled in the art. For example, if there is a structural change such as the cleavage of a domain fragment from the intact polypeptide, such a cleavage can be assessed by assaying for the change in size of the intact polypeptide. Alternatively, such a cleavage can be assessed by assaying for the appearance of the cleaved fragment. Immunoaffinity and electrophoretic methods known to those skilled in the art are amenable for such determinations. Other well known methods also exist and can similarly be used to assess a change in structure of a candidate dependence polypeptide.

Conformational changes can similarly be determined using a variety of methods known to those skilled in the art. For example, changes in conformation can be assessed by, for example, determining the binding of conformation-specific antibodies or other binding probes, construction and testing of methods known or predicted to influence conformational changes or stability of a polypeptide or by biophysical methods known in the art. Such biophysical methods include, for example, nuclear magnetic resonance, (NMR) and x-ray crystallography. In addition, the importance of a conformational change can be determined by altering its conformational state, for example, by examining the effect that multimerization with one or more additional proteins has on its apoptotic activity, as compared to the monomeric state.

Testing of the dependence domain in a candidate dependence polypeptide can be performed by, for example, recombinantly modifying the suspected dependence domain in the candidate polypeptide and testing whether the modified polypeptide maintains its ability to undergo a conformational or structural change with concomitant stimulation of apoptosis. Loss of dependence domain mediated apoptosis localizes the dependence domain to the modified sequences. Such modifications can be made by, for example, deletions, insertions or mutation of selected regions of sequences within the candidate polypeptide.

Alternatively, testing of the dependence domain in a candidate dependence polypeptide can be performed by, for example, synthesizing the domain and determining if it directly induces apoptosis. Such peptides can be made by a variety of methods known to those skilled in the art. For example, peptides can be obtained from commercial vendors or be synthesized on an automated apparatus. Such chemical synthesis enables the introduction of nonnatural and derivatized amino acids as well as structural modifications thereof. Recombinant expression of a dependence domain encoding nucleic acid also can be used to produce large quantities of protein. Mammalian, yeast, bacterial and insect cell systems are examples of expression systems well known in the art which can be used to recombinantly produce proapoptotic dependence domain peptides. Such synthesized or recombinantly produced dependence domain peptides can then be introduced into cells to determine their ability to directly induce apoptosis.

Alternatively, a nucleic acid which encodes the dependence domain portion of the candidate dependence polypeptide can be expressed in cells to determine if it directly induces apoptosis. Various expression systems are well known to those skilled in the art and can be used for constitutive or conditional expression of the encoded dependence domain polypeptide. Such methods and modes of expression are described in, for example, Sambrook et al. *Molecular Cloning: A Laboratory Manual*, 2nd Ed, Vols 1 to 3, Cold Spring Harbor Laboratory Press, New York (1989).

Dependence domain peptides that directly induce apoptosis can be further analyzed to determine which portions, or the portion of the domain which is sufficient to induce cell death. All of such peptides can be considered to be proapoptotic dependence peptides. The analysis can be performed by, for example, producing successively smaller fragments of the domain to identify those regions, or an individual sequence which still exhibits apoptotic activity. Additionally, site-directed mutagenesis can be used to further define the portion of the domain or the amino acids that are required for the proapoptotic activity of the dependence peptides. In addition, randomly generated mutations of a nucleic acid encoding a proapoptotic dependence peptide combined with cell transfections and sequencing analysis of the peptides that have proapoptotic activity can collectively be used to formulate a consensus motif of a proapoptotic dependence peptide.

The apoptotic activity of the dependence domains can be determined by a variety of methods known in the art. Such methods include, for example, induction of mitochondrial swelling, cytochrome c release and caspase-3 cleavage (Ellerby et al. *J. Neurosci.* 17:6165–6178 (1997)). Other methods known in the art exist and can similarly be used for determining the apoptotic activity of dependence polypeptides, domains or peptides.

The proapoptotic dependence peptides can be introduced into cells by methods well known to those skilled in the art. As described previously, a nucleic acid encoding a dependence peptide can be contained within a suitable expression vector, for example, a retroviral vector, and introduced into cells. The viral vector can have a natural or engineered cell tropism which can be used to facilitate cell entry or provide targeting. The use of such a tropic vector can enhance the transfection efficiency of cells. Proapoptotic dependence peptides themselves also can be introduced into cells by nonspecific endocytosis, or through the use of heterologous targeting domain. For example, in a particular embodiment described below, an HIV tat protein, when linked to a dependence peptide, facilitates cellular entry. Lipid carriers also can be used to introduce the nucleic acids encoding proapoptotic dependence peptides, or the peptide itself, directly into cells. Other methods of expressing or introducing proapoptotic dependence peptides into cells are known and can be used by those skilled in the art.

The invention provides a proapoptotic dependence peptide that contains a heterologous functional domain. The invention also provides a heterologous functional domain consisting of a targeting domain or a domain which facilitates cellular entry. The invention additionally provides a heterologous functional domain consisting of a tat peptide. The invention also provides substantially pure proapoptotic dependence peptides having a sequence consisting of SATLDALLAALRRI (SEQ ID NO:3), tat-GG-SATLDALLAALRRI (SEQ ID NO:37), Q14 (SEQ ID NO:7) and tat-GG-Q14 (SEQ ID NO:36). Also provided are substantially pure proapoptotic dependence peptides having a sequence consisting of SATLDALLAALGGI (SEQ ID NO:4), tat-GG-SATLDALLAALGGI (SEQ ID NO:38), SATLDALLAALRGI (SEQ ID NO:5), tat-GG-SATLDALLAALRGI (SEQ ID NO:39), SATLQALLAAL-RRI (SEQ ID NO:6) and tat-GG-SATLQALLAALRRI (SEQ ID NO:40) or functional equivalents thereof.

The proapoptotic dependence peptides can be combined with one or more heterologous functional domains to impart distinct or complimentary functions onto the proapoptotic peptides of the invention. The distinct or complimentary function of the heterologous functional domain can provide targeting functions and additional apoptotic activity onto the proapoptotic peptides of the invention. Additionally, a heterologous functional domain can also function as a regulator of the apoptotic activity of the peptide, for example.

A heterologous functional domain can consist of a domain that facilitates entry of a proapoptotic dependence peptide.

One example of such a heterologous functional domain that facilitates entry into a cell is the HIV tat protein. This protein or functional equivalents thereof, when coupled to a proapoptotic dependence peptide increases the apoptotic activity of the peptide 30-fold compared to the peptide alone. Additional heterologous domains that provide a cell targeting function or facilitate cellular entry also are known to those skilled in the art. Such domains include, for example, ligands to extracellular proteins or receptors, ligands to other cell surface receptors, antibodies, a natural or engineered viral protein with a desired cell tropism, toxin subunits which facilitate toxin entry and functional fragments thereof.

A heterologous functional domain also can augment the cell death activity of the proapoptotic dependence peptide by linking one or more additional cell death or inhibitory activities onto the proapoptotic dependence peptide. Such cell death or inhibitory activities include, for example, domains which exhibit apoptotic, cytotoxic or cytostatic activity. Domains which exhibit apoptotic activity include, for example, ligands or agonists to receptors which induce programmed cell death. Fas ligands or anti-Fas antibodies are two specific examples of such apoptotic domains. A domain which activates caspase protease activity is another example of a heterologous functional domain which exhibits apoptotic activity. Domains which exhibit cytotoxic or cytostatic activity include, for example, toxins and chemotherapeutic agents such as doxorubicin, methotrexate, vincristine and cyclophosphamide can be conjugated to a dependence peptide. Other agents exist as well and are known to those skilled in the art and can be linked to proapoptotic peptides to augment their cell death function.

Additionally, agents which enhance apoptosis through cell cycle regulation can be used as a heterologous functional domain. For example, genes that are required for cell proliferation or cell cycle progression can be inhibited by a heterologous domain that is an antisense nucleic acid of that gene. Cell cycle progression also can be inhibited by a negative regulator of the cell cycle, for example, a suppressor gene such as Rb or p53 or active fragment thereof. Such an inhibitor of cell cycle progression can enhance apoptosis in cells.

Alternatively, in other cell types, the apoptotic machinery can be, for example, more prevalent or more receptive to initiation by an active dependence domain in actively growing cells than cells in stationary phase. In these cells, stimulation of apoptosis by the dependence peptide can be enhanced by a heterologous domain that stimulates proliferation.

A heterologous functional domain also can be a regulatable moiety that modulates the activity of a proapoptotic dependence peptide. When linked to a proapoptotic dependence peptide, a modular domain can impart ligand dependent activation or repression of its proapoptotic activity. For example, many different ligand-dependent transcription factors having inducible ligand-binding domains are known in the art.

A heterologous functional domain also can provide a variety of other useful functions known to those skilled in the art. For example, it can be a lipid-based agent to facilitate cell entry, or an agent that increases or decreases the stability of the proapoptotic dependence peptide either intra- or extra-cellularly. A heterologous functional domain also can provide an imaging and/or visualization function which is mediated by an isotopic, calorimetric or fluorometric agent. Such an imaging function is useful for screening an expression library for interacting proteins, or for detecting or localizing apoptosis in vivo.

A proapoptotic dependence peptide of the invention also can contain more than one heterologous functional domain. For example, a molecule containing a proapoptotic dependence domain attached to two or more identical domains or moieties or attached to two or more different domains or moieties. An example of such a molecule containing two or more different domains is a dependence peptide attached to a cell targeting domain and a chemotherapeutic moiety. The exact chemical nature and structural organization of such a heterologous domain/dependence peptide construct will be known by those skilled in the art and can be determined based on the particular application.

A heterologous functional domain can consist of a variety of different types of moieties ranging from small molecules to large macromolecules. Such moieties can be, for example, nucleic acid, polypeptide or peptide, carbohydrate, lipid, or small molecule compounds. Both natural and non-naturally occurring compounds and derivatives are similarly included.

The invention further provides a method of increasing cell survival. The method consists of inhibiting the function of an active dependence domain.

Dependence domain mediated pathological conditions which are characterized by abnormal or enhanced cellular apoptosis can be treated by inhibiting the function of an active dependence domain. Inhibition can be achieved by, for example, inhibiting the apoptotic stimulus which induces the change. Alternatively, inhibiting the structural or conformational change associated with the formation of an active dependence domain or inhibiting the activity of the active dependence domain or contingency peptide can inhibit the function of an active dependence domain. Depending on the apoptotic stimulus, a variety of different methods known in the art can be used to inhibit the stimulus and, therefore, the induction of an active dependence domain. For example, if the apoptotic stimulus is removal of a cell growth or survival factor, addition of such a factor can be used to inhibit apoptosis. Alternatively, if the apoptotic stimulus is production of a cell death signal, removal of the signal can be used to inhibit apoptosis.

Methods of inhibiting a conformational or structural change in dependence polypeptides are similarly well known in the art and will depend on the type of change sought to be inhibited. Such methods include direct inhibition of active dependence domain formation by, for example, binding a ligand or other specifically reactive molecule to the dependence domain so as to prevent activation or revert it to an inactive conformation. Multimerization of $p75^{NTR}$ inhibits the change in conformation associated with apoptotic activation and can therefore similarly be employed as a direct method of inhibition. An indirect method for inhibition can be, for example, binding a ligand or specifically reactive molecule to an adjacent domain which allosterically inhibits the change in conformation.

For the inhibition of a structural change such as a cleavage event which produces a contingency peptide, agents which bind to or near the cleavage site that mask its recognition motif can be used to prevent cleavage and formation of the apoptotic fragment. Alternatively, inhibitors of the protease which cleaves the dependence polypeptide can also be used to inhibit the structural change.

Finally, pathological conditions mediated by dependence polypeptides activated by a conformational or structural change induced by proteolytic cleavage can be treated by inhibiting an association between a contingency peptide and the cellular apoptotic machinery. Such methods are described in greater detail below and, as with those described above, are similarly well known to those skilled in the art.

The invention further provides a method of increasing cell survival by inhibiting the function of an active dependence domain by selectively binding a ligand to a dependence polypeptide containing the active dependence domain.

The activity of a dependence domain in dependence polypeptides can be inhibited by selectively binding a ligand to the dependence polypeptide so as to prevent negative signaling and apoptosis. Ligand binding can inhibit dependence domain function either indirectly or directly. For example, a ligand can bind to the dependence polypeptide and revert the dependence domain to an apoptotically inactive conformation. Alternatively, a ligand can bind, for example, to an active dependence domain and directly inhibit its interaction with a component of the apoptotic machinery. Similarly, in the case of a dependence polypeptide activated by a structural change, direct inhibition by ligand binding at or near the active dependence domain can prevent its interaction with a component of the cellular apoptotic machinery.

For dependence polypeptides that are activated to their proapoptotic state by ligand binding, antagonists also can be used to inhibit the function of a dependence domain. An antagonist can be in excess of a ligand or exhibit a higher affinity than the ligand in order to displace it from a dependence polypeptide and inhibit a conformational or structural change associated with dependence domain activation.

Ligands that directly or indirectly inhibit the function of an active dependence domain can be identified and used by those skilled in the art. Such ligands can essentially be any compound or macromolecule. Combinatorial libraries of such molecules can be used to identify suitable ligands having a desired property. Once identified, those skilled in the art can determine by titration, for example, the amount to be used to inhibit the function of an active dependence domain to increase cell survival. It should be recognized that ligands, such as agonists, antagonists or those that directly inhibit interaction with the apoptotic machinery can have a high or low binding affinity. Those skilled in the art can select a ligand based on the characteristics desired and the particular application.

The invention further provides a method of inhibiting the function of a dependence domain by inhibiting the association of an active dependence domain with an interacting molecule.

Inhibitors of an association between an active dependence domain and the apoptotic machinery can include, for example, molecules that selectively bind to an active dependence domain as well as those that otherwise bind and inhibit the association. Such molecules that otherwise inhibit an association can do so by, for example, steric hinderence when bound adjacent to an active dependence domain. For example, a peptide domain or mimetic of an interacting component of the apoptotic machinery, can bind to a dependence domain and inhibit its association with the component of the apoptotic machinery to enhance cell survival. Such a mimetic can be derived from or modeled after an interacting component of the apoptotic machinery.

Alternatively, an inhibitor of an association can selectively bind to a component of the apoptotic machinery, for example, a peptide domain or mimetic of an active dependence domain. Such a dependence domain mimetic would mimic binding to a component of the apoptotic machinery, but would not mimic induction of apoptosis. The binding of such a non-apoptotic dependence domain mimetic to a component of the apoptotic machinery can prevent an association between an active dependence domain and a component of apoptotic machinery.

It is noted that inhibition of an association between an active dependence domain and a component of the apoptotic machinery does not require that the binding molecules described above be a peptide domain or mimetic. Rather, any molecule that can bind selectively to an active or inactive dependence domain or a component of the apoptotic machinery can inhibit the association of an active dependence domain with an interacting molecule. A method of identifying selectively-binding molecules that inhibit an association is further described below.

In a similar fashion, a repressor molecule also can directly or indirectly inhibit an association between an active dependence domain and a component of the apoptotic machinery. For example, the ligand-bound neurotrophin receptor $p75^{NTR}$ is apoptotically inactive and forms a homodimer that represses the activity of a dependence domain. In contrast, in the absence of neurotrophin, $p75^{NTR}$ is monomeric and stimulates apoptosis. Thus, a repressor molecule that directly or indirectly promotes $p75^{NTR}$ homodimer or multimer formation can inhibit an association with the apoptotic machinery. Formation of homodimers or multimers also can be induced by, for example, phosphorylation or other post-translational modifications known to those skilled in the art.

The invention provides a method of increasing cell survival by preventing or reducing the rate of formation of an active proapoptotic dependence domain.

The invention provides a method of identifying compounds which prevent or inhibit apoptosis. The method consists of administering a test compound to a cell undergoing proapoptotic dependence domain mediated apoptosis and determining whether the compound increases cell survival. Further provided is a method wherein apoptosis is induced by unliganded $p75^{NTR}$.

Identifying compounds useful for treating pathologies mediated by inappropriate or unregulated proapoptotic dependence domain mediated apoptosis, can be performed using cells that express a dependence polypeptide. The cells are administered a test compound under conditions which allow the induction of apoptosis. An increase in cell survival can be determined by assaying for the ability of the cells to remain viable, proliferate or by measuring other apoptotic determinants known in the art. Viability can be measured by, for example, trypan blue exclusion, whereas proliferation can be determined by, for example, tritium incorporation.

In one embodiment, cells that express the $p75^{NTR}$ neurotrophin receptor can be used to identify compounds that prevent or inhibit apoptosis. The cells can be administered a test compound in the presence and absence of neurotrophin, and cells that survive or proliferate in the absence of neurotrophin can be counted and compared to control cells that were administered neurotrophin. A test compound that increases cell survival in the absence of neurotrophin can be further tested, for example, for the relative efficacy and the concentrations needed to inhibit apoptosis using titration experiments. The test compound also can be administered before, during, or after withdrawal of neurotrophin from the cells to determine the time of optimal efficacy. Such procedures are well known in the art and given the teachings provided herein, can be used to identify and optimize compounds which inhibit proapoptotic dependence domain mediated apoptosis.

Additional cell-based assay systems using other dependence polypeptides and functional equivalents or fragments thereof can similarly identify compounds that increase cell survival by preventing or inhibiting proapoptotic dependence domain mediated apoptosis. For example, cells expressing a proapoptotic dependence peptide under the control of a regulatable promoter, such as an MMTV promoter, can be administered a test compound before, during, or after exposure of the cells to glucocorticoid hormone to determine if the test compound can increase cell survival in the presence of the stimulus which induces active dependence domain formation. Regulatable expression of a dependence peptide in cells is advantageous in that different dependence peptides can be expressed and test compounds administered. Test compounds found to increase cell survival can be tested against a variety of different dependence peptides to determine their range of efficacy. Compounds which display an ability to increase the survival of cells expressing different dependence polypeptides or proapoptotic dependence peptides can be a broad spectrum inhibitor of apoptosis and be useful in the therapeutic methods of the invention.

Compounds that can be tested for their ability to increase cell survival can be small organic molecules, nucleic acids, carbohydrates, proteins or peptides, and mimetics or fragments thereof or combinations thereof. Large scale screening of combinatorial libraries of biologically active substances are known in the art and can be administered as test compounds. The test compounds can be added to the culture media and directly interact with cell surface dependence polypeptides or, if hydrophobic, can directly enter cells. Alternatively, in the event that the dependence polypeptide or functional equivalent is intracellular, a test compound can be conjugated to a targeting moiety, for example, the HIV tat protein, to facilitate cell entry. Incorporation of the test compound into liposomes is another method which can be used to facilitate cell entry. Those skilled in the art can readily determine the appropriate delivery method of a test compound depending on the particular system used.

Apoptosis participates in the maintenance of tissue homeostasis in a number of physiological processes such as embryonic development, hematopoietic cell regulation and normal cell turnover. Recent advances indicate that dysfunction, or loss of regulated apoptosis, can lead to a variety of pathological disease states. For example, the loss of apoptosis in cells can lead to the pathological accumulation of self-reactive lymphocytes, virally infected cells, hyperproliferative cells such as neoplastic or tumor cells and cells that contribute to fibrotic conditions. Inappropriate activation of apoptosis also can contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can alter the progression of many of these diseases.

The invention provides a method of reducing the severity of a proapoptotic dependence domain mediated pathological condition. The method consists of inhibiting the function of an active dependence domain. Further provided is a method of inhibiting the association of an active proapoptotic dependence domain with an interacting molecule. The invention also provides a method of reducing the severity of a dependence domain mediated pathological condition by inhibiting or reducing the rate of formation of an active proapoptotic dependence domain.

Dependence domain mediated pathological conditions that are characterized by cells that exhibit aberrant increases in cell death can be treated by inhibiting the function of an active dependence domain. Dependence domain function can be inhibited by inhibiting the cell death stimulus which induces the conformational or structural change of a dependence polypeptide, as previously described. In addition, ligand agonists, antagonists and other inhibitory binding molecules can inhibit the conformation or structural change of a dependence polypeptide thereby reducing the severity of a dependence domain mediated pathological condition. Such ligands can revert a dependence polypeptide to an apoptotically inactive state or directly or indirectly inhibit the function of the dependence domain by preventing its interaction with a component of the apoptotic machinery. The inhibition of apoptosis using these agents can reduce the severity of the dependence domain mediated pathology.

Methods that inhibit or reduce dependence domain formation by inhibiting a conformational or structural change to increase cell survival have been described previously. Such methods also can be used to reduce the severity of a dependence domain mediated pathological condition.

The severity of pathologies mediated by negative signaling dependence polypeptides can be reduced by administering a therapeutic ligand, such as an agonist, antagonist, protease inhibitor, or other binding inhibitor, as previously described, to inhibit or reduce the rate of formation of an active dependence domain. An individual exhibiting the pathology or an afflicted tissue can be administered such a ligand in a pharmaceutically acceptable carrier. Therapeutic ligands can enter the tissue by passive diffusion, or alternatively, by a delivery vehicle. A lipid-based vessicle is one example of a delivery vehicle that can be used to facilitate entry of a peptide molecule. Additionally, a targeting domain can be associated with the therapeutic ligand or a lipid vessicle carrier which contains the therapeutic ligand. Alternatively, a nucleic acid can encode a peptide or polypeptide therapeutic ligand which can be introduced and expressed into the appropriate cells or tissues by methods known in the art. Such compositions can be administered by intravenous injection into the bloodstream or directly injected into the afflicted region.

Dependence polypeptides containing polyglutamine sequence dependence domains have been identified as mediators of pathologies associated with abnormal induction of apoptosis. For example, a direct correlation exists between polyglutamine sequence expansion of a dependence polypeptide and clinical onset of a disease. In particular, expansion of a huntingtin polypeptide polyglutamine sequence beyond 36 amino acids is associated with Huntingtin's disease (Macdonald et al. *Cell* 72:971–983 (1993)). Similarly, expansion of a polyglutamine sequence in AR from a normal range of about 11 to 33 to about 38 to 66 residues is associated with the manifestation of Spinal and Bulbar muscular atrophy (LaSpada et al. *Nature* 352:77–79(1991)). Furthermore, expansion of a polyglutamine dependence domain of atrophin-1, Machado-Joseph, SCA1, SCA2 and SCA6 is associated with a manifestation of the respective dentatorubropallidoluysian atrophy, Machado-Joseph disease, spinocerebellar ataxia type 1, spinocerebellar ataxia type 2 and spinocerebellar ataxia type 6 pathologies (Koide et al. *Nat. Genet.* 6:9–13(1994)); Kawaguchi et al. *Nat. Genet.* 8:221–228 (1994); Orr et al. *Nat. Genet.* 4:221–226 (1993); Sanpei et al. *Nat. Genet.* 14:277–284 (1996); Zhuchenko et al. *Nat. Genet.* 15:62–69 (1997)).

Diseases characterized by abnormal levels of cellular dependence domain mediated apoptosis can be treated by using the previously described methods that inhibit dependence domain activation thereby altering the course of the disease. Such methods include, for example, inhibiting the apoptotic stimulus that induces a conformational or structural change of a dependence polypeptide. Therapeutic ligands, antagonists and other inhibitory binding molecules can inhibit or prevent an association between an active dependence domain and a component of the apoptotic machinery or inhibit proteolytic cleavage and contingent peptide formation thereby alleviating the pathology. Such therapeutic ligands and binding inhibitors can be administered to a subject at the site of the pathology. Alternatively, a nucleic acid encoding an inhibitory peptide in a suitable expression vector, or an antisense nucleic acid derived from or modeled after a proapoptotic dependence domain can be contained in a lipid-based vessicle or a viral vector and can be administered to a subject to alleviate the pathology. Introduction of such therapeutic ligands, inhibitors and antisense molecules into a sufficient number of diseased cells can inhibit or decrease the rate of dependence-domain mediated apoptosis of these cells which can therefore alter the course of the pathology.

Thus, the invention also provides a method of reducing the severity of a dependence domain-mediated pathological condition of Huntingtin's disease, Alzheimer's disease, Kennedy's disease, Spinocerebellar atrophy, dentatorubropallidoluysian atrophy, Machado-Joseph disease, stroke and head trauma.

The invention provides a method of reducing the severity of a pathological condition mediated by unregulated cell proliferation or cell survival consisting of cytoplasmically administering a proapoptotic dependence peptide. Further provided is a method of reducing the severity of a pathological condition consisting of neoplastic, malignant, autoimmune or fibrotic conditions by cytoplasmically administering a proapoptotic dependence peptide.

A proapoptotic dependence peptide can be administered into the afflicted region or regions characterized by unregulated cell growth or survival to reduce the severity of the pathological condition. Proapoptotic dependence peptides can include, for example, Q14 (SEQ ID NO:7), SATLDALLAALRRI (SEQ ID NO:3), SATLDALLAALRGI (SEQ ID NO:5) or SATLQALLAALRRI (SEQ ID NO:6), or a functional equivalent or fragment thereof. If desired, a dependence peptide that exhibits relatively less apoptotic activity as compared to SATLDALLAALRRI, such as SATLDALLAALGGI (SEQ ID NO:4), can be administered into the afflicted region. The peptides can be introduced into the cell by, for example, a heterologous targeting domain or using a lipid based carrier. A formulation containing a proapoptotic dependence peptide that provides stability or resistance to serum proteases additionally can be used as well as other formulations known in the art. For the treatment of a neoplastic or fibrotic condition, the proapoptotic dependence peptide can be administered by direct injection into a solid tumor mass or into a region of fibrosis. Additional modes of administration are known and can be determined by those skilled in the art depending on the pathological condition to be treated.

The invention further provides a method of reducing the severity of a pathological condition mediated by unregulated cell proliferation or cell survival by cytoplasmically administering a nucleic acid encoding a proapoptotic dependence peptide.

A nucleic acid encoding a proapoptotic dependence peptide or functional equivalent or fragment thereof can be delivered into an appropriate tissue to alleviate the severity of a pathological condition characterized by unregulated cell growth or survival. Expression of the nucleic acid can be provided by a constitutively active or regulatable promoter. For example, a tissue specific promoter can be used to restrict expression of a proapoptotic dependence peptide to those cells and tissues that characterize the pathology. A regulatable promoter can be used to control the induction of apoptosis or to restrict apoptosis to cells exposed to an inducer. Such vectors, promoters and expression constructs for nucleic acids are known to those skilled in the art. Viral vectors containing a natural or engineered envelope protein also can be used to target a nucleic acid encoding a proapoptotic dependence peptide to neoplastic, malignant or autoimmune tissues of cells expressing an appropriate cell surface protein. Thus, disorders characterized by cells that abnormally proliferate can be selectively targeted for apoptosis.

It is understood that modifications which do not substantially affect the activity of the various embodiments of this invention are also included within the definition of the invention provided herein. Accordingly, the following examples are intended to illustrate but not limit the present invention.

EXAMPLE I

Restoration of Neurotrophin Dependence and Negative Apoptotic Signaling in Prostate Carcinoma Cells This Example shows that the restoration of $p75^{NTR}$ expression in prostate carcinoma cells confers neurotrophin dependence and negative apoptotic signaling.

Prostrate carcinoma is characterized by a gradual decline in the level of $p75^{NTR}$ expression from the development of benign prostatic hypertrophy to progression into metastatic carcinoma. Human PC3 prostate carcinoma cells do not express $p75^{NTR}$, nor are they neurotrophin dependent. To determine if $p75^{NTR}$ expression confers a state of neurotrophin dependence in PC3 cells, $p75^{NTR}$ was expressed in the PC3 cells and the viability of the transfected PC3 cells was determined in the presence and absence of neurotrophins.

Briefly, PC3 prostate carcinoma cells were grown in DMEM/F12 (50/50) supplemented with 5% fetal bovine serum (FBS) and seeded at a density of 50% on 10 cm tissue culture dishes. For transfections, 10 µg of the pBabepuro-$p75^{NTR}$ expression vector or insert-less pBabepuro plasmid DNA (Morgenstern and Land Nucl. Acids Res. 18:1068 (1990)) was added to 50 µl of the lipofection reagent DOTAP (Boehringer Mannheim Biochemicals, Indianapolis, Ind.) in a polystyrene tube, mixed, and the volume was adjusted to 500 µl with HBS (20 mM Hepes, 150 mM NaCl). After 30 minutes, the DNA/lipofection solution was added directly to the PC3 cells. PC3 cell transfectants were selected by growing the cells in 5 µg/ml of puromycin. The cells also were incubated in the presence or absence of a 2 mM mixture of the following neurotrophins: nerve growth factor, brain-derived neurotrophic factor, or neurotrophic factor 3. After puromycin selection and propagation of the transformed cells over the course of 15 to 18 days, the number of surviving cells were counted.

The results indicate that in the absence of exogenous neurotrophins, the viability of the $p75^{NTR}$ transfected PC3 cells was approximately 50 to 80% less than control cells transfected with the insert-less pBabepuro plasmid. In addition, the $p75^{NTR}$ transfected PC3 cells incubated in 2 mM of neurotrophin exhibited a significant improvement in colony number. These results show that a state of neurotrophin dependence was created by expressing p75$^{NTR}$ in PC3 cells.

EXAMPLE II

Identification of a Dependence Domain in p75$^{NTR}$

This Example shows that the stimulation of apoptosis by p75$^{NTR}$ can be mediated by a domain near the carboxy-terminus and that mutating a region similar to the Fas/Apo-1 and TNFR I death domains in p75$^{NTR}$ does not affect the apoptotic activity of p75$^{NTR}$ This Example also shows that multimerization of p75$^{NTR}$ can inhibit proapoptotic activity.

Expression constructs containing wild type p75$^{NTR}$, p75$^{NTR}$ variants and p75$^{NTR}$/TNFR II chimeras were constructed and are shown in FIG. 1. The p75$^{NTR}$ variants consisted of single point mutations, double point mutations, carboxy-terminal deletions and internal deletions. The p75$^{NTR}$/TNFR II chimeras consisted of the p75$^{NTR}$ amino-terminal half fused to TNFR II carboxy-terminal half, ECp75, and the TNFR II amino-terminal half fused to the p75$^{NTR}$ carboxy-terminal half, ECp70. Each construct was expressed in NRA5 mutant PC12 neural cells, which do not normally express p75$^{NTR}$, to determine the region of p75$^{NTR}$ that confers neurotrophin dependence. The results are shown in FIG. 1.

Briefly, cloning of the wild type p75$^{NTR}$ and the variant p75$^{NTR}$ cDNAs into the pBabepuro mammalian expression vector was performed as described (Rabizadeh et al. *Science* 261:345–348 (1993)). p75$^{NTR}$ variants containing single point mutations at positions 348, 359 and 370, in which glutamic acid was replaced with alanine (E348A), tryptophan was replaced with glycine (W359G) and leucine was replaced with lysine (L370K), were generated using the Altered Sites II in vitro Mutagenesis System (Promega, Madison, Wis.) with a single stranded template of p75$^{NTR}$ cDNA. The primers used were 5'-CCTTTACCCACGCGGCCTGCCCAGT-3' (E348A; SEQ ID NO: 57), 5'-CTGCTGGCCAGCGGGGGTGCCCAG-3' (W359G; SEQ ID NO:58), and 5'-ACGCTTGATGCCAAATTAGCCGCCCTGCGA-3' (L370K; SEQ ID NO:59).

The p75$^{NTR}$ carboxy-terminal deletion variants of 19 amino acids, p75ΔC19, and 33 amino acids, p75ΔC33, were generated by PCR amplification with the Pfu polymerase enzyme (Stratagene, La Jolla, Calif.). The 5' PCR primer contains the unique Bam HI site located at 700 bp of the rat p75 cDNA and is 5'-ATGGATCCCAAGGTCTACGCC-3' (SEQ ID NO:60). Both 3' PCR primers contained Sal I sites which introduce a stop codon following isoleucine 377 or asparagine 363, and are 5'-CGCTGGTCGACTAGATGCGTCGCAG-3' (SEQ ID NO:61) for p75ΔC19 and 5'-CGCTGGTCGACTAGTCCTGGGCACC-3' (SEQ ID NO:62) for p75ΔC33. The pBabepuro-p75ΔC19 and pBabepuro-p75ΔC33 expression vectors were constructed by replacing the Bam HI-Sal I fragment in pBabepuro-p75 with the corresponding PCR products. A third p75$^{NTR}$ carboxy-terminal deletion variant of 38 amino acids, p75ΔC38, was produced by a partial Pvu II digestion of the p75$^{NTR}$ cDNA in a pUC18 cloning plasmid. The construct was then digested with Xba I and the restriction sites were filled in with the Klenow fragment of DNA Polymerase I to generate blunt ends. The resulting 1.3 kb DNA fragment was agarose gel fractionated, purified and religated to create the pUC18-p75ΔC38 plasmid. The p75ΔC38 cDNA was then excised from this plasmid and cloned into the pBabepuro expression vector as described above.

The p75$^{NTR}$ variant M1 contained two point mutations in which both arginines at positions 375 and 376 were replaced with glycine. The p75$^{NTR}$ variant M2 contained two point mutations in which both leucines at positions 370 and 371 were replaced with lysine and proline, respectively. The M1 and M2 variant p75$^{NTR}$ cDNAs were generated from a pUC18-p75 plasmid by first removing a Bam HI-Xba I fragment from the plasmid and then replacing it with two fragments generated by PCR amplification using Pfu. The first PCR product spanned from the Bam HI site within the p75$^{NTR}$ open reading frame to a new Hind III site which contained the desired mutation. The second PCR product spanned from the same new Hind III site to the Xba I site in the pUC18 plasmid. The PCR products were digested and ligated into the Bam H1 and Xba I digested pUC18-p75 plasmid to generate a cDNA encoding the M1 or M2 variant p75$^{NTR}$. The oligonucleotides used to amplify the first PCR product were 5'-ATCCCTGGTCGATGGATCCCAA-3' (SEQ ID NO:63), which contained the Bam HI site, and 5'-TCTCTGGATCCCTCCCAGGGCG-3' (SEQ ID NO:64) which contained the Hind III site and the M1 mutation, or 5'-CTGGATCCGTCGCAGGGCGGCTGGTTTGG-3' (SEQ ID NO:65), which contained the Hind III site and the M2 mutation. For the second PCR product, the oligonucleotides were 5'-CTGCGACGGATCCAGAGAGCTG-3' (SEQ ID NO:66), which contained the Hind III site and 5'-GCTCTAGAACATCAGTCGTCGGA-3' (SEQ ID NO:67), which contained the Xba I site.

The p75$^{NTR}$ internal deletion variant lacking a Fas/Apo-1 like region spanning amino acids 328 to 348 is denoted p75Δ328-48 and was constructed using a strategy similar to that described above. Briefly, PCR amplification was used to generate two fragments that flanked the desired deletion which contained either one of the restriction sites Bam HI or Xba I. After Bam HI or Xba I digestion, the two flanking sequence fragments were religated into a Bam HI and Xba I digested pUC18-p75 plasmid. The p75$^{NTR}$ internal deletion variant cDNA was excised from this plasmid and cloned into the pBabepuro expression vector as described above.

The chimeric p75$^{NTR}$/TNFR II expression constructs were obtained from E. Shooter (constructed as described by Rovelli et al. *Proc. Natl. Acad. Sci. USA* 90:8717–8721 (1993)) and then subcloned into the pBabepuro expression vector. For the chimeric constructs, the gray regions indicate p75$^{NTR}$ and the white regions indicate TNFR II and are shown in FIG. 1. The nucleotide sequence of all constructs was confirmed by DNA sequencing. The expression of p75$^{NTR}$ protein was detected by flow cytometry using monoclonal antibody 192, and immunoblotting using anti-p75 antiserum (Promega, Madison, Wis.).

The FKBP12-tagging vector MF1E/MF3E, which included an amino-terminal myristylation site for membrane insertion (Spencer et al. *Science* 262:1019–1024 (1993)), contains one and three repeats of the FK-binding protein (FKBP) sequence. The FKBP12 vector served as a PCR template and was amplified using primers flanked by Nhe I (5' primer) or Nde I (3' primer) sites to produce DNA fragments consisting of one or three FK-binding domains (FKBP). The resulting PCR products contained either one or three FKBP sequence repeats and were subcloned into pcDNA3.1. A DNA fragment encoding an intracytoplasmic form of p75$^{NTR}$ was removed from the pUC18-p75 plasmid by digestion with Nde I and Bam HI, and the DNA fragment was ligated to the carboxy-terminus of the FKBP sequences within the pcDNA3.1-FKBP construct. The resulting two expression vectors encoded FKBP/p75$^{NTR}$ chimeras comprising one or three FKBP repeats at the amino-terminus fused to an intracytoplasmic form of p75$^{NTR}$ at the carboxy-terminus.

PC12 NRA5 cells were grown and maintained as described previously (Rabizadeh et al. *Science* 261:345–348 (1993)). For transfection, the cells were exposed to the cationic lipid DOTAP (Boehringer Mannheim Biochemicals, Indianapolis, Ind.) containing the particular p75$^{NTR}$ expression vector using the manufacturer's protocol. To obtain stable transfectants, the cells were selected in 5 µg/ml puromycin, and pools of puromycin resistant cell transfectants were compared in the analysis (Zhong et al. *Proc. Natl. Acad. Sci. USA* 90:4533–4537 (1993)). The expression of p75$^{NTR}$ protein in the transfected cells was detected by flow cytometry using the monoclonal antibody 192 (Baldwin et al. *J. Immunol.* 267:8352–8359 (1992)). Cell death was quantitated by propidium iodide as previously described (Rabizadeh et al. *Science* 261:345–348 (1993) and Kane et al. *J. Neurosci. Res.* 40:269–275 (1995)).

The results shown in FIG. 1 indicate the percentage of cell death stimulated by particular p75$^{NTR}$ constructs after normalization to that stimulated by wild type p75$^{NTR}$. Each p75$^{NTR}$ construct was analyzed in 3 to 7 separate transfections and the statistical significance was assessed by the two-tailed t-test with bars indicating standard error; $p<0.05$ is indicated by *, and $p<0.01$ by **. The asterisks over the constructs indicate mutation sites and the † symbol indicates mutants that induced cell death at least as effectively as p75$^{NTR}$.

The results indicate that wild type p75$^{NTR}$, p75WT, stimulates apoptosis and has an $EC_{50}$ of about 10–50 µm. In contrast, a p75$^{NTR}$/TNFR II chimeric protein having an amino-terminal p75$^{NTR}$ portion fused to a carboxy-terminal TNFR II portion, ECp75, failed to stimulate apoptosis in NRA 5 cells whereas a TNFR II/p75$^{NTR}$ chimeric protein having an amino-terminal TNFR II portion fused to a carboxy-terminal p75$^{NTR}$ portion, ECp70, stimulated apoptosis in NRA 5 cells. These findings indicate that a proapoptotic dependence domain is located in a carboxy-terminal region of p75$^{NTR}$. Therefore, additional mutations within the carboxy-terminal region of p75$^{NTR}$ were analyzed.

The effect of amino acid deletions at or near the carboxy-terminus of p75$^{NTR}$ on the apoptotic activity was determined. Deletion of the carboxy-terminal 19 amino acids of p75$^{NTR}$, p75ΔC19, did not diminish the ability of this p75$^{NTR}$ variant to stimulate apoptosis; in fact, a slight increase in apoptosis was observed. However, extending the carboxy-terminal deletion an additional 14 residues for a total of 33 amino acids, p75ΔC33, abolished the ability of this p75$^{NTR}$ variant to induce apoptosis in the absence of neurotrophin.

The 14 amino acid internal near the carboxy-terminus sequence of p75$^{NTR}$ that confers neurotrophin dependence lies just to the carboxyl side of a sequence region that exhibits sequence similarity to the Fas/Apo-1 and TNFR I death domains. This Fas/Apo-1 and TNFR I like region was tested for its ability to confer neurotrophin dependence in p75$^{NTR}$ by deletion analysis and site directed mutagenesis. An internal deletion of 21 amino acids that removed the Fas/Apo-1 and TNFR I like sequence region, p75Δ328-48, did not inhibit the ability of this p75$^{NTR}$ variant to induce apoptosis. Similarly, point mutations of the native TNFR I protein which abolish TNFR I's ability to stimulate cellular apoptosis, when introduced into the Fas/Apo-1 and TNFR I like region of p75$^{NTR}$, had little or no effect on neurotrophin dependence. Specifically, point mutations in which the tryptophan at position 359 was replaced with glycine, p75W359G, or the glutamic acid at position 369 was replaced with alanine, p75E348A, had little or no effect on the ability of these p75$^{NTR}$ variants to stimulate apoptosis. Thus, a Fas/Apo-1 and TNFR like death domain located immediately to the aminyl side of the 14 amino acid sequence region of p75$^{NTR}$ is not required for the stimulation of apoptosis.

To further confirm the importance of the 14 amino acid domain, p75$^{NTR}$ variants containing single or double point mutations in the domain were analyzed for their ability to stimulate apoptosis. Specifically, replacing leucine with lysine at position 370 (L370K) of p75$^{NTR}$ abolished proapoptotic activity. Similarly, replacing the two arginines with glycine at positions 375 and 376 in p75$^{NTR}$, p75M1, or replacing the two leucines at positions 370 and 371 with lysine and proline in p75$^{NTR}$, respectively, p75M2, decreased the apoptotic activity. Specifically, the p75$^{NTR}$ variants p75M1 and p75M2 exhibited a 75% and 60% decrease in the stimulation of apoptosis, respectively, in comparison to wild type p75$^{NTR}$. These results demonstrate the importance of particular amino acids within the 14 amino acid proapoptotic dependence domain of p75$^{NTR}$ for the stimulation of apoptosis and further demonstrate that this domain confers neurotrophin dependence.

The stimulation of cellular apoptosis by Fas and TNFR I is induced by ligand binding which triggers multimerization of Fas and TNFR I. The assembly of such a death-inducing signaling complex contributes to cellular apoptosis by activating caspase-8. The effect that dimerization or multimerization has on the ability of p75$^{NTR}$ to stimulate apoptosis was analyzed. FKBP/p75$^{NTR}$ protein chimeras containing one or three copies of an FKBP fused to an intracytoplasmic form of p75$^{NTR}$ were expressed in cells. Cross-linking studies indicated that FKBP expressed in cells could be induced to form dimers or multimers by exposing the cells to the FK1012 agent. Therefore, a single copy FKBP/p75$^{NTR}$ protein chimera expressed in cells could be induced to form a dimer in the presence of the FK1012 dimerizing agent. Expression of a triple copy FKBP/p75$^{NTR}$ protein chimera in cells could be induced to form a multimer in the presence of FK1012.

Briefly, 293T cells were grown and maintained in DMEM supplemented with 10% FBS at 37° C. and plated at a density of 5×10$^5$ cells into each well of a 6-well plate. The cells were transiently transfected with 5 µg of plasmid DNA containing either a single copy or triple copy of the FKBP cDNA fused to intracytoplasmic p75$^{NTR}$ in the presence or absence of 2 µM FK1012 using the calcium phosphate method (Sambrook et al. *Molecular Cloning: A Laboratory Manual* Chapter 16 (1989)). After an 18 hour incubation, the cells were washed with DMEM and placed on DMEM supplemented with 3% FBS and 2 µM FK1012 as before. After an additional 18 hour incubation, transfected cells were placed on DMEM supplemented with 1.5% FBS, 2 µM FK1012 as before, and 35 µM tamoxifen to induce apoptosis.

These studies indicated that expression of a monomeric intracytoplasmic form of p75$^{NTR}$ in cells stimulates apoptosis. In contrast, apoptosis was blocked when cells containing the single copy or triple copy FKBP/p75$^{NTR}$ protein chimera were exposed to FK1012. These results demonstrate that dimerization or multimerization of p75$^{NTR}$ with a different protein can inhibit apoptosis and that a monomeric form of p75$^{NTR}$ can stimulate apoptosis.

EXAMPLE III

Induction of Cell Death with Proapoptotic Peptides

This Example shows the induction of cell death by the $p75^{NTR}$ dependence domain proapoptotic peptide SATLDALLAALRRI (SEQ ID NO:3) and by the polyglutamine proapoptotic peptide Q14 (SEQ ID NO:7).

A region of a dependence polypeptide that mediates apoptosis in cells was analyzed for its ability to stimulate apoptosis in cells. Various cell types were treated with peptide fragments modeled after a $p75^{NTR}$ dependence domain SATLDALLAALRRI (blue; SEQ ID NO:3, tat-blue; SEQ ID NO:37) and the polyglutamine-containing dependence domains tat-GG-Q14 (SEQ ID NO:36). The effect of replacing leucine with lysine at position 7 (purple, SATLDAKLAALRRI; SEQ ID NO:41; tat-purple, tat-GG-SATLDAKLAALRRI; SEQ ID NO:42), removing the carboxy-terminal "RRI" sequence (gray, SATLDALLAAL; SEQ ID NO:43; tat-gray, tat-GG--SATLDALLAAL; SEQ ID NO:44) or amino-terminal "SATLD" sequence (green; ALLAALRRI; SEQ ID NO:45) on the proapoptotic activity of a dependence peptide was examined. Negative control peptides, for example, the helicity controls (turquoise, KDRNLRRITRMVLV; SEQ ID NO:46; tat-turquoise, tat-GG-KDRNLRRITRMVLV; SEQ ID NO:47 and red, LDENFKRCFREFCI; SEQ ID NO:48), scrambled sequence (tat-yellow, tat-GG-DLSLARLATARLAI; SEQ ID NO:50), and positive control peptides, for example, the mastoparan peptide (MP, INLKALAALAKKIL; SEQ ID NO:51) also were examined. The 12 amino acid HIV tat protein fragment (GRKKRRQRRRPP; SEQ ID NO:52; hereinafter termed "tat"), which facilitates cellular entry, also was included on the amino terminus of some of the peptides tested. This HIV tat sequence did not affect the function of the peptide to which it was linked, as shown below. For convenience, the hyphen in the above amino acid sequences is a nomenclature intended to set apart the proapoptotic dependence peptides and variants thereof or control peptides from other amino acid residues contained in the peptide.

Briefly, NTera 2 human neuronal cells, R2 neural cells, CSM14.1 neural cells, LNCaP cells, SH-SY5Y human neuroblastoma cells and PC12 NRA5 cells were grown in DMEM/F12 (50/50) supplemented with 5% fetal bovine serum and seeded onto 96-well plates. The peptides were synthesized and HPLC purified (Coast Scientific, San Diego, Calif.). The purified peptides were dissolved in tissue culture grade water and diluted to 50 μM and 100 μM in serum free medium and directly added to the cells in 96-well plates. The cells were incubated at 37° C. for 18 hours and 20 μM propidium iodide was added. Cell viability was determined using a fluorimeter as previously described (Kane et al. *J. Neurosci. Res.* 40:269–275 (1995)). The presence of the dependence peptides lacking the tat sequence in cells was confirmed by confocal microscopy.

The results of these studies shown in Table 1 reveal that cells treated with a SATLDALLAALRRI (blue; SEQ ID NO:3) dependence peptide underwent apoptosis as did cells treated with the positive mastoparan peptide control (MP). Similarly, an all D-enantiomer of the dependence peptide stimulated apoptosis. In contrast, cells treated with either helicity control peptide (turquoise or red) did not undergo apoptosis. The leucine to lysine point mutation at position 7 (purple), the carboxy-terminal "RRI" (gray) and the amino-terminal "SATLD" (green) sequences were critical to the apoptotic function of SATLDALLAALRRI; these forms of the dependence peptide were incapable of stimulating apoptosis.

The proapoptotic dependence peptides containing the HIV tat sequence also stimulated apoptosis in cells. These studies indicated that tat-GG-SATLDALLAALRRI exhibited a 30-fold increase in apoptosis compared to the SATLDALLAALRRI dependence peptide lacking the tat sequence. Similar results were obtained for tat-GG-Q14 in comparison to Q14. Specifically, the viability of cells treated with 50 μM tat-GG-SATLDALLAALRRI was 1.5% for COS-7, 4.2% for PC3, 0% for LNCaP, 1.3% for NTera 2, 0% for R2, and 0% for NRA 5 cells (100 μM peptide). However, cells exposed to the tat sequence alone did not undergo apoptosis.

Peptides which did not exhibit apoptotic activity without the amino-terminal tat sequence similarly did not exhibit apoptotic activity with the linked tat sequence. Specifically, cell viability after exposure to tat-purple was 97.8% for COS-7, 92.8% for PC3 and 69.3% for NTera 2 cells. For tat-gray, cell viability was 97.1% for COS-7, 90.5% for PC3, 59.1% for LNCaP and 76.7% for NTera 2 cells. For tat-turquoise, cell viability was 87.9% for PC3, 46.7% for LNCaP, 67.6% for NTera 2, 92.6% for R2 and 95.7% for NRA 5 cells (100 μM peptide). Similarly, for tat-yellow, PC3 cell viability was 97%. These findings indicate that the tat sequence itself could neither confer apoptotic activity upon a peptide lacking apoptotic activity or inhibit the inherent apoptotic activity of a proapoptotic dependence peptide.

TABLE 1

Induction of Cell Death by Proapoptotic Peptides

| Peptide designation | Sequence | Effect on apoptosis |
|---|---|---|
| Blue | SATL DALL AAL RRI | Apoptotic |
| Purple | SATL DAKL AAL RRI | None |
| Turquoise | KDRN LRRI TRM VLV | None |
| Red | LDEN FKRC FRE FCI | None |
| MP | INLK ALAA LAK KIL | Apoptotic |
| Gray | SATL DALL AAL | None |
| Green | ALL AAL RRI | None |
| tat-blue | tat-GG-SATL DALL AAL RRI | Apoptotic |
| tat-purple | tat-GG-SATL DAKL AAL RRI | None |
| tat-gray | tat-GG-SATL DALL AAL | None |
| tat-turquoise | tat-GG-KDRN LRRI TRM VLV | None |
| tat-yellow | tat-GG-DLSL ARLA TAR LAI | None |
| tat-GG-Q14 | tat-GG-QQQQ QQQQ QQQ QQQ | Apoptotic |
| tat | GRKK RRQR RRP P | None |

The results in Table 1 show the identification of the dependence domains of several dependence polypeptides. In addition, Table 1 shows the effect of carboxy-terminal deletions, amino-terminal deletions and introducing a point mutation on the apoptotic activity of a dependence peptide modeled after a $p75^{NTR}$ dependence domain. The results also show that dependence peptides modeled after dependence domains stimulate apoptosis when introduced into every cell type examined. The stimulation of apoptosis in such diverse cell types indicates that the dependence peptides of the invention can be used to treat many different pathological conditions characterized by different cell types.

Figure 2A:
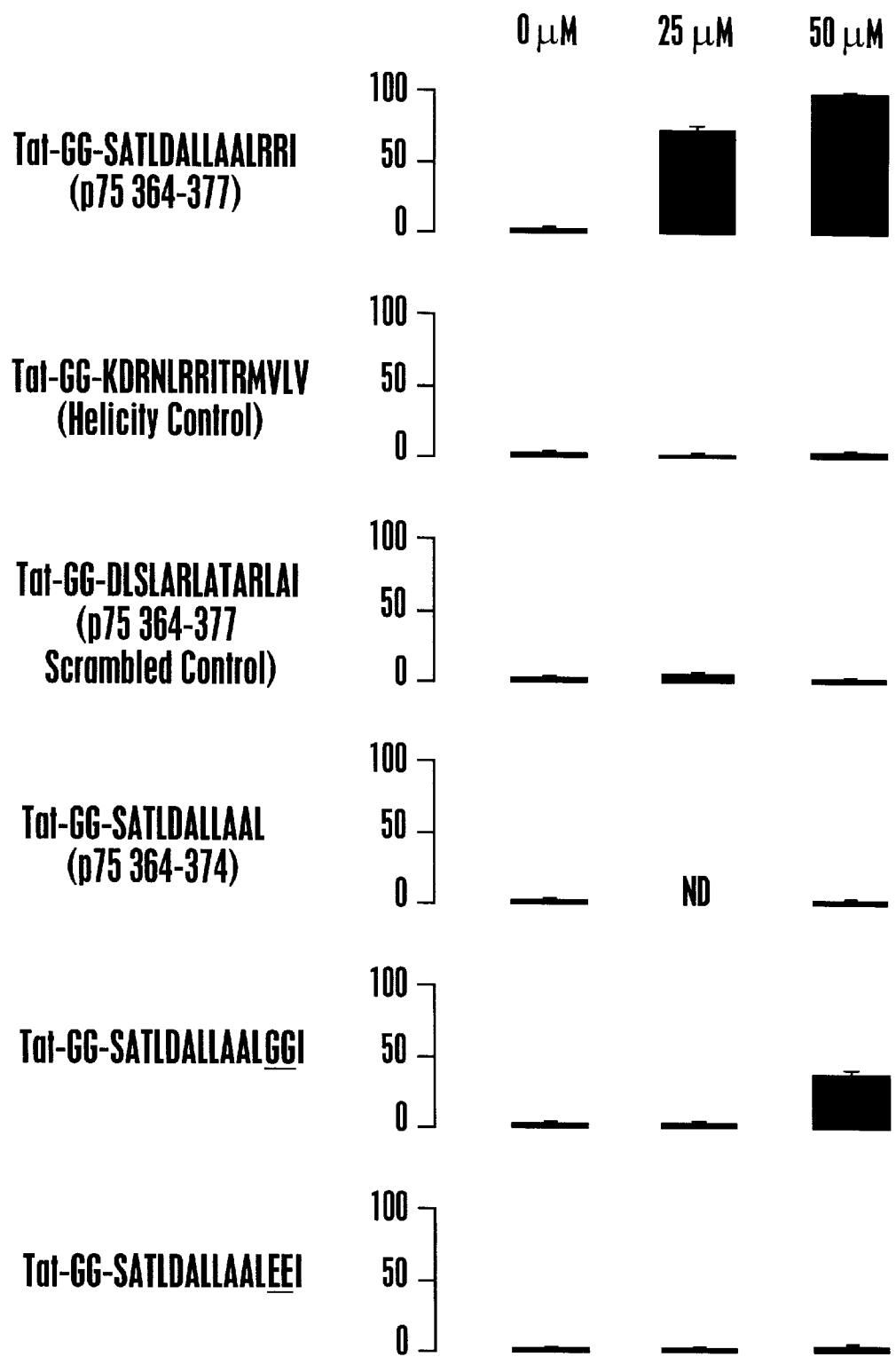
FIG. 2 shows the ability of a proapoptotic dependence peptide and related peptides to stimulate apoptosis.
Figure 2B:
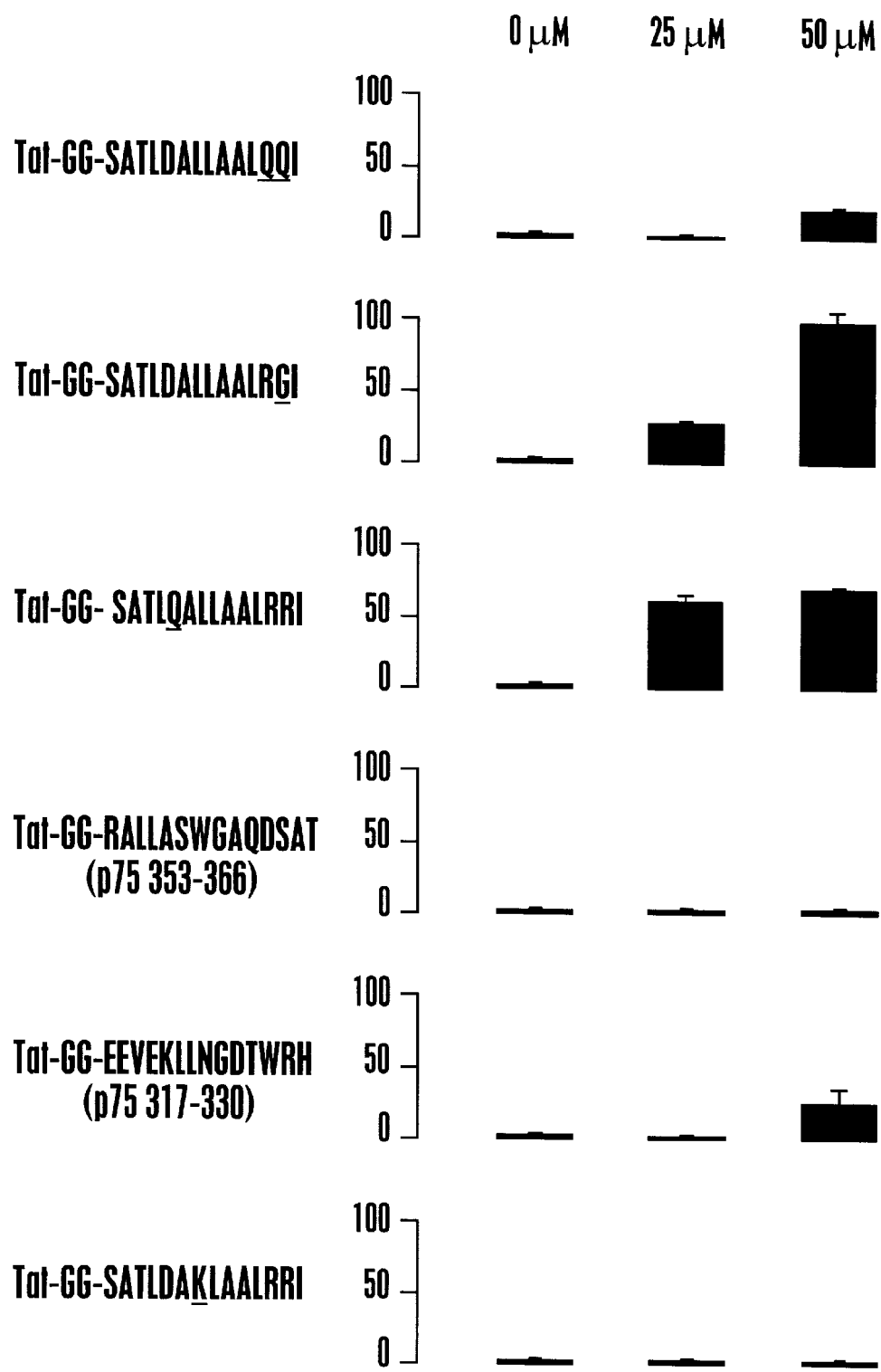

To further analyze the effect of particular point mutations on apoptosis, additional studies employing dependence peptides and mutated variants linked to tat were performed in SH-SY5Y cells. The results shown in FIG. 2 are of studies in which quadruplicate samples were averaged, and the studies were repeated 2 to 10 times for each peptide. Each column represents the percentage cell death and the bars indicate the standard error. The amount of peptide added to the cells is indicated above each column.

These studies demonstrated that the presence or absence of apoptotic activity observed for particular peptides in SH-SY5Y cells is the same as that observed in the other cell lines described above indicating that apoptotic activity is independent of cell line. Specifically, tat-blue (tat-GG-SATLDALLAALRRI) exhibited apoptotic activity whereas tat-turqoise (tat-GG-KDRNLRRITRMVLV), tat-gray (tat-GG-SATLDALLAAL), tat-yellow (tat-GG-DLSLARLATARLAI) and tat-purple (tat-GG-SATLDAKLAALRRI) did not.

These studies also demonstrate that particular amino acid residues are critical to the apoptotic activity of the dependence peptide SATLDALLAALRRI. For example, replacing two arginine residues at positions 12 and 13 with glutamic acid residues (tat-GG-SATLDALLAAL$\underline{EE}$I; SEQ ID NO:53) abolished the ability of the peptide to induce apoptosis. Similarly, replacing the arginine residues with glycine residues (tat-GG-SATLDALLAAL$\underline{GG}$I; SEQ ID NO:38) or glutamine residues (tat-GG-SATLDALLAAL$\underline{QQ}$I; SEQ ID NO:54) at positions 12 and 13 decreased the ability of the peptides to stimulate SH-SY5Y cell death by 70% and 80%, respectively.

The results shown in FIG. 2 also reveal that other amino acids were less critical to the apoptotic activity of the dependence peptide SATLDALLAALRRI. For example, replacing the arginine at position 13 with glycine (tat-GG-SATLDALLAALR$\underline{G}$I; SEQ ID NO:39) had very little effect on the ability of the peptide to stimulate apoptosis. Similarly, replacing an aspartic acid at position 5 with glutamine (tat-GG-SATL$\underline{Q}$ALLAALRRI; SEQ ID NO:40) resulted in a peptide that retained most of its apoptotic function; SH-SY5Y cells were 70% killed as compared to tat-GG-SATLDALLAALRRI.

The results shown in FIG. 2 demonstrate that particular amino acids are extremely important for apoptotic activity whereas other amino acids appear less critical. Furthermore, the results in FIG. 2, in conjunction with the results in FIG. 1, indicate that mutating certain amino acids in a dependence peptide can be a means by which one can decrease (see, for example, tat-GG-SATLDALLAAL$\underline{GG}$I and tat-GG-SATLDALLAAL$\underline{QQ}$I) or increase (see, for example, FIG. 1, p75ΔC19) the ability of a dependence peptide to stimulate apoptosis. Such altered forms of dependence peptides can be useful for modulating the degree of apoptosis in cells.

EXAMPLE IV

Dependence Peptide Mediated Mitochondrial Swelling, Cytochrome c Release and Caspase-3 Cleavage This Example shows that dependence peptides increase mitochondrial swelling, stimulate the release of cytochrome c from mitochondria and activate caspase-3 in a cell free assay system.

Figure 3A:
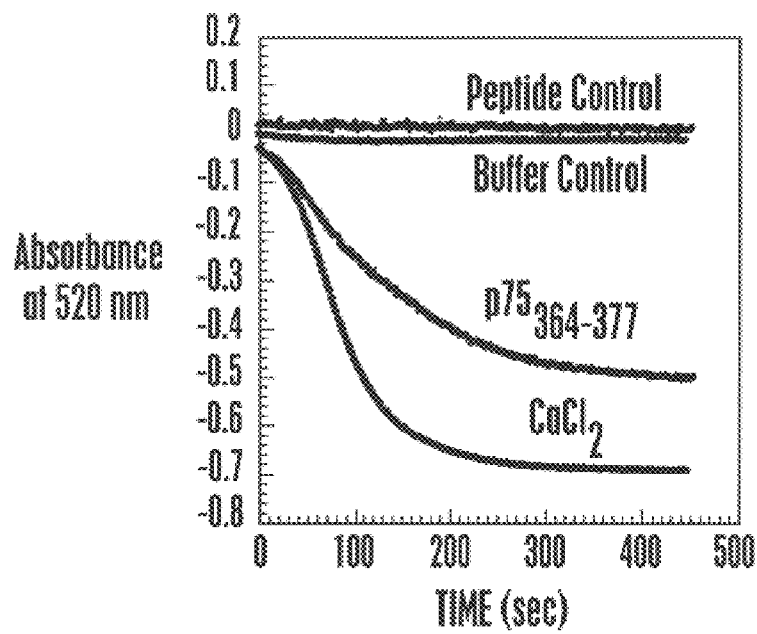
FIG. 3 shows that the stimulation of apoptosis by proapoptotic dependence peptides is accompanied by mitochondrial swelling (A), cytochrome c release (B), and caspase-3 cleavage (C).

Many molecules that stimulate cellular apoptosis such as actactyloside, Bax and mastoparan have been shown to stimulate mitochondrial swelling. Consistent with these observations, molecules such as Bcl-2 which inhibit apoptosis inhibit mitochondrial swelling. The effect of a proapoptotic dependence peptide on mitochondrial swelling was determined and the results are shown in FIG. 3A. Briefly, mitochondria were prepared as previously described (Ellerby et al. *J. Neurosci.* 17:6165–6178 (1997)) except for the following modifications. The rats were sacrificed by $CO_2$ inhalation without fasting and the mitochondria were isolated in MIB buffer (210 mM mannitol, 70 mM sucrose, 0.05% BSA, 1 mM EGTA, 5 mM Hepes-NaOH, pH 7.4). The mitochondrial pellet samples resuspended in MCB buffer (300 mM mannitol, 10 mM $KH_2PO_4$, 0.1% BSA, pH 7.2) and applied to a discontinuous sucrose gradient (1.6 M sucrose, 10 mM $KH_2PO_4$, pH 7.5; 1.2 M sucrose, 10 mM $KH_2PO_4$, pH 7.5) were centrifuged at 48,500 g for 1 hour. Centrifugation resulted in the fractionation of mitochondrial layers which were collected, resuspended in 4 volumes of MCB, and centrifuged at 12,000 g for 10 minutes. The mitochondrial pellets were collected, resuspended in MSB, and stored on ice. After the addition of 50 μM of the peptide, mitochondrial swelling was followed spectrophotometrically at 520 nm (Petronilli et al. *J. Biol. Chem.* 269:16638–16642 (1994)) in CFS (220 mM mannitol, 68 mM sucrose, 2 mM NaCl, 5 mM $KH_2PO_4$, 2 mM $MgCl_2$, 5 mM succinate, 10 mM Hepes-NaOH, 2 mM ATP, 50 μg/ml creatine kinase, 10 mM phosphocreatine, 0.75 μg/ml rotenone, pH 7.4).

The results shown in FIG. 3A indicate that the isolated mitochondria treated with the dependence peptide SATLDALLAALRRI ($p75_{364-377}$) underwent a rapid increase in swelling as indicated by the decreased absorbance at 520 nm. Similarly, mitochondria treated with a 0.5 mM calcium chloride positive control underwent rapid swelling. In contrast, no swelling of mitochondria was observed in incubation buffer alone or after treatment with a scrambled peptide control (yellow, DLSLARLATARLAI; SEQ ID NO:49).

Figure 3B:
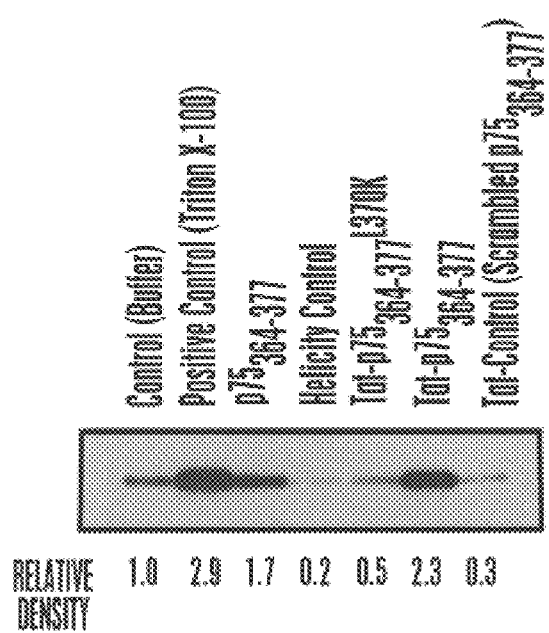

Apoptosis inducing molecules such as actactyloside, Bax and mastoparan also have been shown to stimulate cytochrome c release from mitochondria whereas apoptotic inhibitors such as Bcl-2 inhibit cytochrome c release. The effect of a proapoptotic dependence peptide on cytochrome c release from mitochondria was determined and the results are shown in FIG. 3B. Briefly, cytochrome c release studies (1 hour, 37° C.) were performed as described (Ellerby et al. *J. Neurosci.* 17:6165–6178 (1997)). The mitochondria were prepared as described above, washed and resuspended in CFS (50–10 mg/ml) and peptide was added to the mitochondria at a final concentration of 385 μM. Western blot analysis using a cytochrome c specific antibody monitored the amount of cytochrome c released (Ellerby et al. *J. Neurosci.* 17:6165–6178 (1997)).

The results shown in FIG. 3B indicate the relative amount of cytochrome c, which was normalized to a negative buffer control. Mitochondria treated with Triton X-100 were used as a positive control. The results demonstrate that cytochrome c release by mitochondria was stimulated by 500 μM of the SATLDALLAALRRI ($p75_{364-377}$;) and 385 μM of the tat-GG-SATLDALLAALRRI (tat-$p75_{364-377}$) dependence peptides. In contrast, mitochondria exposed to a helicity control (turqoise, SEQ ID NO:46; helicity determined by Helical Wheel program of GCG), tat-yellow control peptide (SEQ ID NO:56) and a peptide that lacks proapoptotic activity due to a point mutation, tat-purple (tat-$p75_{364-377}$ L370K; SEQ ID NO:42), did not stimulate cytochrome c release from mitochondria.

Figure 3C:
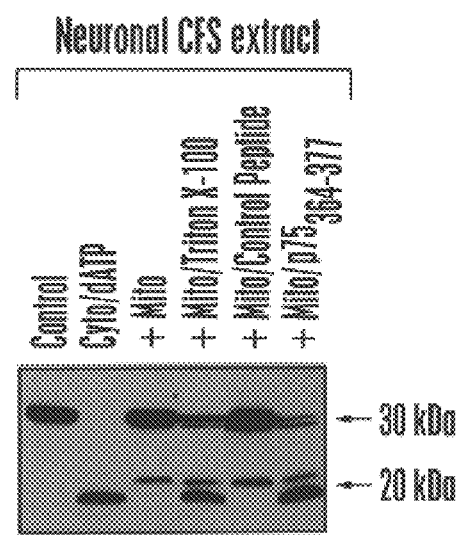

The activation of cellular apoptosis often results in caspase processing which leads to its activation, an event thought to contribute to the apoptotic cascade. For example, the activation of caspase-8 can be triggered by a Fas or TNFR I multimeric death inducing signaling complex. The effect of a proapoptotic dependence peptide on caspase-3 cleavage therefore was determined using a cell free system. The results are shown in FIG. 3C. Briefly, neuronal CFS extracts were prepared and cell-free caspase activation studies were performed. For these studies (3 hour, 37° C.), mitochondria were washed and resuspended in CFS (50–100 mg/ml) and the final peptide concentration was 385 μM. Western blot analyses using the caspase-3 specific antibody, CPP32, was performed as described (Ellerby et al. *J. Neurosci.* 17:6165–6178 (1997)).

The results shown in FIG. 3C demonstrate that cleavage of caspase-3, indicated by the appearance of a prominent band below the 20 kDa marker, is stimulated by treatment of the CFS extracts with a proapoptotic dependence peptide SATLDALLAALRRI ($p75_{364-377}$) modeled after a $p75^{NTR}$ dependence domain. In contrast, no cleavage of caspase-3 was observed in extracts treated with a scrambled control peptide DLSLARLATARLAI (SEQ ID NO:55).

These results demonstrate that the proapoptotic peptides of the invention stimulate mitochondrial swelling, cytochrome c release, and caspase-3 activation. Similarly, an all D-enantiomer of the dependence peptide stimulated mitochondrial swelling, cytochrome c release, and caspase-3 activation indicating that stimulation of apoptosis by dependence peptides is not stereospecific. The observed changes stimulated by proapoptotic dependence peptides may suggest a possible mechanism by which proapoptotic peptides stimulate apoptosis. In addition, such detectable changes provide useful methods to identify dependence polypeptides and their dependence domains.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A substantially pure proapoptotic dependence peptide consisting of sequence SATLDALLAALRRI (SEQ ID NO:3).

2. A substantially pure proapoptotic dependence peptide consisting of sequence SATLDALLAALRRI (SEQ ID NO:3) and further consisting of a heterologous functional domain.

3. The peptide of claim 2, wherein the heterologous function domain is a targeting domain.

4. The peptide of claim 2, wherein the heterologous function domain facilitates cellular entry.

5. The peptide of claim 2, wherein the heterologous function domain is a tat peptide sequence.

6. The peptide of claim 5, wherein the heterologous function domain consists of tat-GG-SATLDALLAALRRI (SEQ ID NO:37).

7. A substantially pure proapoptotic dependence peptide, comprising a sequence selected from the group consisting of SATLDALLAALGGY (SEQ ID NO:4), SATLDALLAALRGI (SEQ ID NO:5) and

SATLQALLAALRRI (SEQ ID NO:6), wherein the peptide has 14 to 250 amino acid residues.

8. The peptide of claim 7, wherein the selected sequence is SATLDALLAALGGI (SEQ ID NO:4).

9. The peptide of claim 7, wherein the selected sequence is SATLDALLAALRGI (SEQ ID NO:5).

10. The peptide of claim 7, wherein the selected sequence is SATLQALLAALRRI (SEQ ID NO:6).

11. The peptide of claim 7, wherein the peptide is less than about 100 amino acid residues in length.

12. The peptide of claim 7, wherein the peptide is no longer than 40 amino acid residues in length.

13. The peptide of claim 7, wherein the peptide is 14 amino acid residues in length.

14. The peptide of claim 7, wherein the peptide further comprises a polypeptide sequence that is a heterologous functional domain.

15. The peptide of claim 14, wherein the polypeptide sequence is a targeting domain.

16. The peptide of claim 14, wherein the polypeptide sequence facilitates cellular entry.

17. The peptide of claim 14, wherein the polypeptide sequence is a tat peptide sequence.

18. A substantially pure proapoptotic dependence peptide, comprising amino acid polglutamine saquence, wherein the peptide has 6 to 250 amino acid residues and the polyglutamine sequence has 6 to 25 amino acid residues, wherein the peptide further comprises a polypeptide sequence that is a heterologous functional domain.

19. The peptide of claim 18, wherein the polypeptide sequence is a targeting domain.

20. The peptide of claim 18, wherein the polypeptide sequence facilitates cellular entry.

21. The peptide of claim 18, wherein the polypeptide sequence is a tat peptide sequence.

22. The peptide of claim 18, wherein the sequence is tat-GG-polyglutamine.

23. The peptide of claim 18, wherein the sequence is tat-GG-Q14 (SEQ ID NO:36).

* * * * *

UNITED STATES PATENT AND TRADEMARK OFFICE
CERTIFICATE OF CORRECTION

PATENT NO. : 6,235,872 B1
DATED : May 22, 2001
INVENTOR(S) : Bredesen et al.

It is certified that error appears in the above-identified patent and that said Letters Patent is hereby corrected as shown below:

<u>Column 219,</u>
Line 20, please delete "SATLDALLAALGGY" replace therefor with
--SATLDALLAALGGI --.

<u>Column 220,</u>
Line 30, please delete "polglutamine saquence," replace therefor with -- polyglutamine sequence, --.

Signed and Sealed this

Thirteenth Day of July, 2004

JON W. DUDAS
*Acting Director of the United States Patent and Trademark Office*

SEQUENCE LISTING (1) GENERAL INFORMATION:

(iii) NUMBER OF SEQUENCES: 72

(2) INFORMATION FOR SEQ ID NO:1:

(i) SEQUENCE CHARACTERISTICS:
      (A) LENGTH: 3386 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 114..1395

(xi) SEQUENCE DESCRIPTION: SEQ ID NO:1:

```
GCCGCGGCCA GCTCCGGCGG GCAGGGGGGG CGCTGGAGCG CAGCGCAGCG CAGCCCCATC      60

AGTCCGCAAA GCGGACCGAG CTGGAAGTCG AGCGCTGCCG CGGGAGGCGG GCG ATG        116
                                                         Met
                                                           1

GGG GCA GGT GCC ACC GGC CGC GCC ATG GAC GGG CCG CGC CTG CTG CTG      164
Gly Ala Gly Ala Thr Gly Arg Ala Met Asp Gly Pro Arg Leu Leu Leu
              5                  10                  15

TTG CTG CTT CTG GGG GTG TCC CTT GGA GGT GCC AAG GAG GCA TGC CCC      212
Leu Leu Leu Leu Gly Val Ser Leu Gly Gly Ala Lys Glu Ala Cys Pro
             20                  25                  30

ACA GGC CTG TAC ACA CAC AGC GGT GAG TGC TGC AAA GCC TGC AAC CTG      260
Thr Gly Leu Tyr Thr His Ser Gly Glu Cys Cys Lys Ala Cys Asn Leu
         35                  40                  45

GGC GAG GGT GTG GCC CAG CCT TGT GGA GCC AAC CAG ACC GTG TGT GAG      308
Gly Glu Gly Val Ala Gln Pro Cys Gly Ala Asn Gln Thr Val Cys Glu
 50                  55                  60                  65

CCC TGC CTG GAC AGC GTG ACG TTC TCC GAC GTG GTG AGC GCG ACC GAG      356
Pro Cys Leu Asp Ser Val Thr Phe Ser Asp Val Val Ser Ala Thr Glu
                 70                  75                  80

CCG TGC AAG CCG TGC ACC GAG TGC GTG GGG CTC CAG AGC ATG TCG GCG      404
Pro Cys Lys Pro Cys Thr Glu Cys Val Gly Leu Gln Ser Met Ser Ala
             85                  90                  95
```

-continued

```
CCG TGC GTG GAG GCC GAC GAC GCC GTG TGC CGC TGC GCC TAC GGC TAC        452
Pro Cys Val Glu Ala Asp Asp Ala Val Cys Arg Cys Ala Tyr Gly Tyr
        100                 105                 110

TAC CAG GAT GAG ACG ACT GGG CGC TGC GAG GCG TGC CGC GTG TGC GAG        500
Tyr Gln Asp Glu Thr Thr Gly Arg Cys Glu Ala Cys Arg Val Cys Glu
115                 120                 125

GCG GGC TCG GGC CTC GTG TTC TCC TGC CAG GAC AAG CAG AAC ACC GTG        548
Ala Gly Ser Gly Leu Val Phe Ser Cys Gln Asp Lys Gln Asn Thr Val
130                 135                 140                 145

TGC GAG GAG TGC CCC GAC GGC ACG TAT TCC GAC GAG GCC AAC CAC GTG        596
Cys Glu Glu Cys Pro Asp Gly Thr Tyr Ser Asp Glu Ala Asn His Val
        150                 155                 160

GAC CCG TGC CTG CCC TGC ACC GTG TGC GAG GAC ACC GAG CGC CAG CTC        644
Asp Pro Cys Leu Pro Cys Thr Val Cys Glu Asp Thr Glu Arg Gln Leu
        165                 170                 175

CGC GAG TGC ACA CGC TGG GCC GAC GCC GAG TGC GAG GAG ATC CCT GGC        692
Arg Glu Cys Thr Arg Trp Ala Asp Ala Glu Cys Glu Glu Ile Pro Gly
    180                 185                 190

CGT TGG ATT ACA CGG TCC ACA CCC CCA GAG GGC TCG GAC AGC ACA GCC        740
Arg Trp Ile Thr Arg Ser Thr Pro Pro Glu Gly Ser Asp Ser Thr Ala
    195                 200                 205

CCC AGC ACC CAG GAG CCT GAG GCA CCT CCA GAA CAA GAC CTC ATA GCC        788
Pro Ser Thr Gln Glu Pro Glu Ala Pro Pro Glu Gln Asp Leu Ile Ala
210                 215                 220                 225

AGC ACG GTG GCA GGT GTG GTG ACC ACA GTG ATG GGC AGC TCC CAG CCC        836
Ser Thr Val Ala Gly Val Val Thr Thr Val Met Gly Ser Ser Gln Pro
        230                 235                 240

GTG GTG ACC CGA GGC ACC ACC GAC AAC CTC ATC CCT GTC TAT TGC TCC        884
Val Val Thr Arg Gly Thr Thr Asp Asn Leu Ile Pro Val Tyr Cys Ser
        245                 250                 255

ATC CTG GCT GCT GTG GTT GTG GGC CTT GTG GCC TAC ATA GCC TTC AAG        932
Ile Leu Ala Ala Val Val Val Gly Leu Val Ala Tyr Ile Ala Phe Lys
        260                 265                 270

AGG TGG AAC AGC TGC AAG CAG AAC AAG CAA GGA GCC AAC AGC CGG CCA        980
Arg Trp Asn Ser Cys Lys Gln Asn Lys Gln Gly Ala Asn Ser Arg Pro
    275                 280                 285

GTG AAC CAG ACG CCC CCA CCA GAG GGA GAA AAA CTC CAC AGC GAC AGT       1028
Val Asn Gln Thr Pro Pro Pro Glu Gly Glu Lys Leu His Ser Asp Ser
290                 295                 300                 305

GGC ATC TCC GTG GAC AGC CAG AGC CTG CAT GAC CAG CAG CCC CAC ACG       1076
Gly Ile Ser Val Asp Ser Gln Ser Leu His Asp Gln Gln Pro His Thr
            310                 315                 320

CAG ACA GCC TCG GGC CAG GCC CTC AAG GGT GAC GGA GGC CTC TAC AGC       1124
Gln Thr Ala Ser Gly Gln Ala Leu Lys Gly Asp Gly Gly Leu Tyr Ser
            325                 330                 335

AGC CTG CCC CCA GCC AAG CGG GAG GAG GTG GAG AAG CTT CTC AAC GGC       1172
Ser Leu Pro Pro Ala Lys Arg Glu Glu Val Glu Lys Leu Leu Asn Gly
        340                 345                 350

TCT GCG GGG GAC ACC TGG CGG CAC CTG GCG GGC GAG CTG GGC TAC CAG       1220
Ser Ala Gly Asp Thr Trp Arg His Leu Ala Gly Glu Leu Gly Tyr Gln
355                 360                 365

CCC GAG CAC ATA GAC TCC TTT ACC CAT GAG GCC TGC CCC GTT CGC GCC       1268
Pro Glu His Ile Asp Ser Phe Thr His Glu Ala Cys Pro Val Arg Ala
370                 375                 380                 385

CTG CTT GCA AGC TGG GCC ACC CAG GAC AGC GCC ACA CTG GAC GCC CTC       1316
Leu Leu Ala Ser Trp Ala Thr Gln Asp Ser Ala Thr Leu Asp Ala Leu
            390                 395                 400

CTG GCC GCC CTG CGC CGC ATC CAG CGA GCC GAC CTC GTG GAG AGT CTG       1364
Leu Ala Ala Leu Arg Arg Ile Gln Arg Ala Asp Leu Val Glu Ser Leu
            405                 410                 415
```

```
TGC AGT GAG TCC ACT GCC ACA TCC CCG GTG T GAGCCCAACC GGGGAGCCCC      1415
Cys Ser Glu Ser Thr Ala Thr Ser Pro Val
        420                 425
```

CGCCCCGCCC ACATTCCGA CAACCGATGC TCCAGCCAAC CCCTGTGGAG CCCGCACCCC      1475

CACCCTTTGG GGGGGGCCCG CCTGGCAGAA CTGAGCTCCT CTGGGCAGGA CCTCAGAGTC      1535

CAGGCCCCAA AACCACAGCC CTGTCAGTGC AGCCCGTGTG GCCCCTTCAC TTCTGACCAC      1595

ACTTCCTGTC CAGAGAGAGA AGTGCCCCTG CTGCCTCCCC AACCCTGCCC CTGCCCCGTC      1655

ACCATCTCAG GCCACCTGCC CCCTTCTCCC ACACTGCTAG GTGGGCCAGC CCCTCCCACC      1715

ACAGCAGGTG TCATATATGG GGGGCCAACA CCAGGGATGG TACTAGGGGG AAGTGACAAG      1775

GCCCCAGAGA CTCAGAGGGA GGAATCGAGG AACCAGAGCC ATGGACTCTA CACTGTGAAC      1835

TTGGGGAACA AGGGTGGCAT CCCAGTGGCC TCAACCCTCC CTCAGCCCCT CTTGCCCCCC      1895

ACCCCAGCCT AAGATGAAGA GGATCGGAGG CTTGTCAGAG CTGGGAGGGG TTTTCGAAGC      1955

TCAGCCCACC CCCCTCATTT TGGATATAGG TCAGTGAGGC CCAGGGAGAG GCCATGATTC      2015

GCCCAAAGCC AGACAGCAAC GGGGAGGCCA AGTGCAGGCT GGCACCGCCT TCTCTAAATG      2075

AGGGGCCTCA GGTTTGCCTG AGGGCGAGGG GAGGGTGGCA GGTGACCTTC TGGGAAATGG      2135

CTTGAAGCCA AGTCAGCTTT GCCTTCCACG CTGTCTCCAG ACCCCACCC CTTCCCCACT       2195

GCCTGCCCAC CCGTGGAGAT GGGATGCTTG CCTAGGGCCT GGTCCATGAT GGAGTCAGGT      2255

TTGGGGTTCG TGGAAAGGGT GCTGCTTCCC TCTGCCTGTC CCTCTCAGGC ATGCCTGTGT      2315

GACATCAGTG GCATGGCTCC AGTCTGCTGC CCTCCATCCC GACATGGACC CGGAGCTAAC      2375

ACTGGCCCCT AGAATCAGCC TAGGGGTCAG GGACCAAGGA CCCCTCACCT TGCAACACAC      2435

AGACACACGC ACACACACAC ACAGGAGGAG AAATCTCACT TTTCTCCATG AGTTTTTTCT      2495

CTTGGGCTGA GACTGGATAC TGCCCGGGGC AGCTGCCAGA GAAGCATCGG AGGGAATTGA      2555

GGTCTGCTCG GCCGTCTTCA CTCGCCCCCG GGTTTGGCGG GCCAAGGACT GCCGACCGAG      2615

GCTGGAGCTG GCGTCTGTCT TCAAGGGCTT ACACGTGGAG GAATGCTCCC CCATCCTCCC      2675

CTTCCCTGCA AACATGGGGT TGGCTGGGCC CAGAAGGTTG CGATGAAGAA AAGCGGGCCA      2735

GTGTGGGAAT GCGGCAAGAA GGAATTGACT TCGACTGTGA CCTGTGGGGA TTTCTCCCAG      2795

CTCTAGACAA CCCTGCAAAG GACTGTTTTT TCCTGAGCTT GGCCAGAAGG GGGCCATGAG      2855

GCCTCAGTGG ACTTTCCACC CCCTCCCTGG CCTGTTCTGT TTTGCCTGAA GTTGGAGTGA      2915

GTGTGGCTCC CCTCTATTTA GCATGACAAG CCCCAGGCAG GCTGTGCGCT GACAACCACC      2975

GCTCCCCAGC CCAGGGTTCC CCCAGCCCTG TGGAAGGGAC TAGGAGCACT GTAGTAAATG      3035

GCAATTCTTT GACCTCAACC TGTGATGAGG GGAGGAAACT CACCTGCTGG CCCCTCACCT      3095

GGGCACCTGG GGAGTGGGAC AGAGTCTGGG TGTATTTATT TTCCTCCCCA GCAGGTGGGG      3155

AGGGGGTTTG GTGGCTTGCA AGTATGTTTT AGCATGTGTT TGGTTCTGGG GCCCCTTTTT      3215

ACTCCCCTTG AGCTGAGATG GAACCCTTTT GGCCCCAGC TGGGGCCAT GAGCTCCAGA        3275

CCCCCAGCAA CCCTCCTATC ACCTCCCCTC CTTGCCTCCT GTGTAATCAT TTCTTGGGCC      3335

CTCCTGAAAC TTACACACAA AACGTTAAGT GATGAACATT AAATAGCAAA G              3386

(2) INFORMATION FOR SEQ ID NO:2:

(i) SEQUENCE CHARACTERISTICS:
        (A) LENGTH: 427 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Ala Gly Ala Thr Gly Arg Ala Met Asp Gly Pro Arg Leu Leu
 1               5                  10                  15

Leu Leu Leu Leu Leu Gly Val Ser Leu Gly Ala Lys Glu Ala Cys
                 20                  25                  30

Pro Thr Gly Leu Tyr Thr His Ser Gly Glu Cys Cys Lys Ala Cys Asn
                 35                  40                  45

Leu Gly Glu Gly Val Ala Gln Pro Cys Gly Ala Asn Gln Thr Val Cys
 50                  55                  60

Glu Pro Cys Leu Asp Ser Val Thr Phe Ser Asp Val Val Ser Ala Thr
 65                  70                  75                  80

Glu Pro Cys Lys Pro Cys Thr Glu Cys Val Gly Leu Gln Ser Met Ser
                 85                  90                  95

Ala Pro Cys Val Glu Ala Asp Asp Ala Val Cys Arg Cys Ala Tyr Gly
                 100                 105                 110

Tyr Tyr Gln Asp Glu Thr Thr Gly Arg Cys Glu Ala Cys Arg Val Cys
                 115                 120                 125

Glu Ala Gly Ser Gly Leu Val Phe Ser Cys Gln Asp Lys Gln Asn Thr
 130                 135                 140

Val Cys Glu Glu Cys Pro Asp Gly Thr Tyr Ser Asp Glu Ala Asn His
145                  150                 155                 160

Val Asp Pro Cys Leu Pro Cys Thr Val Cys Glu Asp Thr Glu Arg Gln
                 165                 170                 175

Leu Arg Glu Cys Thr Arg Trp Ala Asp Ala Glu Cys Glu Glu Ile Pro
                 180                 185                 190

Gly Arg Trp Ile Thr Arg Ser Thr Pro Pro Glu Gly Ser Asp Ser Thr
                 195                 200                 205

Ala Pro Ser Thr Gln Glu Pro Glu Ala Pro Pro Glu Gln Asp Leu Ile
                 210                 215                 220

Ala Ser Thr Val Ala Gly Val Val Thr Thr Val Met Gly Ser Ser Gln
225                  230                 235                 240

Pro Val Val Thr Arg Gly Thr Thr Asp Asn Leu Ile Pro Val Tyr Cys
                 245                 250                 255

Ser Ile Leu Ala Ala Val Val Val Gly Leu Val Ala Tyr Ile Ala Phe
                 260                 265                 270

Lys Arg Trp Asn Ser Cys Lys Gln Asn Lys Gln Gly Ala Asn Ser Arg
                 275                 280                 285

Pro Val Asn Gln Thr Pro Pro Pro Glu Gly Glu Lys Leu His Ser Asp
                 290                 295                 300

Ser Gly Ile Ser Val Asp Ser Gln Ser Leu His Asp Gln Gln Pro His
305                  310                 315                 320

Thr Gln Thr Ala Ser Gly Gln Ala Leu Lys Gly Asp Gly Gly Leu Tyr
                 325                 330                 335

Ser Ser Leu Pro Pro Ala Lys Arg Glu Glu Val Glu Lys Leu Leu Asn
                 340                 345                 350

Gly Ser Ala Gly Asp Thr Trp Arg His Leu Ala Gly Glu Leu Gly Tyr
                 355                 360                 365

Gln Pro Glu His Ile Asp Ser Phe Thr His Glu Ala Cys Pro Val Arg
                 370                 375                 380

Ala Leu Leu Ala Ser Trp Ala Thr Gln Asp Ser Ala Thr Leu Asp Ala
385                  390                 395                 400
```

```
Leu Leu Ala Ala Leu Arg Arg Ile Gln Arg Ala Asp Leu Val Glu Ser
            405                 410                 415
Leu Cys Ser Glu Ser Thr Ala Thr Ser Pro Val
            420                 425

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:3:

Ser Ala Thr Leu Asp Ala Leu Leu Ala Ala Leu Arg Arg Ile
1               5                   10

(2) INFORMATION FOR SEQ ID NO:4:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:4:

Ser Ala Thr Leu Asp Ala Leu Leu Ala Ala Leu Gly Gly Ile
1               5                   10

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:5:

Ser Ala Thr Leu Asp Ala Leu Leu Ala Ala Leu Arg Gly Ile
1               5                   10

(2) INFORMATION FOR SEQ ID NO:6:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:6:

Ser Ala Thr Leu Gln Ala Leu Leu Ala Ala Leu Arg Arg Ile
1               5                   10

(2) INFORMATION FOR SEQ ID NO:7:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:7:

Gln Gln Gln Gln Gln Gln Gln Gln Gln Gln Gln Gln Gln Gln
```

-continued

```
1               5                  10
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:8:

```
Gln Gln Gln Gln Gln Gln Gln Gln Gln Gln
1               5                  10
```

(2) INFORMATION FOR SEQ ID NO:9:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:9:

```
Gln Gln Gln Gln Gln Gln Gln Gln Gln Gln Gln Gln Gln Gln Gln
1               5                  10                 15
Gln Gln Gln Gln Gln Gln Gln Gln Gln
                20                 25
```

(2) INFORMATION FOR SEQ ID NO:10:

(i) SEQUENCE CHARACTERISTICS:
        (A) LENGTH: 3715 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 532..3286

(xi) SEQUENCE DESCRIPTION: SEQ ID NO:10:

```
GAATTCCGGC GGAGAGAACC CTCTGTTTTC CCCCACTCTC TCTCCACCTC CTCCTGCCTT        60

CCCCACCCCG AGTGCGGAGC AGAGATCAAA AGATGAAAAG GCAGTCAGGT CTTCAGTAGC       120

CAAAAACAA AACAAACAAA ACAAAAAAG CCGAAATAAA AGAAAAGAT AATAACTCAG          180

TTCTTATTTG CACCTACTTC AGTGGACACT GAATTTGGAA GGTGGAGGAT TTTGTTTTTT       240

TCTTTTAAGA TCTGGGCATC TTTTGAATCT ACCCTTCAAG TATTAAGAGA CAGACTGTGA       300

GCCTAGCAGG GCAGATCTTG TCCACCGTGT GTCTTCTTCT GCACGAGACT TTGAGGCTGT       360

CAGAGCGCTT TTTGCGTGGT TGCTCCCGCA AGTTTCCTTC TCTGGAGCTT CCCGCAGGTG       420

GGCAGCTAGC TGCAGCGACT ACCGCATCAT CACAGCCTGT TGAACTCTTC TGAGCAAGAG       480

AAGGGGAGGC GGGGTAAGGG AAGTAGGTGG AAGATTCAGC CAAGCTCAAG G ATG GAA       537
                                                        Met Glu
                                                          1

GTG CAG TTA GGG CTG GGA AGG GTC TAC CCT CGG CCG CCG TCC AAG ACC        585
Val Gln Leu Gly Leu Gly Arg Val Tyr Pro Arg Pro Pro Ser Lys Thr
      5                  10                 15

TAC CGA GGA GCT TTC CAG AAT CTG TTC CAG AGC GTG CGC GAA GTG ATC        633
Tyr Arg Gly Ala Phe Gln Asn Leu Phe Gln Ser Val Arg Glu Val Ile
      20                 25                 30
```

```
CAG AAC CCG GGC CCC AGG CAC CCA GAG GCC GCG AGC GCA GCA CCT CCC      681
Gln Asn Pro Gly Pro Arg His Pro Glu Ala Ala Ser Ala Ala Pro Pro
 35                  40                  45                  50

GGC GCC AGT TTG CTG CTG CTG CAG CAG CAG CAG CAG CAG CAG CAG CAG      729
Gly Ala Ser Leu Leu Leu Leu Gln Gln Gln Gln Gln Gln Gln Gln Gln
                 55                  60                  65

CAG CAG CAG CAG CAG CAG CAG CAA GAG ACT AGC CCC AGG CAG CAG CAG      777
Gln Gln Gln Gln Gln Gln Gln Glu Thr Ser Pro Arg Gln Gln Gln
                     70                  75                  80

CAG CAG CAG GGT GAG GAT GGT TCT CCC CAA GCC CAT CGT AGA GGC CCC      825
Gln Gln Gln Gly Glu Asp Gly Ser Pro Gln Ala His Arg Arg Gly Pro
             85                  90                  95

ACA GGC TAC CTG GTC CTG GAT GAG GAA CAG CAA CCT TCA CAG CCG CAG      873
Thr Gly Tyr Leu Val Leu Asp Glu Glu Gln Gln Pro Ser Gln Pro Gln
100                 105                 110

TCG GCC CTG GAG TGC CAC CCC GAG AGA GGT TGC GTC CCA GAG CCT GGA      921
Ser Ala Leu Glu Cys His Pro Glu Arg Gly Cys Val Pro Glu Pro Gly
115                 120                 125                 130

GCC GCC GTG GCC GCC AGC AAG GGG CTG CCG CAG CAG CTG CCA GCA CCT      969
Ala Ala Val Ala Ala Ser Lys Gly Leu Pro Gln Gln Leu Pro Ala Pro
                135                 140                 145

CCG GAC GAG GAT GAC TCA GCT GCC CCA TCC ACG TTG TCC CTG CTG GGC     1017
Pro Asp Glu Asp Asp Ser Ala Ala Pro Ser Thr Leu Ser Leu Leu Gly
                150                 155                 160

CCC ACT TTC CCC GGC TTA AGC AGC TGC TCC GCT GAC CTT AAA GAC ATC     1065
Pro Thr Phe Pro Gly Leu Ser Ser Cys Ser Ala Asp Leu Lys Asp Ile
                165                 170                 175

CTG AGC GAG GCC AGC ACC ATG CAA CTC CTT CAG CAA CAG CAG CAG GAA     1113
Leu Ser Glu Ala Ser Thr Met Gln Leu Leu Gln Gln Gln Gln Gln Glu
                180                 185                 190

GCA GTA TCC GAA GGC AGC AGC AGC GGG AGA GCG AGG GAG GCC TCG GGG     1161
Ala Val Ser Glu Gly Ser Ser Ser Gly Arg Ala Arg Glu Ala Ser Gly
195                 200                 205                 210

GCT CCC ACT TCC TCC AAG GAC AAT TAC TTA GGG GGC ACT TCG ACC ATT     1209
Ala Pro Thr Ser Ser Lys Asp Asn Tyr Leu Gly Gly Thr Ser Thr Ile
                215                 220                 225

TCT GAC AAC GCC AAG GAG TTG TGT AAG GCA GTG TCG GTG TCC ATG GGC     1257
Ser Asp Asn Ala Lys Glu Leu Cys Lys Ala Val Ser Val Ser Met Gly
                230                 235                 240

CTG GGT GTG GAG GCG TTG GAG CAT CTG AGT CCA GGG GAA CAG CTT CGG     1305
Leu Gly Val Glu Ala Leu Glu His Leu Ser Pro Gly Glu Gln Leu Arg
                245                 250                 255

GGG GAT TGC ATG TAC GCC CCA CTT TTG GGA GTT CCA CCC GCT GTG CGT     1353
Gly Asp Cys Met Tyr Ala Pro Leu Leu Gly Val Pro Pro Ala Val Arg
260                 265                 270

CCC ACT CCT TGT GCC CCA TTG GCC GAA TGC AAA GGT TCT CTG CTA GAC     1401
Pro Thr Pro Cys Ala Pro Leu Ala Glu Cys Lys Gly Ser Leu Leu Asp
275                 280                 285                 290

GAC AGC GCA GGC AAG AGC ACT GAA GAT ACT GCT GAG TAT TCC CCT TTC     1449
Asp Ser Ala Gly Lys Ser Thr Glu Asp Thr Ala Glu Tyr Ser Pro Phe
                295                 300                 305

AAG GGA GGT TAC ACC AAA GGG CTA GAA GGC GAG AGC CTA GGC TGC TCT     1497
Lys Gly Gly Tyr Thr Lys Gly Leu Glu Gly Glu Ser Leu Gly Cys Ser
                310                 315                 320

GGC AGC GCT GCA GCA GGG AGC TCC GGG ACA CTT GAA CTG CCG TCT ACC     1545
Gly Ser Ala Ala Ala Gly Ser Ser Gly Thr Leu Glu Leu Pro Ser Thr
                325                 330                 335

CTG TCT CTC TAC AAG TCC GGA GCA CTG GAC GAG GCA GCT GCG TAC CAG     1593
Leu Ser Leu Tyr Lys Ser Gly Ala Leu Asp Glu Ala Ala Ala Tyr Gln
```

```
            340                 345                 350
AGT CGC GAC TAC TAC AAC TTT CCA CTG GCT CTG GCC GGA CCG CCG CCC      1641
Ser Arg Asp Tyr Tyr Asn Phe Pro Leu Ala Leu Ala Gly Pro Pro Pro
355                 360                 365                 370

CCT CCG CCG CCT CCC CAT CCC CAC GCT CGC ATC AAG CTG GAG AAC CCG      1689
Pro Pro Pro Pro Pro His Pro His Ala Arg Ile Lys Leu Glu Asn Pro
                375                 380                 385

CTG GAC TAC GGC AGC GCC TGG GCG GCT GCG GCG GCG CAG TGC CGC TAT      1737
Leu Asp Tyr Gly Ser Ala Trp Ala Ala Ala Ala Ala Gln Cys Arg Tyr
                390                 395                 400

GGG GAC CTG GCG AGC CTG CAT GGC GCG GGT GCA GCG GGA CCC GGT TCT      1785
Gly Asp Leu Ala Ser Leu His Gly Ala Gly Ala Ala Gly Pro Gly Ser
            405                 410                 415

GGG TCA CCC TCA GCC GCC GCT TCC TCA TCC TGG CAC ACT CTC TTC ACA      1833
Gly Ser Pro Ser Ala Ala Ala Ser Ser Ser Trp His Thr Leu Phe Thr
        420                 425                 430

GCC GAA GAA GGC CAG TTG TAT GGA CCG TGT GGT GGT GGG GGT GGT          1881
Ala Glu Glu Gly Gln Leu Tyr Gly Pro Cys Gly Gly Gly Gly Gly Gly
435                 440                 445                 450

GGT GGC GGC GGC GGC GGC GGC GGC GGC GGC GGC GGC GGC GGC GGC GGC      1929
Gly Gly Gly Gly Gly Gly Gly Gly Gly Gly Gly Gly Gly Gly Gly Gly
                455                 460                 465

GGC GGC GGC GGC GGC GAG GCG GAA GCT GTA GCC CCC TAC GGC TAC ACT      1977
Gly Gly Gly Gly Gly Glu Ala Glu Ala Val Ala Pro Tyr Gly Tyr Thr
                470                 475                 480

CGG CCC CCT CAG GGG CTG GCG GGC CAG GAA AGC GAC TTC ACC GCA CCT      2025
Arg Pro Pro Gln Gly Leu Ala Gly Gln Glu Ser Asp Phe Thr Ala Pro
            485                 490                 495

GAT GTG TGG TAC CCT GGC GGC ATG GTG AGC AGA GTG CCC TAT CCC AGT      2073
Asp Val Trp Tyr Pro Gly Gly Met Val Ser Arg Val Pro Tyr Pro Ser
        500                 505                 510

CCC ACT TGT GTC AAA AGC GAA ATG GGC CCC TGG ATG GAT AGC TAC TCC      2121
Pro Thr Cys Val Lys Ser Glu Met Gly Pro Trp Met Asp Ser Tyr Ser
515                 520                 525                 530

GGA CCT TAC GGG GAC ATG CGT TTG GAG ACT GCC AGG GAC CAT GTT TTG      2169
Gly Pro Tyr Gly Asp Met Arg Leu Glu Thr Ala Arg Asp His Val Leu
                535                 540                 545

CCC ATT GAC TAT TAC TTT CCA CCC CAG AAG ACC TGC CTG ATC TGT GGA      2217
Pro Ile Asp Tyr Tyr Phe Pro Pro Gln Lys Thr Cys Leu Ile Cys Gly
                550                 555                 560

GAT GAA GCT TCT GGG TGT CAC TAT GGA GCT CTC ACA TGT GGA AGC TGC      2265
Asp Glu Ala Ser Gly Cys His Tyr Gly Ala Leu Thr Cys Gly Ser Cys
            565                 570                 575

AAG GTC TTC TTC AAA AGA GCC GCT GAA GGG AAA CAG AAG TAC CTG TGC      2313
Lys Val Phe Phe Lys Arg Ala Ala Glu Gly Lys Gln Lys Tyr Leu Cys
        580                 585                 590

GCC AGC AGA AAT GAT TGC ACT ATT GAT AAA TTC CGA AGG AAA AAT TGT      2361
Ala Ser Arg Asn Asp Cys Thr Ile Asp Lys Phe Arg Arg Lys Asn Cys
595                 600                 605                 610

CCA TCT TGT CGT CTT CGG AAA TGT TAT GAA GCA GGG ATG ACT CTG GGA      2409
Pro Ser Cys Arg Leu Arg Lys Cys Tyr Glu Ala Gly Met Thr Leu Gly
                615                 620                 625

GCC CGG AAG CTG AAG AAA CTT GGT AAT CTG AAA CTA CAG GAG GAA GGA      2457
Ala Arg Lys Leu Lys Lys Leu Gly Asn Leu Lys Leu Gln Glu Glu Gly
                630                 635                 640

GAG GCT TCC AGC ACC ACC AGC CCC ACT GAG GAG ACA ACC CAG AAG CTG      2505
Glu Ala Ser Ser Thr Thr Ser Pro Thr Glu Glu Thr Thr Gln Lys Leu
            645                 650                 655

ACA GTG TCA CAC ATT GAA GGC TAT GAA TGT CAG CCC ATC TTT CTG AAT      2553
```

```
Thr Val Ser His Ile Glu Gly Tyr Glu Cys Gln Pro Ile Phe Leu Asn
    660             665             670

GTC CTG GAA GCC ATT GAG CCA GGT GTA GTG TGT GCT GGA CAC GAC AAC      2601
Val Leu Glu Ala Ile Glu Pro Gly Val Val Cys Ala Gly His Asp Asn
675             680             685             690

AAC CAG CCC GAC TCC TTT GCA GCC TTG CTC TCT AGC CTC AAT GAA CTG      2649
Asn Gln Pro Asp Ser Phe Ala Ala Leu Leu Ser Ser Leu Asn Glu Leu
                695             700             705

GGA GAG AGA CAG CTT GTA CAC GTG GTC AAG TGG GCC AAG GCC TTG CCT      2697
Gly Glu Arg Gln Leu Val His Val Val Lys Trp Ala Lys Ala Leu Pro
            710             715             720

GGC TTC CGC AAC TTA CAC GTG GAC GAC CAG ATG GCT GTC ATT CAG TAC      2745
Gly Phe Arg Asn Leu His Val Asp Asp Gln Met Ala Val Ile Gln Tyr
        725             730             735

TCC TGG ATG GGG CTC ATG GTG TTT GCC ATG GGC TGG CGA TCC TTC ACC      2793
Ser Trp Met Gly Leu Met Val Phe Ala Met Gly Trp Arg Ser Phe Thr
    740             745             750

AAT GTC AAC TCC AGG ATG CTC TAC TTC GCC CCT GAT CTG GTT TTC AAT      2841
Asn Val Asn Ser Arg Met Leu Tyr Phe Ala Pro Asp Leu Val Phe Asn
755             760             765             770

GAG TAC CGC ATG CAC AAG TCC CGG ATG TAC AGC CAG TGT GTC CGA ATG      2889
Glu Tyr Arg Met His Lys Ser Arg Met Tyr Ser Gln Cys Val Arg Met
                775             780             785

AGG CAC CTC TCT CAA GAG TTT GGA TGG CTC CAA ATC ACC CCC CAG GAA      2937
Arg His Leu Ser Gln Glu Phe Gly Trp Leu Gln Ile Thr Pro Gln Glu
            790             795             800

TTC CTG TGC ATG AAA GCA CTG CTA CTC TTC AGC ATT ATT CCA GTG GAT      2985
Phe Leu Cys Met Lys Ala Leu Leu Leu Phe Ser Ile Ile Pro Val Asp
        805             810             815

GGG CTG AAA AAT CAA AAA TTC TTT GAT GAA CTT CGA ATG AAC TAC ATC      3033
Gly Leu Lys Asn Gln Lys Phe Phe Asp Glu Leu Arg Met Asn Tyr Ile
    820             825             830

AAG GAA CTC GAT CGT ATC ATT GCA TGC AAA AGA AAA AAT CCC ACA TCC      3081
Lys Glu Leu Asp Arg Ile Ile Ala Cys Lys Arg Lys Asn Pro Thr Ser
835             840             845             850

TGC TCA AGA CGC TTC TAC CAG CTC ACC AAG CTC CTG GAC TCC GTG CAG      3129
Cys Ser Arg Arg Phe Tyr Gln Leu Thr Lys Leu Leu Asp Ser Val Gln
                855             860             865

CCT ATT GCG AGA GAG CTG CAT CAG TTC ACT TTT GAC CTG CTA ATC AAG      3177
Pro Ile Ala Arg Glu Leu His Gln Phe Thr Phe Asp Leu Leu Ile Lys
            870             875             880

TCA CAC ATG GTG AGC GTG GAC TTT CCG GAA ATG ATG GCA GAG ATC ATC      3225
Ser His Met Val Ser Val Asp Phe Pro Glu Met Met Ala Glu Ile Ile
        885             890             895

TCT GTG CAA GTG CCC AAG ATC CTT TCT GGG AAA GTC AAG CCC ATC TAT      3273
Ser Val Gln Val Pro Lys Ile Leu Ser Gly Lys Val Lys Pro Ile Tyr
    900             905             910

TTC CAC ACC CAG T GAAGCATTGG AAACCCTATT TCCCCACCCC AGCTCATGCC        3326
Phe His Thr Gln
915

CCCTTTCAGA TGTCTTCTGC CTGTTATAAC TCTGCACTAC TCCTCTGCAG TGCCTTGTTT    3386

AATTTCCTCT ATTGATGTAC AGTCTGTCAT GGAATTCTAT TTGCTGGGCT TTTTTTTTCT    3446

CTTTCTCTCC TTTCTTTTTC TTCTTCCCTC CCTATCTAAC CCTCCCATGG CACCTTCAGA    3506

CTTTGCTTCC CATTGTGGCT CCTATCTGTG TTTTGAATGG TGTTGTATGC CTTTAAATCT    3566

GTGATGATCC TCTATATGGCC CAGTGTCAAG TTGTGCTTGT TTACAGCACT ACTCTGTGCC   3626

AGCCACACAA ACGTTTACTT ATCTTATGCC ACGGGAAGTT TAGAGAGCTA AGATTATCTG    3686
```

```
GGGAAATCAA AACAAAAACA CCCGAATTC                                              3715
```

(2) INFORMATION FOR SEQ ID NO:11:

(i) SEQUENCE CHARACTERISTICS:
        (A) LENGTH: 918 amino acids
        (B) TYPE: amino acid
        (D) TOPOLOGY: linear (ii) MOLECULE TYPE: protein (xi) SEQUENCE DESCRIPTION: SEQ ID NO:11:

```
Met Glu Val Gln Leu Gly Leu Gly Arg Val Tyr Pro Arg Pro Ser
 1               5                  10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Glu Thr Ser Pro Arg Gln
65                  70                  75                  80

Gln Gln Gln Gln Gln Gly Glu Asp Gly Ser Pro Gln Ala His Arg Arg
                85                  90                  95

Gly Pro Thr Gly Tyr Leu Val Leu Asp Glu Glu Gln Gln Pro Ser Gln
               100                 105                 110

Pro Gln Ser Ala Leu Glu Cys His Pro Glu Arg Gly Cys Val Pro Glu
           115                 120                 125

Pro Gly Ala Ala Val Ala Ala Ser Lys Gly Leu Pro Gln Gln Leu Pro
       130                 135                 140

Ala Pro Pro Asp Glu Asp Asp Ser Ala Ala Pro Ser Thr Leu Ser Leu
145                 150                 155                 160

Leu Gly Pro Thr Phe Pro Gly Leu Ser Ser Cys Ser Ala Asp Leu Lys
               165                 170                 175

Asp Ile Leu Ser Glu Ala Ser Thr Met Gln Leu Leu Gln Gln Gln Gln
           180                 185                 190

Gln Glu Ala Val Ser Glu Gly Ser Ser Gly Arg Ala Arg Glu Ala
       195                 200                 205

Ser Gly Ala Pro Thr Ser Ser Lys Asp Asn Tyr Leu Gly Gly Thr Ser
210                 215                 220

Thr Ile Ser Asp Asn Ala Lys Glu Leu Cys Lys Ala Val Ser Val Ser
225                 230                 235                 240

Met Gly Leu Gly Val Glu Ala Leu Glu His Leu Ser Pro Gly Glu Gln
               245                 250                 255

Leu Arg Gly Asp Cys Met Tyr Ala Pro Leu Leu Gly Val Pro Pro Ala
           260                 265                 270

Val Arg Pro Thr Pro Cys Ala Pro Leu Ala Glu Cys Lys Gly Ser Leu
       275                 280                 285

Leu Asp Asp Ser Ala Gly Lys Ser Thr Glu Asp Thr Ala Glu Tyr Ser
   290                 295                 300

Pro Phe Lys Gly Gly Tyr Thr Lys Gly Leu Glu Gly Glu Ser Leu Gly
305                 310                 315                 320

Cys Ser Gly Ser Ala Ala Ala Gly Ser Ser Gly Thr Leu Glu Leu Pro
               325                 330                 335

Ser Thr Leu Ser Leu Tyr Lys Ser Gly Ala Leu Asp Glu Ala Ala Ala
           340                 345                 350
```

```
Tyr Gln Ser Arg Asp Tyr Tyr Asn Phe Pro Leu Ala Leu Ala Gly Pro
        355                 360                 365

Pro Pro Pro Pro Pro Pro His Pro His Ala Arg Ile Lys Leu Glu
    370                 375                 380

Asn Pro Leu Asp Tyr Gly Ser Ala Trp Ala Ala Ala Ala Gln Cys
385                 390                 395                 400

Arg Tyr Gly Asp Leu Ala Ser Leu His Gly Ala Gly Ala Ala Gly Pro
                405                 410                 415

Gly Ser Gly Ser Pro Ser Ala Ala Ser Ser Ser Trp His Thr Leu
            420                 425                 430

Phe Thr Ala Glu Glu Gly Gln Leu Tyr Gly Pro Cys Gly Gly Gly
        435                 440                 445

Gly Gly Gly Gly Gly Gly Gly Gly Gly Gly Gly Gly Gly Gly Gly
        450                 455                 460

Gly Gly Gly Gly Gly Gly Glu Ala Glu Ala Val Ala Pro Tyr Gly
465                 470                 475                 480

Tyr Thr Arg Pro Pro Gln Gly Leu Ala Gly Gln Glu Ser Asp Phe Thr
                485                 490                 495

Ala Pro Asp Val Trp Tyr Pro Gly Gly Met Val Ser Arg Val Pro Tyr
            500                 505                 510

Pro Ser Pro Thr Cys Val Lys Ser Glu Met Gly Pro Trp Met Asp Ser
        515                 520                 525

Tyr Ser Gly Pro Tyr Gly Asp Met Arg Leu Glu Thr Ala Arg Asp His
        530                 535                 540

Val Leu Pro Ile Asp Tyr Tyr Phe Pro Pro Gln Lys Thr Cys Leu Ile
545                 550                 555                 560

Cys Gly Asp Glu Ala Ser Gly Cys His Tyr Gly Ala Leu Thr Cys Gly
                565                 570                 575

Ser Cys Lys Val Phe Phe Lys Arg Ala Ala Glu Gly Lys Gln Lys Tyr
            580                 585                 590

Leu Cys Ala Ser Arg Asn Asp Cys Thr Ile Asp Lys Phe Arg Arg Lys
        595                 600                 605

Asn Cys Pro Ser Cys Arg Leu Arg Lys Cys Tyr Glu Ala Gly Met Thr
    610                 615                 620

Leu Gly Ala Arg Lys Leu Lys Lys Leu Gly Asn Leu Lys Leu Gln Glu
625                 630                 635                 640

Glu Gly Glu Ala Ser Ser Thr Thr Ser Pro Thr Glu Glu Thr Thr Gln
                645                 650                 655

Lys Leu Thr Val Ser His Ile Glu Gly Tyr Glu Cys Gln Pro Ile Phe
            660                 665                 670

Leu Asn Val Leu Glu Ala Ile Glu Pro Gly Val Val Cys Ala Gly His
        675                 680                 685

Asp Asn Asn Gln Pro Asp Ser Phe Ala Ala Leu Leu Ser Ser Leu Asn
    690                 695                 700

Glu Leu Gly Glu Arg Gln Leu Val His Val Val Lys Trp Ala Lys Ala
705                 710                 715                 720

Leu Pro Gly Phe Arg Asn Leu His Val Asp Asp Gln Met Ala Val Ile
                725                 730                 735

Gln Tyr Ser Trp Met Gly Leu Met Val Phe Ala Met Gly Trp Arg Ser
            740                 745                 750

Phe Thr Asn Val Asn Ser Arg Met Leu Tyr Phe Ala Pro Asp Leu Val
        755                 760                 765
```

```
Phe Asn Glu Tyr Arg Met His Lys Ser Arg Met Tyr Ser Gln Cys Val
    770                 775                 780
Arg Met Arg His Leu Ser Gln Glu Phe Gly Trp Leu Gln Ile Thr Pro
785                 790                 795                 800
Gln Glu Phe Leu Cys Met Lys Ala Leu Leu Leu Phe Ser Ile Ile Pro
                    805                 810                 815
Val Asp Gly Leu Lys Asn Gln Lys Phe Phe Asp Glu Leu Arg Met Asn
                820                 825                 830
Tyr Ile Lys Glu Leu Asp Arg Ile Ile Ala Cys Lys Arg Lys Asn Pro
            835                 840                 845
Thr Ser Cys Ser Arg Arg Phe Tyr Gln Leu Thr Lys Leu Leu Asp Ser
850                 855                 860
Val Gln Pro Ile Ala Arg Glu Leu His Gln Phe Thr Phe Asp Leu Leu
865                 870                 875                 880
Ile Lys Ser His Met Val Ser Val Asp Phe Pro Glu Met Met Ala Glu
                    885                 890                 895
Ile Ile Ser Val Gln Val Pro Lys Ile Leu Ser Gly Lys Val Lys Pro
                900                 905                 910
Ile Tyr Phe His Thr Gln
            915
```

(2) INFORMATION FOR SEQ ID NO:12:

(i) SEQUENCE CHARACTERISTICS:
        (A) LENGTH: 1776 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 36..1116

(xi) SEQUENCE DESCRIPTION: SEQ ID NO:12:

```
TCGGCGTGGG GGCCGTTGGC TCCAGACAAA TAAAC ATG GAG TCC ATC TTC CAC         53
                                      Met Glu Ser Ile Phe His
                                        1               5

GAG AAA CAA GAA GGC TCA CTT TGT GCT CAA CAT TGC CTG AAT AAC TTA       101
Glu Lys Gln Glu Gly Ser Leu Cys Ala Gln His Cys Leu Asn Asn Leu
            10                  15                  20

TTG CAA GGA GAA TAT TTT AGC CCT GTG GAA TTA TCC TCA ATT GCA CAT       149
Leu Gln Gly Glu Tyr Phe Ser Pro Val Glu Leu Ser Ser Ile Ala His
        25                  30                  35

CAG CTG GAT GAG GAG GAG AGG ATG AGA ATG GCA GAA GGA GGA GTT ACT       197
Gln Leu Asp Glu Glu Glu Arg Met Arg Met Ala Glu Gly Gly Val Thr
    40                  45                  50

AGT GAA GAT TAT CGC ACG TTT TTA CAG CAG CCT TCT GGA AAT ATG GAT       245
Ser Glu Asp Tyr Arg Thr Phe Leu Gln Gln Pro Ser Gly Asn Met Asp
55                  60                  65                  70

GAC AGT GGT TTT TTC TCT ATT CAG GTT ATA AGC AAT GCC TTG AAA GTT       293
Asp Ser Gly Phe Phe Ser Ile Gln Val Ile Ser Asn Ala Leu Lys Val
                75                  80                  85

TGG GGT TTA GAA CTA ATC CTG TTC AAC AGT CCA GAG TAT CAG AGG CTC       341
Trp Gly Leu Glu Leu Ile Leu Phe Asn Ser Pro Glu Tyr Gln Arg Leu
            90                  95                 100

AGG ATC GAT CCT ATA AAT GAA AGA TCA TTT ATA TGC AAT TAT AAG GAA       389
Arg Ile Asp Pro Ile Asn Glu Arg Ser Phe Ile Cys Asn Tyr Lys Glu
        105                 110                 115
```

```
CAC TGG TTT ACA GTT AGA AAA TTA GGA AAA CAG TGG TTT AAC TTG AAT    437
His Trp Phe Thr Val Arg Lys Leu Gly Lys Gln Trp Phe Asn Leu Asn
120                 125                 130

TCT CTC TTG ACG GGT CCA GAA TTA ATA TCA GAT ACA TAT CTT GCA CTT    485
Ser Leu Leu Thr Gly Pro Glu Leu Ile Ser Asp Thr Tyr Leu Ala Leu
135                 140                 145                 150

TTC TTG GCT CAA TTA CAA CAG GAA GGT TAT TCT ATA TTT GTT GTT AAG    533
Phe Leu Ala Gln Leu Gln Gln Glu Gly Tyr Ser Ile Phe Val Val Lys
            155                 160                 165

GGT GAT CTG CCA GAT TGC GAA GCT GAC CAA CTC CTG CAG ATG ATT AGG    581
Gly Asp Leu Pro Asp Cys Glu Ala Asp Gln Leu Leu Gln Met Ile Arg
                170                 175                 180

GTC CAA CAG ATG CAT CGA CCA AAA CTT ATT GGA GAA GAA TTA GCA CAA    629
Val Gln Gln Met His Arg Pro Lys Leu Ile Gly Glu Glu Leu Ala Gln
            185                 190                 195

CTA AAA GAG CAA AGA GTC CAT AAA ACA GAC CTG GAA CGA ATG TTA GAA    677
Leu Lys Glu Gln Arg Val His Lys Thr Asp Leu Glu Arg Met Leu Glu
200                 205                 210

GCA AAT GAT GGC TCA GGA ATG TTA GAC GAA GAT GAG GAG GAT TTG CAG    725
Ala Asn Asp Gly Ser Gly Met Leu Asp Glu Asp Glu Glu Asp Leu Gln
215                 220                 225                 230

AGG GCT CTG GCA CTA AGT CGC CAA GAA ATT GAC ATG GAA GAT GAG GAA    773
Arg Ala Leu Ala Leu Ser Arg Gln Glu Ile Asp Met Glu Asp Glu Glu
            235                 240                 245

GCA GAT CTC CGC AGG GCT ATT CAG CTA AGT ATG CAA GGT AGT TCC AGA    821
Ala Asp Leu Arg Arg Ala Ile Gln Leu Ser Met Gln Gly Ser Ser Arg
                250                 255                 260

AAC ATA TCT CAA GAT ATG ACA CAG ACA TCA GGT ACA AAT CTT ACT TCA    869
Asn Ile Ser Gln Asp Met Thr Gln Thr Ser Gly Thr Asn Leu Thr Ser
            265                 270                 275

GAA GAG CTT CGG AAG AGA CGA GAA GCC TAC TTT GAA AAA CAG CAG CAA    917
Glu Glu Leu Arg Lys Arg Arg Glu Ala Tyr Phe Glu Lys Gln Gln Gln
280                 285                 290

AAG CAG CAA CAG CAG CAG CAG CAG CAG CAG CAG CAG CAG CAG CAG CAG    965
Lys Gln Gln Gln Gln Gln Gln Gln Gln Gln Gln Gln Gln Gln Gln Gln
295                 300                 305                 310

CAG CAG CAG CAG CAG CAG CAG CGG GAC CTA TCA GGA CAG AGT TCA CAT    1013
Gln Gln Gln Gln Gln Gln Gln Arg Asp Leu Ser Gly Gln Ser Ser His
            315                 320                 325

CCA TGT GAA AGG CCA GCC ACC AGT TCA GGA GCA CTT GGG AGT GAT CTA    1061
Pro Cys Glu Arg Pro Ala Thr Ser Ser Gly Ala Leu Gly Ser Asp Leu
                330                 335                 340

GGT AAG GCC TGC TCA CCA TTC ATC ATG TTC GCT ACC TTC ACA CTT TAT    1109
Gly Lys Ala Cys Ser Pro Phe Ile Met Phe Ala Thr Phe Thr Leu Tyr
            345                 350                 355

CTG ACA T AAGAGCTCCA TGTGATTTTT GCTTTACATT ATTCTTCATT CCCTCTTTAA    1166
Leu Thr
360

TCATATTAAG ACTCTTAAGT AAATTTGTAA TCTACTAAAT TTCCCTGGAT TAAGGAGCAA    1226

GGTTACCAAA AAAAAAAAAA AAAAAAAAAG CTAGATGTGG TGGCTCACAT CTGTAATCCC    1286

AGCACTTTGG GAAACCAAGG CAGGAGAGGA TTGCTAGAAC ATTAATGAA TACTTTAACA    1346

TAATAATTTA AACTTCACAG TAATTTGTAC AGTCTCCAGA AATTCCTTAG ACATCATGAA    1406

TATTTTTCTT TTTTTGGGGT GACAGGGCAA AACTCTGTCT CAAAAAAAAA AAAAAAAAA    1466

AAAGGGCTGG ACACGGTGGC TTACGCCTGT TATCCCGGCA CTTTGGGAGG CCAAGGCCGA    1526

TGGATCACCT GAGGTCAGGA GTTCAAGACC AGCCTGGCCA ACATGGTGAA ACCCCATCTC    1586

TACTAAAAAT ACAAAAATTT GCTGGGCATG GTGGTGGGCA CCTGTAATCC CAGGAGGCTG    1646
```

```
AGGCAGGAGA ATCACTTGAA CCTGGGAGCG GAGATTGCAG TGAGCCAAGA TTGTGCCATT    1706

GAACTCCAGC CTGGGTGACA AGACCAAAAC TCCATCTCAA AAAAAAAAAA AAAAAAAGCG    1766

ACAGCAACGG                                                            1776
```

(2) INFORMATION FOR SEQ ID NO:13:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO:13:

```
Met Glu Ser Ile Phe His Glu Lys Gln Glu Gly Ser Leu Cys Ala Gln
  1               5                  10                  15

His Cys Leu Asn Asn Leu Leu Gln Gly Glu Tyr Phe Ser Pro Val Glu
             20                  25                  30

Leu Ser Ser Ile Ala His Gln Leu Asp Glu Glu Arg Met Arg Met
         35                  40                  45

Ala Glu Gly Gly Val Thr Ser Glu Asp Tyr Arg Thr Phe Leu Gln Gln
 50                  55                  60

Pro Ser Gly Asn Met Asp Asp Ser Gly Phe Phe Ser Ile Gln Val Ile
 65                  70                  75                  80

Ser Asn Ala Leu Lys Val Trp Gly Leu Glu Leu Ile Leu Phe Asn Ser
                 85                  90                  95

Pro Glu Tyr Gln Arg Leu Arg Ile Asp Pro Ile Asn Glu Arg Ser Phe
                100                 105                 110

Ile Cys Asn Tyr Lys Glu His Trp Phe Thr Val Arg Lys Leu Gly Lys
            115                 120                 125

Gln Trp Phe Asn Leu Asn Ser Leu Leu Thr Gly Pro Glu Leu Ile Ser
    130                 135                 140

Asp Thr Tyr Leu Ala Leu Phe Leu Ala Gln Leu Gln Gln Glu Gly Tyr
145                 150                 155                 160

Ser Ile Phe Val Val Lys Gly Asp Leu Pro Asp Cys Glu Ala Asp Gln
                165                 170                 175

Leu Leu Gln Met Ile Arg Val Gln Gln Met His Arg Pro Lys Leu Ile
            180                 185                 190

Gly Glu Glu Leu Ala Gln Leu Lys Glu Gln Arg Val His Lys Thr Asp
        195                 200                 205

Leu Glu Arg Met Leu Glu Ala Asn Asp Gly Ser Gly Met Leu Asp Glu
    210                 215                 220

Asp Glu Glu Asp Leu Gln Arg Ala Leu Ala Leu Ser Arg Gln Glu Ile
225                 230                 235                 240

Asp Met Glu Asp Glu Glu Ala Asp Leu Arg Arg Ala Ile Gln Leu Ser
                245                 250                 255

Met Gln Gly Ser Ser Arg Asn Ile Ser Gln Asp Met Thr Gln Thr Ser
            260                 265                 270

Gly Thr Asn Leu Thr Ser Glu Glu Leu Arg Lys Arg Arg Glu Ala Tyr
        275                 280                 285

Phe Glu Lys Gln Gln Gln Lys Gln Gln Gln Gln Gln Gln Gln Gln Gln
    290                 295                 300

Gln Gln Gln Gln Gln Gln Gln Gln Gln Gln Gln Gln Gln Arg Asp Leu
305                 310                 315                 320
```

```
Ser Gly Gln Ser Ser His Pro Cys Glu Arg Pro Ala Thr Ser Ser Gly
            325                 330                 335

Ala Leu Gly Ser Asp Leu Gly Lys Ala Cys Ser Pro Phe Ile Met Phe
            340                 345                 350

Ala Thr Phe Thr Leu Tyr Leu Thr
            355                 360

(2) INFORMATION FOR SEQ ID NO:14:

(i) SEQUENCE CHARACTERISTICS:
        (A) LENGTH: 10348 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 316..9748

(xi) SEQUENCE DESCRIPTION: SEQ ID NO:14:

TTGCTGTGTG AGGCAGAACC TGCGGGGGCA GGGGCGGGCT GGTTCCCTGG CCAGCCATTG      60

GCAGAGTCCG CAGGCTAGGG CTGTCAATCA TGCTGGCCGG CGTGGCCCCG CCTCCGCCGG     120

CGCGGCCCCG CCTCCGCCGG CGCACGTCTG GGACGCAAGG CGCCGTGGGG GCTGCCGGGA     180

CGGGTCCAAG ATGGACGGCC GCTCAGGTTC TGCTTTTACC TGCGGCCCAG AGCCCCATTC     240

ATTGCCCCGG TGCTGAGCGG CGCCGCGAGT CGGCCCGAGG CCTCCGGGGA CTGCCGTGCC     300

GGGCGGGAGA CCGCC ATG GCG ACC CTG GAA AAG CTG ATG AAG GCC TTC GAG      351
               Met Ala Thr Leu Glu Lys Leu Met Lys Ala Phe Glu
                1               5                   10

TCC CTC AAG TCC TTC CAG CAG CAG CAG CAG CAG CAG CAG CAG CAG CAG       399
Ser Leu Lys Ser Phe Gln Gln Gln Gln Gln Gln Gln Gln Gln Gln Gln
        15                  20                  25

CAG CAG CAG CAG CAG CAG CAG CAG CAG CAG CAA CAG CCG CCA CCG CCG       447
Gln Gln Gln Gln Gln Gln Gln Gln Gln Gln Gln Gln Pro Pro Pro Pro
    30                  35                  40

CCG CCG CCG CCG CCG CCT CCT CAG CTT CCT CAG CCG CCG CCG CAG GCA       495
Pro Pro Pro Pro Pro Pro Pro Gln Leu Pro Gln Pro Pro Pro Gln Ala
45                  50                  55                  60

CAG CCG CTG CTG CCT CAG CCG CAG CCG CCC CCG CCG CCG CCC CCG CCG       543
Gln Pro Leu Leu Pro Gln Pro Gln Pro Pro Pro Pro Pro Pro Pro Pro
            65                  70                  75

CCA CCC GGC CCG GCT GTG GCT GAG GAG CCG CTG CAC CGA CCA AAG AAA       591
Pro Pro Gly Pro Ala Val Ala Glu Glu Pro Leu His Arg Pro Lys Lys
        80                  85                  90

GAA CTT TCA GCT ACC AAG AAA GAC CGT GTG AAT CAT TGT CTG ACA ATA       639
Glu Leu Ser Ala Thr Lys Lys Asp Arg Val Asn His Cys Leu Thr Ile
        95                  100                 105

TGT GAA AAC ATA GTG GCA CAG TCT GTC AGA AAT TCT CCA GAA TTT CAG       687
Cys Glu Asn Ile Val Ala Gln Ser Val Arg Asn Ser Pro Glu Phe Gln
        110                 115                 120

AAA CTT CTG GGC ATC GCT ATG GAA CTT TTT CTG CTG TGC AGT GAT GAC       735
Lys Leu Leu Gly Ile Ala Met Glu Leu Phe Leu Leu Cys Ser Asp Asp
125                 130                 135                 140

GCA GAG TCA GAT GTC AGG ATG GTG GCT GAC GAA TGC CTC AAC AAA GTT       783
Ala Glu Ser Asp Val Arg Met Val Ala Asp Glu Cys Leu Asn Lys Val
                145                 150                 155

ATC AAA GCT TTG ATG GAT TCT AAT CTT CCA AGG TTA CAG CTC GAG CTC       831
Ile Lys Ala Leu Met Asp Ser Asn Leu Pro Arg Leu Gln Leu Glu Leu
            160                 165                 170
```

```
TAT AAG GAA ATT AAA AAG AAT GGT GCC CCT CGG AGT TTG CGT GCT GCC      879
Tyr Lys Glu Ile Lys Lys Asn Gly Ala Pro Arg Ser Leu Arg Ala Ala
        175             180                 185

CTG TGG AGG TTT GCT GAG CTG GCT CAC CTG GTT CGG CCT CAG AAA TGC      927
Leu Trp Arg Phe Ala Glu Leu Ala His Leu Val Arg Pro Gln Lys Cys
    190             195                 200

AGG CCT TAC CTG GTG AAC CTT CTG CCG TGC CTG ACT CGA ACA AGC AAG      975
Arg Pro Tyr Leu Val Asn Leu Leu Pro Cys Leu Thr Arg Thr Ser Lys
205             210                 215                 220

AGA CCC GAA GAA TCA GTC CAG GAG ACC TTG GCT GCA GCT GTT CCC AAA     1023
Arg Pro Glu Glu Ser Val Gln Glu Thr Leu Ala Ala Ala Val Pro Lys
                225                 230                 235

ATT ATG GCT TCT TTT GGC AAT TTT GCA AAT GAC AAT GAA ATT AAG GTT     1071
Ile Met Ala Ser Phe Gly Asn Phe Ala Asn Asp Asn Glu Ile Lys Val
            240                 245                 250

TTG TTA AAG GCC TTC ATA GCG AAC CTG AAG TCA AGC TCC CCC ACC ATT     1119
Leu Leu Lys Ala Phe Ile Ala Asn Leu Lys Ser Ser Ser Pro Thr Ile
        255                 260                 265

CGG CGG ACA GCG GCT GGA TCA GCA GTG AGC ATC TGC CAG CAC TCA AGA     1167
Arg Arg Thr Ala Ala Gly Ser Ala Val Ser Ile Cys Gln His Ser Arg
    270                 275                 280

AGG ACA CAA TAT TTC TAT AGT TGG CTA CTA AAT GTG CTC TTA GGC TTA     1215
Arg Thr Gln Tyr Phe Tyr Ser Trp Leu Leu Asn Val Leu Leu Gly Leu
285             290                 295                 300

CTC GTT CCT GTC GAG GAT GAA CAC TCC ACT CTG CTG ATT CTT GGC GTG     1263
Leu Val Pro Val Glu Asp Glu His Ser Thr Leu Leu Ile Leu Gly Val
                305                 310                 315

CTG CTC ACC CTG AGG TAT TTG GTG CCC TTG CTG CAG CAG CAG GTC AAG     1311
Leu Leu Thr Leu Arg Tyr Leu Val Pro Leu Leu Gln Gln Gln Val Lys
            320                 325                 330

GAC ACA AGC CTG AAA GGC AGC TTC GGA GTG ACA AGG AAA GAA ATG GAA     1359
Asp Thr Ser Leu Lys Gly Ser Phe Gly Val Thr Arg Lys Glu Met Glu
        335                 340                 345

GTC TCT CCT TCT GCA GAG CAG CTT GTC CAG GTT TAT GAA CTG ACG TTA     1407
Val Ser Pro Ser Ala Glu Gln Leu Val Gln Val Tyr Glu Leu Thr Leu
    350                 355                 360

CAT CAT ACA CAG CAC CAA GAC CAC AAT GTT GTG ACC GGA GCC CTG GAG     1455
His His Thr Gln His Gln Asp His Asn Val Val Thr Gly Ala Leu Glu
365             370                 375                 380

CTG TTG CAG CAG CTC TTC AGA ACG CCT CCA CCC GAG CTT CTG CAA ACC     1503
Leu Leu Gln Gln Leu Phe Arg Thr Pro Pro Pro Glu Leu Leu Gln Thr
                385                 390                 395

CTG ACC GCA GTC GGG GGC ATT GGG CAG CTC ACC GCT GCT AAG GAG GAG     1551
Leu Thr Ala Val Gly Gly Ile Gly Gln Leu Thr Ala Ala Lys Glu Glu
            400                 405                 410

TCT GGT GGC CGA AGC CGT AGT GGG AGT ATT GTG GAA CTT ATA GCT GGA     1599
Ser Gly Gly Arg Ser Arg Ser Gly Ser Ile Val Glu Leu Ile Ala Gly
        415                 420                 425

GGG GGT TCC TCA TGC AGC CCT GTC CTT TCA AGA AAA CAA AAA GGC AAA     1647
Gly Gly Ser Ser Cys Ser Pro Val Leu Ser Arg Lys Gln Lys Gly Lys
    430                 435                 440

GTG CTC TTA GGA GAA GAA GAA GCC TTG GAG GAT GAC TCT GAA TCG AGA     1695
Val Leu Leu Gly Glu Glu Glu Ala Leu Glu Asp Asp Ser Glu Ser Arg
445             450                 455                 460

TCG GAT GTC AGC AGC TCT GCC TTA ACA GCC TCA GTG AAG GAT GAG ATC     1743
Ser Asp Val Ser Ser Ser Ala Leu Thr Ala Ser Val Lys Asp Glu Ile
                465                 470                 475

AGT GGA GAG CTG GCT GCT TCT TCA GGG GTT TCC ACT CCA GGG TCA GCA     1791
Ser Gly Glu Leu Ala Ala Ser Ser Gly Val Ser Thr Pro Gly Ser Ala
```

-continued

```
                      480                 485                 490
GGT CAT GAC ATC ATC ACA GAA CAG CCA CGG TCA CAG CAC ACA CTG CAG        1839
Gly His Asp Ile Ile Thr Glu Gln Pro Arg Ser Gln His Thr Leu Gln
        495                 500                 505

GCG GAC TCA GTG GAT CTG GCC AGC TGT GAC TTG ACA AGC TCT GCC ACT        1887
Ala Asp Ser Val Asp Leu Ala Ser Cys Asp Leu Thr Ser Ser Ala Thr
510                 515                 520

GAT GGG GAT GAG GAG GAT ATC TTG AGC CAC AGC TCC AGC CAG GTC AGC        1935
Asp Gly Asp Glu Glu Asp Ile Leu Ser His Ser Ser Ser Gln Val Ser
525                 530                 535                 540

GCC GTC CCA TCT GAC CCT GCC ATG GAC CTG AAT GAT GGG ACC CAG GCC        1983
Ala Val Pro Ser Asp Pro Ala Met Asp Leu Asn Asp Gly Thr Gln Ala
                545                 550                 555

TCG TCG CCC ATC AGC GAC AGC TCC CAG ACC ACC ACC GAA GGG CCT GAT        2031
Ser Ser Pro Ile Ser Asp Ser Ser Gln Thr Thr Thr Glu Gly Pro Asp
                560                 565                 570

TCA GCT GTT ACC CCT TCA GAC AGT TCT GAA ATT GTG TTA GAC GGT ACC        2079
Ser Ala Val Thr Pro Ser Asp Ser Ser Glu Ile Val Leu Asp Gly Thr
                575                 580                 585

GAC AAC CAG TAT TTG GGC CTG CAG ATT GGA CAG CCC CAG GAT GAA GAT        2127
Asp Asn Gln Tyr Leu Gly Leu Gln Ile Gly Gln Pro Gln Asp Glu Asp
590                 595                 600

GAG GAA GCC ACA GGT ATT CTT CCT GAT GAA GCC TCG GAG GCC TTC AGG        2175
Glu Glu Ala Thr Gly Ile Leu Pro Asp Glu Ala Ser Glu Ala Phe Arg
605                 610                 615                 620

AAC TCT TCC ATG GCC CTT CAA CAG GCA CAT TTA TTG AAA AAC ATG AGT        2223
Asn Ser Ser Met Ala Leu Gln Gln Ala His Leu Leu Lys Asn Met Ser
                625                 630                 635

CAC TGC AGG CAG CCT TCT GAC AGC AGT GTT GAT AAA TTT GTG TTG AGA        2271
His Cys Arg Gln Pro Ser Asp Ser Ser Val Asp Lys Phe Val Leu Arg
                640                 645                 650

GAT GAA GCT ACT GAA CCG GGT GAT CAA GAA AAC AAG CCT TGC CGC ATC        2319
Asp Glu Ala Thr Glu Pro Gly Asp Gln Glu Asn Lys Pro Cys Arg Ile
                655                 660                 665

AAA GGT GAC ATT GGA CAG TCC ACT GAT GAT GAC TCT GCA CCT CTT GTC        2367
Lys Gly Asp Ile Gly Gln Ser Thr Asp Asp Asp Ser Ala Pro Leu Val
            670                 675                 680

CAT TGT GTC CGC CTT TTA TCT GCT TCG TTT TTG CTA ACA GGG GGA AAA        2415
His Cys Val Arg Leu Leu Ser Ala Ser Phe Leu Leu Thr Gly Gly Lys
685                 690                 695                 700

AAT GTG CTG GTT CCG GAC AGG GAT GTG AGG GTC AGC GTG AAG GCC CTG        2463
Asn Val Leu Val Pro Asp Arg Asp Val Arg Val Ser Val Lys Ala Leu
                705                 710                 715

GCC CTC AGC TGT GTG GGA GCA GCT GTG GCC CTC CAC CCG GAA TCT TTC        2511
Ala Leu Ser Cys Val Gly Ala Ala Val Ala Leu His Pro Glu Ser Phe
                720                 725                 730

TTC AGC AAA CTC TAT AAA GTT CCT CTT GAC ACC ACG GAA TAC CCT GAG        2559
Phe Ser Lys Leu Tyr Lys Val Pro Leu Asp Thr Thr Glu Tyr Pro Glu
                735                 740                 745

GAA CAG TAT GTC TCA GAC ATC TTG AAC TAC ATC GAT CAT GGA GAC CCA        2607
Glu Gln Tyr Val Ser Asp Ile Leu Asn Tyr Ile Asp His Gly Asp Pro
                750                 755                 760

CAG GTT CGA GGA GCC ACT GCC ATT CTC TGT GGG ACC CTC ATC TGC TCC        2655
Gln Val Arg Gly Ala Thr Ala Ile Leu Cys Gly Thr Leu Ile Cys Ser
765                 770                 775                 780

ATC CTC AGC AGG TCC CGC TTC CAC GTG GGA GAT TGG ATG GGC ACC ATT        2703
Ile Leu Ser Arg Ser Arg Phe His Val Gly Asp Trp Met Gly Thr Ile
                785                 790                 795

AGA ACC CTC ACA GGA AAT ACA TTT TCT TTG GCG GAT TGC ATT CCT TTG        2751
```

```
                Arg Thr Leu Thr Gly Asn Thr Phe Ser Leu Ala Asp Cys Ile Pro Leu
                                800                 805                 810

CTG CGG AAA ACA CTG AAG GAT GAG TCT TCT GTT ACT TGC AAG TTA GCT           2799
Leu Arg Lys Thr Leu Lys Asp Glu Ser Ser Val Thr Cys Lys Leu Ala
            815                 820                 825

TGT ACA GCT GTG AGG AAC TGT GTC ATG AGT CTC TGC AGC AGC AGC TAC           2847
Cys Thr Ala Val Arg Asn Cys Val Met Ser Leu Cys Ser Ser Ser Tyr
    830                 835                 840

AGT GAG TTA GGA CTG CAG CTG ATC ATC GAT GTG CTG ACT CTG AGG AAC           2895
Ser Glu Leu Gly Leu Gln Leu Ile Ile Asp Val Leu Thr Leu Arg Asn
845                 850                 855                 860

AGT TCC TAT TGG CTG GTG AGG ACA GAG CTT CTG GAA ACC CTT GCA GAG           2943
Ser Ser Tyr Trp Leu Val Arg Thr Glu Leu Leu Glu Thr Leu Ala Glu
                865                 870                 875

ATT GAC TTC AGG CTG GTG AGC TTT TTG GAG GCA AAA GCA GAA AAC TTA           2991
Ile Asp Phe Arg Leu Val Ser Phe Leu Glu Ala Lys Ala Glu Asn Leu
            880                 885                 890

CAC AGA GGG GCT CAT CAT TAT ACA GGG CTT TTA AAA CTG CAA GAA CGA           3039
His Arg Gly Ala His His Tyr Thr Gly Leu Leu Lys Leu Gln Glu Arg
    895                 900                 905

GTG CTC AAT AAT GTT GTC ATC CAT TTG CTT GGA GAT GAA GAC CCC AGG           3087
Val Leu Asn Asn Val Val Ile His Leu Leu Gly Asp Glu Asp Pro Arg
910                 915                 920

GTG CGA CAT GTT GCC GCA GCA TCA CTA ATT AGG CTT GTC CCA AAG CTG           3135
Val Arg His Val Ala Ala Ala Ser Leu Ile Arg Leu Val Pro Lys Leu
925                 930                 935                 940

TTT TAT AAA TGT GAC CAA GGA CAA GCT GAT CCA GTA GTG GCC GTG GCA           3183
Phe Tyr Lys Cys Asp Gln Gly Gln Ala Asp Pro Val Val Ala Val Ala
                945                 950                 955

AGA GAT CAA AGC AGT GTT TAC CTG AAA CTT CTC ATG CAT GAG ACG CAG           3231
Arg Asp Gln Ser Ser Val Tyr Leu Lys Leu Leu Met His Glu Thr Gln
            960                 965                 970

CCT CCA TCT CAT TTC TCC GTC AGC ACA ATA ACC AGA ATA TAT AGA GGC           3279
Pro Pro Ser His Phe Ser Val Ser Thr Ile Thr Arg Ile Tyr Arg Gly
    975                 980                 985

TAT AAC CTA CTA CCA AGC ATA ACA GAC GTC ACT ATG GAA AAT AAC CTT           3327
Tyr Asn Leu Leu Pro Ser Ile Thr Asp Val Thr Met Glu Asn Asn Leu
990                 995                 1000

TCA AGA GTT ATT GCA GCA GTT TCT CAT GAA CTA ATC ACA TCA ACC ACC           3375
Ser Arg Val Ile Ala Ala Val Ser His Glu Leu Ile Thr Ser Thr Thr
1005                1010                1015                1020

AGA GCA CTC ACA TTT GGA TGC TGT GAA GCT TTG TGT CTT CTT TCC ACT           3423
Arg Ala Leu Thr Phe Gly Cys Cys Glu Ala Leu Cys Leu Leu Ser Thr
                1025                1030                1035

GCC TTC CCA GTT TGC ATT TGG AGT TTA GGT TGG CAC TGT GGA GTG CCT           3471
Ala Phe Pro Val Cys Ile Trp Ser Leu Gly Trp His Cys Gly Val Pro
            1040                1045                1050

CCA CTG AGT GCC TCA GAT GAG TCT AGG AAG AGC TGT ACC GTT GGG ATG           3519
Pro Leu Ser Ala Ser Asp Glu Ser Arg Lys Ser Cys Thr Val Gly Met
    1055                1060                1065

GCC ACA ATG ATT CTG ACC CTG CTC TCG TCA GCT TGG TTC CCA TTG GAT           3567
Ala Thr Met Ile Leu Thr Leu Leu Ser Ser Ala Trp Phe Pro Leu Asp
1070                1075                1080

CTC TCA GCC CAT CAA GAT GCT TTG ATT TTG GCC GGA AAC TTG CTT GCA           3615
Leu Ser Ala His Gln Asp Ala Leu Ile Leu Ala Gly Asn Leu Leu Ala
1085                1090                1095                1100

GCC AGT GCT CCC AAA TCT CTG AGA AGT TCA TGG GCC TCT GAA GAA GAA           3663
Ala Ser Ala Pro Lys Ser Leu Arg Ser Ser Trp Ala Ser Glu Glu Glu
                1105                1110                1115
```

```
                                            -continued

GCC AAC CCA GCA GCC ACC AAG CAA GAG GAG GTC TGG CCA GCC CTG GGG        3711
Ala Asn Pro Ala Ala Thr Lys Gln Glu Glu Val Trp Pro Ala Leu Gly
            1120                1125                1130

GAC CGG GCC CTG GTG CCC ATG GTG GAG CAG CTC TTC TCT CAC CTG CTG        3759
Asp Arg Ala Leu Val Pro Met Val Glu Gln Leu Phe Ser His Leu Leu
            1135                1140                1145

AAG GTG ATT AAC ATT TGT GCC CAC GTC CTG GAT GAC GTG GCT CCT GGA        3807
Lys Val Ile Asn Ile Cys Ala His Val Leu Asp Asp Val Ala Pro Gly
            1150                1155                1160

CCC GCA ATA AAG GCA GCC TTG CCT TCT CTA ACA AAC CCC CCT TCT CTA        3855
Pro Ala Ile Lys Ala Ala Leu Pro Ser Leu Thr Asn Pro Pro Ser Leu
1165                1170                1175                1180

AGT CCC ATC CGA CGA AAG GGG AAG GAG AAA GAA CCA GGA GAA CAA GCA        3903
Ser Pro Ile Arg Arg Lys Gly Lys Glu Lys Glu Pro Gly Glu Gln Ala
                1185                1190                1195

TCT GTA CCG TTG AGT CCC AAG AAA GGC AGT GAG GCC AGT GCA GCT TCT        3951
Ser Val Pro Leu Ser Pro Lys Lys Gly Ser Glu Ala Ser Ala Ala Ser
                1200                1205                1210

AGA CAA TCT GAT ACC TCA GGT CCT GTT ACA ACA AGT AAA TCC TCA TCA        3999
Arg Gln Ser Asp Thr Ser Gly Pro Val Thr Thr Ser Lys Ser Ser Ser
            1215                1220                1225

CTG GGG AGT TTC TAT CAT CTT CCT TCA TAC CTC AAA CTG CAT GAT GTC        4047
Leu Gly Ser Phe Tyr His Leu Pro Ser Tyr Leu Lys Leu His Asp Val
            1230                1235                1240

CTG AAA GCT ACA CAC GCT AAC TAC AAG GTC ACG CTG GAT CTT CAG AAC        4095
Leu Lys Ala Thr His Ala Asn Tyr Lys Val Thr Leu Asp Leu Gln Asn
1245                1250                1255                1260

AGC ACG GAA AAG TTT GGA GGG TTT CTC CGC TCA GCC TTG GAT GTT CTT        4143
Ser Thr Glu Lys Phe Gly Gly Phe Leu Arg Ser Ala Leu Asp Val Leu
                1265                1270                1275

TCT CAG ATA CTA GAG CTG GCC ACA CTG CAG GAC ATT GGG AAG TGT GTT        4191
Ser Gln Ile Leu Glu Leu Ala Thr Leu Gln Asp Ile Gly Lys Cys Val
                1280                1285                1290

GAA GAG ATC CTA GGA TAC CTG AAA TCC TGC TTT AGT CGA GAA CCA ATG        4239
Glu Glu Ile Leu Gly Tyr Leu Lys Ser Cys Phe Ser Arg Glu Pro Met
            1295                1300                1305

ATG GCA ACT GTT TGT GTT CAA CAA TTG TTG AAG ACT CTC TTT GGC ACA        4287
Met Ala Thr Val Cys Val Gln Gln Leu Leu Lys Thr Leu Phe Gly Thr
            1310                1315                1320

AAC TTG GCC TCC CAG TTT GAT GGC TTA TCT TCC AAC CCC AGC AAG TCA        4335
Asn Leu Ala Ser Gln Phe Asp Gly Leu Ser Ser Asn Pro Ser Lys Ser
1325                1330                1335                1340

CAA GGC CGA GCA CAG CGC CTT GGC TCC TCC AGT GTG AGG CCA GGC TTG        4383
Gln Gly Arg Ala Gln Arg Leu Gly Ser Ser Ser Val Arg Pro Gly Leu
                1345                1350                1355

TAC CAC TAC TGC TTC ATG GCC CCG TAC ACC CAC TTC ACC CAG GCC CTC        4431
Tyr His Tyr Cys Phe Met Ala Pro Tyr Thr His Phe Thr Gln Ala Leu
                1360                1365                1370

GCT GAC GCC AGC CTG AGG AAC ATG GTG CAG GCG GAG CAG GAG AAC GAC        4479
Ala Asp Ala Ser Leu Arg Asn Met Val Gln Ala Glu Gln Glu Asn Asp
            1375                1380                1385

ACC TCG GGA TGG TTT GAT GTC CTC CAG AAA GTG TCT ACC CAG TTG AAG        4527
Thr Ser Gly Trp Phe Asp Val Leu Gln Lys Val Ser Thr Gln Leu Lys
            1390                1395                1400

ACA AAC CTC ACG AGT GTC ACA AAG AAC CGT GCA GAT AAG AAT GCT ATT        4575
Thr Asn Leu Thr Ser Val Thr Lys Asn Arg Ala Asp Lys Asn Ala Ile
1405                1410                1415                1420

CAT AAT CAC ATT CGT TTG TTT GAA CCT CTT GTT ATA AAA GCT TTA AAA        4623
His Asn His Ile Arg Leu Phe Glu Pro Leu Val Ile Lys Ala Leu Lys
                1425                1430                1435
```

```
CAG TAC ACG ACT ACA ACA TGT GTG CAG TTA CAG AAG CAG GTT TTA GAT        4671
Gln Tyr Thr Thr Thr Thr Cys Val Gln Leu Gln Lys Gln Val Leu Asp
            1440                1445                1450

TTG CTG GCG CAG CTG GTT CAG TTA CGG GTT AAT TAC TGT CTT CTG GAT        4719
Leu Leu Ala Gln Leu Val Gln Leu Arg Val Asn Tyr Cys Leu Leu Asp
        1455                1460                1465

TCA GAT CAG GTG TTT ATT GGC TTT GTA TTG AAA CAG TTT GAA TAC ATT        4767
Ser Asp Gln Val Phe Ile Gly Phe Val Leu Lys Gln Phe Glu Tyr Ile
        1470                1475                1480

GAA GTG GGC CAG TTC AGG GAA TCA GAG GCA ATC ATT CCA AAC ATC TTT        4815
Glu Val Gly Gln Phe Arg Glu Ser Glu Ala Ile Ile Pro Asn Ile Phe
1485                1490                1495                1500

TTC TTC TTG GTA TTA CTA TCT TAT GAA CGC TAT CAT TCA AAA CAG ATC        4863
Phe Phe Leu Val Leu Leu Ser Tyr Glu Arg Tyr His Ser Lys Gln Ile
                1505                1510                1515

ATT GGA ATT CCT AAA ATC ATT CAG CTC TGT GAT GGC ATC ATG GCC AGT        4911
Ile Gly Ile Pro Lys Ile Ile Gln Leu Cys Asp Gly Ile Met Ala Ser
            1520                1525                1530

GGA AGG AAG GCT GTG ACA CAT GCC ATA CCG GCT CTG CAG CCC ATA GTC        4959
Gly Arg Lys Ala Val Thr His Ala Ile Pro Ala Leu Gln Pro Ile Val
        1535                1540                1545

CAC GAC CTC TTT GTA TTA AGA GGA ACA AAT AAA GCT GAT GCA GGA AAA        5007
His Asp Leu Phe Val Leu Arg Gly Thr Asn Lys Ala Asp Ala Gly Lys
        1550                1555                1560

GAG CTT GAA ACC CAA AAA GAG GTG GTG GTG TCA ATG TTA CTG AGA CTC        5055
Glu Leu Glu Thr Gln Lys Glu Val Val Val Ser Met Leu Leu Arg Leu
1565                1570                1575                1580

ATC CAG TAC CAT CAG GTG TTG GAG ATG TTC ATT CTT GTC CTG CAG CAG        5103
Ile Gln Tyr His Gln Val Leu Glu Met Phe Ile Leu Val Leu Gln Gln
            1585                1590                1595

TGC CAC AAG GAG AAT GAA GAC AAG TGG AAG CGA CTG TCT CGA CAG ATA        5151
Cys His Lys Glu Asn Glu Asp Lys Trp Lys Arg Leu Ser Arg Gln Ile
            1600                1605                1610

GCT GAC ATC ATC CTC CCA ATG TTA GCC AAA CAG CAG ATG CAC ATT GAC        5199
Ala Asp Ile Ile Leu Pro Met Leu Ala Lys Gln Gln Met His Ile Asp
        1615                1620                1625

TCT CAT GAA GCC CTT GGA GTG TTA AAT ACA TTA TTT GAG ATT TTG GCC        5247
Ser His Glu Ala Leu Gly Val Leu Asn Thr Leu Phe Glu Ile Leu Ala
        1630                1635                1640

CCT TCC TCC CTC CGT CCG GTA GAC ATG CTT TTA CGG AGT ATG TTC GTC        5295
Pro Ser Ser Leu Arg Pro Val Asp Met Leu Leu Arg Ser Met Phe Val
1645                1650                1655                1660

ACT CCA AAC ACA ATG GCG TCC GTG AGC ACT GTT CAA CTG TGG ATA TCG        5343
Thr Pro Asn Thr Met Ala Ser Val Ser Thr Val Gln Leu Trp Ile Ser
            1665                1670                1675

GGA ATT CTG GCC ATT TTG AGG GTT CTG ATT TCC CAG TCA ACT GAA GAT        5391
Gly Ile Leu Ala Ile Leu Arg Val Leu Ile Ser Gln Ser Thr Glu Asp
            1680                1685                1690

ATT GTT CTT TCT CGT ATT CAG GAG CTC TCC TTC TCT CCG TAT TTA ATC        5439
Ile Val Leu Ser Arg Ile Gln Glu Leu Ser Phe Ser Pro Tyr Leu Ile
        1695                1700                1705

TCC TGT ACA GTA ATT AAT AGG TTA AGA GAT GGG GAC AGT ACT TCA ACG        5487
Ser Cys Thr Val Ile Asn Arg Leu Arg Asp Gly Asp Ser Thr Ser Thr
        1710                1715                1720

CTA GAA GAA CAC AGT GAA GGG AAA CAA ATA AAG AAT TTG CCA GAA GAA        5535
Leu Glu Glu His Ser Glu Gly Lys Gln Ile Lys Asn Leu Pro Glu Glu
1725                1730                1735                1740

ACA TTT TCA AGG TTT CTA TTA CAA CTG GTT GGT ATT CTT TTA GAA GAC        5583
Thr Phe Ser Arg Phe Leu Leu Gln Leu Val Gly Ile Leu Leu Glu Asp
```

-continued

```
                 1745                    1750                    1755
ATT GTT ACA AAA CAG CTG AAG GTG GAA ATG AGT GAG CAG CAA CAT ACT         5631
Ile Val Thr Lys Gln Leu Lys Val Glu Met Ser Glu Gln Gln His Thr
            1760                    1765                    1770

TTC TAT TGC CAG GAA CTA GGC ACA CTG CTA ATG TGT CTG ATC CAC ATC         5679
Phe Tyr Cys Gln Glu Leu Gly Thr Leu Leu Met Cys Leu Ile His Ile
        1775                    1780                    1785

TTC AAG TCT GGA ATG TTC CGG AGA ATC ACA GCA GCT GCC ACT AGG CTG         5727
Phe Lys Ser Gly Met Phe Arg Arg Ile Thr Ala Ala Ala Thr Arg Leu
    1790                    1795                    1800

TTC CGC AGT GAT GGC TGT GGC GGC AGT TTC TAC ACC CTG GAC AGC TTG         5775
Phe Arg Ser Asp Gly Cys Gly Gly Ser Phe Tyr Thr Leu Asp Ser Leu
1805                    1810                    1815                    1820

AAC TTG CGG GCT CGT TCC ATG ATC ACC ACC CAC CCG GCC CTG GTG CTG         5823
Asn Leu Arg Ala Arg Ser Met Ile Thr Thr His Pro Ala Leu Val Leu
            1825                    1830                    1835

CTC TGG TGT CAG ATA CTG CTG CTT GTC AAC CAC ACC GAC TAC CGC TGG         5871
Leu Trp Cys Gln Ile Leu Leu Leu Val Asn His Thr Asp Tyr Arg Trp
        1840                    1845                    1850

TGG GCA GAA GTG CAG CAG ACC CCG AAA AGA CAC AGT CTG TCC AGC ACA         5919
Trp Ala Glu Val Gln Gln Thr Pro Lys Arg His Ser Leu Ser Ser Thr
    1855                    1860                    1865

AAG TTA CTT AGT CCC CAG ATG TCT GGA GAA GAG GAG GAT TCT GAC TTG         5967
Lys Leu Leu Ser Pro Gln Met Ser Gly Glu Glu Glu Asp Ser Asp Leu
    1870                    1875                    1880

GCA GCC AAA CTT GGA ATG TGC AAT AGA GAA ATA GTA CGA AGA GGG GCT         6015
Ala Ala Lys Leu Gly Met Cys Asn Arg Glu Ile Val Arg Arg Gly Ala
1885                    1890                    1895                    1900

CTC ATT CTC TTC TGT GAT TAT GTC TGT CAG AAC CTC CAT GAC TCC GAG         6063
Leu Ile Leu Phe Cys Asp Tyr Val Cys Gln Asn Leu His Asp Ser Glu
            1905                    1910                    1915

CAC TTA ACG TGG CTC ATT GTA AAT CAC ATT CAA GAT CTG ATC AGC CTT         6111
His Leu Thr Trp Leu Ile Val Asn His Ile Gln Asp Leu Ile Ser Leu
            1920                    1925                    1930

TCC CAC GAG CCT CCA GTA CAG GAC TTC ATC AGT GCC GTT CAT CGG AAC         6159
Ser His Glu Pro Pro Val Gln Asp Phe Ile Ser Ala Val His Arg Asn
        1935                    1940                    1945

TCT GCT GCC AGC GGC CTG TTC ATC CAG GCA ATT CAG TCT CGT TGT GAA         6207
Ser Ala Ala Ser Gly Leu Phe Ile Gln Ala Ile Gln Ser Arg Cys Glu
    1950                    1955                    1960

AAC CTT TCA ACT CCA ACC ATG CTG AAG AAA ACT CTT CAG TGC TTG GAG         6255
Asn Leu Ser Thr Pro Thr Met Leu Lys Lys Thr Leu Gln Cys Leu Glu
1965                    1970                    1975                    1980

GGG ATC CAT CTC AGC CAG TCG GGA GCT GTG CTC ACG CTG TAT GTG GAC         6303
Gly Ile His Leu Ser Gln Ser Gly Ala Val Leu Thr Leu Tyr Val Asp
            1985                    1990                    1995

AGG CTT CTG TGC ACC CCT TTC CGT GTG CTG GCT CGC ATG GTC GAC ATC         6351
Arg Leu Leu Cys Thr Pro Phe Arg Val Leu Ala Arg Met Val Asp Ile
        2000                    2005                    2010

CTT GCT TGT CGC CGG GTA GAA ATG CTT CTG GCT GCA AAT TTA CAG AGC         6399
Leu Ala Cys Arg Arg Val Glu Met Leu Leu Ala Ala Asn Leu Gln Ser
    2015                    2020                    2025

AGC ATG GCC CAG TTG CCA ATG GAA GAA CTC AAC AGA ATC CAG GAA TAC         6447
Ser Met Ala Gln Leu Pro Met Glu Glu Leu Asn Arg Ile Gln Glu Tyr
    2030                    2035                    2040

CTT CAG AGC AGC GGG CTC GCT CAG AGA CAC CAA AGG CTC TAT TCC CTG         6495
Leu Gln Ser Ser Gly Leu Ala Gln Arg His Gln Arg Leu Tyr Ser Leu
2045                    2050                    2055                    2060

CTG GAC AGG TTT CGT CTC TCC ACC ATG CAA GAC TCA CTT AGT CCC TCT         6543
```

```
                    -continued

Leu Asp Arg Phe Arg Leu Ser Thr Met Gln Asp Ser Leu Ser Pro Ser
                2065                2070                2075

CCT CCA GTC TCT TCC CAC CCG CTG GAC GGG GAT GGG CAC GTG TCA CTG         6591
Pro Pro Val Ser Ser His Pro Leu Asp Gly Asp Gly His Val Ser Leu
                2080                2085                2090

GAA ACA GTG AGT CCG GAC AAA GAC TGG TAC GTT CAT CTT GTC AAA TCC         6639
Glu Thr Val Ser Pro Asp Lys Asp Trp Tyr Val His Leu Val Lys Ser
                2095                2100                2105

CAG TGT TGG ACC AGG TCA GAT TCT GCA CTG CTG GAA GGT GCA GAG CTG         6687
Gln Cys Trp Thr Arg Ser Asp Ser Ala Leu Leu Glu Gly Ala Glu Leu
        2110                2115                2120

GTG AAT CGG ATT CCT GCT GAA GAT ATG AAT GCC TTC ATG ATG AAC TCG         6735
Val Asn Arg Ile Pro Ala Glu Asp Met Asn Ala Phe Met Met Asn Ser
2125                2130                2135                2140

GAG TTC AAC CTA AGC CTG CTA GCT CCA TGC TTA AGC CTA GGG ATG AGT         6783
Glu Phe Asn Leu Ser Leu Leu Ala Pro Cys Leu Ser Leu Gly Met Ser
                2145                2150                2155

GAA ATT TCT GGT GGC CAG AAG AGT GCC CTT TTT GAA GCA GCC CGT GAG         6831
Glu Ile Ser Gly Gly Gln Lys Ser Ala Leu Phe Glu Ala Ala Arg Glu
        2160                2165                2170

GTG ACT CTG GCC CGT GTG AGC GGC ACC GTG CAG CAG CTC CCT GCT GTC         6879
Val Thr Leu Ala Arg Val Ser Gly Thr Val Gln Gln Leu Pro Ala Val
                2175                2180                2185

CAT CAT GTC TTC CAG CCC GAG CTG CCT GCA GAG CCG GCG GCC TAC TGG         6927
His His Val Phe Gln Pro Glu Leu Pro Ala Glu Pro Ala Ala Tyr Trp
                2190                2195                2200

AGC AAG TTG AAT GAT CTG TTT GGG GAT GCT GCA CTG TAT CAG TCC CTG         6975
Ser Lys Leu Asn Asp Leu Phe Gly Asp Ala Ala Leu Tyr Gln Ser Leu
2205                2210                2215                2220

CCC ACT CTG GCC CGG GCC CTG GCA CAG TAC CTG GTG GTG GTC TCC AAA         7023
Pro Thr Leu Ala Arg Ala Leu Ala Gln Tyr Leu Val Val Val Ser Lys
                2225                2230                2235

CTG CCC AGT CAT TTG CAC CTT CCT CCT GAG AAA GAG AAG GAC ATT GTG         7071
Leu Pro Ser His Leu His Leu Pro Pro Glu Lys Glu Lys Asp Ile Val
                2240                2245                2250

AAA TTC GTG GTG GCA ACC CTT GAG GCC CTG TCC TGG CAT TTG ATC CAT         7119
Lys Phe Val Val Ala Thr Leu Glu Ala Leu Ser Trp His Leu Ile His
                2255                2260                2265

GAG CAG ATC CCG CTG AGT CTG GAT CTC CAG GCA GGG CTG GAC TGC TGC         7167
Glu Gln Ile Pro Leu Ser Leu Asp Leu Gln Ala Gly Leu Asp Cys Cys
        2270                2275                2280

TGC CTG GCC CTG CAG CTG CCT GGC CTC TGG AGC GTG GTC TCC TCC ACA         7215
Cys Leu Ala Leu Gln Leu Pro Gly Leu Trp Ser Val Val Ser Ser Thr
2285                2290                2295                2300

GAG TTT GTG ACC CAC GCC TGC TCC CTC ATC TAC TGT GTG CAC TTC ATC         7263
Glu Phe Val Thr His Ala Cys Ser Leu Ile Tyr Cys Val His Phe Ile
                2305                2310                2315

CTG GAG GCC GTT GCA GTG CAG CCT GGA GAG CAG CTT CTT AGT CCA GAA         7311
Leu Glu Ala Val Ala Val Gln Pro Gly Glu Gln Leu Leu Ser Pro Glu
                2320                2325                2330

AGA AGG ACA AAT ACC CCA AAA GCC ATC AGC GAG GAG GAG GAG GAA GTA         7359
Arg Arg Thr Asn Thr Pro Lys Ala Ile Ser Glu Glu Glu Glu Glu Val
                2335                2340                2345

GAT CCA AAC ACA CAG AAT CCT AAG TAT ATC ACT GCA GCC TGT GAG ATG         7407
Asp Pro Asn Thr Gln Asn Pro Lys Tyr Ile Thr Ala Ala Cys Glu Met
        2350                2355                2360

GTG GCA GAA ATG GTG GAG TCT CTG CAG TCG GTG TTG GCC TTG GGT CAT         7455
Val Ala Glu Met Val Glu Ser Leu Gln Ser Val Leu Ala Leu Gly His
2365                2370                2375                2380
```

```
AAA AGG AAT AGC GGC GTG CCG GCG TTT CTC ACG CCA TTG CTC AGG AAC      7503
Lys Arg Asn Ser Gly Val Pro Ala Phe Leu Thr Pro Leu Leu Arg Asn
            2385                2390                2395

ATC ATC ATC AGC CTG GCC CGC CTG CCC CTT GTC AAC AGC TAC ACA CGT      7551
Ile Ile Ile Ser Leu Ala Arg Leu Pro Leu Val Asn Ser Tyr Thr Arg
                2400                2405                2410

GTG CCC CCA CTG GTG TGG AAG CTT GGA TGG TCA CCC AAA CCG GGA GGG      7599
Val Pro Pro Leu Val Trp Lys Leu Gly Trp Ser Pro Lys Pro Gly Gly
                2415                2420                2425

GAT TTT GGC ACA GCA TTC CCT GAG ATC CCC GTG GAG TTC CTC CAG GAA      7647
Asp Phe Gly Thr Ala Phe Pro Glu Ile Pro Val Glu Phe Leu Gln Glu
            2430                2435                2440

AAG GAA GTC TTT AAG GAG TTC ATC TAC CGC ATC AAC ACA CTA GGC TGG      7695
Lys Glu Val Phe Lys Glu Phe Ile Tyr Arg Ile Asn Thr Leu Gly Trp
2445                2450                2455                2460

ACC AGT CGT ACT CAG TTT GAA GAA ACT TGG GCC ACC CTC CTT GGT GTC      7743
Thr Ser Arg Thr Gln Phe Glu Glu Thr Trp Ala Thr Leu Leu Gly Val
                2465                2470                2475

CTG GTG ACG CAG CCC CTC GTG ATG GAG CAG GAG GAG AGC CCA CCA GAA      7791
Leu Val Thr Gln Pro Leu Val Met Glu Gln Glu Glu Ser Pro Pro Glu
            2480                2485                2490

GAA GAC ACA GAG AGG ACC CAG ATC AAC GTC CTG GCC GTG CAG GCC ATC      7839
Glu Asp Thr Glu Arg Thr Gln Ile Asn Val Leu Ala Val Gln Ala Ile
                2495                2500                2505

ACC TCA CTG GTG CTC AGT GCA ATG ACT GTG CCT GTG GCC GGC AAC CCA      7887
Thr Ser Leu Val Leu Ser Ala Met Thr Val Pro Val Ala Gly Asn Pro
            2510                2515                2520

GCT GTA AGC TGC TTG GAG CAG CAG CCC CGG AAC AAG CCT CTG AAA GCT      7935
Ala Val Ser Cys Leu Glu Gln Gln Pro Arg Asn Lys Pro Leu Lys Ala
2525                2530                2535                2540

CTC GAC ACC AGG TTT GGG AGG AAG CTG AGC ATT ATC AGA GGG ATT GTG      7983
Leu Asp Thr Arg Phe Gly Arg Lys Leu Ser Ile Ile Arg Gly Ile Val
                2545                2550                2555

GAG CAA GAG ATT CAA GCA ATG GTT TCA AAG AGA GAG AAT ATT GCC ACC      8031
Glu Gln Glu Ile Gln Ala Met Val Ser Lys Arg Glu Asn Ile Ala Thr
            2560                2565                2570

CAT CAT TTA TAT CAG GCA TGG GAT CCT GTC CCT TCT CTG TCT CCG GCT      8079
His His Leu Tyr Gln Ala Trp Asp Pro Val Pro Ser Leu Ser Pro Ala
                2575                2580                2585

ACT ACA GGT GCC CTC ATC AGC CAC GAG AAG CTG CTG CTA CAG ATC AAC      8127
Thr Thr Gly Ala Leu Ile Ser His Glu Lys Leu Leu Leu Gln Ile Asn
            2590                2595                2600

CCC GAG CGG GAG CTG GGG AGC ATG AGC TAC AAA CTC GGC CAG GTG TCC      8175
Pro Glu Arg Glu Leu Gly Ser Met Ser Tyr Lys Leu Gly Gln Val Ser
2605                2610                2615                2620

ATA CAC TCC GTG TGG CTG GGG AAC AGC ATC ACA CCC CTG AGG GAG GAG      8223
Ile His Ser Val Trp Leu Gly Asn Ser Ile Thr Pro Leu Arg Glu Glu
                2625                2630                2635

GAA TGG GAC GAG GAA GAG GAG GAG GAG GCC GAC GCC CCT GCA CCT TCG      8271
Glu Trp Asp Glu Glu Glu Glu Glu Glu Ala Asp Ala Pro Ala Pro Ser
            2640                2645                2650

TCA CCA CCC ACG TCT CCA GTC AAC TCC AGG AAA CAC CGG GCT GGA GTT      8319
Ser Pro Pro Thr Ser Pro Val Asn Ser Arg Lys His Arg Ala Gly Val
                2655                2660                2665

GAC ATC CAC TCC TGT TCG CAG TTT TTG CTT GAG TTG TAC AGC CGC TGG      8367
Asp Ile His Ser Cys Ser Gln Phe Leu Leu Glu Leu Tyr Ser Arg Trp
            2670                2675                2680

ATC CTG CCG TCC AGC TCA GCC AGG AGG ACC CCG GCC ATC CTG ATC AGT      8415
Ile Leu Pro Ser Ser Ser Ala Arg Arg Thr Pro Ala Ile Leu Ile Ser
2685                2690                2695                2700
```

```
GAG GTG GTC AGA TCC CTT CTA GTG GTC TCA GAC TTG TTC ACC GAG CGC                    8463
Glu Val Val Arg Ser Leu Leu Val Val Ser Asp Leu Phe Thr Glu Arg
              2705                2710                2715

AAC CAG TTT GAG CTG ATG TAT GTG ACG CTG ACA GAA CTG CGA AGG GTG                    8511
Asn Gln Phe Glu Leu Met Tyr Val Thr Leu Thr Glu Leu Arg Arg Val
              2720                2725                2730

CAC CCT TCA GAA GAC GAG ATC CTC GCT CAG TAC CTG GTG CCT GCC ACC                    8559
His Pro Ser Glu Asp Glu Ile Leu Ala Gln Tyr Leu Val Pro Ala Thr
              2735                2740                2745

TGC AAG GCA GCT GCC GTC CTT GGG ATG GAC AAG GCC GTG GCG GAG CCT                    8607
Cys Lys Ala Ala Ala Val Leu Gly Met Asp Lys Ala Val Ala Glu Pro
              2750                2755                2760

GTC AGC CGC CTG CTG GAG AGC ACG CTC AGG AGC AGC CAC CTG CCC AGC                    8655
Val Ser Arg Leu Leu Glu Ser Thr Leu Arg Ser Ser His Leu Pro Ser
2765                2770                2775                2780

AGG GTT GGA GCC CTG CAC GGC GTC CTC TAT GTG CTG GAG TGC GAC CTG                    8703
Arg Val Gly Ala Leu His Gly Val Leu Tyr Val Leu Glu Cys Asp Leu
              2785                2790                2795

CTG GAC GAC ACT GCC AAG CAG CTC ATC CCG GTC ATC AGC GAC TAT CTC                    8751
Leu Asp Asp Thr Ala Lys Gln Leu Ile Pro Val Ile Ser Asp Tyr Leu
              2800                2805                2810

CTC TCC AAC CTG AAA GGG ATC GCC CAC TGC GTG AAC ATT CAC AGC CAG                    8799
Leu Ser Asn Leu Lys Gly Ile Ala His Cys Val Asn Ile His Ser Gln
              2815                2820                2825

CAG CAC GTA CTG GTC ATG TGT GCC ACT GCG TTT TAC CTC ATT GAG AAC                    8847
Gln His Val Leu Val Met Cys Ala Thr Ala Phe Tyr Leu Ile Glu Asn
              2830                2835                2840

TAT CCT CTG GAC GTA GGG CCG GAA TTT TCA GCA TCA ATA ATA CAG ATG                    8895
Tyr Pro Leu Asp Val Gly Pro Glu Phe Ser Ala Ser Ile Ile Gln Met
2845                2850                2855                2860

TGT GGG GTG ATG CTG TCT GGA AGT GAG GAG TCC ACC CCC TCC ATC ATT                    8943
Cys Gly Val Met Leu Ser Gly Ser Glu Glu Ser Thr Pro Ser Ile Ile
              2865                2870                2875

TAC CAC TGT GCC CTC AGA GGC CTG GAG CGC CTC CTG CTC TCT GAG CAG                    8991
Tyr His Cys Ala Leu Arg Gly Leu Glu Arg Leu Leu Leu Ser Glu Gln
              2880                2885                2890

CTC TCC CGC CTG GAT GCA GAA TCG CTG GTC AAG CTG AGT GTG GAC AGA                    9039
Leu Ser Arg Leu Asp Ala Glu Ser Leu Val Lys Leu Ser Val Asp Arg
              2895                2900                2905

GTG AAC GTG CAC AGC CCG CAC CGG GCC ATG GCG GCT CTG GGC CTG ATG                    9087
Val Asn Val His Ser Pro His Arg Ala Met Ala Ala Leu Gly Leu Met
              2910                2915                2920

CTC ACC TGC ATG TAC ACA GGA AAG GAG AAA GTC AGT CCG GGT AGA ACT                    9135
Leu Thr Cys Met Tyr Thr Gly Lys Glu Lys Val Ser Pro Gly Arg Thr
2925                2930                2935                2940

TCA GAC CCT AAT CCT GCA GCC CCC GAC AGC GAG TCA GTG ATT GTT GCT                    9183
Ser Asp Pro Asn Pro Ala Ala Pro Asp Ser Glu Ser Val Ile Val Ala
              2945                2950                2955

ATG GAG CGG GTA TCT GTT CTT TTT GAT AGG ATC AGG AAA GGC TTT CCT                    9231
Met Glu Arg Val Ser Val Leu Phe Asp Arg Ile Arg Lys Gly Phe Pro
              2960                2965                2970

TGT GAA GCC AGA GTG GTG GCC AGG ATC CTG CCC CAG TTT CTA GAC GAC                    9279
Cys Glu Ala Arg Val Val Ala Arg Ile Leu Pro Gln Phe Leu Asp Asp
              2975                2980                2985

TTC TTC CCA CCC CAG GAC ATC ATG AAC AAA GTC ATC GGA GAG TTT CTG                    9327
Phe Phe Pro Pro Gln Asp Ile Met Asn Lys Val Ile Gly Glu Phe Leu
              2990                2995                3000

TCC AAC CAG CAG CCA TAC CCC CAG TTC ATG GCC ACC GTG GTG TAT AAG                    9375
Ser Asn Gln Gln Pro Tyr Pro Gln Phe Met Ala Thr Val Val Tyr Lys
```

```
                                                                 -continued 3005              3010              3015              3020
GTG TTT CAG ACT CTG CAC AGC ACC GGG CAG TCG TCC ATG GTC CGG GAC     9423
Val Phe Gln Thr Leu His Ser Thr Gly Gln Ser Ser Met Val Arg Asp
              3025              3030              3035

TGG GTC ATG CTG TCC CTC TCC AAC TTC ACG CAG AGG GCC CCG GTC GCC     9471
Trp Val Met Leu Ser Leu Ser Asn Phe Thr Gln Arg Ala Pro Val Ala
              3040              3045              3050

ATG GCC ACG TGG AGC CTC TCC TGC TTC TTT GTC AGC GCG TCC ACC AGC     9519
Met Ala Thr Trp Ser Leu Ser Cys Phe Phe Val Ser Ala Ser Thr Ser
              3055              3060              3065

CCG TGG GTC GCG GCG ATC CTC CCA CAT GTC ATC AGC AGG ATG GGC AAG     9567
Pro Trp Val Ala Ala Ile Leu Pro His Val Ile Ser Arg Met Gly Lys
              3070              3075              3080

CTG GAG CAG GTG GAC GTG AAC CTT TTC TGC CTG GTC GCC ACA GAC TTC     9615
Leu Glu Gln Val Asp Val Asn Leu Phe Cys Leu Val Ala Thr Asp Phe
3085              3090              3095              3100

TAC AGA CAC CAG ATA GAG GAG GAG CTC GAC CGC AGG GCC TTC CAG TCT     9663
Tyr Arg His Gln Ile Glu Glu Glu Leu Asp Arg Arg Ala Phe Gln Ser
              3105              3110              3115

GTG CTT GAG GTG GTT GCA GCC CCA GGA AGC CCA TAT CAC CGG CTG CTG     9711
Val Leu Glu Val Val Ala Ala Pro Gly Ser Pro Tyr His Arg Leu Leu
              3120              3125              3130

ACT TGT TTA CGA AAT GTC CAC AAG GTC ACC ACC TGC T GAGCGCCATG        9758
Thr Cys Leu Arg Asn Val His Lys Val Thr Thr Cys
              3135              3140

GTGGGAGAGA CTGTGAGGCG GCAGCTGGGG CCGGAGCCTT TGGAAGTCTG TGCCCTTGTG   9818

CCCTGCCTCC ACCGAGCCAG CTTGGTCCCT ATGGGCTTCC GCACATGCCG CGGGCGGCCA   9878

GGCAACGTGC GTGTCTCTGC CATGTGGCAG AAGTGCTCTT TGTGGCAGTG GCCAGGCAGG   9938

GAGTGTCTGC AGTCCTGGTG GGGCTGAGCC TGAGGCCTTC CAGAAAGCAG GAGCAGCTGT   9998

GCTGCACCCC ATGTGGGTGA CCAGGTCCTT TCTCCTGATA GTCACCTGCT GGTTGTTGCC   10058

AGGTTGCAGC TGCTCTTGCA TCTGGGCCAG AAGTCCTCCC TCCTGCAGGC TGGCTGTTGG   10118

CCCCTCTGCT GTCCTGCAGT AGAAGGTGCC GTGAGCAGGG TTTGGGAACA CTGGCCTGGG   10178

TCTCCCTGGT GGGGTGTGCA TGCCACGCCC CGTGTCTGGA TGCACAGATG CCATGGCCTG   10238

TGCTGGGCCA GTGGCTGGGG GTGCTAGACA CCCCGGCACCA TTCTCCCTTC TCTCTTTTCT  10298

TCTCAGGATT TAAAATTTAA TTATATCAGT AAAGAGATTA ATTTTAACGT              10348

(2) INFORMATION FOR SEQ ID NO:15:

(i) SEQUENCE CHARACTERISTICS:
        (A) LENGTH: 3144 amino acids
        (B) TYPE: amino acid
        (D) TOPOLOGY: linear (ii) MOLECULE TYPE: protein (xi) SEQUENCE DESCRIPTION: SEQ ID NO:15:

Met Ala Thr Leu Glu Lys Leu Met Lys Ala Phe Glu Ser Leu Lys Ser
 1               5                  10                  15

Phe Gln Gln Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro Pro Pro
            35                  40                  45

Pro Pro Pro Gln Leu Pro Gln Pro Pro Pro Gln Ala Gln Pro Leu Leu
        50                  55                  60

Pro Gln Pro Gln Pro Pro Pro Pro Pro Pro Pro Pro Pro Pro Gly Pro
```

```
                65                  70                  75                  80
Ala Val Ala Glu Glu Pro Leu His Arg Pro Lys Lys Glu Leu Ser Ala
                    85                  90                  95
Thr Lys Lys Asp Arg Val Asn His Cys Leu Thr Ile Cys Glu Asn Ile
                    100                 105                 110
Val Ala Gln Ser Val Arg Asn Ser Pro Glu Phe Gln Lys Leu Leu Gly
                    115                 120                 125
Ile Ala Met Glu Leu Phe Leu Leu Cys Ser Asp Asp Ala Glu Ser Asp
                    130                 135                 140
Val Arg Met Val Ala Asp Glu Cys Leu Asn Lys Val Ile Lys Ala Leu
145                 150                 155                 160
Met Asp Ser Asn Leu Pro Arg Leu Gln Leu Glu Leu Tyr Lys Glu Ile
                    165                 170                 175
Lys Lys Asn Gly Ala Pro Arg Ser Leu Arg Ala Ala Leu Trp Arg Phe
                    180                 185                 190
Ala Glu Leu Ala His Leu Val Arg Pro Gln Lys Cys Arg Pro Tyr Leu
                    195                 200                 205
Val Asn Leu Leu Pro Cys Leu Thr Arg Thr Ser Lys Arg Pro Glu Glu
                    210                 215                 220
Ser Val Gln Glu Thr Leu Ala Ala Ala Val Pro Lys Ile Met Ala Ser
225                 230                 235                 240
Phe Gly Asn Phe Ala Asn Asp Asn Glu Ile Lys Val Leu Leu Lys Ala
                    245                 250                 255
Phe Ile Ala Asn Leu Lys Ser Ser Pro Thr Ile Arg Arg Thr Ala
                    260                 265                 270
Ala Gly Ser Ala Val Ser Ile Cys Gln His Ser Arg Arg Thr Gln Tyr
                    275                 280                 285
Phe Tyr Ser Trp Leu Leu Asn Val Leu Leu Gly Leu Leu Val Pro Val
                    290                 295                 300
Glu Asp Glu His Ser Thr Leu Leu Ile Leu Gly Val Leu Leu Thr Leu
305                 310                 315                 320
Arg Tyr Leu Val Pro Leu Leu Gln Gln Gln Val Lys Asp Thr Ser Leu
                    325                 330                 335
Lys Gly Ser Phe Gly Val Thr Arg Lys Glu Met Glu Val Ser Pro Ser
                    340                 345                 350
Ala Glu Gln Leu Val Gln Val Tyr Glu Leu Thr Leu His His Thr Gln
                    355                 360                 365
His Gln Asp His Asn Val Val Thr Gly Ala Leu Glu Leu Leu Gln Gln
                    370                 375                 380
Leu Phe Arg Thr Pro Pro Glu Leu Leu Gln Thr Leu Thr Ala Val
385                 390                 395                 400
Gly Gly Ile Gly Gln Leu Thr Ala Ala Lys Glu Glu Ser Gly Gly Arg
                    405                 410                 415
Ser Arg Ser Gly Ser Ile Val Glu Leu Ile Ala Gly Gly Ser Ser
                    420                 425                 430
Cys Ser Pro Val Leu Ser Arg Lys Gln Lys Gly Lys Val Leu Leu Gly
                    435                 440                 445
Glu Glu Glu Ala Leu Glu Asp Asp Ser Glu Ser Arg Ser Asp Val Ser
                    450                 455                 460
Ser Ser Ala Leu Thr Ala Ser Val Lys Asp Glu Ile Ser Gly Glu Leu
465                 470                 475                 480
Ala Ala Ser Ser Gly Val Ser Thr Pro Gly Ser Ala Gly His Asp Ile
                    485                 490                 495
```

-continued

```
Ile Thr Glu Gln Pro Arg Ser Gln His Thr Leu Gln Ala Asp Ser Val
            500                 505                 510

Asp Leu Ala Ser Cys Asp Leu Thr Ser Ser Ala Thr Asp Gly Asp Glu
            515                 520                 525

Glu Asp Ile Leu Ser His Ser Ser Ser Gln Val Ser Ala Val Pro Ser
            530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
            580                 585                 590

Leu Gly Leu Gln Ile Gly Gln Pro Gln Asp Glu Asp Glu Glu Ala Thr
            595                 600                 605

Gly Ile Leu Pro Asp Glu Ala Ser Glu Ala Phe Arg Asn Ser Ser Met
            610                 615                 620

Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
            660                 665                 670

Gly Gln Ser Thr Asp Asp Ser Ala Pro Leu Val His Cys Val Arg
            675                 680                 685

Leu Leu Ser Ala Ser Phe Leu Leu Thr Gly Gly Lys Asn Val Leu Val
            690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
            755                 760                 765

Ala Thr Ala Ile Leu Cys Gly Thr Leu Ile Cys Ser Ile Leu Ser Arg
770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Ser Tyr Ser Glu Leu Gly
            835                 840                 845

Leu Gln Leu Ile Ile Asp Val Leu Thr Leu Arg Asn Ser Ser Tyr Trp
            850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910
```

-continued

```
Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
        930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
                980                 985                 990

Pro Ser Ile Thr Asp Val Thr Met Glu Asn Asn Leu Ser Arg Val Ile
            995                 1000                1005

Ala Ala Val Ser His Glu Leu Ile Thr Ser Thr Thr Arg Ala Leu Thr
        1010                1015                1020

Phe Gly Cys Cys Glu Ala Leu Cys Leu Leu Ser Thr Ala Phe Pro Val
1025                1030                1035                1040

Cys Ile Trp Ser Leu Gly Trp His Cys Gly Val Pro Pro Leu Ser Ala
            1045                1050                1055

Ser Asp Glu Ser Arg Lys Ser Cys Thr Val Gly Met Ala Thr Met Ile
            1060                1065                1070

Leu Thr Leu Leu Ser Ser Ala Trp Phe Pro Leu Asp Leu Ser Ala His
        1075                1080                1085

Gln Asp Ala Leu Ile Leu Ala Gly Asn Leu Leu Ala Ala Ser Ala Pro
1090                1095                1100

Lys Ser Leu Arg Ser Ser Trp Ala Ser Glu Glu Ala Asn Pro Ala
1105                1110                1115                1120

Ala Thr Lys Gln Glu Glu Val Trp Pro Ala Leu Gly Asp Arg Ala Leu
            1125                1130                1135

Val Pro Met Val Glu Gln Leu Phe Ser His Leu Leu Lys Val Ile Asn
        1140                1145                1150

Ile Cys Ala His Val Leu Asp Asp Val Ala Pro Gly Pro Ala Ile Lys
            1155                1160                1165

Ala Ala Leu Pro Ser Leu Thr Asn Pro Pro Ser Leu Ser Pro Ile Arg
        1170                1175                1180

Arg Lys Gly Lys Glu Lys Glu Pro Gly Glu Gln Ala Ser Val Pro Leu
1185                1190                1195                1200

Ser Pro Lys Lys Gly Ser Glu Ala Ser Ala Ala Ser Arg Gln Ser Asp
            1205                1210                1215

Thr Ser Gly Pro Val Thr Thr Ser Lys Ser Ser Ser Leu Gly Ser Phe
            1220                1225                1230

Tyr His Leu Pro Ser Tyr Leu Lys Leu His Asp Val Leu Lys Ala Thr
        1235                1240                1245

His Ala Asn Tyr Lys Val Thr Leu Asp Leu Gln Asn Ser Thr Glu Lys
        1250                1255                1260

Phe Gly Gly Phe Leu Arg Ser Ala Leu Asp Val Leu Ser Gln Ile Leu
1265                1270                1275                1280

Glu Leu Ala Thr Leu Gln Asp Ile Gly Lys Cys Val Glu Glu Ile Leu
            1285                1290                1295

Gly Tyr Leu Lys Ser Cys Phe Ser Arg Glu Pro Met Met Ala Thr Val
            1300                1305                1310

Cys Val Gln Gln Leu Leu Lys Thr Leu Phe Gly Thr Asn Leu Ala Ser
        1315                1320                1325

Gln Phe Asp Gly Leu Ser Ser Asn Pro Ser Lys Ser Gln Gly Arg Ala
```

-continued

```
            1330              1335              1340
Gln Arg Leu Gly Ser Ser Val Arg Pro Gly Leu Tyr His Tyr Cys
1345              1350              1355              1360
Phe Met Ala Pro Tyr Thr His Phe Thr Gln Ala Leu Ala Asp Ala Ser
                  1365              1370              1375
Leu Arg Asn Met Val Gln Ala Glu Gln Glu Asn Asp Thr Ser Gly Trp
            1380              1385              1390
Phe Asp Val Leu Gln Lys Val Ser Thr Gln Leu Lys Thr Asn Leu Thr
            1395              1400              1405
Ser Val Thr Lys Asn Arg Ala Asp Lys Asn Ala Ile His Asn His Ile
            1410              1415              1420
Arg Leu Phe Glu Pro Leu Val Ile Lys Ala Leu Lys Gln Tyr Thr Thr
1425              1430              1435              1440
Thr Thr Cys Val Gln Leu Gln Lys Gln Val Leu Asp Leu Leu Ala Gln
                  1445              1450              1455
Leu Val Gln Leu Arg Val Asn Tyr Cys Leu Leu Asp Ser Asp Gln Val
                  1460              1465              1470
Phe Ile Gly Phe Val Leu Lys Gln Phe Glu Tyr Ile Glu Val Gly Gln
            1475              1480              1485
Phe Arg Glu Ser Glu Ala Ile Ile Pro Asn Ile Phe Phe Phe Leu Val
            1490              1495              1500
Leu Leu Ser Tyr Glu Arg Tyr His Ser Lys Gln Ile Gly Ile Pro
1505              1510              1515              1520
Lys Ile Ile Gln Leu Cys Asp Gly Ile Met Ala Ser Gly Arg Lys Ala
                  1525              1530              1535
Val Thr His Ala Ile Pro Ala Leu Gln Pro Ile Val His Asp Leu Phe
                  1540              1545              1550
Val Leu Arg Gly Thr Asn Lys Ala Asp Ala Gly Lys Glu Leu Glu Thr
            1555              1560              1565
Gln Lys Glu Val Val Ser Met Leu Leu Arg Leu Ile Gln Tyr His
            1570              1575              1580
Gln Val Leu Glu Met Phe Ile Leu Val Leu Gln Gln Cys His Lys Glu
1585              1590              1595              1600
Asn Glu Asp Lys Trp Lys Arg Leu Ser Arg Gln Ile Ala Asp Ile Ile
                  1605              1610              1615
Leu Pro Met Leu Ala Lys Gln Gln Met His Ile Asp Ser His Glu Ala
                  1620              1625              1630
Leu Gly Val Leu Asn Thr Leu Phe Glu Ile Leu Ala Pro Ser Ser Leu
            1635              1640              1645
Arg Pro Val Asp Met Leu Leu Arg Ser Met Phe Val Thr Pro Asn Thr
            1650              1655              1660
Met Ala Ser Val Ser Thr Val Gln Leu Trp Ile Ser Gly Ile Leu Ala
1665              1670              1675              1680
Ile Leu Arg Val Leu Ile Ser Gln Ser Thr Glu Asp Ile Val Leu Ser
                  1685              1690              1695
Arg Ile Gln Glu Leu Ser Phe Ser Pro Tyr Leu Ile Ser Cys Thr Val
                  1700              1705              1710
Ile Asn Arg Leu Arg Asp Gly Asp Ser Thr Ser Thr Leu Glu Glu His
            1715              1720              1725
Ser Glu Gly Lys Gln Ile Lys Asn Leu Pro Glu Glu Thr Phe Ser Arg
            1730              1735              1740
Phe Leu Leu Gln Leu Val Gly Ile Leu Leu Glu Asp Ile Val Thr Lys
1745              1750              1755              1760
```

```
Gln Leu Lys Val Glu Met Ser Glu Gln Gln His Thr Phe Tyr Cys Gln
                1765                1770                1775
Glu Leu Gly Thr Leu Leu Met Cys Leu Ile His Ile Phe Lys Ser Gly
                1780                1785                1790
Met Phe Arg Arg Ile Thr Ala Ala Thr Arg Leu Phe Arg Ser Asp
                1795                1800                1805
Gly Cys Gly Gly Ser Phe Tyr Thr Leu Asp Ser Leu Asn Leu Arg Ala
                1810                1815                1820
Arg Ser Met Ile Thr Thr His Pro Ala Leu Val Leu Leu Trp Cys Gln
1825                1830                1835                1840
Ile Leu Leu Leu Val Asn His Thr Asp Tyr Arg Trp Trp Ala Glu Val
                1845                1850                1855
Gln Gln Thr Pro Lys Arg His Ser Leu Ser Ser Thr Lys Leu Leu Ser
                1860                1865                1870
Pro Gln Met Ser Gly Glu Glu Asp Ser Asp Leu Ala Ala Lys Leu
                1875                1880                1885
Gly Met Cys Asn Arg Glu Ile Val Arg Arg Gly Ala Leu Ile Leu Phe
                1890                1895                1900
Cys Asp Tyr Val Cys Gln Asn Leu His Asp Ser Glu His Leu Thr Trp
1905                1910                1915                1920
Leu Ile Val Asn His Ile Gln Asp Leu Ile Ser Leu Ser His Glu Pro
                1925                1930                1935
Pro Val Gln Asp Phe Ile Ser Ala Val His Arg Asn Ser Ala Ala Ser
                1940                1945                1950
Gly Leu Phe Ile Gln Ala Ile Gln Ser Arg Cys Glu Asn Leu Ser Thr
                1955                1960                1965
Pro Thr Met Leu Lys Lys Thr Leu Gln Cys Leu Glu Gly Ile His Leu
                1970                1975                1980
Ser Gln Ser Gly Ala Val Leu Thr Leu Tyr Val Asp Arg Leu Leu Cys
1985                1990                1995                2000
Thr Pro Phe Arg Val Leu Ala Arg Met Val Asp Ile Leu Ala Cys Arg
                2005                2010                2015
Arg Val Glu Met Leu Leu Ala Ala Asn Leu Gln Ser Ser Met Ala Gln
                2020                2025                2030
Leu Pro Met Glu Glu Leu Asn Arg Ile Gln Glu Tyr Leu Gln Ser Ser
                2035                2040                2045
Gly Leu Ala Gln Arg His Gln Arg Leu Tyr Ser Leu Leu Asp Arg Phe
                2050                2055                2060
Arg Leu Ser Thr Met Gln Asp Ser Leu Ser Pro Ser Pro Val Ser
2065                2070                2075                2080
Ser His Pro Leu Asp Gly Asp Gly His Val Ser Leu Glu Thr Val Ser
                2085                2090                2095
Pro Asp Lys Asp Trp Tyr Val His Leu Val Lys Ser Gln Cys Trp Thr
                2100                2105                2110
Arg Ser Asp Ser Ala Leu Leu Glu Gly Ala Glu Leu Val Asn Arg Ile
                2115                2120                2125
Pro Ala Glu Asp Met Asn Ala Phe Met Met Asn Ser Glu Phe Asn Leu
                2130                2135                2140
Ser Leu Leu Ala Pro Cys Leu Ser Leu Gly Met Ser Glu Ile Ser Gly
2145                2150                2155                2160
Gly Gln Lys Ser Ala Leu Phe Glu Ala Ala Arg Glu Val Thr Leu Ala
                2165                2170                2175
```

-continued

```
Arg Val Ser Gly Thr Val Gln Gln Leu Pro Ala Val His His Val Phe
                2180                2185                2190

Gln Pro Glu Leu Pro Ala Glu Pro Ala Ala Tyr Trp Ser Lys Leu Asn
                2195                2200                2205

Asp Leu Phe Gly Asp Ala Ala Leu Tyr Gln Ser Leu Pro Thr Leu Ala
                2210                2215                2220

Arg Ala Leu Ala Gln Tyr Leu Val Val Ser Lys Leu Pro Ser His
2225                2230                2235                2240

Leu His Leu Pro Pro Glu Lys Glu Lys Asp Ile Val Lys Phe Val Val
                2245                2250                2255

Ala Thr Leu Glu Ala Leu Ser Trp His Leu Ile His Glu Gln Ile Pro
                2260                2265                2270

Leu Ser Leu Asp Leu Gln Ala Gly Leu Asp Cys Cys Cys Leu Ala Leu
                2275                2280                2285

Gln Leu Pro Gly Leu Trp Ser Val Val Ser Ser Thr Glu Phe Val Thr
                2290                2295                2300

His Ala Cys Ser Leu Ile Tyr Cys Val His Phe Ile Leu Glu Ala Val
2305                2310                2315                2320

Ala Val Gln Pro Gly Glu Gln Leu Leu Ser Pro Glu Arg Arg Thr Asn
                2325                2330                2335

Thr Pro Lys Ala Ile Ser Glu Glu Glu Glu Val Asp Pro Asn Thr
                2340                2345                2350

Gln Asn Pro Lys Tyr Ile Thr Ala Ala Cys Glu Met Val Ala Glu Met
                2355                2360                2365

Val Glu Ser Leu Gln Ser Val Leu Ala Leu Gly His Lys Arg Asn Ser
                2370                2375                2380

Gly Val Pro Ala Phe Leu Thr Pro Leu Leu Arg Asn Ile Ile Ile Ser
2385                2390                2395                2400

Leu Ala Arg Leu Pro Leu Val Asn Ser Tyr Thr Arg Val Pro Pro Leu
                2405                2410                2415

Val Trp Lys Leu Gly Trp Ser Pro Lys Pro Gly Gly Asp Phe Gly Thr
                2420                2425                2430

Ala Phe Pro Glu Ile Pro Val Glu Phe Leu Gln Glu Lys Glu Val Phe
                2435                2440                2445

Lys Glu Phe Ile Tyr Arg Ile Asn Thr Leu Gly Trp Thr Ser Arg Thr
                2450                2455                2460

Gln Phe Glu Glu Thr Trp Ala Thr Leu Leu Gly Val Leu Val Thr Gln
2465                2470                2475                2480

Pro Leu Val Met Glu Gln Glu Glu Ser Pro Pro Glu Glu Asp Thr Glu
                2485                2490                2495

Arg Thr Gln Ile Asn Val Leu Ala Val Gln Ala Ile Thr Ser Leu Val
                2500                2505                2510

Leu Ser Ala Met Thr Val Pro Val Ala Gly Asn Pro Ala Val Ser Cys
                2515                2520                2525

Leu Glu Gln Gln Pro Arg Asn Lys Pro Leu Lys Ala Leu Asp Thr Arg
                2530                2535                2540

Phe Gly Arg Lys Leu Ser Ile Ile Arg Gly Ile Val Glu Gln Glu Ile
2545                2550                2555                2560

Gln Ala Met Val Ser Lys Arg Glu Asn Ile Ala Thr His His Leu Tyr
                2565                2570                2575

Gln Ala Trp Asp Pro Val Pro Ser Leu Ser Pro Ala Thr Thr Gly Ala
                2580                2585                2590

Leu Ile Ser His Glu Lys Leu Leu Leu Gln Ile Asn Pro Glu Arg Glu
```

-continued

```
              2595                2600                2605

Leu Gly Ser Met Ser Tyr Lys Leu Gly Gln Val Ser Ile His Ser Val
              2610                2615                2620

Trp Leu Gly Asn Ser Ile Thr Pro Leu Arg Glu Glu Trp Asp Glu
2625                2630                2635                2640

Glu Glu Glu Glu Glu Ala Asp Ala Pro Ala Pro Ser Ser Pro Pro Thr
                  2645                2650                2655

Ser Pro Val Asn Ser Arg Lys His Arg Ala Gly Val Asp Ile His Ser
              2660                2665                2670

Cys Ser Gln Phe Leu Leu Glu Leu Tyr Ser Arg Trp Ile Leu Pro Ser
              2675                2680                2685

Ser Ser Ala Arg Arg Thr Pro Ala Ile Leu Ile Ser Glu Val Val Arg
              2690                2695                2700

Ser Leu Leu Val Val Ser Asp Leu Phe Thr Glu Arg Asn Gln Phe Glu
2705                2710                2715                2720

Leu Met Tyr Val Thr Leu Thr Glu Leu Arg Arg Val His Pro Ser Glu
                  2725                2730                2735

Asp Glu Ile Leu Ala Gln Tyr Leu Val Pro Ala Thr Cys Lys Ala Ala
                  2740                2745                2750

Ala Val Leu Gly Met Asp Lys Ala Val Ala Glu Pro Val Ser Arg Leu
                  2755                2760                2765

Leu Glu Ser Thr Leu Arg Ser Ser His Leu Pro Ser Arg Val Gly Ala
              2770                2775                2780

Leu His Gly Val Leu Tyr Val Leu Glu Cys Asp Leu Leu Asp Asp Thr
2785                2790                2795                2800

Ala Lys Gln Leu Ile Pro Val Ile Ser Asp Tyr Leu Leu Ser Asn Leu
                  2805                2810                2815

Lys Gly Ile Ala His Cys Val Asn Ile His Ser Gln Gln His Val Leu
                  2820                2825                2830

Val Met Cys Ala Thr Ala Phe Tyr Leu Ile Glu Asn Tyr Pro Leu Asp
                  2835                2840                2845

Val Gly Pro Glu Phe Ser Ala Ser Ile Ile Gln Met Cys Gly Val Met
              2850                2855                2860

Leu Ser Gly Ser Glu Glu Ser Thr Pro Ser Ile Ile Tyr His Cys Ala
2865                2870                2875                2880

Leu Arg Gly Leu Glu Arg Leu Leu Leu Ser Glu Gln Leu Ser Arg Leu
                  2885                2890                2895

Asp Ala Glu Ser Leu Val Lys Leu Ser Val Asp Arg Val Asn Val His
                  2900                2905                2910

Ser Pro His Arg Ala Met Ala Ala Leu Gly Leu Met Leu Thr Cys Met
                  2915                2920                2925

Tyr Thr Gly Lys Glu Lys Val Ser Pro Gly Arg Thr Ser Asp Pro Asn
              2930                2935                2940

Pro Ala Ala Pro Asp Ser Glu Ser Val Ile Val Ala Met Glu Arg Val
2945                2950                2955                2960

Ser Val Leu Phe Asp Arg Ile Arg Lys Gly Phe Pro Cys Glu Ala Arg
                  2965                2970                2975

Val Val Ala Arg Ile Leu Pro Gln Phe Leu Asp Asp Phe Phe Pro Pro
                  2980                2985                2990

Gln Asp Ile Met Asn Lys Val Ile Gly Glu Phe Leu Ser Asn Gln Gln
                  2995                3000                3005

Pro Tyr Pro Gln Phe Met Ala Thr Val Val Tyr Lys Val Phe Gln Thr
                  3010                3015                3020
```

```
Leu His Ser Thr Gly Gln Ser Ser Met Val Arg Asp Trp Val Met Leu
3025                3030                3035                3040

Ser Leu Ser Asn Phe Thr Gln Arg Ala Pro Val Ala Met Ala Thr Trp
            3045                3050                3055

Ser Leu Ser Cys Phe Phe Val Ser Ala Ser Thr Ser Pro Trp Val Ala
            3060                3065                3070

Ala Ile Leu Pro His Val Ile Ser Arg Met Gly Lys Leu Glu Gln Val
        3075                3080                3085

Asp Val Asn Leu Phe Cys Leu Val Ala Thr Asp Phe Tyr Arg His Gln
    3090                3095                3100

Ile Glu Glu Leu Asp Arg Arg Ala Phe Gln Ser Val Leu Glu Val
3105                3110                3115                3120

Val Ala Ala Pro Gly Ser Pro Tyr His Arg Leu Leu Thr Cys Leu Arg
            3125                3130                3135

Asn Val His Lys Val Thr Thr Cys
            3140
```

(2) INFORMATION FOR SEQ ID NO:16:

(i) SEQUENCE CHARACTERISTICS:
        (A) LENGTH: 10660 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 936..3384

(xi) SEQUENCE DESCRIPTION: SEQ ID NO:16:

```
CTACTACAGT GGCGGACGTA CAGGACCTGT TCACTGCAG GGGGATCCAA AACAAGCCCC      60

GTGGAGCAAC AGCCAGAGCA ACAGCAGCTG CAAGACATTG TTTCTCTCCC TCTGCCCCCC    120

CTTCCCCACG CAACCCCAGA TCCATTTACA CTTTACAGTT TTACCTCACA AAAACTACTA    180

CAAGCACCAA GCTCCCTGAT GGAAAGGAGC ATCGTGCATC AAGTCACCAG GGTGGTCCAT    240

TCAAGCTGCA GATTTGTTTG TCATCCTTGT ACAGCAATCT CCTCCTCCAC TGCCACTACA    300

GGGAAGTGCA TCACATGTCA GCATACTGGA GCATAGTGAA AGAGTCTATT TTGAAGCTTC    360

AAACTTAGTG CTGCTGCAGA CCAGGAACAA GAGAGAAAGA GTGGATTTCA GCCTGCACGG    420

ATGGTCTTGA ACACAAATG GTTTTTGGTC TAGGCGTTTT ACACTGAGAT TCTCCACTGC    480

CACCCTTTCT ACTCAAGCAA AATCTTCGTG AAAAGATCTG CTGCAAGGAA CTGATAGCTT    540

ATGGTTCTCC ATTGTGATGA AAGCACATGG TACAGTTTTC CAAAGAAATT AGACCATTTT    600

CTTCGTGAGA AAGAAATCGA CGTGCTGTTT TCATAGGGTA TTTCTCACTT CTCTGTGAAA    660

GGAAGAAAGA ACACGCCTGA GCCCAAGAGC CCTCAGGAGC CCTCCAGAGC CTGTGGGAAG    720

TCTCCATGGT GAAGTATAGG CTGAGGCTAC CTGTGAACAG TACGCAGTGA ATGTTCATCC    780

AGAGCTGCTG TTGGCGGATT GTACCCACGG GGAGATGATT CCTCATGAAG AGCCTGGATC    840

CCCTACAGAA ATCAAATGTG ACTTTCCGTT TATCAGACTA AAATCAGAGC CATCCAGACA    900

GTGAAACAGT CACCGTGGAG GGGGGACGGC GAAAA ATG AAA TCC AAC CAA GAG      953
                                  Met Lys Ser Asn Gln Glu
                                   1               5

CGG AGC AAC GAA TGC CTG CCT CCC AAG AAG CGC GAG ATC CCC GCC ACC     1001
Arg Ser Asn Glu Cys Leu Pro Pro Lys Lys Arg Glu Ile Pro Ala Thr
        10                  15                  20
```

```
AGC CGG TCC TCC GAG GAG AAG GCC CCT ACC CTG CCC AGC GAC AAC CAC      1049
Ser Arg Ser Ser Glu Glu Lys Ala Pro Thr Leu Pro Ser Asp Asn His
         25                  30                  35

CGG GTG GAG GGC ACA GCA TGG CTC CCG GGC AAC CCT GGT GGC CGG GGC      1097
Arg Val Glu Gly Thr Ala Trp Leu Pro Gly Asn Pro Gly Gly Arg Gly
 40                  45                  50

CAC GGG GGC GGG AGG CAT GGG CCG GCA GGG ACC TCG GTG GAG CTT GGT      1145
His Gly Gly Gly Arg His Gly Pro Ala Gly Thr Ser Val Glu Leu Gly
 55                  60                  65                  70

TTA CAA CAG GGA ATA GGT TTA CAC AAA GCA TTG TCC ACA GGG CTG GAC      1193
Leu Gln Gln Gly Ile Gly Leu His Lys Ala Leu Ser Thr Gly Leu Asp
             75                  80                  85

TAC TCC CCG CCC AGC GCT CCC AGG TCT GTC CCC GTG GCC ACC ACG CTG      1241
Tyr Ser Pro Pro Ser Ala Pro Arg Ser Val Pro Val Ala Thr Thr Leu
         90                  95                 100

CCT GCC GCG TAC GCC ACC CCG CAG CCA GGG ACC CCG GTG TCC CCC GTG      1289
Pro Ala Ala Tyr Ala Thr Pro Gln Pro Gly Thr Pro Val Ser Pro Val
            105                 110                 115

CAG TAC GCT CAC CTG CCG CAC ACC TTC CAG TTC ATT GGG TCC TCC CAA      1337
Gln Tyr Ala His Leu Pro His Thr Phe Gln Phe Ile Gly Ser Ser Gln
120                 125                 130

TAC AGT GGA ACC TAT GCC AGC TTC ATC CCA TCA CAG CTG ATC CCC CCA      1385
Tyr Ser Gly Thr Tyr Ala Ser Phe Ile Pro Ser Gln Leu Ile Pro Pro
135                 140                 145                 150

ACC GCC AAC CCC GTC ACC AGT GCA GTG GCC TCG GCC GCA GGG GCC ACC      1433
Thr Ala Asn Pro Val Thr Ser Ala Val Ala Ser Ala Ala Gly Ala Thr
                155                 160                 165

ACT CCA TCC CAG CGC TCC CAG CTG GAG GCC TAT TCC ACT CTG CTG GCC      1481
Thr Pro Ser Gln Arg Ser Gln Leu Glu Ala Tyr Ser Thr Leu Leu Ala
            170                 175                 180

AAC ATG GGC AGT CTG AGC CAG ACG CCG GGA CAC AAG GCT GAG CAG CAG      1529
Asn Met Gly Ser Leu Ser Gln Thr Pro Gly His Lys Ala Glu Gln Gln
                185                 190                 195

CAG CAG CAG CAG CAG CAG CAG CAG CAG CAT CAG CAT CAG CAG CAG          1577
Gln Gln Gln Gln Gln Gln Gln Gln Gln His Gln His Gln Gln Gln
200                 205                 210

CAG CAG CAG CAG CAG CAG CAG CAG CAG CAG CAG CAG CAC CTC AGC AGG      1625
Gln Gln Gln Gln Gln Gln Gln Gln Gln Gln Gln Gln His Leu Ser Arg
215                 220                 225                 230

GCT CCG GGG CTC ATC ACC CCG GGG TCC CCC CCA CCA GCC CAG CAG AAC      1673
Ala Pro Gly Leu Ile Thr Pro Gly Ser Pro Pro Pro Ala Gln Gln Asn
                235                 240                 245

CAG TAC GTC CAC ATT TCC AGT TCT CCG CAG AAC ACC GGC CGC ACC GCC      1721
Gln Tyr Val His Ile Ser Ser Ser Pro Gln Asn Thr Gly Arg Thr Ala
            250                 255                 260

TCT CCT CCG GCC ATC CCC GTC CAC CTC CAC CCC CAC CAG ACG ATG ATC      1769
Ser Pro Pro Ala Ile Pro Val His Leu His Pro His Gln Thr Met Ile
                265                 270                 275

CCA CAC ACG CTC ACC CTG GGG CCC CCC TCC CAG GTC GTC ATG CAA TAC      1817
Pro His Thr Leu Thr Leu Gly Pro Pro Ser Gln Val Val Met Gln Tyr
                280                 285                 290

GCC GAC TCC GGC AGC CAC TTT GTC CCT CGG GAG GCC ACC AAG AAA GCT      1865
Ala Asp Ser Gly Ser His Phe Val Pro Arg Glu Ala Thr Lys Lys Ala
295                 300                 305                 310

GAG AGC AGC CGG CTG CAG CAG GCC ATC CAG GCC AAG GAG GTC CTG AAC      1913
Glu Ser Ser Arg Leu Gln Gln Ala Ile Gln Ala Lys Glu Val Leu Asn
            315                 320                 325

GGT GAG ATG GAG AAG AGC CGG CGG TAC GGG GCC CCG TCC TCA GCC GAC      1961
Gly Glu Met Glu Lys Ser Arg Arg Tyr Gly Ala Pro Ser Ser Ala Asp
```

-continued

```
              330                     335                     340
CTG GGC CTG GGC AAG GCA GGC GGC AAG TCG GTT CCT CAC CCG TAC GAG    2009
Leu Gly Leu Gly Lys Ala Gly Gly Lys Ser Val Pro His Pro Tyr Glu
            345                     350                     355

TCC AGG CAC GTG GTG GTC CAC CCG AGC CCC TCA GAC TAC AGC AGT CGT    2057
Ser Arg His Val Val Val His Pro Ser Pro Ser Asp Tyr Ser Ser Arg
        360                     365                     370

GAT CCT TCG GGG GTC CGG GCC TCT GTG ATG GTC CTG CCC AAC AGC AAC    2105
Asp Pro Ser Gly Val Arg Ala Ser Val Met Val Leu Pro Asn Ser Asn
375                     380                     385                     390

ACG CCC GCA GCT GAC CTG GAG GTG CAA CAG GCC ACT CAT CGT GAA GCC    2153
Thr Pro Ala Ala Asp Leu Glu Val Gln Gln Ala Thr His Arg Glu Ala
                395                     400                     405

TCC CCT TCT ACC CTC AAC GAC AAA AGT GGC CTG CAT TTA GGG AAG CCT    2201
Ser Pro Ser Thr Leu Asn Asp Lys Ser Gly Leu His Leu Gly Lys Pro
            410                     415                     420

GGC CAC CGG TCC TAC GCG CTC TCA CCC CAC ACG GTC ATT CAG ACC ACA    2249
Gly His Arg Ser Tyr Ala Leu Ser Pro His Thr Val Ile Gln Thr Thr
        425                     430                     435

CAC AGT GCT TCA GAG CCA CTC CCG GTG GGA CTG CCA GCC ACG GCC TTC    2297
His Ser Ala Ser Glu Pro Leu Pro Val Gly Leu Pro Ala Thr Ala Phe
    440                     445                     450

TAC GCA GGG ACT CAA CCC CCT GTC ATC GGC TAC CTG AGC GGC CAG CAG    2345
Tyr Ala Gly Thr Gln Pro Pro Val Ile Gly Tyr Leu Ser Gly Gln Gln
455                     460                     465                     470

CAA GCA ATC ACC TAC GCC GGC AGC CTG CCC CAG CAC CTG GTG ATC CCC    2393
Gln Ala Ile Thr Tyr Ala Gly Ser Leu Pro Gln His Leu Val Ile Pro
                475                     480                     485

GGC ACA CAG CCC CTG CTC ATC CCG GTC GGC AGC ACT GAC ATG GAA GCG    2441
Gly Thr Gln Pro Leu Leu Ile Pro Val Gly Ser Thr Asp Met Glu Ala
            490                     495                     500

TCG GGG GCA GCC CCG GCC ATA GTC ACG TCA TCC CCC CAG TTT GCT GCA    2489
Ser Gly Ala Ala Pro Ala Ile Val Thr Ser Ser Pro Gln Phe Ala Ala
        505                     510                     515

GTG CCT CAC ACG TTC GTC ACC ACC GCC CTT CCC AAG AGC GAG AAC TTC    2537
Val Pro His Thr Phe Val Thr Thr Ala Leu Pro Lys Ser Glu Asn Phe
    520                     525                     530

AAC CCT GAG GCC CTG GTC ACC CAG GCC GCC TAC CCA GCC ATG GTG CAG    2585
Asn Pro Glu Ala Leu Val Thr Gln Ala Ala Tyr Pro Ala Met Val Gln
535                     540                     545                     550

GCC CAG ATC CAC CTG CCT GTG GTG CAG TCC GTG GCC TCC CCG GCG GCG    2633
Ala Gln Ile His Leu Pro Val Val Gln Ser Val Ala Ser Pro Ala Ala
                555                     560                     565

GCT CCC CCT ACG CTG CCT CCC TAC TTC ATG AAA GGC TCC ATC ATC CAG    2681
Ala Pro Pro Thr Leu Pro Pro Tyr Phe Met Lys Gly Ser Ile Ile Gln
            570                     575                     580

TTG GCC AAC GGG GAG CTA AAG AAG GTG GAA GAC TTA AAA ACA GAA GAT    2729
Leu Ala Asn Gly Glu Leu Lys Lys Val Glu Asp Leu Lys Thr Glu Asp
        585                     590                     595

TTC ATC CAG AGT GCA GAG ATA AGC AAC GAC CTG AAG ATC GAC TCC AGC    2777
Phe Ile Gln Ser Ala Glu Ile Ser Asn Asp Leu Lys Ile Asp Ser Ser
    600                     605                     610

ACC GTA GAG AGG ATT GAA GAC AGC CAT AGC CCG GGC GTG GCC GTG ATA    2825
Thr Val Glu Arg Ile Glu Asp Ser His Ser Pro Gly Val Ala Val Ile
615                     620                     625                     630

CAG TTC GCC GTC GGG GAG CAC CGA GCC CAG GTC AGC GTT GAA GTT TTG    2873
Gln Phe Ala Val Gly Glu His Arg Ala Gln Val Ser Val Glu Val Leu
                635                     640                     645

GTA GAG TAT CCT TTT TTT GTG TTT GGA CAG GGC TGG TCA TCC TGC TGT    2921
```

```
                                                                                    -continued Val Glu Tyr Pro Phe Phe Val Phe Gly Gln Gly Trp Ser Ser Cys Cys
            650                 655                 660

CCG GAG AGA ACC AGC CAG CTC TTT GAT TTG CCG TGT TCC AAA CTC TCA      2969
Pro Glu Arg Thr Ser Gln Leu Phe Asp Leu Pro Cys Ser Lys Leu Ser
            665                 670                 675

GTT GGG GAT GTC TGC ATC TCG CTT ACC CTC AAG AAC CTG AAG AAC GGC      3017
Val Gly Asp Val Cys Ile Ser Leu Thr Leu Lys Asn Leu Lys Asn Gly
680                 685                 690

TCT GTT AAA AAG GGC CAG CCC GTG GAT CCC GCC AGC GTC CTG CTG AAG      3065
Ser Val Lys Lys Gly Gln Pro Val Asp Pro Ala Ser Val Leu Leu Lys
695                 700                 705                 710

CAC TCA AAG GCC GAC GGC CTG GCG GGC AGC AGA CAC AGG TAT GCC GAG      3113
His Ser Lys Ala Asp Gly Leu Ala Gly Ser Arg His Arg Tyr Ala Glu
                715                 720                 725

CAG GAA AAC GGA ATC AAC CAG GGG AGT GCC CAG ATG CTC TCT GAG AAT      3161
Gln Glu Asn Gly Ile Asn Gln Gly Ser Ala Gln Met Leu Ser Glu Asn
            730                 735                 740

GGC GAA CTG AAG TTT CCA GAG AAA ATG GGA TTG CCT GCA GCG CCC TTC      3209
Gly Glu Leu Lys Phe Pro Glu Lys Met Gly Leu Pro Ala Ala Pro Phe
            745                 750                 755

CTC ACC AAA ATA GAA CCC AGC AAG CCC GCG GCA ACG AGG AAG AGG AGG      3257
Leu Thr Lys Ile Glu Pro Ser Lys Pro Ala Ala Thr Arg Lys Arg Arg
        760                 765                 770

TGG TCG GCG CCA GAG AGC CGC AAA CTG GAG AAG TCA GAA GAC GAA CCA      3305
Trp Ser Ala Pro Glu Ser Arg Lys Leu Glu Lys Ser Glu Asp Glu Pro
775                 780                 785                 790

CCT TTG ACT CTT CCT AAG CCT TCT CTA ATT CCT CAG GAG GTT AAG ATT      3353
Pro Leu Thr Leu Pro Lys Pro Ser Leu Ile Pro Gln Glu Val Lys Ile
                795                 800                 805

TGC ATT GAA GGC CGG TCT AAT GTA GGC AAG T AGAGGCAGCG TGGGGAAAG       3404
Cys Ile Glu Gly Arg Ser Asn Val Gly Lys
            810                 815

GAAACGTGGC TCTCCCTTAT CATTTGTATC CAGATTACTG TACTGTAGGC TAAAATAACA    3464

CAGTATTTAC ATGTTATCTT CTTAATTTTA GGTTTCTGTT CTAACCTTGT CATTAGAGTT    3524

ACAGCAGGTG TGTCGCAGGA GACTGGTGCA TATGCTTTTT CCACGAGTGT CTGTCAGTGA    3584

GCGGGCGGGA GGAAGGGCAC AGCAGGAGCG GTCAGGGCTC CAGGCATCCC CGGGGAAGAA    3644

AGGAACGGGG CTTCACAGTG CCTGCCTTCT CTAGCGGCAC AGAAGCAGCC GGGGGCGCTG    3704

ACTCCCGCTA GTGTCAGGAG AAAAGTCCCG TGGGAAGAGT CCTGCAGGGG TGCAGGGTTG    3764

CACGCATGTG GGGGTGCACA GGCGCTGTGG CGGCGAGTGA GGGTCTCTTT TTCTCTGCCT    3824

CCCTCTGCCT CACTCTCTTG CTATCGGCAT GGGCCGGGGG GGTTCAGAGC AGTGTCCTCC    3884

TGGGGTTCCC ACGTGCAAAA TCAACATCAG GAACCCAGCT TCAGGGCATC GCGGAGACGC    3944

GTCAGATGGC AGATTTGGAA AGTTAACCAT TTAAAAGAAC ATTTTTCTCT CCAACATATT    4004

TTACAATAAA AGCAACTTTT AATTGTATAG ATATATATTT CCCCCTATGG GGCCTGACTG    4064

CACTGATATA TATTTTTTTT AAAGAGCAAC TGCCACATGC GGGATTTCAT TTCTGCTTTT    4124

TACTAGTGCA GCGATGTCAC CAGGGTGTTG TGGTGGACAG GGAAGCCCCT GCTGTCATGG    4184

CCCCACATGG GGTAAGGGGG GTTGGGGGTG GGGAGAGGG AGAGAGCGAA CACCCACGCT     4244

GGTTTCTGTG CAGTGTTAGG AAAACCAATC AGGTTATTGC ATTGACTTCA CTCCCAAGAG    4304

GTAGATGCAA ACTGCCCTTC AGTGAGAGCA ACAGAAGCTC TTCACGTTGA GTTTGCGAAA    4364

TCTTTTTGTC TTTGAACTCT AGTACTGTTT ATAGTTCATG ACTATGGACA ACTCGGGTGC    4424

CACTTTTTTT TTTTTCAGAT TCCAGTGTGA CATGAGGAAT TAGATTTTGA AGATGAGCAT    4484
```

```
ATATTACTAT CTTTAAGCAT TTAAAAATAC TGTTCACACT TTATTACCAA GCATCTTGGT    4544

CTCTCATTCA ACAAGTACTG TATCTCACTT TAAACTCTTT GGGGAAAAAA CAAAAACAAA    4604

AAAAACTAAG TTGCTTTCTT TTTTTCAACA CTGTAACTAC ATTTCAGCTC TGCAGAATTG    4664

CTGAAGAGCA AGATATTGAA AGTTTCAATG TGGTTTAAAG GGATGAATGT GAATTATGAA    4724

CTAGTATGTG ACAATAAATG ACCACCAAGT ACTACCTGAC GGGAGGCACT TTTCACTTTG    4784

ATGTCTGAGA ATCAGTTCAA GGCATATGCA GAGTTGGCAG AGAAACTGAG AGAAAAGGGA    4844

TGGAGAAGAG AATACTCATT TTTGTCCAGT GTTTTTCTTT TTAAGATGAA CTTTTAAAGA    4904

ACCTTGCGAT TTGCACATAT TGAGTTTATA ACTTGTGTGA TATTCCTGCA GTTTTTATCC    4964

AATAACATTG TGGGAAAGGT TTGGGGGACT GAACGAGCAT AAATAAATGT AGCAAAATTT    5024

CTTTCTAACC TGCCTAAACT CTAGGCCATT TTATAAGGTT ATGTTCCTTT GAAAATTCAT    5084

TTTGGTCTTT TTACCACATC TGTCACAAAA AGCCAGGTCT TAGCGGGCTC TTAGAAACTC    5144

TGAGAATTTT CTTCAGATTC ATTGAGAGAG TTTTCCATAA AGACATTTAT ATATGTGAGC    5204

AAGATTTTTT TTAAACAATT ACTTTATTAT TGTTGTTATT AATGTTATTT TCAGAATGGC    5264

TTTTTTTTTC TATTCAAAAT CAAATCGAGA TTTAATGTTT GGTACAAACC CAGAAAGGGT    5324

ATTTCATAGT TTTTAAACCT TTCATTCCCA GAGATCCGAA ATATCATTTG TGGGTTTTGA    5384

ATGCATCTTT AAAGTGCTTT AAAAAAAAGT TTTATAAGTA GGGAGAAATT TTTAAATATT    5444

CTTACTTGGA TGGCTGCAAC TAAACTGAAC AAATACCTGA CTTTTCTTTT ACCCCATTGA    5504

AAATAGTACT TTCTTCGTTT CACAAATTAA AAAAAAAATC TGGTATCAAC CCACATTTTG    5564

GCTGTCTAGT ATTCATTTAC ATTTAGGGTT CACCAGGACT AATGATTTTT ATAAACCGTT    5624

TTCTGGGGTG TACCAAAAAC ATTTGAATAG GTTTAGAATA GCTAGAATAG TTCCTTGACT    5684

TTCCTCGAAT TTCATTACCC TCTCAGCATG CTTGCAGAGA GCTGGGTGGG CTCATTCTTG    5744

CAGTCATACT GCTTATTTAG TGCTGTATTT TTTAAACGTT TCTGTTCAGA GAACTTGCTT    5804

AATCTTCCAT ATATTCTGCT CAGGGCACTT GCAATTATTA GGTTTTGTTT TTCTTTTTGT    5864

TTTTTAGCCT TTGATGGTAA GAGGAATACG GGCTGCCACA TAGACTTTGT TCTCATTAAT    5924

ATCACTATTT ACAACTCATG TGGACTCAGA AAAACACACA CCACCTTTTG GCTTACTTCG    5984

AGTATTGAAT TGACTGGATC CACTAAACCA ACACTAAGAT GGGAAAACAC ACATGGTTTG    6044

GAGCAATAGG AACATCATCA TAATTTTTGT GGTTCTATTT CAGGTATAGG AATTATAAAA    6104

TAATTGGTTC TTTCTAAACA CTTGTCCCAT TTCATTCTCT TGCTTTTTTA GCATGTGCAA    6164

TACTTTCTGT GCCAATAGAG TCTGACCAGT GTGCTATATA GTTAAAGCTC ATTCCCTTTT    6224

GGCTTTTTCC TTGTTTGGTT GATCTTCCCC ATTCTGGCCA GAGCAGGGCT GGAGGGAAGG    6284

AGCCAGGAGG GAGAGAGCCT CCCACCTTTC CCCTGCTGCG GATGCTGAGT GCTGGGCGG    6344

GGAGCCTTCA GGAGCCCCGT GCGTCTGCCG CCACGTTGCA GAAAGAGCCA GCCAAGGAGA    6404

CCCGGGGGAG GAACCGCAGT GTCCCCTGTC ACCACACGGA ATAGTGAATG TGGAGTGTGG    6464

AGAGGAAGGA GGCAGATTCA TTTCTAAGAC GCACTCTGGA GCCATGTAGC CTGGAGTCAA    6524

CCCATTTTCC ACGGTCTTTT CTGCAAGTGG GCAGGCCCCT CCTCGGGGTC TGTGTCCTTG    6584

AGACTTGGAG CCCTGCCTCT GAGCCTGGAC GGGAAGTGTG GCCTGTTGTG TGTGTGCGTT    6644

CTGAGCGTGT TGGCCAGTGG CTGTGGAGGG GACCACCTGC CACCCACGGT CACCACTCCC    6704

TTGTGGCAGC TTTCTCTTCA AATAGGAAGA ACGCACAGAG GGCAGGAGCC TCCTGTTTGC    6764

AGACGTTGGC GGGCCCCGAG GCTCCCAGAG CAGCCTCTGT CACCGCTTCT GTGTAGCAAA    6824

CATTAACGAT GACAGGGGTA GAAATTCTTC GGTGCCGTTC AGCTTACAAG GATCAGCCAT    6884
```

```
GTGCCTCTGT ACTATGTCCA CTTTGCAATA TTTACCGACA GCCGTCTTTT GTTCTTTCTT      6944

TCCTGTTTTC CATTTTTAAA CTAGTAACAG CAGGCCTTTT GCGTTACAA TGGAACACAA       7004

TCACCAAGAA ATTAGTCAGG GCGAAAAGAA AAAAATAATA CTATTAATAA GAAACCAACA      7064

AACAAGAACC TCTCTTTCTA GGGATTTCTA AATATATAAA ATGACTGTTC CTTAGAATGT      7124

TTAACTTAAG AATTATTTCA GTTTGTCTGG GCCACACTGG GGCAGAGGGG GGAGGGAGGG      7184

ATACAGAGAT GGATGCCACT TACCTCAGAT CTTTTAAAGT GGAAATCCAA ATTGAATTTT      7244

CATTTGGACT TTCAGGATAA TTTTCTATGT TGGTCAACTT TTCGTTTTCC CTAACTCACC      7304

CAGTTTAGTT TGGGATGATT TGATTTCTGT TGTTGTTGAT CCCATTTCTA ACTTGGAATT      7364

GTGAGCCTCT ATGTTTTCTG TTAGGTGAGT GTGTTGGGTT TTTTCCCCCC ACCAGGAAGT      7424

GGCAGCATCC CTCCTTCTCC CCTAAAGGGA CTCTGCGGAA CCTTTCACAC CTCTTTCTCA      7484

GGGACGGGGC AGGTGTGTGT GTGGTACACT GACGTGTCCA GAAGCAGCAC TTTGACTGCT      7544

CTGGAGTAGG GTTGTACAAT TTCAAGGAAT GTTTGGATTT CCTGCATCTT GTGGATTACT      7604

CCTTAGATAC CGCATAGATT GCAATATAAT GCTGCATGTT CAAGATGAAC AGTAGCTCCT      7664

AGTAATCATA AAATCCACTC TTTGCACAGT TGATCTTTA CTGAAATATG TTGCCAAAAT       7724

TTATTTTTGT TGTTGTAGCT CTGGATTTTG TTTTGTTTTG TTTTTTAAGG AAACGATTGA      7784

CAATACCCTT TAACATCTGT GACTACTAAG GAAACCTATT TCTTTCATAG AGAGAAAAAT      7844

CTCCAATGCT TTTGAAGACA CTAATACCGT GCTATTTCAG ATATGGGTGA GGAAGCAGAG      7904

CTCTCGGTAC CGAAGGCCGG GCTTCTTGAG CTGTGTTGGT TGTCATGGCT ACTGTTTCAT      7964

GAACCACAAG CAGCTCAACA GACTGGTCTG TTGCCTTCTG AAACCCTTTG CACTTCAATT      8024

TGCACCAGGT GAAAACAGGG CCAGCAGACT CCATGGCCCA ATTCGGTTTC TTCGGTGGTG      8084

ATGTGAAAGG AGAGAATTAC ACTTTTTTTT TTTTTAAGTG GCGTGGAGGC CTTTGCTTCC      8144

ACATTTGTTT TTAACCCAGA ATTTCTGAAA TAGAGAATTT AAGAACACAT CAAGTAATAA      8204

ATATACAGAG AATATACTTT TTTATAAAGC ACATGCATCT GCTATTGTGT TGGGTTGGTT      8264

TCCTCTCTTT TCCACGGACA GTGTTGTGTT CTGGCATAG GGAAACTCCA AACAACTTGC       8324

ACACCTCTAC TCCGGAGCTG AGATTTCTTT TACATAGATG ACCTCGCTTC AAATACGTTA      8384

CCTTACTGAT GATAGGATCT TTTCTTGTAG CACTATACCT TGTGGGAATT TTTTTTTAAA      8444

TGTACACCTG ATTTGAGAAG CTGAAGAAAA CAAAATTTTG AAGCACTCAC TTTGAGGAGT      8504

ACAGGTAATG TTTTAAAAAA TTGCACAAAA GAAAAATGAA TGTCGAAATG ATTCATTCAG      8564

TGTTTGAAAG ATATGGCTCT GTTGAAACAA TGAGTTTCAT ACTTTGTTTG TAAAAAAAAA      8624

AAGCAGAGAA GGGTTGAAAG TTACATGTTT TTTTGTATAT AGAAATTTGT CATGTCTAAA     8684

TGATCAGATT TGTATGGTTA TGGCCTGGAA GAATTACTAC GTAAAAGGCT CTTAAACTAT      8744

ACCTATGCTT ATTGTTATTT TTGTTACATA TAGCCCTCGT CTGAGGGAGG GGAACTCGGT      8804

ATTCTGCGAT TTGAGAATAC TGTTCATTCC TATGCTGAAA GTACTTCTCT GAGCTCCCTT      8864

CTTAGTCTAA ACTCTTAAGC CATTGCAACT TCTTTTTCTT CAGAGATGAT GTTTGACATT      8924

TTCAGCACTT CCTGTTCCTA TAAACCCAAA GAATATAATC TTGAACACGA AGTGTTTGTA      8984

ACAAGGGATC CAGGCTACCA ATCAAACAGG ACTCATTATG GGACAAAAA AAAAAAAAT       9044

TATTTCACCT TCTTTCCCCC CACACCTCAT TTAAATGGGG GGAGTAAAAA CATGATTTCA     9104

ATGTAAATGC CTCATTTTAT TTTAGTTTTA TTTTGATTTT TATTTAATAT AAAGAGGCCA     9164

GAATAAATAC GGAGCATCTT CTCAGAATAG TATTCCTGTC CAAAAATCAA GCCGGACAGT     9224
```

-continued

```
GGAAACTGGA CAGCTGTGGG GATATTAAGC ACCCCCACTT ACAATTCTTA AATTCAGAAT    9284

CTCGTCCCCT CCCTTCTCGT TGAAGGCAAC TGTTCTGGTA GCTAACTTTC TCCTGTGTAA    9344

TGGCGGGAGG GAACACCGGC TTCAGTTTTT CATGTCCCCA TGACTTGCAT ACAAATGGTT    9404

CAACTGTATT AAAATTAAGT GCATTTGGCC AATAGGTAGT ATCTATACAA TAACAACAAT    9464

CTCTAAGAAT TTCCATAACT TTTCTTATCT GAAAGGACTC AAGTCTTCCA CTGCAGATAC    9524

ATTGGAGGCT TCACCCACGT TTTCTTTCCC TTTAGTTTGT TTGCTGTCTG GATGGCCAAT    9584

GAGCCTGTCT CCTTTTCTGT GGCCAATCTG AAGGCCTTCG TTGGAAGTGT TGTTCACAGT    9644

AATCCTTACC AAGATAACAT ACTGTCCTCC AGAATACCAA GTATTAGGTG ACACTAGCTC    9704

AAGCTGTTGT CTTCAGAGCA GTTACCAAGA AGCTCGGTGC ACAGGTTTTC TCTGGTTCTT    9764

ACAGGAACCA CCTACTCTTT CAGTTTTCTG GCCCAGGAGT GGGGTAAATC CTTTAGTTAG    9824

TGCATTTGAA CTTGGTACCT GTGCATTCAG TTCTGTGAAT ACTGCCCTTT TTGGCGGGGT    9884

TTCCTCATCT CCCCAGCCTG AACTGCTCAA CTCTAAACCC AAATTAGTGT CAGCCGAAAG    9944

GAGGTTTCAA GATAGTCCTG TCAGTATTTG TGGTGACCTT CAGATTAGAC AGTCTTCATT   10004

TCCAGCCAGT GGAGTCCTGG CTCCAGAGCC ATCTCTGAGA CTCCGTACTA CTGGATGTTT   10064

TAATATCAGA TCATTACCCA CCATATGCCT CCCACAGGCC AAGGGAAAAC AGACACCAGA   10124

ACTTGGGTTG AGGGCACTAC CAGACTGACA TGGCCAGTAC AGAGGAGAAC TAGGGAAGGA   10184

ATGATGTTTT GCACCTTATT GAAAAGAAAA TTTTAAGTGC ATACATAATA GTTAAGAGCT   10244

TTTATTGTGA CAGGAGAACT TTTTTCCATA TGCGTGCATA CTCTCTGTAA TTCCAGTGTA   10304

AAATATTGTA CTTGCACTAG CTTTTTTAAA CAAATATTAA AAAATGGAAG AATTCATATT   10364

CTATTTTCTA ATCGTGGTGT GTCTATTTGT AGGATACACT CGAGTCTGTT TATTGAATTT   10424

TATGGTCCCT TTCTTTGATG GTGCTTGCAG GTTTTCTAGG TAGAAATTAT TTCATTATTA   10484

TAATAAAACA ATGTTTGATT CAAAATTTGA ACAAAATTGT TTTAAATAAA TTGTCTGTAT   10544

ACCAGTACAA GTTTATTGTT TCAGTATACT CGTACTAATA AATAACAGT GCCAATTGCA    10604

AAAAAAAAAA AAAAAAAAAA AAAAAAAAAA AAAAAAAAAA AAAAAAAAA AAAAAA        10660
```

(2) INFORMATION FOR SEQ ID NO:17:

(i) SEQUENCE CHARACTERISTICS:
        (A) LENGTH: 816 amino acids
        (B) TYPE: amino acid
        (D) TOPOLOGY: linear (ii) MOLECULE TYPE: protein (xi) SEQUENCE DESCRIPTION: SEQ ID NO:17:

```
Met Lys Ser Asn Gln Glu Arg Ser Asn Glu Cys Leu Pro Pro Lys Lys
  1               5                  10                  15

Arg Glu Ile Pro Ala Thr Ser Arg Ser Ser Glu Glu Lys Ala Pro Thr
             20                  25                  30

Leu Pro Ser Asp Asn His Arg Val Glu Gly Thr Ala Trp Leu Pro Gly
         35                  40                  45

Asn Pro Gly Gly Arg Gly His Gly Gly Gly Arg His Gly Pro Ala Gly
     50                  55                  60

Thr Ser Val Glu Leu Gly Leu Gln Gln Gly Ile Gly Leu His Lys Ala
 65                  70                  75                  80

Leu Ser Thr Gly Leu Asp Tyr Ser Pro Pro Ser Ala Pro Arg Ser Val
                 85                  90                  95

Pro Val Ala Thr Thr Leu Pro Ala Ala Tyr Ala Thr Pro Gln Pro Gly
```

```
                  100                 105                 110
Thr Pro Val Ser Pro Val Gln Tyr Ala His Leu Pro His Thr Phe Gln
            115                 120                 125
Phe Ile Gly Ser Ser Gln Tyr Ser Gly Thr Tyr Ala Ser Phe Ile Pro
        130                 135                 140
Ser Gln Leu Ile Pro Pro Thr Ala Asn Pro Val Thr Ser Ala Val Ala
145                 150                 155                 160
Ser Ala Ala Gly Ala Thr Thr Pro Ser Gln Arg Ser Gln Leu Glu Ala
                165                 170                 175
Tyr Ser Thr Leu Leu Ala Asn Met Gly Ser Leu Ser Gln Thr Pro Gly
            180                 185                 190
His Lys Ala Glu Gln Gln Gln Gln Gln Gln Gln Gln Gln Gln Gln Gln
        195                 200                 205
His Gln His Gln Gln Gln Gln Gln Gln Gln Gln Gln Gln Gln Gln Gln
        210                 215                 220
Gln Gln His Leu Ser Arg Ala Pro Gly Leu Ile Thr Pro Gly Ser Pro
225                 230                 235                 240
Pro Pro Ala Gln Gln Asn Gln Tyr Val His Ile Ser Ser Ser Pro Gln
                245                 250                 255
Asn Thr Gly Arg Thr Ala Ser Pro Pro Ala Ile Pro Val His Leu His
            260                 265                 270
Pro His Gln Thr Met Ile Pro His Thr Leu Thr Leu Gly Pro Pro Ser
        275                 280                 285
Gln Val Val Met Gln Tyr Ala Asp Ser Gly Ser His Phe Val Pro Arg
        290                 295                 300
Glu Ala Thr Lys Lys Ala Glu Ser Ser Arg Leu Gln Gln Ala Ile Gln
305                 310                 315                 320
Ala Lys Glu Val Leu Asn Gly Glu Met Glu Lys Ser Arg Arg Tyr Gly
                325                 330                 335
Ala Pro Ser Ser Ala Asp Leu Gly Leu Gly Lys Ala Gly Gly Lys Ser
            340                 345                 350
Val Pro His Pro Tyr Glu Ser Arg His Val Val His Pro Ser Pro
        355                 360                 365
Ser Asp Tyr Ser Ser Arg Asp Pro Ser Gly Val Arg Ala Ser Val Met
370                 375                 380
Val Leu Pro Asn Ser Asn Thr Pro Ala Ala Asp Leu Glu Val Gln Gln
385                 390                 395                 400
Ala Thr His Arg Glu Ala Ser Pro Ser Thr Leu Asn Asp Lys Ser Gly
                405                 410                 415
Leu His Leu Gly Lys Pro Gly His Arg Ser Tyr Ala Leu Ser Pro His
            420                 425                 430
Thr Val Ile Gln Thr Thr His Ser Ala Ser Glu Pro Leu Pro Val Gly
        435                 440                 445
Leu Pro Ala Thr Ala Phe Tyr Ala Gly Thr Gln Pro Pro Val Ile Gly
    450                 455                 460
Tyr Leu Ser Gly Gln Gln Ala Ile Thr Tyr Ala Gly Ser Leu Pro
465                 470                 475                 480
Gln His Leu Val Ile Pro Gly Thr Gln Pro Leu Leu Ile Pro Val Gly
                485                 490                 495
Ser Thr Asp Met Glu Ala Ser Gly Ala Ala Pro Ala Ile Val Thr Ser
            500                 505                 510
Ser Pro Gln Phe Ala Ala Val Pro His Thr Phe Val Thr Thr Ala Leu
        515                 520                 525
```

```
Pro Lys Ser Glu Asn Phe Asn Pro Glu Ala Leu Val Thr Gln Ala Ala
    530                 535                 540

Tyr Pro Ala Met Val Gln Ala Gln Ile His Leu Pro Val Val Gln Ser
545                 550                 555                 560

Val Ala Ser Pro Ala Ala Pro Pro Thr Leu Pro Pro Tyr Phe Met
                565                 570                 575

Lys Gly Ser Ile Ile Gln Leu Ala Asn Gly Glu Leu Lys Lys Val Glu
                580                 585                 590

Asp Leu Lys Thr Glu Asp Phe Ile Gln Ser Ala Glu Ile Ser Asn Asp
                595                 600                 605

Leu Lys Ile Asp Ser Ser Thr Val Glu Arg Ile Glu Asp Ser His Ser
    610                 615                 620

Pro Gly Val Ala Val Ile Gln Phe Ala Val Gly Glu His Arg Ala Gln
625                 630                 635                 640

Val Ser Val Glu Val Leu Val Glu Tyr Pro Phe Phe Val Phe Gly Gln
                645                 650                 655

Gly Trp Ser Ser Cys Cys Pro Glu Arg Thr Ser Gln Leu Phe Asp Leu
                660                 665                 670

Pro Cys Ser Lys Leu Ser Val Gly Asp Val Cys Ile Ser Leu Thr Leu
    675                 680                 685

Lys Asn Leu Lys Asn Gly Ser Val Lys Lys Gly Gln Pro Val Asp Pro
    690                 695                 700

Ala Ser Val Leu Leu Lys His Ser Lys Ala Asp Gly Leu Ala Gly Ser
705                 710                 715                 720

Arg His Arg Tyr Ala Glu Gln Glu Asn Gly Ile Asn Gln Gly Ser Ala
                725                 730                 735

Gln Met Leu Ser Glu Asn Gly Glu Leu Lys Phe Pro Glu Lys Met Gly
                740                 745                 750

Leu Pro Ala Ala Pro Phe Leu Thr Lys Ile Glu Pro Ser Lys Pro Ala
                755                 760                 765

Ala Thr Arg Lys Arg Arg Trp Ser Ala Pro Glu Ser Arg Lys Leu Glu
                770                 775                 780

Lys Ser Glu Asp Glu Pro Pro Leu Thr Leu Pro Lys Pro Ser Leu Ile
785                 790                 795                 800

Pro Gln Glu Val Lys Ile Cys Ile Glu Gly Arg Ser Asn Val Gly Lys
                805                 810                 815

(2) INFORMATION FOR SEQ ID NO:18:

(i) SEQUENCE CHARACTERISTICS:
        (A) LENGTH: 4481 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 163..4099

(xi) SEQUENCE DESCRIPTION: SEQ ID NO:18:

ACCCCCGAGA AAGCAACCCA GCGCGCCGCC CGCTCCTCAC GTGTCCCTCC CGGCCCCGGG        60

GCCACCTCAC GTTCTGCTTC CGTCTGACCC CTCCGACTTC CGGTAAAGAG TCCCTATCCG      120

CACCTCCGCT CCCACCCGGC GCCTCGGCGC GCCCGCCCTC CG ATG CGC TCA GCG        174
                                                Met Arg Ser Ala
                                                  1
```

| | | | | | | | | | | | | | | | |
|---|---|---|---|---|---|---|---|---|---|---|---|---|---|---|---|
| GCC | GCA | GCT | CCT | CGG | AGT | CCC | GCG | GTG | GCC | ACC | GAG | TCT | CGC | CGC | TTC | 222 |
| Ala | Ala | Ala | Pro | Arg | Ser | Pro | Ala | Val | Ala | Thr | Glu | Ser | Arg | Arg | Phe |
| 5 | | | | 10 | | | | | 15 | | | | | 20 | |

| | | | | | | | | | | | | | | |
|---|---|---|---|---|---|---|---|---|---|---|---|---|---|---|
| GCC GCA GCC AGG TGG CCC GGG TGG CGC TCG CTC CAG CGG CCG GCG CGG | 270 |
| Ala Ala Ala Arg Trp Pro Gly Trp Arg Ser Leu Gln Arg Pro Ala Arg |
| 25 30 35 |

| CGG AGC GGG CGG GGC GGC GGT GGC GCG GCC CCG GGA CCG TAT CCC TCC | 318 |
|---|---|
| Arg Ser Gly Arg Gly Gly Gly Gly Ala Ala Pro Gly Pro Tyr Pro Ser |
| 40 45 50 |

| GCC GCC CCT CCC CCG CCC GGC CCC GGC CCC CCT CCC TCC CGG CAG AGC | 366 |
|---|---|
| Ala Ala Pro Pro Pro Pro Gly Pro Gly Pro Pro Pro Ser Arg Gln Ser |
| 55 60 65 |

| TCG CCT CCC TCC GCC TCA GAC TGT TTT GGT AGC AAC GGC AAC GGC GGC | 414 |
|---|---|
| Ser Pro Pro Ser Ala Ser Asp Cys Phe Gly Ser Asn Gly Asn Gly Gly |
| 70 75 80 |

| GGC GCG TTT CGG CCC GGC TCC CGG CGG CTC CTT GGT CTC GGC GGG CCT | 462 |
|---|---|
| Gly Ala Phe Arg Pro Gly Ser Arg Arg Leu Leu Gly Leu Gly Gly Pro |
| 85 90 95 100 |

| CCC CGC CCC TTC GTC GTC GTC CTT CTC CCC CTC GCC AGC CCG GGC GCC | 510 |
|---|---|
| Pro Arg Pro Phe Val Val Val Leu Leu Pro Leu Ala Ser Pro Gly Ala |
| 105 110 115 |

| CCT CCG GCC GCG CCA ACC CGC GCC TCC CCG CTC GGC GCC CGT GCG TCC | 558 |
|---|---|
| Pro Pro Ala Ala Pro Thr Arg Ala Ser Pro Leu Gly Ala Arg Ala Ser |
| 120 125 130 |

| CCG CCG CGT TCC GGC GTC TCC TTG GCG CGC CCG GCT CCC GGC TGT CCC | 606 |
|---|---|
| Pro Pro Arg Ser Gly Val Ser Leu Ala Arg Pro Ala Pro Gly Cys Pro |
| 135 140 145 |

| CGC CCG GCG TGC GAG CCG GTG TAT GGG CCC CTC ACC ATG TCG CTG AAG | 654 |
|---|---|
| Arg Pro Ala Cys Glu Pro Val Tyr Gly Pro Leu Thr Met Ser Leu Lys |
| 150 155 160 |

| CCC CAG CAG CAG CAG CAG CAG CAG CAA CAG CAG CAG CAG CAA CAG | 702 |
|---|---|
| Pro Gln Gln Gln Gln Gln Gln Gln Gln Gln Gln Gln Gln Gln Gln |
| 165 170 175 180 |

| CAG CAG CAG CAG CAG CAG CAG CCG CCG CCC GCG GCT GCC AAT GTC CGC | 750 |
|---|---|
| Gln Gln Gln Gln Gln Gln Gln Pro Pro Pro Ala Ala Ala Asn Val Arg |
| 185 190 195 |

| AAG CCC GGC GGC AGC GGC CTT CTA GCG TCG CCC GCC GCC GCG CCT TCG | 798 |
|---|---|
| Lys Pro Gly Gly Ser Gly Leu Leu Ala Ser Pro Ala Ala Ala Pro Ser |
| 200 205 210 |

| CCG TCC TCG TCC TCG GTC TCC TCG TCC TCG GCC ACG GCT CCC TCC TCG | 846 |
|---|---|
| Pro Ser Ser Ser Ser Val Ser Ser Ser Ser Ala Thr Ala Pro Ser Ser |
| 215 220 225 |

| GTG GTC GCG GCG ACC TCC GGC GGC GGG AGG CCC GGC CTG GGC AGA GGT | 894 |
|---|---|
| Val Val Ala Ala Thr Ser Gly Gly Gly Arg Pro Gly Leu Gly Arg Gly |
| 230 235 240 |

| CGA AAC AGT AAC AAA GGA CTG CCT CAG TCT ACG ATT TCT TTT GAT GGA | 942 |
|---|---|
| Arg Asn Ser Asn Lys Gly Leu Pro Gln Ser Thr Ile Ser Phe Asp Gly |
| 245 250 255 260 |

| ATC TAT GCA AAT ATG AGG ATG GTT CAT ATA CTT ACA TCA GTT GTT GGC | 990 |
|---|---|
| Ile Tyr Ala Asn Met Arg Met Val His Ile Leu Thr Ser Val Val Gly |
| 265 270 275 |

| TCC AAA TGT GAA GTA CAA GTG AAA AAT GGA GGT ATA TAT GAA GGA GTT | 1038 |
|---|---|
| Ser Lys Cys Glu Val Gln Val Lys Asn Gly Gly Ile Tyr Glu Gly Val |
| 280 285 290 |

| TTT AAA ACT TAC AGT CCG AAG TGT GAT TTG GTA CTT GAT GCC GCA CAT | 1086 |
|---|---|
| Phe Lys Thr Tyr Ser Pro Lys Cys Asp Leu Val Leu Asp Ala Ala His |
| 295 300 305 |

| GAG AAA AGT ACA GAA TCC AGT TCG GGG CCG AAA CGT GAA GAA ATA ATG | 1134 |
|---|---|
| Glu Lys Ser Thr Glu Ser Ser Ser Gly Pro Lys Arg Glu Glu Ile Met |

```
                310                     315                     320
GAG AGT ATT TTG TTC AAA TGT TCA GAC TTT GTT GTG GTA CAG TTT AAA      1182
Glu Ser Ile Leu Phe Lys Cys Ser Asp Phe Val Val Val Gln Phe Lys
325                 330                     335                 340

GAT ATG GAC TCC AGT TAT GCA AAA AGA GAT GCT TTT ACT GAC TCT GCT      1230
Asp Met Asp Ser Ser Tyr Ala Lys Arg Asp Ala Phe Thr Asp Ser Ala
                    345                     350                 355

ATC AGT GCT AAA GTG AAT GGC GAA CAC AAA GAG AAG GAC CTG GAG CCC      1278
Ile Ser Ala Lys Val Asn Gly Glu His Lys Glu Lys Asp Leu Glu Pro
                360                     365                 370

TGG GAT GCA GGT GAA CTC ACA GCC AAT GAG GAA CTT GAG GCT TTG GAA      1326
Trp Asp Ala Gly Glu Leu Thr Ala Asn Glu Glu Leu Glu Ala Leu Glu
            375                     380                 385

AAT GAC GTA TCT AAT GGA TGG GAT CCC AAT GAT ATG TTT CGA TAT AAT      1374
Asn Asp Val Ser Asn Gly Trp Asp Pro Asn Asp Met Phe Arg Tyr Asn
390                     395                     400

GAA GAA AAT TAT GGT GTA GTG TCT ACG TAT GAT AGC AGT TTA TCT TCG      1422
Glu Glu Asn Tyr Gly Val Val Ser Thr Tyr Asp Ser Ser Leu Ser Ser
405                     410                     415                 420

TAT ACA GTG CCC TTA GAA AGA GAT AAC TCA GAA GAA TTT TTA AAA CGG      1470
Tyr Thr Val Pro Leu Glu Arg Asp Asn Ser Glu Glu Phe Leu Lys Arg
                    425                     430                 435

GAA GCA AGG GCA AAC CAG TTA GCA GAA GAA ATT GAG TCA AGT GCC CAG      1518
Glu Ala Arg Ala Asn Gln Leu Ala Glu Glu Ile Glu Ser Ser Ala Gln
                440                     445                 450

TAC AAA GCT CGA GTG GCC CTG GAA AAT GAT GAT AGG AGT GAG GAA GAA      1566
Tyr Lys Ala Arg Val Ala Leu Glu Asn Asp Asp Arg Ser Glu Glu Glu
            455                     460                 465

AAA TAC ACA GCA GTT CAG AGA AAT TCC AGT GAA CGT GAG GGG CAC AGC      1614
Lys Tyr Thr Ala Val Gln Arg Asn Ser Ser Glu Arg Glu Gly His Ser
470                     475                     480

ATA AAC ACT AGG GAA AAT AAA TAT ATT CCT CCT GGA CAA AGA AAT AGA      1662
Ile Asn Thr Arg Glu Asn Lys Tyr Ile Pro Pro Gly Gln Arg Asn Arg
485                     490                     495                 500

GAA GTC ATA TCC TGG GGA AGT GGG AGA CAG AAT TCA CCG CGT ATG GGC      1710
Glu Val Ile Ser Trp Gly Ser Gly Arg Gln Asn Ser Pro Arg Met Gly
                    505                     510                 515

CAG CCT GGA TCG GGC TCC ATG CCA TCA AGA TCC ACT TCT CAC ACT TCA      1758
Gln Pro Gly Ser Gly Ser Met Pro Ser Arg Ser Thr Ser His Thr Ser
                520                     525                 530

GAT TTC AAC CCG AAT TCT GGT TCA GAC CAA AGA GTA GTT AAT GGA GGT      1806
Asp Phe Asn Pro Asn Ser Gly Ser Asp Gln Arg Val Val Asn Gly Gly
            535                     540                 545

GTT CCC TGG CCA TCG CCT TGC CCA TCT CCT TCC TCT CGC CCA CCT TCT      1854
Val Pro Trp Pro Ser Pro Cys Pro Ser Pro Ser Ser Arg Pro Pro Ser
550                     555                     560

CGC TAC CAG TCA GGT CCC AAC TCT CTT CCA CCT CGG GCA GCC ACC CCT      1902
Arg Tyr Gln Ser Gly Pro Asn Ser Leu Pro Pro Arg Ala Ala Thr Pro
565                     570                     575                 580

ACA CGG CCG CCC TCC AGG CCC CCC TCG CGG CCA TCC AGA CCC CCG TCT      1950
Thr Arg Pro Pro Ser Arg Pro Pro Ser Arg Pro Ser Arg Pro Pro Ser
                    585                     590                 595

CAC CCC TCT GCT CAT GGT TCT CCA GCT CCT GTC TCT ACT ATG CCT AAA      1998
His Pro Ser Ala His Gly Ser Pro Ala Pro Val Ser Thr Met Pro Lys
                600                     605                 610

CGC ATG TCT TCA GAA GGG CCT CCA AGG ATG TCC CCA AAG GCC CAG CGA      2046
Arg Met Ser Ser Glu Gly Pro Pro Arg Met Ser Pro Lys Ala Gln Arg
            615                     620                 625

CAT CCT CGA AAT CAC AGA GTT TCT GCT GGG AGG GGT TCC ATA TCC AGT      2094
```

```
His Pro Arg Asn His Arg Val Ser Ala Gly Arg Gly Ser Ile Ser Ser
            630                 635                 640

GGC CTA GAA TTT GTA TCC CAC AAC CCA CCC AGT GAA GCA GCT ACT CCT       2142
Gly Leu Glu Phe Val Ser His Asn Pro Pro Ser Glu Ala Ala Thr Pro
645                 650                 655                 660

CCA GTA GCA AGG ACC AGT CCC TCG GGG GGA ACG TGG TCA TCA GTG GTC       2190
Pro Val Ala Arg Thr Ser Pro Ser Gly Gly Thr Trp Ser Ser Val Val
                665                 670                 675

AGT GGG GTT CCA AGA TTA TCC CCT AAA ACT CAT AGA CCC AGG TCT CCC       2238
Ser Gly Val Pro Arg Leu Ser Pro Lys Thr His Arg Pro Arg Ser Pro
            680                 685                 690

AGA CAG AAC AGT ATT GGA AAT ACC CCC AGT GGG CCA GTT CTT GCT TCT       2286
Arg Gln Asn Ser Ile Gly Asn Thr Pro Ser Gly Pro Val Leu Ala Ser
                695                 700                 705

CCC CAA GCT GGT ATT ATT CCA ACT GAA GCT GTT GCC ATG CCT ATT CCA       2334
Pro Gln Ala Gly Ile Ile Pro Thr Glu Ala Val Ala Met Pro Ile Pro
    710                 715                 720

GCT GCA TCT CCT ACG CCT GCT AGT CCT GCA TCG AAC AGA GCT GTT ACC       2382
Ala Ala Ser Pro Thr Pro Ala Ser Pro Ala Ser Asn Arg Ala Val Thr
725                 730                 735                 740

CCT TCT AGT GAG GCT AAA GAT TCC AGG CTT CAA GAT CAG AGG CAG AAC       2430
Pro Ser Ser Glu Ala Lys Asp Ser Arg Leu Gln Asp Gln Arg Gln Asn
                745                 750                 755

TCT CCT GCA GGG AAT AAA GAA AAT ATT AAA CCC AAT GAA ACA TCA CCT       2478
Ser Pro Ala Gly Asn Lys Glu Asn Ile Lys Pro Asn Glu Thr Ser Pro
            760                 765                 770

AGC TTC TCA AAA GCT GAA AAC AAA GGT ATA TCA CCA GTT GTT TCT GAA       2526
Ser Phe Ser Lys Ala Glu Asn Lys Gly Ile Ser Pro Val Val Ser Glu
                775                 780                 785

CAT AGA AAA CAG ATT GAT GAT TTA AAG AAA TTT AAG AAT GAT TTT AGG       2574
His Arg Lys Gln Ile Asp Asp Leu Lys Lys Phe Lys Asn Asp Phe Arg
    790                 795                 800

TTA CAG CCA AGT TCT ACT TCT GAA TCT ATG GAT CAA CTA CTA AAC AAA       2622
Leu Gln Pro Ser Ser Thr Ser Glu Ser Met Asp Gln Leu Leu Asn Lys
805                 810                 815                 820

AAT AGA GAG GGA GAA AAA TCA AGA GAT TTG ATC AAA GAC AAA ATT GAA       2670
Asn Arg Glu Gly Glu Lys Ser Arg Asp Leu Ile Lys Asp Lys Ile Glu
                825                 830                 835

CCA AGT GCT AAG GAT TCT TTC ATT GAA AAT AGC AGC AGC AAC TGT ACC       2718
Pro Ser Ala Lys Asp Ser Phe Ile Glu Asn Ser Ser Ser Asn Cys Thr
            840                 845                 850

AGT GGC AGC AGC AAG CCG AAT AGC CCC AGC ATT TCC CCT TCA ATA CTT       2766
Ser Gly Ser Ser Lys Pro Asn Ser Pro Ser Ile Ser Pro Ser Ile Leu
                855                 860                 865

AGT AAC ACG GAG CAC AAG AGG GGA CCT GAG GTC ACT TCC CAA GGG GTT       2814
Ser Asn Thr Glu His Lys Arg Gly Pro Glu Val Thr Ser Gln Gly Val
    870                 875                 880

CAG ACT TCC AGC CCA GCA TGT AAA CAA GAG AAA GAC GAT AAG GAA GAG       2862
Gln Thr Ser Ser Pro Ala Cys Lys Gln Glu Lys Asp Asp Lys Glu Glu
885                 890                 895                 900

AAG AAA GAC GCA GCT GAG CAA GTT AGG AAA TCA ACA TTG AAT CCC AAT       2910
Lys Lys Asp Ala Ala Glu Gln Val Arg Lys Ser Thr Leu Asn Pro Asn
                905                 910                 915

GCA AAG GAG TTC AAC CCA CGT TCC TTC TCT CAG CCA AAG CCT TCT ACT       2958
Ala Lys Glu Phe Asn Pro Arg Ser Phe Ser Gln Pro Lys Pro Ser Thr
            920                 925                 930

ACC CCA ACT TCA CCT CGG CCT CAA GCA CAA CCT AGC CCA TCT ATG GTG       3006
Thr Pro Thr Ser Pro Arg Pro Gln Ala Gln Pro Ser Pro Ser Met Val
                935                 940                 945
```

-continued

```
GGT CAT CAA CAG CCA ACT CCA GTT TAT ACT CAG CCT GTT TGT TTT GCA      3054
Gly His Gln Gln Pro Thr Pro Val Tyr Thr Gln Pro Val Cys Phe Ala
        950                 955                 960

CCA AAT ATG ATG TAT CCA GTC CCA GTG AGC CCA GGC GTG CAA CCT TTA      3102
Pro Asn Met Met Tyr Pro Val Pro Val Ser Pro Gly Val Gln Pro Leu
965                 970                 975                 980

TAC CCA ATA CCT ATG ACG CCC ATG CCA GTG AAT CAA GCC AAG ACA TAT      3150
Tyr Pro Ile Pro Met Thr Pro Met Pro Val Asn Gln Ala Lys Thr Tyr
                985                 990                 995

AGA GCA GTA CCA AAT ATG CCC CAA CAG CGG CAA GAC CAG CAT CAT CAG      3198
Arg Ala Val Pro Asn Met Pro Gln Gln Arg Gln Asp Gln His His Gln
        1000                1005                1010

AGT GCC ATG ATG CAC CCA GCG TCA GCA GCG GGC CCA CCG ATT GCA GCC      3246
Ser Ala Met Met His Pro Ala Ser Ala Ala Gly Pro Pro Ile Ala Ala
        1015                1020                1025

ACC CCA CCA GCT TAC TCC ACG CAA TAT GTT GCC TAC AGT CCT CAG CAG      3294
Thr Pro Pro Ala Tyr Ser Thr Gln Tyr Val Ala Tyr Ser Pro Gln Gln
        1030                1035                1040

TTC CCA AAT CAG CCC CTT GTT CAG CAT GTG CCA CAT TAT CAG TCT CAG      3342
Phe Pro Asn Gln Pro Leu Val Gln His Val Pro His Tyr Gln Ser Gln
1045                1050                1055                1060

CAT CCT CAT GTC TAT AGT CCT GTA ATA CAG GGT AAT GCT AGA ATG ATG      3390
His Pro His Val Tyr Ser Pro Val Ile Gln Gly Asn Ala Arg Met Met
                1065                1070                1075

GCA CCA CCA ACA CAC GCC CAG CCT GGT TTA GTA TCT TCT TCA GCA ACT      3438
Ala Pro Pro Thr His Ala Gln Pro Gly Leu Val Ser Ser Ser Ala Thr
        1080                1085                1090

CAG TAC GGG GCT CAT GAG CAG ACG CAT GCG ATG TAT GCA TGT CCC AAA      3486
Gln Tyr Gly Ala His Glu Gln Thr His Ala Met Tyr Ala Cys Pro Lys
        1095                1100                1105

TTA CCA TAC AAC AAG GAG ACA AGC CCT TCT TTC TAC TTT GCC ATT TCC      3534
Leu Pro Tyr Asn Lys Glu Thr Ser Pro Ser Phe Tyr Phe Ala Ile Ser
1110                1115                1120

ACG GGC TCC CTT GCT CAG CAG TAT GCG CAC CCT AAC GCT ACC CTG CAC      3582
Thr Gly Ser Leu Ala Gln Gln Tyr Ala His Pro Asn Ala Thr Leu His
1125                1130                1135                1140

CCA CAT ACT CCA CAC CCT CAG CCT TCA GCT ACC CCC ACT GGA CAG CAG      3630
Pro His Thr Pro His Pro Gln Pro Ser Ala Thr Pro Thr Gly Gln Gln
                1145                1150                1155

CAA AGC CAA CAT GGT GGA AGT CAT CCT GCA CCC AGT CCT GTT CAG CAC      3678
Gln Ser Gln His Gly Gly Ser His Pro Ala Pro Ser Pro Val Gln His
        1160                1165                1170

CAT CAG CAC CAG GCC GCC CAG GCT CTC CAT CTG GCC AGT CCA CAG CAG      3726
His Gln His Gln Ala Ala Gln Ala Leu His Leu Ala Ser Pro Gln Gln
        1175                1180                1185

CAG TCA GCC ATT TAC CAC GCG GGG CTT GCG CCA ACT CCA CCC TCC ATG      3774
Gln Ser Ala Ile Tyr His Ala Gly Leu Ala Pro Thr Pro Pro Ser Met
        1190                1195                1200

ACA CCT GCC TCC AAC ACG CAG TCG CCA CAG AAT AGT TTC CCA GCA GCA      3822
Thr Pro Ala Ser Asn Thr Gln Ser Pro Gln Asn Ser Phe Pro Ala Ala
1205                1210                1215                1220

CAA CAG ACT GTC TTT ACG ATC CAT CCT TCT CAC GTT CAG CCG GCG TAT      3870
Gln Gln Thr Val Phe Thr Ile His Pro Ser His Val Gln Pro Ala Tyr
                1225                1230                1235

ACC AAC CCA CCC CAC ATG GCC CAC GTA CCT CAG GCT CAT GTA CAG TCA      3918
Thr Asn Pro Pro His Met Ala His Val Pro Gln Ala His Val Gln Ser
                1240                1245                1250

GGA ATG GTT CCT TCT CAT CCA ACT GCC CAT GCG CCA ATG ATG CTA ATG      3966
Gly Met Val Pro Ser His Pro Thr Ala His Ala Pro Met Met Leu Met
                1255                1260                1265
```

```
ACG ACA CAG CCA CCC GGC GGT CCC CAG GCC GCC CTC GCT CAA AGT GCA    4014
Thr Thr Gln Pro Pro Gly Gly Pro Gln Ala Ala Leu Ala Gln Ser Ala
    1270            1275                1280

CTA CAG CCC ATT CCA GTC TCG ACA ACA GCG CAT TTC CCC TAT ATG ACG    4062
Leu Gln Pro Ile Pro Val Ser Thr Thr Ala His Phe Pro Tyr Met Thr
1285            1290                1295                    1300

CAC CCT TCA GTA CAA GCC CAC CAC CAA CAG CAG TTG T AAGGCTGCCC       4109
His Pro Ser Val Gln Ala His His Gln Gln Gln Leu
                1305            1310

TGGAGGAACC GAAAGGCCAA ATTCCCTCCT CCCTTCTACT GCTTCTACCA ACTGGAAGCA  4169

CAGAAAACTA GAATTTCATT TATTTTGTTT TTAAAATATA TATGTTGATT TCTTGTAACA  4229

TCCAATAGGA ATGCTAACAG TTCACTTGCA GTGGAAGATA CTTGGACCGA GTAGAGGCAT  4289

TTAGGAACTT GGGGGCTATT CCATAATTCC ATATGCTGTT TCAGAGTCCC GCAGGTACCC  4349

CAGCTCTGCT TGCCGAAACT GGAAGTTATT TATTTTTTAA TAACCCTTGA AAGTCATGAA  4409

CACATCAGCT AGCAAAGAA GTAACAAGAG TGATTCTTGC TGCTATTACT GCTAAAAAAA   4469

AAAAAAAAA AA                                                       4481
```

(2) INFORMATION FOR SEQ ID NO:19:

(i) SEQUENCE CHARACTERISTICS:
        (A) LENGTH: 1312 amino acids
        (B) TYPE: amino acid
        (D) TOPOLOGY: linear (ii) MOLECULE TYPE: protein (xi) SEQUENCE DESCRIPTION: SEQ ID NO:19:

```
Met Arg Ser Ala Ala Ala Ala Pro Arg Ser Pro Ala Val Ala Thr Glu
 1               5                  10                  15

Ser Arg Arg Phe Ala Ala Ala Arg Trp Pro Gly Trp Arg Ser Leu Gln
                20                  25                  30

Arg Pro Ala Arg Arg Ser Gly Arg Gly Gly Gly Ala Ala Pro Gly
        35                  40                  45

Pro Tyr Pro Ser Ala Ala Pro Pro Pro Gly Pro Gly Pro Pro Pro
    50                  55                  60

Ser Arg Gln Ser Ser Pro Pro Ser Ala Ser Asp Cys Phe Gly Ser Asn
65                  70                  75                  80

Gly Asn Gly Gly Gly Ala Phe Arg Pro Gly Ser Arg Arg Leu Leu Gly
                85                  90                  95

Leu Gly Gly Pro Pro Arg Pro Phe Val Val Leu Leu Pro Leu Ala
                100                 105                 110

Ser Pro Gly Ala Pro Pro Ala Ala Pro Thr Arg Ala Ser Pro Leu Gly
            115                 120                 125

Ala Arg Ala Ser Pro Pro Arg Ser Gly Val Ser Leu Ala Arg Pro Ala
        130                 135                 140

Pro Gly Cys Pro Arg Pro Ala Cys Glu Pro Val Tyr Gly Pro Leu Thr
145                 150                 155                 160

Met Ser Leu Lys Pro Gln Gln Gln Gln Gln Gln Gln Gln Gln
                165                 170                 175

Gln Gln Gln Gln Gln Gln Gln Gln Gln Pro Pro Pro Ala Ala
            180                 185                 190

Ala Asn Val Arg Lys Pro Gly Gly Ser Gly Leu Leu Ala Ser Pro Ala
        195                 200                 205

Ala Ala Pro Ser Pro Ser Ser Ser Ser Val Ser Ser Ser Ser Ala Thr
```

```
            210                 215                 220
Ala Pro Ser Ser Val Val Ala Ala Thr Ser Gly Gly Arg Pro Gly
225                 230                 235                 240
Leu Gly Arg Gly Arg Asn Ser Asn Lys Gly Leu Pro Gln Ser Thr Ile
                245                 250                 255
Ser Phe Asp Gly Ile Tyr Ala Asn Met Arg Met Val His Ile Leu Thr
            260                 265                 270
Ser Val Val Gly Ser Lys Cys Glu Val Gln Val Lys Asn Gly Gly Ile
                275                 280                 285
Tyr Glu Gly Val Phe Lys Thr Tyr Ser Pro Lys Cys Asp Leu Val Leu
            290                 295                 300
Asp Ala Ala His Glu Lys Ser Thr Glu Ser Ser Gly Pro Lys Arg
305                 310                 315                 320
Glu Glu Ile Met Glu Ser Ile Leu Phe Lys Cys Ser Asp Phe Val Val
                325                 330                 335
Val Gln Phe Lys Asp Met Asp Ser Ser Tyr Ala Lys Arg Asp Ala Phe
                340                 345                 350
Thr Asp Ser Ala Ile Ser Ala Lys Val Asn Gly Glu His Lys Glu Lys
            355                 360                 365
Asp Leu Glu Pro Trp Asp Ala Gly Glu Leu Thr Ala Asn Glu Glu Leu
370                 375                 380
Glu Ala Leu Glu Asn Asp Val Ser Asn Gly Trp Asp Pro Asn Asp Met
385                 390                 395                 400
Phe Arg Tyr Asn Glu Glu Asn Tyr Gly Val Val Ser Thr Tyr Asp Ser
                405                 410                 415
Ser Leu Ser Ser Tyr Thr Val Pro Leu Glu Arg Asp Asn Ser Glu Glu
                420                 425                 430
Phe Leu Lys Arg Glu Ala Arg Ala Asn Gln Leu Ala Glu Glu Ile Glu
            435                 440                 445
Ser Ser Ala Gln Tyr Lys Ala Arg Val Ala Leu Glu Asn Asp Asp Arg
            450                 455                 460
Ser Glu Glu Glu Lys Tyr Thr Ala Val Gln Arg Asn Ser Ser Glu Arg
465                 470                 475                 480
Glu Gly His Ser Ile Asn Thr Arg Glu Asn Lys Tyr Ile Pro Pro Gly
                485                 490                 495
Gln Arg Asn Arg Glu Val Ile Ser Trp Gly Ser Gly Arg Gln Asn Ser
                500                 505                 510
Pro Arg Met Gly Gln Pro Gly Ser Gly Ser Met Pro Ser Arg Ser Thr
            515                 520                 525
Ser His Thr Ser Asp Phe Asn Pro Asn Ser Gly Ser Asp Gln Arg Val
            530                 535                 540
Val Asn Gly Gly Val Pro Trp Pro Ser Pro Cys Pro Ser Pro Ser Ser
545                 550                 555                 560
Arg Pro Pro Ser Arg Tyr Gln Ser Gly Pro Asn Ser Leu Pro Pro Arg
                565                 570                 575
Ala Ala Thr Pro Thr Arg Pro Pro Ser Arg Pro Pro Ser Arg Pro Ser
            580                 585                 590
Arg Pro Pro Ser His Pro Ser Ala His Gly Ser Pro Ala Pro Val Ser
            595                 600                 605
Thr Met Pro Lys Arg Met Ser Ser Glu Gly Pro Pro Arg Met Ser Pro
            610                 615                 620
Lys Ala Gln Arg His Pro Arg Asn His Arg Val Ser Ala Gly Arg Gly
625                 630                 635                 640
```

-continued

```
Ser Ile Ser Ser Gly Leu Glu Phe Val Ser His Asn Pro Pro Ser Glu
            645                 650                 655
Ala Ala Thr Pro Pro Val Ala Arg Thr Ser Pro Ser Gly Gly Thr Trp
            660                 665                 670
Ser Ser Val Val Ser Gly Val Pro Arg Leu Ser Pro Lys Thr His Arg
            675                 680                 685
Pro Arg Ser Pro Arg Gln Asn Ser Ile Gly Asn Thr Pro Ser Gly Pro
        690                 695                 700
Val Leu Ala Ser Pro Gln Ala Gly Ile Ile Pro Thr Glu Ala Val Ala
705                 710                 715                 720
Met Pro Ile Pro Ala Ala Ser Pro Thr Pro Ala Ser Pro Ala Ser Asn
            725                 730                 735
Arg Ala Val Thr Pro Ser Ser Glu Ala Lys Asp Ser Arg Leu Gln Asp
            740                 745                 750
Gln Arg Gln Asn Ser Pro Ala Gly Asn Lys Glu Asn Ile Lys Pro Asn
            755                 760                 765
Glu Thr Ser Pro Ser Phe Ser Lys Ala Glu Asn Lys Gly Ile Ser Pro
    770                 775                 780
Val Val Ser Glu His Arg Lys Gln Ile Asp Asp Leu Lys Lys Phe Lys
785                 790                 795                 800
Asn Asp Phe Arg Leu Gln Pro Ser Ser Thr Ser Glu Ser Met Asp Gln
            805                 810                 815
Leu Leu Asn Lys Asn Arg Glu Gly Glu Lys Ser Arg Asp Leu Ile Lys
            820                 825                 830
Asp Lys Ile Glu Pro Ser Ala Lys Asp Ser Phe Ile Glu Asn Ser Ser
        835                 840                 845
Ser Asn Cys Thr Ser Gly Ser Ser Lys Pro Asn Ser Pro Ser Ile Ser
850                 855                 860
Pro Ser Ile Leu Ser Asn Thr Glu His Lys Arg Gly Pro Glu Val Thr
865                 870                 875                 880
Ser Gln Gly Val Gln Thr Ser Ser Pro Ala Cys Lys Gln Glu Lys Asp
            885                 890                 895
Asp Lys Glu Glu Lys Lys Asp Ala Ala Glu Gln Val Arg Lys Ser Thr
            900                 905                 910
Leu Asn Pro Asn Ala Lys Glu Phe Asn Pro Arg Ser Phe Ser Gln Pro
        915                 920                 925
Lys Pro Ser Thr Thr Pro Thr Ser Pro Arg Pro Gln Ala Gln Pro Ser
    930                 935                 940
Pro Ser Met Val Gly His Gln Pro Thr Pro Val Tyr Thr Gln Pro
945                 950                 955                 960
Val Cys Phe Ala Pro Asn Met Met Tyr Pro Val Pro Val Ser Pro Gly
            965                 970                 975
Val Gln Pro Leu Tyr Pro Ile Pro Met Thr Pro Met Pro Val Asn Gln
            980                 985                 990
Ala Lys Thr Tyr Arg Ala Val Pro Asn Met Pro Gln Gln Arg Gln Asp
        995                 1000                1005
Gln His His Gln Ser Ala Met Met His Pro Ala Ser Ala Ala Gly Pro
    1010                1015                1020
Pro Ile Ala Ala Thr Pro Pro Ala Tyr Ser Thr Gln Tyr Val Ala Tyr
1025                1030                1035                1040
Ser Pro Gln Gln Phe Pro Asn Gln Pro Leu Val Gln His Val Pro His
            1045                1050                1055
```

```
Tyr Gln Ser Gln His Pro His Val Tyr Ser Pro Val Ile Gln Gly Asn
            1060                1065                1070

Ala Arg Met Met Ala Pro Pro Thr His Ala Gln Pro Gly Leu Val Ser
        1075                1080                1085

Ser Ser Ala Thr Gln Tyr Gly Ala His Glu Gln Thr His Ala Met Tyr
    1090                1095                1100

Ala Cys Pro Lys Leu Pro Tyr Asn Lys Glu Thr Ser Pro Ser Phe Tyr
1105                1110                1115                1120

Phe Ala Ile Ser Thr Gly Ser Leu Ala Gln Gln Tyr Ala His Pro Asn
            1125                1130                1135

Ala Thr Leu His Pro His Thr Pro His Pro Gln Pro Ser Ala Thr Pro
            1140                1145                1150

Thr Gly Gln Gln Gln Ser Gln His Gly Gly Ser His Pro Ala Pro Ser
            1155                1160                1165

Pro Val Gln His His Gln His Gln Ala Ala Gln Ala Leu His Leu Ala
            1170                1175                1180

Ser Pro Gln Gln Gln Ser Ala Ile Tyr His Ala Gly Leu Ala Pro Thr
1185                1190                1195                1200

Pro Pro Ser Met Thr Pro Ala Ser Asn Thr Gln Ser Pro Gln Asn Ser
            1205                1210                1215

Phe Pro Ala Ala Gln Gln Thr Val Phe Thr Ile His Pro Ser His Val
            1220                1225                1230

Gln Pro Ala Tyr Thr Asn Pro Pro His Met Ala His Val Pro Gln Ala
            1235                1240                1245

His Val Gln Ser Gly Met Val Pro Ser His Pro Thr Ala His Ala Pro
    1250                1255                1260

Met Met Leu Met Thr Thr Gln Pro Pro Gly Gly Pro Gln Ala Ala Leu
1265                1270                1275                1280

Ala Gln Ser Ala Leu Gln Pro Ile Pro Val Ser Thr Thr Ala His Phe
            1285                1290                1295

Pro Tyr Met Thr His Pro Ser Val Gln Ala His His Gln Gln Gln Leu
            1300                1305                1310

(2) INFORMATION FOR SEQ ID NO:20:

(i) SEQUENCE CHARACTERISTICS:
        (A) LENGTH: 3563 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..3550

(xi) SEQUENCE DESCRIPTION: SEQ ID NO:20:

GA ATT CTT CCA CTC GAC TTC ATA GTG GTC AGT GGG GCC CTG GTA GCC        47
   Ile Leu Pro Leu Asp Phe Ile Val Val Ser Gly Ala Leu Val Ala
   1               5                   10                  15

TTT GCC TTC ACT GGC AAT AGC AAA GGA AAA GAC ATC AAC ACG ATT AAA       95
Phe Ala Phe Thr Gly Asn Ser Lys Gly Lys Asp Ile Asn Thr Ile Lys
                20                  25                  30

TCC CTC CGA GTC CTC CGG GTG CTA CGA CCT CTT AAA ACC ATC AAG CGG      143
Ser Leu Arg Val Leu Arg Val Leu Arg Pro Leu Lys Thr Ile Lys Arg
            35                  40                  45

CTG CCA AAG CTC AAG GCT GTG TTT GAC TGT GTG GTG AAC TCA CTT AAA      191
Leu Pro Lys Leu Lys Ala Val Phe Asp Cys Val Val Asn Ser Leu Lys
```

```
                50                      55                      60
AAC GTC TTC AAC ATC CTC ATC GTC TAC ATG CTA TTC ATG TTC ATC TTC    239
Asn Val Phe Asn Ile Leu Ile Val Tyr Met Leu Phe Met Phe Ile Phe
         65                  70                  75

GCC GTG GTG GCT GTG CAG CTC TTC AAG GGG AAA TTC TTC CAC TGC ACT    287
Ala Val Val Ala Val Gln Leu Phe Lys Gly Lys Phe Phe His Cys Thr
 80                  85                  90                  95

GAC GAG TCC AAA GAG TTT GAG AAA GAT TGT CGA GGC AAA TAC CTC CTC    335
Asp Glu Ser Lys Glu Phe Glu Lys Asp Cys Arg Gly Lys Tyr Leu Leu
                    100                 105                 110

TAC GAG AAG AAT GAG GTG AAG GCG CGA GAC CGG GAG TGG AAG AAG TAT    383
Tyr Glu Lys Asn Glu Val Lys Ala Arg Asp Arg Glu Trp Lys Lys Tyr
             115                 120                 125

GAA TTC CAT TAC GAC AAT GTG CTG TGG GCT CTG CTG ACC CTC TTC ACC    431
Glu Phe His Tyr Asp Asn Val Leu Trp Ala Leu Leu Thr Leu Phe Thr
         130                 135                 140

GTG TCC ACG GGA GAA GGC TGG CCA CAG GTC CTC AAG CAT TCG GTG GAC    479
Val Ser Thr Gly Glu Gly Trp Pro Gln Val Leu Lys His Ser Val Asp
 145                 150                 155

GCC ACC TTT GAG AAC CAG GGC CCC AGC CCC GGG TAC CGC ATG GAG ATG    527
Ala Thr Phe Glu Asn Gln Gly Pro Ser Pro Gly Tyr Arg Met Glu Met
160                 165                 170                 175

TCC ATT TTC TAC GTC GTC TAC TTT GTG GTG TTC CCC TTC TTC TTT GTC    575
Ser Ile Phe Tyr Val Val Tyr Phe Val Val Phe Pro Phe Phe Phe Val
                    180                 185                 190

AAT ATC TTT GTG GCC TTG ATC ATC ATC ACC TTC AGG GAG CAA GGG GAC    623
Asn Ile Phe Val Ala Leu Ile Ile Ile Thr Phe Gln Glu Gln Gly Asp
             195                 200                 205

AAG ATG ATG GAG GAA TAC AGC CTG GAG AAA AAT GAG AGG GCC TGC ATT    671
Lys Met Met Glu Glu Tyr Ser Leu Glu Lys Asn Glu Arg Ala Cys Ile
         210                 215                 220

GAT TTC GCC ATC AGC GCC AAG CCG CTG ACC CGA CAC ATG CCG CAG AAC    719
Asp Phe Ala Ile Ser Ala Lys Pro Leu Thr Arg His Met Pro Gln Asn
 225                 230                 235

AAG CAG AGC TTC CAG TAC CGC ATG TGG CAG TTC GTG GTG TCT CCG CCT    767
Lys Gln Ser Phe Gln Tyr Arg Met Trp Gln Phe Val Val Ser Pro Pro
240                 245                 250                 255

TTC GAG TAC ACG ATC ATG GCC ATG ATC GCC CTC AAC ACC ATC GTG CTT    815
Phe Glu Tyr Thr Ile Met Ala Met Ile Ala Leu Asn Thr Ile Val Leu
                    260                 265                 270

ATG ATG AAG TTC TAT GGG GCT TCT GTT GCT TAT GAA AAT GCC CTG CGG    863
Met Met Lys Phe Tyr Gly Ala Ser Val Ala Tyr Glu Asn Ala Leu Arg
             275                 280                 285

GTG TTC AAC ATC GTC TTC ACC TCC CTC TTC TCT CTG GAA TGT GTG CTG    911
Val Phe Asn Ile Val Phe Thr Ser Leu Phe Ser Leu Glu Cys Val Leu
         290                 295                 300

AAA GTC ATG GCT TTT GGG ATT CTG AAT TAT TTC CGC GAT GCC TGG AAC    959
Lys Val Met Ala Phe Gly Ile Leu Asn Tyr Phe Arg Asp Ala Trp Asn
 305                 310                 315

ATC TTC GAC TTT GTG ACT GTT CTG GGC AGC ATC ACC GAT ATC CTC GTG    1007
Ile Phe Asp Phe Val Thr Val Leu Gly Ser Ile Thr Asp Ile Leu Val
320                 325                 330                 335

ACT GAG TTT GGG AAT AAC TTC ATC AAC CTG AGC TTT CTC CGC CTC TTC    1055
Thr Glu Phe Gly Asn Asn Phe Ile Asn Leu Ser Phe Leu Arg Leu Phe
                    340                 345                 350

CGA GCT GCC CGG CTC ATC AAA CTT CTC CGT CAG GGT TAC ACC ATC CGC    1103
Arg Ala Ala Arg Leu Ile Lys Leu Leu Arg Gln Gly Tyr Thr Ile Arg
             355                 360                 365

ATT CTT CTC TGG ACC TTT GTG CAG TCC TTC AAG GCC CTG CCT TAT GTC    1151
```

```
                                                                         -continued Ile Leu Leu Trp Thr Phe Val Gln Ser Phe Lys Ala Leu Pro Tyr Val
        370                 375                 380

TGT CTG CTG ATC GCC ATG CTC TTC TTC ATC TAT GCC ATC ATT GGG ATG    1199
Cys Leu Leu Ile Ala Met Leu Phe Phe Ile Tyr Ala Ile Ile Gly Met
385                 390                 395

CAG GTG TTT GGT AAC ATT GGC ATC GAC GTG GAG GAC GAG GAC AGT GAT    1247
Gln Val Phe Gly Asn Ile Gly Ile Asp Val Glu Asp Glu Asp Ser Asp
400                 405                 410                 415

GAA GAT GAG TTC CAA ATC ACT GAG CAC AAT AAC TTC CGG ACC TTC TTC    1295
Glu Asp Glu Phe Gln Ile Thr Glu His Asn Asn Phe Arg Thr Phe Phe
                420                 425                 430

CAG GCC CTC ATG CTT CTC TTC CGG AGT GCC ACC GGG GAA GCT TGG CAC    1343
Gln Ala Leu Met Leu Leu Phe Arg Ser Ala Thr Gly Glu Ala Trp His
            435                 440                 445

AAC ATC ATG CTT TCC TGC CTC AGC GGG AAA CCG TGT GAT AAG AAC TCT    1391
Asn Ile Met Leu Ser Cys Leu Ser Gly Lys Pro Cys Asp Lys Asn Ser
        450                 455                 460

GGC ATC CTG ACT CGA GAG TGT GGC AAT GAA TTT GCT TAT TTT TAC TTT    1439
Gly Ile Leu Thr Arg Glu Cys Gly Asn Glu Phe Ala Tyr Phe Tyr Phe
    465                 470                 475

GTT TCC TTC ATC TTC CTC TGC TCG TTT CTG ATG CTG AAT CTC TTT GTC    1487
Val Ser Phe Ile Phe Leu Cys Ser Phe Leu Met Leu Asn Leu Phe Val
480                 485                 490                 495

GCC GTC ATC ATG GAC AAC TTT GAG TAC CTC ACC CGA GAC TCC TCC ATC    1535
Ala Val Ile Met Asp Asn Phe Glu Tyr Leu Thr Arg Asp Ser Ser Ile
                500                 505                 510

CTG GGC CCC CAC CAC CTG GAT GAG TAC GTG CGT GTC TGG GCC GAG TAT    1583
Leu Gly Pro His His Leu Asp Glu Tyr Val Arg Val Trp Ala Glu Tyr
            515                 520                 525

GAC CCC GCA GCT TGG GGC CGC ATG CCT TAC CTG GAC ATG TAT CAG ATG    1631
Asp Pro Ala Ala Trp Gly Arg Met Pro Tyr Leu Asp Met Tyr Gln Met
        530                 535                 540

CTG AGA CAC ATG TCT CCG CCC CTG GGT CTG GGG AAG AAG TGT CCG GCC    1679
Leu Arg His Met Ser Pro Pro Leu Gly Leu Gly Lys Lys Cys Pro Ala
    545                 550                 555

AGA GTG GCT TAC AAG CGG CTT CTG CGG ATG GAC CTG CCC GTC GCA GAT    1727
Arg Val Ala Tyr Lys Arg Leu Leu Arg Met Asp Leu Pro Val Ala Asp
560                 565                 570                 575

GAC AAC ACC GTC CAC TTC AAT TCC ACC CTC ATG GCT CTG ATC CGC ACA    1775
Asp Asn Thr Val His Phe Asn Ser Thr Leu Met Ala Leu Ile Arg Thr
                580                 585                 590

GCC CTG GAC ATC AAG ATT GCC AAG GGA GGA GCC GAC AAA CAG CAG ATG    1823
Ala Leu Asp Ile Lys Ile Ala Lys Gly Gly Ala Asp Lys Gln Gln Met
            595                 600                 605

GAC GCT GAG CTG CGG AAG GAG ATG ATG GCG ATT TGG CCC AAT CTG TCC    1871
Asp Ala Glu Leu Arg Lys Glu Met Met Ala Ile Trp Pro Asn Leu Ser
        610                 615                 620

CAG AAG ACG CTA GAC CTG CTG GTC ACA CCT CAC AAG TCC ACG GAC CTC    1919
Gln Lys Thr Leu Asp Leu Leu Val Thr Pro His Lys Ser Thr Asp Leu
    625                 630                 635

ACC GTG GGG AAG ATC TAC GCA GCC ATG ATG ATC ATG GAG TAC TAC CGG    1967
Thr Val Gly Lys Ile Tyr Ala Ala Met Met Ile Met Glu Tyr Tyr Arg
640                 645                 650                 655

CAG AGC AAG GCC AAG AAG CTG CAG GCC ATG CGC GAG GAG CAG GAC CGG    2015
Gln Ser Lys Ala Lys Lys Leu Gln Ala Met Arg Glu Glu Gln Asp Arg
                660                 665                 670

ACA CCC CTC ATG TTC CAG CGC ATG GAG CCC CCG TCC CCA ACG CAG GAA    2063
Thr Pro Leu Met Phe Gln Arg Met Glu Pro Pro Ser Pro Thr Gln Glu
            675                 680                 685
```

```
GGG GGA CCT GGC CAG AAC GCC CTC CCC TCC ACC CAG CTG GAC CCA GGA      2111
Gly Gly Pro Gly Gln Asn Ala Leu Pro Ser Thr Gln Leu Asp Pro Gly
            690                 695                 700

GGA GCC CTG ATG GCT CAC GAA AGC GGC CTC AAG GAG AGC CCG TCC TGG      2159
Gly Ala Leu Met Ala His Glu Ser Gly Leu Lys Glu Ser Pro Ser Trp
    705                 710                 715

GTG ACC CAG CGT GCC CAG GAG ATG TTC CAG AAG ACG GGC ACA TGG AGT      2207
Val Thr Gln Arg Ala Gln Glu Met Phe Gln Lys Thr Gly Thr Trp Ser
720                 725                 730                 735

CCG GAA CAA GGC CCC CCT ACC GAC ATG CCC AAC AGC CAG CCT AAC TCT      2255
Pro Glu Gln Gly Pro Pro Thr Asp Met Pro Asn Ser Gln Pro Asn Ser
                740                 745                 750

CAG TCC GTG GAG ATG CGA GAG ATG GGC AGA GAT GGC TAC TCC GAC AGC      2303
Gln Ser Val Glu Met Arg Glu Met Gly Arg Asp Gly Tyr Ser Asp Ser
            755                 760                 765

GAG CAC TAC CTC CCC ATG GAA GGC CAG GGC CGG GCT GCC TCC ATG CCC      2351
Glu His Tyr Leu Pro Met Glu Gly Gln Gly Arg Ala Ala Ser Met Pro
    770                 775                 780

CGC CTC CCT GCA GAG AAC CAG ACC ATC TCA GAC ACC AGC CCC ATG AAG      2399
Arg Leu Pro Ala Glu Asn Gln Thr Ile Ser Asp Thr Ser Pro Met Lys
785                 790                 795

CGT TCA GCC TCC GTG CTG GGC CCC AAG GCC CGA CGC CTG GAC GAT TAC      2447
Arg Ser Ala Ser Val Leu Gly Pro Lys Ala Arg Arg Leu Asp Asp Tyr
800                 805                 810                 815

TCG CTG GAG CGG GTC CCG CCC GAG GAG AAC CAG CGG CAC CAC CAG CGG      2495
Ser Leu Glu Arg Val Pro Pro Glu Glu Asn Gln Arg His His Gln Arg
                820                 825                 830

CGC CGC GAC CGC AGC CAC CGC GCC TCT GAG CGC TCC CTG GGC CGC TAC      2543
Arg Arg Asp Arg Ser His Arg Ala Ser Glu Arg Ser Leu Gly Arg Tyr
            835                 840                 845

ACC GAT GTG GAC ACA GGC TTG GGG ACA GAC CTG AGC ATG ACC ACC CAA      2591
Thr Asp Val Asp Thr Gly Leu Gly Thr Asp Leu Ser Met Thr Thr Gln
    850                 855                 860

TCC GGG GAC CTG CCG TCG AAG GAG CGG GAC CAG GAG CGG GGC CGG CCC      2639
Ser Gly Asp Leu Pro Ser Lys Glu Arg Asp Gln Glu Arg Gly Arg Pro
865                 870                 875

AAG GAT CGG AAG CAT CGA CAG CAC CAC CAC CAC CAC CAC CAC CAC CAC      2687
Lys Asp Arg Lys His Arg Gln His His His His His His His His His
                880                 885                 890                 895

CAT CCC CCG CCC CCC GAC AAG GAC CGC TAT GCC CAG GAA CGG CCG GAC      2735
His Pro Pro Pro Pro Asp Lys Asp Arg Tyr Ala Gln Glu Arg Pro Asp
            900                 905                 910

CAC GGC CGG GCA CGG GCT CGG GAC CAG CGC TGG TCC CGC TCG CCC AGC      2783
His Gly Arg Ala Arg Ala Arg Asp Gln Arg Trp Ser Arg Ser Pro Ser
    915                 920                 925

GAG GGC CGA GAG CAC ATG GCG CAC CGG CAG GGC AGT AGT TCC GTA AGT      2831
Glu Gly Arg Glu His Met Ala His Arg Gln Gly Ser Ser Ser Val Ser
930                 935                 940

GGA AGC CCA GCC CCC TCA ACA TCT GGT ACC AGC ACT CCG CGG CGG GGC      2879
Gly Ser Pro Ala Pro Ser Thr Ser Gly Thr Ser Thr Pro Arg Arg Gly
            945                 950                 955

CGC CGC CAG CTC CCC CAG ACC CCC TCC ACC CCC CGG CCA CAC GTG TCC      2927
Arg Arg Gln Leu Pro Gln Thr Pro Ser Thr Pro Arg Pro His Val Ser
960                 965                 970                 975

TAT TCC CCT GTG ATC CGT AAG GCC GGC GGC TCG GGG CCC CCG CAG CAG      2975
Tyr Ser Pro Val Ile Arg Lys Ala Gly Gly Ser Gly Pro Pro Gln Gln
                980                 985                 990

CAG CAG CAG CAG CAG CAG CAG CAG CAG GCG GTG GCC AGG CCG GGC           3023
Gln Gln Gln Gln Gln Gln Gln Gln Gln Ala Val Ala Arg Pro Gly
            995                 1000                1005
```

```
CGG GCG GCC ACC AGC GGC CCT CGG AGG TAC CCA GGC CCC ACG GCC GAG    3071
Arg Ala Ala Thr Ser Gly Pro Arg Arg Tyr Pro Gly Pro Thr Ala Glu
        1010                1015                1020

CCT CTG GCC GGA GAT CGG CCG CCC ACG GGG GGC CAC AGC AGC GGC CGC    3119
Pro Leu Ala Gly Asp Arg Pro Pro Thr Gly Gly His Ser Ser Gly Arg
        1025                1030                1035

TCG CCC AGG ATG GAG AGG CGG GTC CCA GGC CCG GCC CGG AGC GAG TCC    3167
Ser Pro Arg Met Glu Arg Arg Val Pro Gly Pro Ala Arg Ser Glu Ser
1040                1045                1050                1055

CCC AGG GCC TGT CGA CAC GGC GGG GCC CGG TGG CCG GCA TCT GGC CCG    3215
Pro Arg Ala Cys Arg His Gly Gly Ala Arg Trp Pro Ala Ser Gly Pro
                1060                1065                1070

CAC GTG TCC GAG GGG CCC CCG GGT CCC CGG CAC CAT GGC TAC TAC CGG    3263
His Val Ser Glu Gly Pro Pro Gly Pro Arg His His Gly Tyr Tyr Arg
        1075                1080                1085

GGC TCC GAC TAC GAC GAG GCC GAT GGC CCG GGC AGC GGG GGC GGC GAG    3311
Gly Ser Asp Tyr Asp Glu Ala Asp Gly Pro Gly Ser Gly Gly Gly Glu
        1090                1095                1100

GAG GCC ATG GCC GGG GCC TAC GAC GCG CCA CCC CCC GTA CGA CAC GCG    3359
Glu Ala Met Ala Gly Ala Tyr Asp Ala Pro Pro Pro Val Arg His Ala
        1105                1110                1115

TCC TCG GGC GCC ACC GGG CGC TCG CCC AGG ACT CCC CGG GCC TCG GGC    3407
Ser Ser Gly Ala Thr Gly Arg Ser Pro Arg Thr Pro Arg Ala Ser Gly
1120                1125                1130                1135

CCG GCC TGC GCC TCG CCT TCT CGG CAC GGC CGG CGA CTC CCC AAC GGC    3455
Pro Ala Cys Ala Ser Pro Ser Arg His Gly Arg Arg Leu Pro Asn Gly
                1140                1145                1150

TAC TAC CCG GCG CAC GGA CTG GCC AGG CCC CGC GGG CCG GGC TCC AGG    3503
Tyr Tyr Pro Ala His Gly Leu Ala Arg Pro Arg Gly Pro Gly Ser Arg
        1155                1160                1165

AAG GGC CTG CAC GAA CCC TAC AGC GAG AGT GAC GAT GAT TGG TGC TA     3550
Lys Gly Leu His Glu Pro Tyr Ser Glu Ser Asp Asp Asp Trp Cys
        1170                1175                1180

AGCCCGGGCG AGG                                                      3563

(2) INFORMATION FOR SEQ ID NO:21:

(i) SEQUENCE CHARACTERISTICS:
        (A) LENGTH: 1182 amino acids
        (B) TYPE: amino acid
        (D) TOPOLOGY: linear (ii) MOLECULE TYPE: protein (xi) SEQUENCE DESCRIPTION: SEQ ID NO:21:

Ile Leu Pro Leu Asp Phe Ile Val Val Ser Gly Ala Leu Val Ala Phe
 1               5                  10                  15

Ala Phe Thr Gly Asn Ser Lys Gly Lys Asp Ile Asn Thr Ile Lys Ser
                20                  25                  30

Leu Arg Val Leu Arg Val Leu Arg Pro Leu Lys Thr Ile Lys Arg Leu
        35                  40                  45

Pro Lys Leu Lys Ala Val Phe Asp Cys Val Val Asn Ser Leu Lys Asn
    50                  55                  60

Val Phe Asn Ile Leu Ile Val Tyr Met Leu Phe Met Phe Ile Phe Ala
65                  70                  75                  80

Val Val Ala Val Gln Leu Phe Lys Gly Lys Phe Phe His Cys Thr Asp
                85                  90                  95

Glu Ser Lys Glu Phe Glu Lys Asp Cys Arg Gly Lys Tyr Leu Leu Tyr
            100                 105                 110
```

-continued

```
Glu Lys Asn Glu Val Lys Ala Arg Asp Arg Glu Trp Lys Lys Tyr Glu
            115                 120                 125
Phe His Tyr Asp Asn Val Leu Trp Ala Leu Leu Thr Leu Phe Thr Val
        130                 135                 140
Ser Thr Gly Glu Gly Trp Pro Gln Val Leu Lys His Ser Val Asp Ala
145                 150                 155                 160
Thr Phe Glu Asn Gln Gly Pro Ser Pro Gly Tyr Arg Met Glu Met Ser
                165                 170                 175
Ile Phe Tyr Val Val Tyr Phe Val Val Phe Pro Phe Phe Val Asn
            180                 185                 190
Ile Phe Val Ala Leu Ile Ile Ile Thr Phe Gln Glu Gln Gly Asp Lys
            195                 200                 205
Met Met Glu Glu Tyr Ser Leu Glu Lys Asn Glu Arg Ala Cys Ile Asp
    210                 215                 220
Phe Ala Ile Ser Ala Lys Pro Leu Thr Arg His Met Pro Gln Asn Lys
225                 230                 235                 240
Gln Ser Phe Gln Tyr Arg Met Trp Gln Phe Val Val Ser Pro Pro Phe
                245                 250                 255
Glu Tyr Thr Ile Met Ala Met Ile Ala Leu Asn Thr Ile Val Leu Met
                260                 265                 270
Met Lys Phe Tyr Gly Ala Ser Val Ala Tyr Glu Asn Ala Leu Arg Val
            275                 280                 285
Phe Asn Ile Val Phe Thr Ser Leu Phe Ser Leu Glu Cys Val Leu Lys
            290                 295                 300
Val Met Ala Phe Gly Ile Leu Asn Tyr Phe Arg Asp Ala Trp Asn Ile
305                 310                 315                 320
Phe Asp Phe Val Thr Val Leu Gly Ser Ile Thr Asp Ile Leu Val Thr
                325                 330                 335
Glu Phe Gly Asn Asn Phe Ile Asn Leu Ser Phe Leu Arg Leu Phe Arg
                340                 345                 350
Ala Ala Arg Leu Ile Lys Leu Leu Arg Gln Gly Tyr Thr Ile Arg Ile
            355                 360                 365
Leu Leu Trp Thr Phe Val Gln Ser Phe Lys Ala Leu Pro Tyr Val Cys
370                 375                 380
Leu Leu Ile Ala Met Leu Phe Phe Ile Tyr Ala Ile Ile Gly Met Gln
385                 390                 395                 400
Val Phe Gly Asn Ile Gly Ile Asp Val Glu Asp Glu Asp Ser Asp Glu
                405                 410                 415
Asp Glu Phe Gln Ile Thr Glu His Asn Asn Phe Arg Thr Phe Phe Gln
                420                 425                 430
Ala Leu Met Leu Leu Phe Arg Ser Ala Thr Gly Glu Ala Trp His Asn
            435                 440                 445
Ile Met Leu Ser Cys Leu Ser Gly Lys Pro Cys Asp Lys Asn Ser Gly
    450                 455                 460
Ile Leu Thr Arg Glu Cys Gly Asn Glu Phe Ala Tyr Phe Tyr Phe Val
465                 470                 475                 480
Ser Phe Ile Phe Leu Cys Ser Phe Leu Met Leu Asn Leu Phe Val Ala
                485                 490                 495
Val Ile Met Asp Asn Phe Glu Tyr Leu Thr Arg Asp Ser Ser Ile Leu
                500                 505                 510
Gly Pro His His Leu Asp Glu Tyr Val Arg Val Trp Ala Glu Tyr Asp
            515                 520                 525
```

-continued

```
Pro Ala Ala Trp Gly Arg Met Pro Tyr Leu Asp Met Tyr Gln Met Leu
530                 535                 540
Arg His Met Ser Pro Pro Leu Gly Leu Gly Lys Lys Cys Pro Ala Arg
545                 550                 555                 560
Val Ala Tyr Lys Arg Leu Leu Arg Met Asp Leu Pro Val Ala Asp Asp
                565                 570                 575
Asn Thr Val His Phe Asn Ser Thr Leu Met Ala Leu Ile Arg Thr Ala
            580                 585                 590
Leu Asp Ile Lys Ile Ala Lys Gly Gly Ala Asp Lys Gln Gln Met Asp
        595                 600                 605
Ala Glu Leu Arg Lys Glu Met Met Ala Ile Trp Pro Asn Leu Ser Gln
610                 615                 620
Lys Thr Leu Asp Leu Leu Val Thr Pro His Lys Ser Thr Asp Leu Thr
625                 630                 635                 640
Val Gly Lys Ile Tyr Ala Ala Met Met Ile Met Glu Tyr Tyr Arg Gln
                645                 650                 655
Ser Lys Ala Lys Lys Leu Gln Ala Met Arg Glu Glu Gln Asp Arg Thr
            660                 665                 670
Pro Leu Met Phe Gln Arg Met Glu Pro Pro Ser Pro Thr Gln Glu Gly
        675                 680                 685
Gly Pro Gly Gln Asn Ala Leu Pro Ser Thr Gln Leu Asp Pro Gly Gly
690                 695                 700
Ala Leu Met Ala His Glu Ser Gly Leu Lys Glu Ser Pro Ser Trp Val
705                 710                 715                 720
Thr Gln Arg Ala Gln Glu Met Phe Gln Lys Thr Gly Thr Trp Ser Pro
                725                 730                 735
Glu Gln Gly Pro Pro Thr Asp Met Pro Asn Ser Gln Pro Asn Ser Gln
            740                 745                 750
Ser Val Glu Met Arg Glu Met Gly Arg Asp Gly Tyr Ser Asp Ser Glu
        755                 760                 765
His Tyr Leu Pro Met Glu Gly Gln Gly Arg Ala Ala Ser Met Pro Arg
770                 775                 780
Leu Pro Ala Glu Asn Gln Thr Ile Ser Asp Thr Ser Pro Met Lys Arg
785                 790                 795                 800
Ser Ala Ser Val Leu Gly Pro Lys Ala Arg Arg Leu Asp Asp Tyr Ser
                805                 810                 815
Leu Glu Arg Val Pro Pro Glu Glu Asn Gln Arg His His Gln Arg Arg
            820                 825                 830
Arg Asp Arg Ser His Arg Ala Ser Glu Arg Ser Leu Gly Arg Tyr Thr
        835                 840                 845
Asp Val Asp Thr Gly Leu Gly Thr Asp Leu Ser Met Thr Thr Gln Ser
850                 855                 860
Gly Asp Leu Pro Ser Lys Glu Arg Asp Gln Glu Arg Gly Arg Pro Lys
865                 870                 875                 880
Asp Arg Lys His Arg Gln His His His His His His His His His His
                885                 890                 895
Pro Pro Pro Pro Asp Lys Asp Arg Tyr Ala Gln Glu Arg Pro Asp His
            900                 905                 910
Gly Arg Ala Arg Ala Arg Asp Gln Arg Trp Ser Arg Ser Pro Ser Glu
        915                 920                 925
Gly Arg Glu His Met Ala His Arg Gln Gly Ser Ser Val Ser Gly
930                 935                 940
Ser Pro Ala Pro Ser Thr Ser Gly Thr Ser Thr Pro Arg Arg Gly Arg
```

```
945                 950                 955                 960
Arg Gln Leu Pro Gln Thr Pro Ser Thr Pro Arg Pro His Val Ser Tyr
                965                 970                 975
Ser Pro Val Ile Arg Lys Ala Gly Gly Ser Gly Pro Pro Gln Gln Gln
            980                 985                 990
Gln Gln Gln Gln Gln Gln Gln Gln Ala Val Ala Arg Pro Gly Arg
        995                 1000                1005
Ala Ala Thr Ser Gly Pro Arg Arg Tyr Pro Gly Pro Thr Ala Glu Pro
    1010                1015                1020
Leu Ala Gly Asp Arg Pro Pro Thr Gly Gly His Ser Ser Gly Arg Ser
1025                1030                1035                1040
Pro Arg Met Glu Arg Arg Val Pro Gly Pro Ala Arg Ser Glu Ser Pro
                1045                1050                1055
Arg Ala Cys Arg His Gly Gly Ala Arg Trp Pro Ala Ser Gly Pro His
                1060                1065                1070
Val Ser Glu Gly Pro Pro Gly Pro Arg His His Gly Tyr Tyr Arg Gly
            1075                1080                1085
Ser Asp Tyr Asp Glu Ala Asp Gly Pro Gly Ser Gly Gly Gly Glu Glu
    1090                1095                1100
Ala Met Ala Gly Ala Tyr Asp Ala Pro Pro Val Arg His Ala Ser
1105                1110                1115                1120
Ser Gly Ala Thr Gly Arg Ser Pro Arg Thr Pro Arg Ala Ser Gly Pro
                1125                1130                1135
Ala Cys Ala Ser Pro Ser Arg His Gly Arg Arg Leu Pro Asn Gly Tyr
                1140                1145                1150
Tyr Pro Ala His Gly Leu Ala Arg Pro Arg Gly Pro Gly Ser Arg Lys
            1155                1160                1165
Gly Leu His Glu Pro Tyr Ser Glu Ser Asp Asp Asp Trp Cys
    1170                1175                1180
```

(2) INFORMATION FOR SEQ ID NO:22:

(i) SEQUENCE CHARACTERISTICS:
        (A) LENGTH: 4279 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 239..3794

(xi) SEQUENCE DESCRIPTION: SEQ ID NO:22:

```
GAATTCCGCC CCCCTCAGAG GCGCCGGAGC CCGGAATCCC GCTCGGAGCC AGCCAGCCGT      60

CCCGAGCTAC CAGCAGGTTT CATTGAAAAC AGATCCTGCA AAAGTTCCAG GTGCCCACAC     120

TGGAAACTTG GAGATCCTGC TTCCCAGACC ACAGCTGTGG GGAACTTGGG GTGGAGCAGA     180

GAAGTTTCTG TATTCAGCTG CCCAGGCAGA GGAGAATGGG GTCTCCACAG CCTGAAGA      238

ATG AAG ACA CGA CAG AAT AAA GAC TCG ATG TCA ATG AGG AGT GGA CGG      286
Met Lys Thr Arg Gln Asn Lys Asp Ser Met Ser Met Arg Ser Gly Arg
  1               5                  10                  15

AAG AAA GAG GCC CCT GGG CCC CGG GAA GAA CTG AGA TCG AGG GGC CGG      334
Lys Lys Glu Ala Pro Gly Pro Arg Glu Glu Leu Arg Ser Arg Gly Arg
                 20                  25                  30

GCC TCC CCT GGA GGG GTC AGC ACG TCC AGC AGT GAT GGC AAA GCT GAG      382
Ala Ser Pro Gly Gly Val Ser Thr Ser Ser Ser Asp Gly Lys Ala Glu
```

```
               35                   40                   45
AAG TCC AGG CAG ACA GCC AAG AAG GCC CGA GTA GAG GAA GCC TCC ACC        430
Lys Ser Arg Gln Thr Ala Lys Lys Ala Arg Val Glu Glu Ala Ser Thr
         50                   55                   60

CCA AAG GTC AAC AAG CAG GGT CGG AGT GAG GAG ATC TCA GAG AGT GAA        478
Pro Lys Val Asn Lys Gln Gly Arg Ser Glu Glu Ile Ser Glu Ser Glu
 65                   70                   75                   80

AGT GAG GAG ACC AAT GCA CCA AAA AAG ACC AAA ACT GAG CAG GAA CTC        526
Ser Glu Glu Thr Asn Ala Pro Lys Lys Thr Lys Thr Glu Gln Glu Leu
                 85                   90                   95

CCT CGG CCA CAG TCT CCC TCC GAT CTG GAT AGC TTG GAC GGG CGG AGC        574
Pro Arg Pro Gln Ser Pro Ser Asp Leu Asp Ser Leu Asp Gly Arg Ser
             100                  105                  110

CTT AAT GAT GAT GGC AGC AGC GAC CCT AGG GAT ATC GAC CAG GAC AAC        622
Leu Asn Asp Asp Gly Ser Ser Asp Pro Arg Asp Ile Asp Gln Asp Asn
         115                  120                  125

CGA AGC ACG TCC CCC AGT ATC TAC AGC CCT GGA AGT GTG GAG AAT GAC        670
Arg Ser Thr Ser Pro Ser Ile Tyr Ser Pro Gly Ser Val Glu Asn Asp
     130                  135                  140

TCT GAC TCA TCT TCT GGC CTG TCC CAG GGC CCA GCC CGC CCC TAC CAC        718
Ser Asp Ser Ser Ser Gly Leu Ser Gln Gly Pro Ala Arg Pro Tyr His
145                  150                  155                  160

CCA CCT CCA CTC TTT CCT CCT TCC CCT CAA CCG CCA GAC AGC ACC CCT        766
Pro Pro Pro Leu Phe Pro Pro Ser Pro Gln Pro Pro Asp Ser Thr Pro
                 165                  170                  175

CGA CAG CCA GAG GCT AGC TTT GAA CCC CAT CCT TCT GTG ACA CCC ACT        814
Arg Gln Pro Glu Ala Ser Phe Glu Pro His Pro Ser Val Thr Pro Thr
             180                  185                  190

GGA TAT CAT GCT CCC ATG GAG CCC CCC ACA TCT CGA ATG TTC CAG GCT        862
Gly Tyr His Ala Pro Met Glu Pro Pro Thr Ser Arg Met Phe Gln Ala
         195                  200                  205

CCT CCT GGG GCC CCT CCC CCT CAC CCA CAG CTC TAT CCT GGG GGC ACT        910
Pro Pro Gly Ala Pro Pro Pro His Pro Gln Leu Tyr Pro Gly Gly Thr
     210                  215                  220

GGT GGT GTT TTG TCT GGA CCC CCA ATG GGT CCC AAG GGG GGA GGG GCT        958
Gly Gly Val Leu Ser Gly Pro Pro Met Gly Pro Lys Gly Gly Gly Ala
225                  230                  235                  240

GCC TCA TCA GTG GGG GGC CCT AAT GGG GGT AAG CAG CAC CCC CCA CCC       1006
Ala Ser Ser Val Gly Gly Pro Asn Gly Gly Lys Gln His Pro Pro Pro
                 245                  250                  255

ACT ACT CCC ATT TCA GTA TCA AGC TCT GGG GCT AGT GGT GCT CCC CCA       1054
Thr Thr Pro Ile Ser Val Ser Ser Ser Gly Ala Ser Gly Ala Pro Pro
             260                  265                  270

ACA AAG CCG CCT ACC ACT CCA GTG GGT GGT GGG AAC CTA CCT TCT GCT       1102
Thr Lys Pro Pro Thr Thr Pro Val Gly Gly Gly Asn Leu Pro Ser Ala
         275                  280                  285

CCA CCA CCA GCC AAC TTC CCC CAT GTG ACA CCG AAC CTG CCT CCC CCA       1150
Pro Pro Pro Ala Asn Phe Pro His Val Thr Pro Asn Leu Pro Pro Pro
     290                  295                  300

CCT GCC CTG AGA CCC CTC AAC AAT GCA TCA GCC TCT CCC CCT GGC CTG       1198
Pro Ala Leu Arg Pro Leu Asn Asn Ala Ser Ala Ser Pro Pro Gly Leu
305                  310                  315                  320

GGG GCC CAA CCA CTA CCT GGT CAT CTG CCC TCT CCC TAC GCC ATG GGA       1246
Gly Ala Gln Pro Leu Pro Gly His Leu Pro Ser Pro Tyr Ala Met Gly
                 325                  330                  335

CAG GGT ATG GGT GGA CTT CCT CCT GGC CCA GAG AAG GGC CCA ACT CTG       1294
Gln Gly Met Gly Gly Leu Pro Pro Gly Pro Glu Lys Gly Pro Thr Leu
             340                  345                  350

GCT CCT TCA CCC CAC TCT CTG CCT CCT GCT TCC TCT TCT GCT CCA GCG       1342
```

```
                                                          -continued

Ala Pro Ser Pro His Ser Leu Pro Ala Ser Ser Ala Pro Ala
        355                 360             365

CCC CCC ATG AGG TTT CCT TAT TCA TCC TCT AGT AGT AGC TCT GCA GCA      1390
Pro Pro Met Arg Phe Pro Tyr Ser Ser Ser Ser Ser Ser Ala Ala
        370                 375             380

GCC TCC TCT TCC AGT TCT TCC TCC TCT TCC TCT GCC TCC CCC TTC CCA      1438
Ala Ser Ser Ser Ser Ser Ser Ser Ser Ser Ser Ala Ser Pro Phe Pro
385                 390                 395                 400

GCT TCC CAG GCA TTG CCC AGC TAC CCC CAC TCT TTC CCT CCC CCA ACA      1486
Ala Ser Gln Ala Leu Pro Ser Tyr Pro His Ser Phe Pro Pro Pro Thr
                    405                 410                 415

AGC CTC TCT GTC TCC AAT CAG CCC CCC AAG TAT ACT CAG CCT TCT CTC      1534
Ser Leu Ser Val Ser Asn Gln Pro Pro Lys Tyr Thr Gln Pro Ser Leu
                420                 425                 430

CCA TCC CAG GCT GTG TGG AGC CAG GGT CCC CCA CCA CCT CCT CCC TAT      1582
Pro Ser Gln Ala Val Trp Ser Gln Gly Pro Pro Pro Pro Pro Pro Tyr
            435                 440                 445

GGC CGC CTC TTA GCC AAC AGC AAT GCC CAT CCA GGC CCC TTC CCT CCC      1630
Gly Arg Leu Leu Ala Asn Ser Asn Ala His Pro Gly Pro Phe Pro Pro
        450                 455                 460

TCT ACT GGG GCC CAG TCC ACC GCC CAC CCA CCA GTC TCA ACA CAT CAC      1678
Ser Thr Gly Ala Gln Ser Thr Ala His Pro Pro Val Ser Thr His His
465                 470                 475                 480

CAT CAC CAC CAG CAA CAG CAA CAG CAG CAG CAG CAG CAG CAG CAG CAG      1726
His His His Gln Gln Gln Gln Gln Gln Gln Gln Gln Gln Gln Gln Gln
                    485                 490                 495

CAG CAT CAC GGA AAC TCT GGG CCC CCT CCT CCT GGA GCA TTT CCC CAC      1774
Gln His His Gly Asn Ser Gly Pro Pro Pro Pro Gly Ala Phe Pro His
                500                 505                 510

CCA CTG GAG GGC GGT AGC TCC CAC CAC GCA CAC CCT TAC GCC ATG TCT      1822
Pro Leu Glu Gly Gly Ser Ser His His Ala His Pro Tyr Ala Met Ser
            515                 520                 525

CCC TCC CTG GGG TCT CTG AGG CCC TAC CCA CCA GGG CCA GCA CAC CTG      1870
Pro Ser Leu Gly Ser Leu Arg Pro Tyr Pro Pro Gly Pro Ala His Leu
        530                 535                 540

CCC CCA CCT CAC AGC CAG GTG TCC TAC AGC CAA GCA GGC CCC AAT GGC      1918
Pro Pro Pro His Ser Gln Val Ser Tyr Ser Gln Ala Gly Pro Asn Gly
545                 550                 555                 560

CCT CCA GTC TCT TCC TCT TCC AAC TCT TCC TCT TCC ACT TCT CAA GGG      1966
Pro Pro Val Ser Ser Ser Ser Asn Ser Ser Ser Ser Thr Ser Gln Gly
                565                 570                 575

TCC TAC CCA TGT TCA CAC CCC TCC CCT TCC CAG GGC CCT CAA GGG GCG      2014
Ser Tyr Pro Cys Ser His Pro Ser Pro Ser Gln Gly Pro Gln Gly Ala
            580                 585                 590

CCC TAC CCT TTC CCA CCG GTG CCT ACG GTC ACC ACC TCT TCG GCT ACC      2062
Pro Tyr Pro Phe Pro Pro Val Pro Thr Val Thr Thr Ser Ser Ala Thr
        595                 600                 605

CTT TCC ACG GTC ATT GCC ACC GTG GCT TCC TCG CCA GCA GGC TAC AAA      2110
Leu Ser Thr Val Ile Ala Thr Val Ala Ser Ser Pro Ala Gly Tyr Lys
    610                 615                 620

ACG GCC TCC CCA CCT GGG CCC CCA CCG TAC GGA AAG AGA GCC CCG TCC      2158
Thr Ala Ser Pro Pro Gly Pro Pro Pro Tyr Gly Lys Arg Ala Pro Ser
625                 630                 635                 640

CCG GGG GCC TAC AAG ACA GCC ACC CCA CCC GGA TAC AAA CCC GGG TCG      2206
Pro Gly Ala Tyr Lys Thr Ala Thr Pro Pro Gly Tyr Lys Pro Gly Ser
                    645                 650                 655

CCT CCC TCC TTC CGA ACG GGG ACC CCA CCG GGC TAT CGA GGA ACC TCG      2254
Pro Pro Ser Phe Arg Thr Gly Thr Pro Pro Gly Tyr Arg Gly Thr Ser
                660                 665                 670
```

```
CCA CCT GCA GGC CCA GGG ACC TTC AAG CCG GGC TCG CCC ACC GTG GGA      2302
Pro Pro Ala Gly Pro Gly Thr Phe Lys Pro Gly Ser Pro Thr Val Gly
            675                 680                 685

CCT GGG CCC CTG CCA CCT GCG GGG CCC TCA GGC CTG CCA TCG CTG CCA      2350
Pro Gly Pro Leu Pro Pro Ala Gly Pro Ser Gly Leu Pro Ser Leu Pro
690                 695                 700

CCA CCA CCT GCG GCC CCT GCC TCA GGG CCG CCC CTG AGC GCC ACG CAG      2398
Pro Pro Pro Ala Ala Pro Ala Ser Gly Pro Pro Leu Ser Ala Thr Gln
705                 710                 715                 720

ATC AAA CAG GAG CCG GCT GAG GAG TAT GAG ACC CCC GAG AGC CCG GTG      2446
Ile Lys Gln Glu Pro Ala Glu Glu Tyr Glu Thr Pro Glu Ser Pro Val
            725                 730                 735

CCC CCA GCC CGC AGC CCC TCG CCC CCT CCC AAG GTG GTA GAT GTA CCC      2494
Pro Pro Ala Arg Ser Pro Ser Pro Pro Pro Lys Val Val Asp Val Pro
            740                 745                 750

AGC CAT GCC AGT CAG TCT GCC AGG TTC AAC AAA CAC CTG GAT CGC GGC      2542
Ser His Ala Ser Gln Ser Ala Arg Phe Asn Lys His Leu Asp Arg Gly
            755                 760                 765

TTC AAC TCG TGC GCG CGC AGC GAC CTG TAC TTC GTG CCA CTG GAG GGC      2590
Phe Asn Ser Cys Ala Arg Ser Asp Leu Tyr Phe Val Pro Leu Glu Gly
770                 775                 780

TCC AAG CTG GCC AAG AAG CGG GCC GAC CTG GTG GAG AAG GTG CGG CGC      2638
Ser Lys Leu Ala Lys Lys Arg Ala Asp Leu Val Glu Lys Val Arg Arg
785                 790                 795                 800

GAG GCC GAG CAG CGC GCG CGC GAA GAA AAG GAG CGC GAG CGC GAG CGG      2686
Glu Ala Glu Gln Arg Ala Arg Glu Glu Lys Glu Arg Glu Arg Glu Arg
                805                 810                 815

GAA CGC GAG AAA GAG CGC GAG CGC GAG AAG GAG CGC GAG CTT GAA CGC      2734
Glu Arg Glu Lys Glu Arg Glu Arg Glu Lys Glu Arg Glu Leu Glu Arg
            820                 825                 830

AGC GTG AAG TTG GCT CAG GAG GGC CGT GCT CCG GTG GAA TGC CCA TCT      2782
Ser Val Lys Leu Ala Gln Glu Gly Arg Ala Pro Val Glu Cys Pro Ser
            835                 840                 845

CTG GGC CCA GTG CCC CAT CGC CCT CCA TTT GAA CCG GGC AGT GCG GTG      2830
Leu Gly Pro Val Pro His Arg Pro Pro Phe Glu Pro Gly Ser Ala Val
850                 855                 860

GCT ACA GTG CCC CCC TAC CTG GGT CCT GAC ACT CCA GCC TTG CGC ACT      2878
Ala Thr Val Pro Pro Tyr Leu Gly Pro Asp Thr Pro Ala Leu Arg Thr
865                 870                 875                 880

CTC AGT GAA TAT GCC CGG CCT CAT GTC ATG TCT CCT GGC AAT CGC AAC      2926
Leu Ser Glu Tyr Ala Arg Pro His Val Met Ser Pro Gly Asn Arg Asn
                885                 890                 895

CAT CCA TTC TAC GTG CCC CTG GGG GCA GTG GAC CCG GGG CTC CTG GGT      2974
His Pro Phe Tyr Val Pro Leu Gly Ala Val Asp Pro Gly Leu Leu Gly
            900                 905                 910

TAC AAT GTC CCG GCC CTG TAC AGC AGT GAT CCA GCT GCC CGG GAG AGG      3022
Tyr Asn Val Pro Ala Leu Tyr Ser Ser Asp Pro Ala Ala Arg Glu Arg
            915                 920                 925

GAA CGG GAA GCC CGT GAA CGA GAC CTC CGT GAC CGC CTC AAG CCT GGC      3070
Glu Arg Glu Ala Arg Glu Arg Asp Leu Arg Asp Arg Leu Lys Pro Gly
930                 935                 940

TTT GAG GTG AAG CCT AGT GAG CTG GAA CCC CTA CAT GGG GTC CCT GGG      3118
Phe Glu Val Lys Pro Ser Glu Leu Glu Pro Leu His Gly Val Pro Gly
945                 950                 955                 960

CCG GGC TTG GAT CCC TTT CCC CGA CAT GGG GCT GGC TCT GCA GCC T        3166
Pro Gly Leu Asp Pro Phe Pro Arg His Gly Gly Leu Ala Leu Gln Pro
            965                 970                 975

GGC CCA CCT GGC CTG CAC CCT TTC CCC TTT CAT CCG AGC CTG GGG CCC      3214
Gly Pro Pro Gly Leu His Pro Phe Pro Phe His Pro Ser Leu Gly Pro
            980                 985                 990
```

-continued

| | |
|---|---|
| CTG GAG CGA GAA CGT CTA GCG CTG GCA GCT GGG CCA GCC CTG CGG CCT<br>Leu Glu Arg Glu Arg Leu Ala Leu Ala Ala Gly Pro Ala Leu Arg Pro<br>        995                    1000                    1005 | 3262 |
| GAC ATG TCC TAT GCT GAG CGG CTG GCA GCT GAG AGG CAG CAC GCA GAA<br>Asp Met Ser Tyr Ala Glu Arg Leu Ala Ala Glu Arg Gln His Ala Glu<br>        1010                    1015                    1020 | 3310 |
| AGG GTG GCG GGC CTG GGC AAT GAC CCA CTG GCC CGG CTG CAG ATG CTC<br>Arg Val Ala Gly Leu Gly Asn Asp Pro Leu Ala Arg Leu Gln Met Leu<br>1025                    1030                    1035                    1040 | 3358 |
| AAT GTG ACT CCC CAT CAC CAC CAG CAC TCC CAC ATC CAC TCG CAC CTG<br>Asn Val Thr Pro His His His Gln His Ser His Ile His Ser His Leu<br>                1045                    1050                    1055 | 3406 |
| CAC CTG CAC CAG CAA GAT GCT ATC CAT GCA GCC TCT GCC TCG GTG CAC<br>His Leu His Gln Gln Asp Ala Ile His Ala Ala Ser Ala Ser Val His<br>        1060                    1065                    1070 | 3454 |
| CCT CTC ATT GAC CCC CTG GCC TCA GGG TCT CAC CTT ACC CGG ATC CCC<br>Pro Leu Ile Asp Pro Leu Ala Ser Gly Ser His Leu Thr Arg Ile Pro<br>        1075                    1080                    1085 | 3502 |
| TAC CCA GCT GGA ACT CTC CCT AAC CCC CTG CTT CCT CAC CCT CTG CAC<br>Tyr Pro Ala Gly Thr Leu Pro Asn Pro Leu Leu Pro His Pro Leu His<br>        1090                    1095                    1100 | 3550 |
| GAG AAC GAA GTT CTT CGT CAC CAG CTC TTT GCT GCC CCT TAC CGG GAC<br>Glu Asn Glu Val Leu Arg His Gln Leu Phe Ala Ala Pro Tyr Arg Asp<br>1105                    1110                    1115                    1120 | 3598 |
| CTG CCG GCC TCC CTT TCT GCC CCG ATG TCA GCA GCT CAT CAG CTG CAG<br>Leu Pro Ala Ser Leu Ser Ala Pro Met Ser Ala Ala His Gln Leu Gln<br>                1125                    1130                    1135 | 3646 |
| GCC ATG CAC GCA CAG TCA GCT GAG CTG CAG CGC TTG GCG CTG GAA CAG<br>Ala Met His Ala Gln Ser Ala Glu Leu Gln Arg Leu Ala Leu Glu Gln<br>        1140                    1145                    1150 | 3694 |
| CAG CAG TGG CTG CAT GCC CAT CAC CCG CTG CAC AGT GTG CCG CTG CCT<br>Gln Gln Trp Leu His Ala His His Pro Leu His Ser Val Pro Leu Pro<br>        1155                    1160                    1165 | 3742 |
| GCC CAG GAG GAC TAC TAC AGT CAC CTG AAG AAG GAA AGC GAC AAG CCA<br>Ala Gln Glu Asp Tyr Tyr Ser His Leu Lys Lys Glu Ser Asp Lys Pro<br>        1170                    1175                    1180 | 3790 |
| CTG T AGAACCTGCG ATCAAGAGAG CACCATGGCT CCTACATTGG ACCTTGGAGC<br>Leu<br>118 | 3844 |
| ACCCCCACCC TCCCCCCACC GTGCCCTTGG CCTGCCACCC AGAGCCAAGA GGGTACTGCT | 3904 |
| CAGTTGCAGG GCCTCCGCAG CTGGACAGAG AGTGGGGGAG GGAGGGACAG ACAGAAGGCC | 3964 |
| AAGGCCCGAT GTGGTGTGCA GAGGTGGGGA GGTGGCGAGG ATGGGGACAG AAAGGGAACA | 4024 |
| GAATCTTGGA CCAGGTCTCT CTTCCTTGTC CCCCCTGCTT TTCTCCTCCC CCATGCCCAA | 4084 |
| CCCCTGTGGC CGCCGCCCCT CCCCTGCCCC GTTGGTGTGA TTATTTCATC TGTTAGATGT | 4144 |
| GGCTGTTTTG CGTAGCATCG TGTGCCACCC CTGCCCCTCC CCGATCCCTG TGTGCGCGCC | 4204 |
| CCCTCTGCAA TGTATGCCCC TTGCCCCTTC CCCACACTAA TAATTTATAT ATATAAATAT | 4264 |
| CTATATGACG CTCTT | 4279 |

(2) INFORMATION FOR SEQ ID NO:23:

(i) SEQUENCE CHARACTERISTICS:
        (A) LENGTH: 1185 amino acids
        (B) TYPE: amino acid
        (D) TOPOLOGY: linear (ii) MOLECULE TYPE: protein -continued (xi) SEQUENCE DESCRIPTION: SEQ ID NO:23:

```
Met Lys Thr Arg Gln Asn Lys Asp Ser Met Ser Met Arg Ser Gly Arg
 1               5                  10                  15

Lys Lys Glu Ala Pro Gly Pro Arg Glu Glu Leu Arg Ser Arg Gly Arg
            20                  25                  30

Ala Ser Pro Gly Gly Val Ser Thr Ser Ser Ser Asp Gly Lys Ala Glu
        35                  40                  45

Lys Ser Arg Gln Thr Ala Lys Lys Ala Arg Val Glu Glu Ala Ser Thr
    50                  55                  60

Pro Lys Val Asn Lys Gln Gly Arg Ser Glu Glu Ile Ser Glu Ser Glu
65                  70                  75                  80

Ser Glu Glu Thr Asn Ala Pro Lys Lys Thr Lys Thr Glu Gln Glu Leu
                85                  90                  95

Pro Arg Pro Gln Ser Pro Ser Asp Leu Asp Ser Leu Asp Gly Arg Ser
            100                 105                 110

Leu Asn Asp Asp Gly Ser Ser Asp Pro Arg Asp Ile Asp Gln Asp Asn
        115                 120                 125

Arg Ser Thr Ser Pro Ser Ile Tyr Ser Pro Gly Ser Val Glu Asn Asp
    130                 135                 140

Ser Asp Ser Ser Ser Gly Leu Ser Gln Gly Pro Ala Arg Pro Tyr His
145                 150                 155                 160

Pro Pro Pro Leu Phe Pro Pro Ser Pro Gln Pro Pro Asp Ser Thr Pro
                165                 170                 175

Arg Gln Pro Glu Ala Ser Phe Glu Pro His Pro Ser Val Thr Pro Thr
            180                 185                 190

Gly Tyr His Ala Pro Met Glu Pro Pro Thr Ser Arg Met Phe Gln Ala
        195                 200                 205

Pro Pro Gly Ala Pro Pro His Pro Gln Leu Tyr Pro Gly Gly Thr
    210                 215                 220

Gly Gly Val Leu Ser Gly Pro Pro Met Gly Pro Lys Gly Gly Gly Ala
225                 230                 235                 240

Ala Ser Ser Val Gly Gly Pro Asn Gly Lys Gln His Pro Pro Pro
                245                 250                 255

Thr Thr Pro Ile Ser Val Ser Ser Ser Gly Ala Ser Gly Ala Pro Pro
            260                 265                 270

Thr Lys Pro Pro Thr Thr Pro Val Gly Gly Gly Asn Leu Pro Ser Ala
        275                 280                 285

Pro Pro Pro Ala Asn Phe Pro His Val Thr Pro Asn Leu Pro Pro Pro
    290                 295                 300

Pro Ala Leu Arg Pro Leu Asn Asn Ala Ser Ala Ser Pro Pro Gly Leu
305                 310                 315                 320

Gly Ala Gln Pro Leu Pro Gly His Leu Pro Ser Pro Tyr Ala Met Gly
                325                 330                 335

Gln Gly Met Gly Gly Leu Pro Gly Pro Glu Lys Gly Pro Thr Leu
            340                 345                 350

Ala Pro Ser Pro His Ser Leu Pro Ala Ser Ser Ala Pro Ala
        355                 360                 365

Pro Pro Met Arg Phe Pro Tyr Ser Ser Ser Ser Ser Ser Ala Ala
    370                 375                 380

Ala Ser Ser Ser Ser Ser Ser Ser Ser Ala Ser Pro Phe Pro
385                 390                 395                 400

Ala Ser Gln Ala Leu Pro Ser Tyr Pro His Ser Phe Pro Pro Thr
                405                 410                 415
```

-continued

```
Ser Leu Ser Val Ser Asn Gln Pro Pro Lys Tyr Thr Gln Pro Ser Leu
            420                 425                 430

Pro Ser Gln Ala Val Trp Ser Gln Gly Pro Pro Pro Pro Tyr
        435                 440                 445

Gly Arg Leu Leu Ala Asn Ser Asn Ala His Pro Gly Pro Phe Pro Pro
        450                 455                 460

Ser Thr Gly Ala Gln Ser Thr Ala His Pro Pro Val Ser Thr His His
465                 470                 475                 480

His His His Gln Gln Gln Gln Gln Gln Gln Gln Gln Gln Gln
                485                 490                 495

Gln His His Gly Asn Ser Gly Pro Pro Pro Gly Ala Phe Pro His
        500                 505                 510

Pro Leu Glu Gly Gly Ser Ser His His Ala His Pro Tyr Ala Met Ser
        515                 520                 525

Pro Ser Leu Gly Ser Leu Arg Pro Tyr Pro Pro Gly Pro Ala His Leu
        530                 535                 540

Pro Pro Pro His Ser Gln Val Ser Tyr Ser Gln Ala Gly Pro Asn Gly
545                 550                 555                 560

Pro Pro Val Ser Ser Ser Asn Ser Ser Ser Thr Ser Gln Gly
                565                 570                 575

Ser Tyr Pro Cys Ser His Pro Ser Pro Ser Gln Gly Pro Gln Gly Ala
                580                 585                 590

Pro Tyr Pro Phe Pro Pro Val Pro Thr Val Thr Thr Ser Ser Ala Thr
        595                 600                 605

Leu Ser Thr Val Ile Ala Thr Val Ala Ser Ser Pro Ala Gly Tyr Lys
        610                 615                 620

Thr Ala Ser Pro Pro Gly Pro Pro Pro Tyr Gly Lys Arg Ala Pro Ser
625                 630                 635                 640

Pro Gly Ala Tyr Lys Thr Ala Thr Pro Pro Gly Tyr Lys Pro Gly Ser
                645                 650                 655

Pro Pro Ser Phe Arg Thr Gly Thr Pro Pro Gly Tyr Arg Gly Thr Ser
                660                 665                 670

Pro Pro Ala Gly Pro Gly Thr Phe Lys Pro Gly Ser Pro Thr Val Gly
        675                 680                 685

Pro Gly Pro Leu Pro Pro Ala Gly Pro Ser Gly Leu Pro Ser Leu Pro
        690                 695                 700

Pro Pro Pro Ala Ala Pro Ala Ser Gly Pro Pro Leu Ser Ala Thr Gln
705                 710                 715                 720

Ile Lys Gln Glu Pro Ala Glu Tyr Glu Thr Pro Glu Ser Pro Val
        725                 730                 735

Pro Pro Ala Arg Ser Pro Ser Pro Pro Lys Val Val Asp Val Pro
            740                 745                 750

Ser His Ala Ser Gln Ser Ala Arg Phe Asn Lys His Leu Asp Arg Gly
        755                 760                 765

Phe Asn Ser Cys Ala Arg Ser Asp Leu Tyr Phe Val Pro Leu Glu Gly
        770                 775                 780

Ser Lys Leu Ala Lys Lys Arg Ala Asp Leu Val Glu Lys Val Arg Arg
785                 790                 795                 800

Glu Ala Glu Gln Arg Ala Arg Glu Glu Lys Glu Arg Glu Arg Glu Arg
                805                 810                 815

Glu Arg Glu Lys Glu Arg Glu Arg Glu Lys Glu Arg Glu Leu Glu Arg
                820                 825                 830
```

```
Ser Val Lys Leu Ala Gln Glu Gly Arg Ala Pro Val Glu Cys Pro Ser
        835                 840                 845

Leu Gly Pro Val Pro His Arg Pro Pro Phe Glu Pro Gly Ser Ala Val
    850                 855                 860

Ala Thr Val Pro Pro Tyr Leu Gly Pro Asp Thr Pro Ala Leu Arg Thr
865                 870                 875                 880

Leu Ser Glu Tyr Ala Arg Pro His Val Met Ser Pro Gly Asn Arg Asn
                885                 890                 895

His Pro Phe Tyr Val Pro Leu Gly Ala Val Asp Pro Gly Leu Leu Gly
            900                 905                 910

Tyr Asn Val Pro Ala Leu Tyr Ser Ser Asp Pro Ala Ala Arg Glu Arg
        915                 920                 925

Glu Arg Glu Ala Arg Glu Arg Asp Leu Arg Asp Arg Leu Lys Pro Gly
    930                 935                 940

Phe Glu Val Lys Pro Ser Glu Leu Glu Pro Leu His Gly Val Pro Gly
945                 950                 955                 960

Pro Gly Leu Asp Pro Phe Pro Arg His Gly Gly Leu Ala Leu Gln Pro
                965                 970                 975

Gly Pro Pro Gly Leu His Pro Phe Pro Phe His Pro Ser Leu Gly Pro
            980                 985                 990

Leu Glu Arg Glu Arg Leu Ala Leu Ala Ala Gly Pro Ala Leu Arg Pro
        995                 1000                1005

Asp Met Ser Tyr Ala Glu Arg Leu Ala Ala Glu Arg Gln His Ala Glu
    1010                1015                1020

Arg Val Ala Gly Leu Gly Asn Asp Pro Leu Ala Arg Leu Gln Met Leu
1025                1030                1035                1040

Asn Val Thr Pro His His His Gln His Ser His Ile His Ser His Leu
                1045                1050                1055

His Leu His Gln Gln Asp Ala Ile His Ala Ala Ser Ala Ser Val His
            1060                1065                1070

Pro Leu Ile Asp Pro Leu Ala Ser Gly Ser His Leu Thr Arg Ile Pro
        1075                1080                1085

Tyr Pro Ala Gly Thr Leu Pro Asn Pro Leu Leu Pro His Pro Leu His
    1090                1095                1100

Glu Asn Glu Val Leu Arg His Gln Leu Phe Ala Ala Pro Tyr Arg Asp
1105                1110                1115                1120

Leu Pro Ala Ser Leu Ser Ala Pro Met Ser Ala His Gln Leu Gln
                1125                1130                1135

Ala Met His Ala Gln Ser Ala Glu Leu Gln Arg Leu Ala Leu Glu Gln
            1140                1145                1150

Gln Gln Trp Leu His Ala His Pro Leu His Ser Val Pro Leu Pro
        1155                1160                1165

Ala Gln Glu Asp Tyr Tyr Ser His Leu Lys Lys Glu Ser Asp Lys Pro
    1170                1175                1180

Leu
1185

(2) INFORMATION FOR SEQ ID NO:24:

(i) SEQUENCE CHARACTERISTICS:
        (A) LENGTH: 4608 base pairs
        (B) TYPE: nucleic acid
        (C) STRANDEDNESS: single
        (D) TOPOLOGY: linear (ii) MOLECULE TYPE: DNA (genomic)
```

(ix) FEATURE:
    (A) NAME/KEY: CDS
    (B) LOCATION: 1..4342

(xi) SEQUENCE DESCRIPTION: SEQ ID NO:24:

```
ATG GAG AAT AGT CTT AGA TGT GTT TGG GTA CCC AAG CTG GCT TTT GTA        48
Met Glu Asn Ser Leu Arg Cys Val Trp Val Pro Lys Leu Ala Phe Val
1               5                  10                  15

CTC TTC GGA GCT TCC TTG CTC AGC GCG CAT CTT CAA GTA ACC GGT TTT        96
Leu Phe Gly Ala Ser Leu Leu Ser Ala His Leu Gln Val Thr Gly Phe
              20                  25                  30

CAA ATT AAA GCT TTC ACA GCA CTG CGC TTC CTC TCA GAA CCT TCT GAT       144
Gln Ile Lys Ala Phe Thr Ala Leu Arg Phe Leu Ser Glu Pro Ser Asp
          35                  40                  45

GCC GTC ACA ATG CGG GGA GGA AAT GTC CTC CTC GAC TGC TCC GCG GAG       192
Ala Val Thr Met Arg Gly Gly Asn Val Leu Leu Asp Cys Ser Ala Glu
      50                  55                  60

TCC GAC CGA GGA GTT CCA GTG ATC AAG TGG AAG AAA GAT GGC ATT CAT       240
Ser Asp Arg Gly Val Pro Val Ile Lys Trp Lys Lys Asp Gly Ile His
65                  70                  75                  80

CTG GCC TTG GGA ATG GAT GAA AGG AAG CAG CAA CTT TCA AAT GGG TCT       288
Leu Ala Leu Gly Met Asp Glu Arg Lys Gln Gln Leu Ser Asn Gly Ser
              85                  90                  95

CTG CTG ATA CAA AAC ATA CTT CAT TCC AGA CAC CAC AAG CCA GAT GAG       336
Leu Leu Ile Gln Asn Ile Leu His Ser Arg His His Lys Pro Asp Glu
         100                 105                 110

GGA CTT TAC CAA TGT GAG GCA TCT TTA GGA GAT TCT GGC TCA ATT ATT       384
Gly Leu Tyr Gln Cys Glu Ala Ser Leu Gly Asp Ser Gly Ser Ile Ile
     115                 120                 125

AGT CGG ACA GCA AAA GTT GCA GTA GCA GGA CCA CTG AGG TTC CTT TCA       432
Ser Arg Thr Ala Lys Val Ala Val Ala Gly Pro Leu Arg Phe Leu Ser
 130                 135                 140

CAG ACA GAA TCT GTC ACA GCC TTC ATG GGA GAC ACA GTG CTA CTC AAG       480
Gln Thr Glu Ser Val Thr Ala Phe Met Gly Asp Thr Val Leu Leu Lys
145                 150                 155                 160

TGT GAA GTC ATT GGG GAG CCC ATG CCA ACA ATC CAC TGG CAG AAG AAC       528
Cys Glu Val Ile Gly Glu Pro Met Pro Thr Ile His Trp Gln Lys Asn
             165                 170                 175

CAA CAA GAC CTG ACT CCA ATC CCA GGT GAC TCC CGA GTG GTG GTC TTG       576
Gln Gln Asp Leu Thr Pro Ile Pro Gly Asp Ser Arg Val Val Val Leu
         180                 185                 190

CCC TCT GGA GCA TTG CAG ATC AGC CGA CTC CAA CCG GGG GAC ATT GGA       624
Pro Ser Gly Ala Leu Gln Ile Ser Arg Leu Gln Pro Gly Asp Ile Gly
     195                 200                 205

ATT TAC CGA TGC TCA GCT CGA AAT CCA GCC AGC TCA AGA ACA GGA AAT       672
Ile Tyr Arg Cys Ser Ala Arg Asn Pro Ala Ser Ser Arg Thr Gly Asn
 210                 215                 220

GAA GCA GAA GTC AGA ATT TTA TCA GAT CCA GGA CTG CAT AGA CAG CTG       720
Glu Ala Glu Val Arg Ile Leu Ser Asp Pro Gly Leu His Arg Gln Leu
225                 230                 235                 240

TAT TTT CTG CAA AGA CCA TCC AAT GTA GTA GCC ATT GAA GGA AAA GAT       768
Tyr Phe Leu Gln Arg Pro Ser Asn Val Val Ala Ile Glu Gly Lys Asp
             245                 250                 255

GCT GTC CTG GAA TGT TGT GTT TCT GGC TAT CCT CCA CCA AGT TTT ACC       816
Ala Val Leu Glu Cys Cys Val Ser Gly Tyr Pro Pro Pro Ser Phe Thr
         260                 265                 270

TGG TTA CGA GGC GAG GAA GTC ATC CAA CTC AGG TCT AAA AAG TAT TCT       864
Trp Leu Arg Gly Glu Glu Val Ile Gln Leu Arg Ser Lys Lys Tyr Ser
     275                 280                 285
```

```
TTA TTG GGT GGA AGC AAC TTG CTT ATC TCC AAT GTG ACA GAT GAT GAC          912
Leu Leu Gly Gly Ser Asn Leu Leu Ile Ser Asn Val Thr Asp Asp Asp
    290                 295                 300

AGT GGA ATG TAT ACC TGT GTT GTC ACA TAT AAA AAT GAG AAT ATT AGT          960
Ser Gly Met Tyr Thr Cys Val Val Thr Tyr Lys Asn Glu Asn Ile Ser
305                 310                 315                 320

GCC TCT GCA GAG CTC ACA GTC TTG GTT CCG CCA TGG TTT TTA AAT CAT         1008
Ala Ser Ala Glu Leu Thr Val Leu Val Pro Pro Trp Phe Leu Asn His
                325                 330                 335

CCT TCC AAC CTG TAT GCC TAT GAA AGC ATG GAT ATT GAG TTT GAA TGT         1056
Pro Ser Asn Leu Tyr Ala Tyr Glu Ser Met Asp Ile Glu Phe Glu Cys
        340                 345                 350

ACA GTC TCT GGA AAG CCT GTG CCC ACT GTG AAT TGG ATG AAG AAT GGA         1104
Thr Val Ser Gly Lys Pro Val Pro Thr Val Asn Trp Met Lys Asn Gly
            355                 360                 365

GAT GTG GTC ATT CCT AGT GAT TAT TTT CAG ATA GTG GGA GGA AGC AAC         1152
Asp Val Val Ile Pro Ser Asp Tyr Phe Gln Ile Val Gly Gly Ser Asn
370                 375                 380

TTA CGG ATA CTT GGG GTG GTG AAG TCA GAT GAA GGC TTT TAT CAA TGT         1200
Leu Arg Ile Leu Gly Val Val Lys Ser Asp Glu Gly Phe Tyr Gln Cys
385                 390                 395                 400

GTG GCT GAA AAT GAG GCT GGA AAT GCC CAG ACC AGT GCA CAG CTC ATT         1248
Val Ala Glu Asn Glu Ala Gly Asn Ala Gln Thr Ser Ala Gln Leu Ile
                405                 410                 415

GTC CCT AAG CCT GCA ATC CCA AGC TCC AGT GTC CTC CCT TCG GCT CCC         1296
Val Pro Lys Pro Ala Ile Pro Ser Ser Ser Val Leu Pro Ser Ala Pro
        420                 425                 430

AGA GAT GTG GTC CCT GTC TTG GTT TCC AGC CGA TTT GTC CGT CTC AGC         1344
Arg Asp Val Val Pro Val Leu Val Ser Ser Arg Phe Val Arg Leu Ser
            435                 440                 445

TGG CGC CCA CCT GCA GAA GCG AAA GGG AAC ATT CAA ACT TTC ACG GTC         1392
Trp Arg Pro Pro Ala Glu Ala Lys Gly Asn Ile Gln Thr Phe Thr Val
450                 455                 460

TTT TTC TCC AGA GAA GGT GAC AAC AGG GAA CGA GCA TTG AAT ACA ACA         1440
Phe Phe Ser Arg Glu Gly Asp Asn Arg Glu Arg Ala Leu Asn Thr Thr
465                 470                 475                 480

CAG CCT GGG TCC CTT CAG CTC ACT GTG GGA AAC CTG AAG CCA GAA GCC         1488
Gln Pro Gly Ser Leu Gln Leu Thr Val Gly Asn Leu Lys Pro Glu Ala
                485                 490                 495

ATG TAC ACC TTT CGA GTT GTG GCT TAC AAT GAA TGG GGA CCG GGA GAG         1536
Met Tyr Thr Phe Arg Val Val Ala Tyr Asn Glu Trp Gly Pro Gly Glu
        500                 505                 510

AGT TCT CAA CCC ATC AAG GTG GCC ACA CAG CCT GAG TTG CAA GTT CCA         1584
Ser Ser Gln Pro Ile Lys Val Ala Thr Gln Pro Glu Leu Gln Val Pro
            515                 520                 525

GGG CCA GTA GAA AAC CTG CAA GCT GTA TCT ACC TCA CCT ACC TCA ATT         1632
Gly Pro Val Glu Asn Leu Gln Ala Val Ser Thr Ser Pro Thr Ser Ile
530                 535                 540

CTT ATT ACC TGG GAA CCC CCT GCC TAT GCA AAC GGT CCA GTC CAA GGT         1680
Leu Ile Thr Trp Glu Pro Pro Ala Tyr Ala Asn Gly Pro Val Gln Gly
545                 550                 555                 560

TAC AGA TTG TTC TGC ACT GAG GTG TCC ACA GGA AAA GAA CAG AAT ATA         1728
Tyr Arg Leu Phe Cys Thr Glu Val Ser Thr Gly Lys Glu Gln Asn Ile
                565                 570                 575

GAG GTT GAT GGA CTA TCT TAT AAA CTG GAA GGC CTG AAA AAA TTC ACC         1776
Glu Val Asp Gly Leu Ser Tyr Lys Leu Glu Gly Leu Lys Lys Phe Thr
        580                 585                 590

GAA TAT AGT CTT CGA TTC TTA GCT TAT AAT CGC TAT GGT CCG GGC GTC         1824
Glu Tyr Ser Leu Arg Phe Leu Ala Tyr Asn Arg Tyr Gly Pro Gly Val
            595                 600                 605
```

```
TCT ACT GAT GAT ATA ACA GTG GTT ACA CTT TCT GAC GTG CCA AGT GCC    1872
Ser Thr Asp Asp Ile Thr Val Val Thr Leu Ser Asp Val Pro Ser Ala
        610             615             620

CCG CCT CAG AAC GTC TCC CTG GAA GTG GTC AAT TCA AGA AGT ATC AAA    1920
Pro Pro Gln Asn Val Ser Leu Glu Val Val Asn Ser Arg Ser Ile Lys
625             630             635                         640

GTT AGC TGG CTG CCT CCT CCA TCA GGA ACA CAA AAT GGA TTT ATT ACC    1968
Val Ser Trp Leu Pro Pro Pro Ser Gly Thr Gln Asn Gly Phe Ile Thr
                645             650             655

GGC TAT AAA ATT CGA CAC AGA AAG ACG ACC CGC AGG GGT GAG ATG GAA    2016
Gly Tyr Lys Ile Arg His Arg Lys Thr Thr Arg Arg Gly Glu Met Glu
            660             665             670

ACA CTG GAG CCA AAC AAC CTC TGG TAC CTA TTC ACA GGA CTG GAG AAA    2064
Thr Leu Glu Pro Asn Asn Leu Trp Tyr Leu Phe Thr Gly Leu Glu Lys
                675             680             685

GGA AGT CAG TAC AGT TTC CAG GTG TCA GCC ATG ACA GTC AAT GGT ACT    2112
Gly Ser Gln Tyr Ser Phe Gln Val Ser Ala Met Thr Val Asn Gly Thr
        690             695             700

GGA CCA CCT TCC AAC TGG TAT ACT GCA GAG ACT CCA GAG AAT GAT CTA    2160
Gly Pro Pro Ser Asn Trp Tyr Thr Ala Glu Thr Pro Glu Asn Asp Leu
705             710             715             720

GAT GAA TCT CAA GTT CCT GAT CAA CCA AGC TCT CTT CAT GTG AGG CCC    2208
Asp Glu Ser Gln Val Pro Asp Gln Pro Ser Ser Leu His Val Arg Pro
                725             730             735

CAG ACT AAC TGC ATC ATC ATG AGT TGG ACT CCT CCC TTG AAC CCA AAC    2256
Gln Thr Asn Cys Ile Ile Met Ser Trp Thr Pro Pro Leu Asn Pro Asn
            740             745             750

ATC GTG GTG CGA GGT TAT ATT ATC GGT TAT GGC GTT GGG AGC CCT TAC    2304
Ile Val Val Arg Gly Tyr Ile Ile Gly Tyr Gly Val Gly Ser Pro Tyr
                755             760             765

GCT GAG ACA GTG CGT GTG GAC AGC AAG CAG CGA TAT TAT TCC ATT GAG    2352
Ala Glu Thr Val Arg Val Asp Ser Lys Gln Arg Tyr Tyr Ser Ile Glu
        770             775             780

AGG TTA GAG TCA AGT TCC CAT TAT GTA ATC TCC CTA AAA GCT TTT AAC    2400
Arg Leu Glu Ser Ser Ser His Tyr Val Ile Ser Leu Lys Ala Phe Asn
785             790             795             800

AAT GCC GGA GAA GGA GTT CCT CTT TAT GAA AGT GCC ACC ACC AGG TCT    2448
Asn Ala Gly Glu Gly Val Pro Leu Tyr Glu Ser Ala Thr Thr Arg Ser
                805             810             815

ATA ACC GAT CCC ACT GAC CCA GTT GAT TAT TAT CCT TTG CTT GAT GAT    2496
Ile Thr Asp Pro Thr Asp Pro Val Asp Tyr Tyr Pro Leu Leu Asp Asp
            820             825             830

TTC CCC ACC TCG GTC CCA GAT CTC TCC ACC CCC ATG CTC CCA CCA GTA    2544
Phe Pro Thr Ser Val Pro Asp Leu Ser Thr Pro Met Leu Pro Pro Val
                835             840             845

GGT GTA CAG GCT GTG GCT CTT ACC CAT GAT GCT GTG AGG GTC AGC TGG    2592
Gly Val Gln Ala Val Ala Leu Thr His Asp Ala Val Arg Val Ser Trp
850             855             860

GCA GAC AAC TCT GTC CCT AAG AAC CAA AAG ACG TCT GAG GTG CGA CTT    2640
Ala Asp Asn Ser Val Pro Lys Asn Gln Lys Thr Ser Glu Val Arg Leu
865             870             875             880

TAC ACC GTC CGG TGG AGA ACC AGC TTT TCT GCA AGT GCA AAA TAC AAG    2688
Tyr Thr Val Arg Trp Arg Thr Ser Phe Ser Ala Ser Ala Lys Tyr Lys
                885             890             895

TCA GAA GAC ACA ACA TCT CTA AGT TAC ACA GCA ACA GGC CTC AAA CCA    2736
Ser Glu Asp Thr Thr Ser Leu Ser Tyr Thr Ala Thr Gly Leu Lys Pro
            900             905             910

AAC ACA ATG TAT GAA TTC TCG GTC ATG GTA ACA AAA AAC AGA AGG TCC    2784
Asn Thr Met Tyr Glu Phe Ser Val Met Val Thr Lys Asn Arg Arg Ser
```

```
                    915                 920                 925
AGT ACT TGG AGC ATG ACT GCA CAT GCC ACC ACG TAT GAA GCA GCC CCC        2832
Ser Thr Trp Ser Met Thr Ala His Ala Thr Thr Tyr Glu Ala Ala Pro
        930                 935                 940

ACC TCT GCT CCC AAG GAC TTT ACA GTC ATT ACT AGG GAA GGG AAG CCT        2880
Thr Ser Ala Pro Lys Asp Phe Thr Val Ile Thr Arg Glu Gly Lys Pro
945                 950                 955                 960

CGT GCC GTC ATT GTG AGT TGG CAG CCT CCC TTG GAA GCC AAT GGG AAA        2928
Arg Ala Val Ile Val Ser Trp Gln Pro Pro Leu Glu Ala Asn Gly Lys
                965                 970                 975

ATT ACT GCT TAC ATC TTA TTT TAT ACC TTG GAC AAG AAC ATC CCA ATT        2976
Ile Thr Ala Tyr Ile Leu Phe Tyr Thr Leu Asp Lys Asn Ile Pro Ile
        980                 985                 990

GAT GAC TGG ATT ATG GAA ACA ATC AGT GGT GAT AGG CTT ACT CAT CAA        3024
Asp Asp Trp Ile Met Glu Thr Ile Ser Gly Asp Arg Leu Thr His Gln
        995                 1000                1005

ATC ATG GAT CTC AAC CTT GAT ACT ATG TAT TAC TTT CGA ATT CAA GCA        3072
Ile Met Asp Leu Asn Leu Asp Thr Met Tyr Tyr Phe Arg Ile Gln Ala
        1010                1015                1020

CGA AAT TCA AAA GGA GTG GGG CCA CTC TCT GAT CCC ATC CTC TTC AGG        3120
Arg Asn Ser Lys Gly Val Gly Pro Leu Ser Asp Pro Ile Leu Phe Arg
1025                1030                1035                1040

ACT CTG AAA GTG GAA CAC CCT GAC AAA ATG GCT AAT GAC CAA GGT CGT        3168
Thr Leu Lys Val Glu His Pro Asp Lys Met Ala Asn Asp Gln Gly Arg
                1045                1050                1055

CAT GGA GAT GGA GGT TAT TGG CCA GTT GAT ACT AAT TTG ATT GAT AGA        3216
His Gly Asp Gly Gly Tyr Trp Pro Val Asp Thr Asn Leu Ile Asp Arg
        1060                1065                1070

AGC ACC CTA AAT GAG CCG CCA ATT GGA CAA ATG CAC CCC CCG CAT GGC        3264
Ser Thr Leu Asn Glu Pro Pro Ile Gly Gln Met His Pro Pro His Gly
        1075                1080                1085

AGT GTC ACT CCT CAG AAG AAC AGC AAC CTG CTT GTG ATC ATT GTG GTC        3312
Ser Val Thr Pro Gln Lys Asn Ser Asn Leu Leu Val Ile Ile Val Val
        1090                1095                1100

ACC GTT GGT GTC ATC ACA GTG CTG GTA GTG GTC ATC GTG GCT GTG ATT        3360
Thr Val Gly Val Ile Thr Val Leu Val Val Val Ile Val Ala Val Ile
1105                1110                1115                1120

TGC ACC CGA CGC TCT TCA GCC CAG CAG AGA AAG AAA CGG GCC ACC CAC        3408
Cys Thr Arg Arg Ser Ser Ala Gln Gln Arg Lys Lys Arg Ala Thr His
                1125                1130                1135

AGT GCT GGC AAA AGG AAG GGC AGC CAG AAG GAC CTC CGA CCC CCT GAT        3456
Ser Ala Gly Lys Arg Lys Gly Ser Gln Lys Asp Leu Arg Pro Pro Asp
        1140                1145                1150

CTT TGG ATC CAT CAT GAA GAA ATG GAG ATG AAA AAT ATT GAA AAG CCA        3504
Leu Trp Ile His His Glu Glu Met Glu Met Lys Asn Ile Glu Lys Pro
        1155                1160                1165

TCT GGC ACT GAC CCT GCA GGA AGG GAC TCT CCC ATC CAA AGT TGC CAA        3552
Ser Gly Thr Asp Pro Ala Gly Arg Asp Ser Pro Ile Gln Ser Cys Gln
        1170                1175                1180

GAC CTC ACA CCA GTC AGC CAC AGC CAG TCA GAA ACC CAA CTG GGA AGC        3600
Asp Leu Thr Pro Val Ser His Ser Gln Ser Glu Thr Gln Leu Gly Ser
1185                1190                1195                1200

AAA AGC ACC TCT CAT TCA GGT CAA GAC ACT GAG GAA GCA GGG AGC TCT        3648
Lys Ser Thr Ser His Ser Gly Gln Asp Thr Glu Glu Ala Gly Ser Ser
                1205                1210                1215

ATG TCC ACT CTG GAG AGG TCG CTG GCT GCA CGC CGA GCC CCC GGG GCC        3696
Met Ser Thr Leu Glu Arg Ser Leu Ala Ala Arg Arg Ala Pro Arg Ala
        1220                1225                1230

AAG CTC ATG ATT CCC ATG GAT GCC CAG TCC AAC AAT CCT GCT GTC GTG        3744
```

| | | |
|---|---|---|
| Lys Leu Met Ile Pro Met Asp Ala Gln Ser Asn Asn Pro Ala Val Val<br>     1235                  1240                   1245 | | |

```
AGC GCC ATC CCG GTG CCA ACG CTA GAA AGT GCC CAG TAC CCA GGA ATC      3792
Ser Ala Ile Pro Val Pro Thr Leu Glu Ser Ala Gln Tyr Pro Gly Ile
    1250                1255                1260

CTC CCG TCT CCC ACC TGT GGA TAT CCC CAC CCG CAG TTC ACT CTC CGG      3840
Leu Pro Ser Pro Thr Cys Gly Tyr Pro His Pro Gln Phe Thr Leu Arg
1265                1270                1275                1280

CCT GTG CCA TTC CCA ACA CTC TCA GTG GAC CGA GGT TTC GGA GCA GGA      3888
Pro Val Pro Phe Pro Thr Leu Ser Val Asp Arg Gly Phe Gly Ala Gly
                1285                1290                1295

AGA AGT CAG TCA GTG AGT GAA GGA CCA ACT ACC CAA CAA CCA CCT ATG      3936
Arg Ser Gln Ser Val Ser Glu Gly Pro Thr Thr Gln Gln Pro Pro Met
    1300                1305                1310

CTG CCC CCA TCT CAG CCT GAG CAT TCT AGC AGC GAG GAG GCA CCA AGC      3984
Leu Pro Pro Ser Gln Pro Glu His Ser Ser Ser Glu Glu Ala Pro Ser
1315                1320                1325

AGA ACC ATC CCC ACA GCT TGT GTT CGA CCA ACT CAC CCA CTC CGC AGC      4032
Arg Thr Ile Pro Thr Ala Cys Val Arg Pro Thr His Pro Leu Arg Ser
        1330                1335                1340

TTT GCT AAT CCT TTG CTA CCT CCA CCA ATG AGT GCA ATA GAA CCG AAA      4080
Phe Ala Asn Pro Leu Leu Pro Pro Pro Met Ser Ala Ile Glu Pro Lys
1345                1350                1355                1360

GTC CCT TAC ACA CCA CTT TTG TCT CAG CCA GGG CCC ACT CTT CCT AAG      4128
Val Pro Tyr Thr Pro Leu Leu Ser Gln Pro Gly Pro Thr Leu Pro Lys
                1365                1370                1375

ACC CAT GTG AAA ACA GCC TCC CTT GGG TTG GCT GGA AAA GCA AGA TCC      4176
Thr His Val Lys Thr Ala Ser Leu Gly Leu Ala Gly Lys Ala Arg Ser
            1380                1385                1390

CCT TTG CTT CCT GTG TCT GTG CCA ACA GCC CCT GAA GTG TCT GAG GAG      4224
Pro Leu Leu Pro Val Ser Val Pro Thr Ala Pro Glu Val Ser Glu Glu
        1395                1400                1405

AGC CAC AAA CCA ACA GAG GAT TCA GCC AAT GTG TAT GAA CAG GAT GAT      4272
Ser His Lys Pro Thr Glu Asp Ser Ala Asn Val Tyr Glu Gln Asp Asp
    1410                1415                1420

CTG AGT GAA CAA ATG GCA AGT TTG GAA GGA CTC ATG AAG CAG CTT AAT      4320
Leu Ser Glu Gln Met Ala Ser Leu Glu Gly Leu Met Lys Gln Leu Asn
1425                1430                1435                1440

GCC ATC ACA GGC TCA GCC TTT T AACATGTATT TCTGAATGGA TGAGGTGAAT      4372
Ala Ile Thr Gly Ser Ala Phe
                1445

TTTCCGGGAA CTTTGCAGCA TACCAATTAC CCATAAACAG CACACCTGTG TCCAAGAACT   4432

CTAACCAGTG TACAGGTCAC CCATCAGGAC CACTCAGTTA AGGAAGATCC TGAAGCAGTT   4492

CAGAAGGAAT AAGCATTCCT TCTTTCACAG GCATCAGGAA TTGTCAAATG ATGATTATGA   4552

GTTCCCTAAA CAAAAGCAAA GATGCATTTT CACTGCAATG TCAAAGTTTA GCTGCT       4608
```

(2) INFORMATION FOR SEQ ID NO:25:

(i) SEQUENCE CHARACTERISTICS:
        (A) LENGTH: 1447 amino acids
        (B) TYPE: amino acid
        (D) TOPOLOGY: linear (ii) MOLECULE TYPE: protein (xi) SEQUENCE DESCRIPTION: SEQ ID NO:25:

```
Met Glu Asn Ser Leu Arg Cys Val Trp Val Pro Lys Leu Ala Phe Val
  1               5                  10                  15

Leu Phe Gly Ala Ser Leu Leu Ser Ala His Leu Gln Val Thr Gly Phe
```

```
                    20                      25                      30
Gln Ile Lys Ala Phe Thr Ala Leu Arg Phe Leu Ser Glu Pro Ser Asp
                35                      40                      45

Ala Val Thr Met Arg Gly Gly Asn Val Leu Leu Asp Cys Ser Ala Glu
            50                      55                      60

Ser Asp Arg Gly Val Pro Val Ile Lys Trp Lys Lys Asp Gly Ile His
65                      70                      75                      80

Leu Ala Leu Gly Met Asp Glu Arg Lys Gln Gln Leu Ser Asn Gly Ser
                    85                      90                      95

Leu Leu Ile Gln Asn Ile Leu His Ser Arg His His Lys Pro Asp Glu
                100                     105                     110

Gly Leu Tyr Gln Cys Glu Ala Ser Leu Gly Asp Ser Gly Ser Ile Ile
            115                     120                     125

Ser Arg Thr Ala Lys Val Ala Val Ala Gly Pro Leu Arg Phe Leu Ser
130                     135                     140

Gln Thr Glu Ser Val Thr Ala Phe Met Gly Asp Thr Val Leu Leu Lys
145                     150                     155                     160

Cys Glu Val Ile Gly Glu Pro Met Pro Thr Ile His Trp Gln Lys Asn
                165                     170                     175

Gln Gln Asp Leu Thr Pro Ile Pro Gly Asp Ser Arg Val Val Val Leu
                180                     185                     190

Pro Ser Gly Ala Leu Gln Ile Ser Arg Leu Gln Pro Gly Asp Ile Gly
            195                     200                     205

Ile Tyr Arg Cys Ser Ala Arg Asn Pro Ala Ser Ser Arg Thr Gly Asn
        210                     215                     220

Glu Ala Glu Val Arg Ile Leu Ser Asp Pro Gly Leu His Arg Gln Leu
225                     230                     235                     240

Tyr Phe Leu Gln Arg Pro Ser Asn Val Val Ala Ile Glu Gly Lys Asp
                245                     250                     255

Ala Val Leu Glu Cys Cys Val Ser Gly Tyr Pro Pro Ser Phe Thr
                260                     265                     270

Trp Leu Arg Gly Glu Glu Val Ile Gln Leu Arg Ser Lys Lys Tyr Ser
            275                     280                     285

Leu Leu Gly Gly Ser Asn Leu Leu Ile Ser Asn Val Thr Asp Asp Asp
290                     295                     300

Ser Gly Met Tyr Thr Cys Val Val Thr Tyr Lys Asn Glu Asn Ile Ser
305                     310                     315                     320

Ala Ser Ala Glu Leu Thr Val Leu Val Pro Pro Trp Phe Leu Asn His
                325                     330                     335

Pro Ser Asn Leu Tyr Ala Tyr Glu Ser Met Asp Ile Glu Phe Glu Cys
                340                     345                     350

Thr Val Ser Gly Lys Pro Val Pro Thr Val Asn Trp Met Lys Asn Gly
            355                     360                     365

Asp Val Val Ile Pro Ser Asp Tyr Phe Gln Ile Val Gly Gly Ser Asn
        370                     375                     380

Leu Arg Ile Leu Gly Val Lys Ser Asp Glu Gly Phe Tyr Gln Cys
385                     390                     395                     400

Val Ala Glu Asn Glu Ala Gly Asn Ala Gln Thr Ser Ala Gln Leu Ile
                405                     410                     415

Val Pro Lys Pro Ala Ile Pro Ser Ser Ser Val Leu Pro Ser Ala Pro
                420                     425                     430

Arg Asp Val Val Pro Val Leu Val Ser Ser Arg Phe Val Arg Leu Ser
            435                     440                     445
```

```
Trp Arg Pro Pro Ala Glu Ala Lys Gly Asn Ile Gln Thr Phe Thr Val
450                 455                 460

Phe Phe Ser Arg Glu Gly Asp Asn Arg Glu Arg Ala Leu Asn Thr Thr
465                 470                 475                 480

Gln Pro Gly Ser Leu Gln Leu Thr Val Gly Asn Leu Lys Pro Glu Ala
            485                 490                 495

Met Tyr Thr Phe Arg Val Val Ala Tyr Asn Glu Trp Gly Pro Gly Glu
                500                 505                 510

Ser Ser Gln Pro Ile Lys Val Ala Thr Gln Pro Glu Leu Gln Val Pro
            515                 520                 525

Gly Pro Val Glu Asn Leu Gln Ala Val Ser Thr Ser Pro Thr Ser Ile
530                 535                 540

Leu Ile Thr Trp Glu Pro Pro Ala Tyr Ala Asn Gly Pro Val Gln Gly
545                 550                 555                 560

Tyr Arg Leu Phe Cys Thr Glu Val Ser Thr Gly Lys Glu Gln Asn Ile
                565                 570                 575

Glu Val Asp Gly Leu Ser Tyr Lys Leu Glu Gly Leu Lys Lys Phe Thr
            580                 585                 590

Glu Tyr Ser Leu Arg Phe Leu Ala Tyr Asn Arg Tyr Gly Pro Gly Val
            595                 600                 605

Ser Thr Asp Asp Ile Thr Val Val Thr Leu Ser Asp Val Pro Ser Ala
610                 615                 620

Pro Pro Gln Asn Val Ser Leu Glu Val Val Asn Ser Arg Ser Ile Lys
625                 630                 635                 640

Val Ser Trp Leu Pro Pro Ser Gly Thr Gln Asn Gly Phe Ile Thr
                645                 650                 655

Gly Tyr Lys Ile Arg His Arg Lys Thr Thr Arg Arg Gly Glu Met Glu
                660                 665                 670

Thr Leu Glu Pro Asn Asn Leu Trp Tyr Leu Phe Thr Gly Leu Glu Lys
            675                 680                 685

Gly Ser Gln Tyr Ser Phe Gln Val Ser Ala Met Thr Val Asn Gly Thr
690                 695                 700

Gly Pro Pro Ser Asn Trp Tyr Thr Ala Glu Thr Pro Glu Asn Asp Leu
705                 710                 715                 720

Asp Glu Ser Gln Val Pro Asp Gln Pro Ser Ser Leu His Val Arg Pro
                725                 730                 735

Gln Thr Asn Cys Ile Ile Met Ser Trp Thr Pro Pro Leu Asn Pro Asn
            740                 745                 750

Ile Val Val Arg Gly Tyr Ile Ile Gly Tyr Gly Val Gly Ser Pro Tyr
            755                 760                 765

Ala Glu Thr Val Arg Val Asp Ser Lys Gln Arg Tyr Tyr Ser Ile Glu
770                 775                 780

Arg Leu Glu Ser Ser Ser His Tyr Val Ile Ser Leu Lys Ala Phe Asn
785                 790                 795                 800

Asn Ala Gly Glu Gly Val Pro Leu Tyr Glu Ser Ala Thr Thr Arg Ser
                805                 810                 815

Ile Thr Asp Pro Thr Asp Pro Val Asp Tyr Tyr Pro Leu Leu Asp Asp
                820                 825                 830

Phe Pro Thr Ser Val Pro Asp Leu Ser Thr Pro Met Leu Pro Pro Val
            835                 840                 845

Gly Val Gln Ala Val Ala Leu Thr His Asp Ala Val Arg Val Ser Trp
850                 855                 860
```

```
Ala Asp Asn Ser Val Pro Lys Asn Gln Lys Thr Ser Glu Val Arg Leu
865                 870                 875                 880

Tyr Thr Val Arg Trp Arg Thr Ser Phe Ser Ala Ser Ala Lys Tyr Lys
            885                 890                 895

Ser Glu Asp Thr Thr Ser Leu Ser Tyr Thr Ala Thr Gly Leu Lys Pro
            900                 905                 910

Asn Thr Met Tyr Glu Phe Ser Val Met Val Thr Lys Asn Arg Arg Ser
            915                 920                 925

Ser Thr Trp Ser Met Thr Ala His Ala Thr Thr Tyr Glu Ala Ala Pro
        930                 935                 940

Thr Ser Ala Pro Lys Asp Phe Thr Val Ile Thr Arg Glu Gly Lys Pro
945                 950                 955                 960

Arg Ala Val Ile Val Ser Trp Gln Pro Pro Leu Glu Ala Asn Gly Lys
                965                 970                 975

Ile Thr Ala Tyr Ile Leu Phe Tyr Thr Leu Asp Lys Asn Ile Pro Ile
                980                 985                 990

Asp Asp Trp Ile Met Glu Thr Ile Ser Gly Asp Arg Leu Thr His Gln
                995                 1000                1005

Ile Met Asp Leu Asn Leu Asp Thr Met Tyr Tyr Phe Arg Ile Gln Ala
        1010                1015                1020

Arg Asn Ser Lys Gly Val Gly Pro Leu Ser Asp Pro Ile Leu Phe Arg
1025                1030                1035                1040

Thr Leu Lys Val Glu His Pro Asp Lys Met Ala Asn Asp Gln Gly Arg
            1045                1050                1055

His Gly Asp Gly Gly Tyr Trp Pro Val Asp Thr Asn Leu Ile Asp Arg
            1060                1065                1070

Ser Thr Leu Asn Glu Pro Pro Ile Gly Gln Met His Pro Pro His Gly
            1075                1080                1085

Ser Val Thr Pro Gln Lys Asn Ser Asn Leu Leu Val Ile Ile Val Val
            1090                1095                1100

Thr Val Gly Val Ile Thr Val Leu Val Val Ile Val Ala Val Ile
1105                1110                1115                1120

Cys Thr Arg Arg Ser Ser Ala Gln Gln Arg Lys Lys Arg Ala Thr His
                1125                1130                1135

Ser Ala Gly Lys Arg Lys Gly Ser Gln Lys Asp Leu Arg Pro Pro Asp
            1140                1145                1150

Leu Trp Ile His His Glu Glu Met Glu Met Lys Asn Ile Glu Lys Pro
            1155                1160                1165

Ser Gly Thr Asp Pro Ala Gly Arg Asp Ser Pro Ile Gln Ser Cys Gln
            1170                1175                1180

Asp Leu Thr Pro Val Ser His Ser Gln Ser Glu Thr Gln Leu Gly Ser
1185                1190                1195                1200

Lys Ser Thr Ser His Ser Gly Gln Asp Thr Glu Glu Ala Gly Ser Ser
            1205                1210                1215

Met Ser Thr Leu Glu Arg Ser Leu Ala Ala Arg Arg Ala Pro Arg Ala
            1220                1225                1230

Lys Leu Met Ile Pro Met Asp Ala Gln Ser Asn Asn Pro Ala Val Val
        1235                1240                1245

Ser Ala Ile Pro Val Pro Thr Leu Glu Ser Ala Gln Tyr Pro Gly Ile
        1250                1255                1260

Leu Pro Ser Pro Thr Cys Gly Tyr Pro His Pro Gln Phe Thr Leu Arg
1265                1270                1275                1280

Pro Val Pro Phe Pro Thr Leu Ser Val Asp Arg Gly Phe Gly Ala Gly
```

-continued

```
                  1285                1290                1295
Arg Ser Gln Ser Val Ser Glu Gly Pro Thr Thr Gln Pro Pro Met
                1300                1305                1310

Leu Pro Pro Ser Gln Pro Glu His Ser Ser Glu Glu Ala Pro Ser
                1315                1320                1325

Arg Thr Ile Pro Thr Ala Cys Val Arg Pro Thr His Pro Leu Arg Ser
                1330                1335                1340

Phe Ala Asn Pro Leu Leu Pro Pro Met Ser Ala Ile Glu Pro Lys
1345                1350                1355                1360

Val Pro Tyr Thr Pro Leu Leu Ser Gln Pro Gly Pro Thr Leu Pro Lys
                1365                1370                1375

Thr His Val Lys Thr Ala Ser Leu Gly Leu Ala Gly Lys Ala Arg Ser
                1380                1385                1390

Pro Leu Leu Pro Val Ser Val Pro Thr Ala Pro Glu Val Ser Glu Glu
                1395                1400                1405

Ser His Lys Pro Thr Glu Asp Ser Ala Asn Val Tyr Glu Gln Asp Asp
                1410                1415                1420

Leu Ser Glu Gln Met Ala Ser Leu Glu Gly Leu Met Lys Gln Leu Asn
1425                1430                1435                1440

Ala Ile Thr Gly Ser Ala Phe
                1445
```

(2) INFORMATION FOR SEQ ID NO:26:

(i) SEQUENCE CHARACTERISTICS:
        (A) LENGTH: 1004 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 48..876

(xi) SEQUENCE DESCRIPTION: SEQ ID NO:26:

```
GCCTCGCTCG GGCGCCCAGT GGTCCTGCCG CCTGGTCTCA CCTCGCC ATG GTT CGT       56
                                                 Met Val Arg
                                                   1

CTG CCT CTG CAG TGC GTC CTC TGG GGC TGC TTG CTG ACC GCT GTC CAT      104
Leu Pro Leu Gln Cys Val Leu Trp Gly Cys Leu Leu Thr Ala Val His
  5                  10                  15

CCA GAA CCA CCC ACT GCA TGC AGA GAA AAA CAG TAC CTA ATA AAC AGT      152
Pro Glu Pro Pro Thr Ala Cys Arg Glu Lys Gln Tyr Leu Ile Asn Ser
 20                  25                  30                  35

CAG TGC TGT TCT TTG TGC CAG CCA GGA CAG AAA CTG GTG AGT GAC TGC      200
Gln Cys Cys Ser Leu Cys Gln Pro Gly Gln Lys Leu Val Ser Asp Cys
                 40                  45                  50

ACA GAG TTC ACT GAA ACG GAA TGC CTT CCT TGC GGT GAA AGC GAA TTC      248
Thr Glu Phe Thr Glu Thr Glu Cys Leu Pro Cys Gly Glu Ser Glu Phe
             55                  60                  65

CTA GAC ACC TGG AAC AGA GAG ACA CAC TGC CAC CAG CAC AAA TAC TGC      296
Leu Asp Thr Trp Asn Arg Glu Thr His Cys His Gln His Lys Tyr Cys
         70                  75                  80

GAC CCC AAC CTA GGG CTT CGG GTC CAG CAG AAG GGC ACC TCA GAA ACA      344
Asp Pro Asn Leu Gly Leu Arg Val Gln Gln Lys Gly Thr Ser Glu Thr
     85                  90                  95

GAC ACC ATC TGC ACC TGT GAA GAA GGC TGG CAC TGT ACG AGT GAG GCC      392
Asp Thr Ile Cys Thr Cys Glu Glu Gly Trp His Cys Thr Ser Glu Ala
```

```
                100                     105                     110                      115
TGT GAG AGC TGT GTC CTG CAC CGC TCA TGC TCG CCC GGC TTT GGG GTC                    440
Cys Glu Ser Cys Val Leu His Arg Ser Cys Ser Pro Gly Phe Gly Val
                    120                     125                 130

AAG CAG ATT GCT ACA GGG GTT TCT GAT ACC ATC TGC GAG CCC TGC CCA                    488
Lys Gln Ile Ala Thr Gly Val Ser Asp Thr Ile Cys Glu Pro Cys Pro
                135                     140                 145

GTC GGC TTC TTC TCC AAT GTG TCA TCT GCT TTC GAA AAA TGT CAC CCT                    536
Val Gly Phe Phe Ser Asn Val Ser Ser Ala Phe Glu Lys Cys His Pro
            150                     155                 160

TGG ACA AGC TGT GAG ACC AAA GAC CTG GTT GTG CAA CAG GCA GGC ACA                    584
Trp Thr Ser Cys Glu Thr Lys Asp Leu Val Val Gln Gln Ala Gly Thr
        165                     170                 175

AAC AAG ACT GAT GTT GTC TGT GGT CCC CAG GAT CGG CTG AGA GCC CTG                    632
Asn Lys Thr Asp Val Val Cys Gly Pro Gln Asp Arg Leu Arg Ala Leu
180                     185                 190                     195

GTG GTG ATC CCC ATC ATC TTC GGG ATC CTG TTT GCC ATC CTC TTG GTG                    680
Val Val Ile Pro Ile Ile Phe Gly Ile Leu Phe Ala Ile Leu Leu Val
                    200                     205                 210

CTG GTC TTT ATC AAA AAG GTG GCC AAG AAG CCA ACC AAT AAG GCC CCC                    728
Leu Val Phe Ile Lys Lys Val Ala Lys Lys Pro Thr Asn Lys Ala Pro
                215                     220                 225

CAC CCC AAG CAG GAA CCC CAG GAG ATC AAT TTT CCC GAC GAT CTT CCT                    776
His Pro Lys Gln Glu Pro Gln Glu Ile Asn Phe Pro Asp Asp Leu Pro
            230                     235                 240

GGC TCC AAC ACT GCT GCT CCA GTG CAG GAG ACT TTA CAT GGA TGC CAA                    824
Gly Ser Asn Thr Ala Ala Pro Val Gln Glu Thr Leu His Gly Cys Gln
        245                     250                 255

CCG GTC ACC CAG GAG GAT GGC AAA GAG AGT CGC ATC TCA GTG CAG GAG                    872
Pro Val Thr Gln Glu Asp Gly Lys Glu Ser Arg Ile Ser Val Gln Glu
260                     265                     270                     275

AGA C AGTGAGGCTG CACCCACCCA GGAGTGTGGC CACGTGGGCA AACAGGCAGT                       926
Arg

TGGCCAGAGA GCCTGGTGCT GCTGCTGCAG GGGTGCAGGC AGAAGCGGGG AGCTATGCCC                  986

AGTCAGTGCC AGCCCCTC                                                               1004

(2) INFORMATION FOR SEQ ID NO:27:

(i) SEQUENCE CHARACTERISTICS:
        (A) LENGTH: 276 amino acids
        (B) TYPE: amino acid
        (D) TOPOLOGY: linear (ii) MOLECULE TYPE: protein (xi) SEQUENCE DESCRIPTION: SEQ ID NO:27:

Met Val Arg Leu Pro Leu Gln Cys Val Leu Trp Gly Cys Leu Leu Thr
 1               5                  10                      15

Ala Val His Pro Glu Pro Pro Thr Ala Cys Arg Glu Lys Gln Tyr Leu
                20                  25                      30

Ile Asn Ser Gln Cys Cys Ser Leu Cys Gln Pro Gly Gln Lys Leu Val
            35                  40                      45

Ser Asp Cys Thr Glu Phe Thr Glu Thr Glu Cys Leu Pro Cys Gly Glu
        50                  55                      60

Ser Glu Phe Leu Asp Thr Trp Asn Arg Glu Thr His Cys His Gln His
65                  70                      75                      80

Lys Tyr Cys Asp Pro Asn Leu Gly Leu Arg Val Gln Gln Lys Gly Thr
                85                  90                      95
```

-continued

```
Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg
275
```

(2) INFORMATION FOR SEQ ID NO:28:

(i) SEQUENCE CHARACTERISTICS:
        (A) LENGTH: 513 amino acids
        (B) TYPE: amino acid
        (D) TOPOLOGY: linear (ii) MOLECULE TYPE: peptide (xi) SEQUENCE DESCRIPTION: SEQ ID NO:28:

```
Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Pro Pro Pro Pro Pro Pro Pro Pro Pro
        35                  40                  45

Pro Pro Pro Gln Leu Pro Gln Pro Pro Pro Gln Ala Gln Pro Leu Leu
50                  55                  60

Pro Gln Pro Gln Pro Pro Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
```

```
                        165                 170                 175
Lys Lys Asn Gly Ala Pro Arg Ser Leu Arg Ala Ala Leu Trp Arg Phe
                    180                 185                 190

Ala Glu Leu Ala His Leu Val Arg Pro Gln Lys Cys Arg Pro Tyr Leu
                195                 200                 205

Val Asn Leu Leu Pro Cys Leu Thr Arg Thr Ser Lys Arg Pro Glu Glu
            210                 215                 220

Ser Val Gln Glu Thr Leu Ala Ala Val Pro Lys Ile Met Ala Ser
225                 230                 235                 240

Phe Gly Asn Phe Ala Asn Asp Asn Glu Ile Lys Val Leu Leu Lys Ala
                    245                 250                 255

Phe Ile Ala Asn Leu Lys Ser Ser Pro Thr Ile Arg Arg Thr Ala
                260                 265                 270

Ala Gly Ser Ala Val Ser Ile Cys Gln His Ser Arg Arg Thr Gln Tyr
                275                 280                 285

Phe Tyr Ser Trp Leu Leu Asn Val Leu Leu Gly Leu Leu Val Pro Val
            290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Gln Val Lys Asp Thr Ser Leu
                    325                 330                 335

Lys Gly Ser Phe Gly Val Thr Arg Lys Glu Met Glu Val Ser Pro Ser
                340                 345                 350

Ala Glu Gln Leu Val Gln Val Tyr Glu Leu Thr Leu His His Thr Gln
                355                 360                 365

His Gln Asp His Asn Val Val Thr Gly Ala Leu Glu Leu Leu Gln Gln
            370                 375                 380

Leu Phe Arg Thr Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                    405                 410                 415

Ser Arg Ser Gly Ser Ile Val Glu Leu Ile Ala Gly Gly Ser Ser
                420                 425                 430

Cys Ser Pro Val Leu Ser Arg Lys Gln Lys Gly Lys Val Leu Leu Gly
                435                 440                 445

Glu Glu Glu Ala Leu Glu Asp Asp Ser Glu Ser Arg Ser Asp Val Ser
450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                    485                 490                 495

Ile Thr Glu Gln Pro Arg Ser Gln His Thr Leu Gln Ala Asp Ser Val
                500                 505                 510

Asp
```

(2) INFORMATION FOR SEQ ID NO:29:

(i) SEQUENCE CHARACTERISTICS:
        (A) LENGTH: 530 amino acids
        (B) TYPE: amino acid
        (D) TOPOLOGY: linear (ii) MOLECULE TYPE: peptide (xi) SEQUENCE DESCRIPTION: SEQ ID NO:29:

-continued

```
Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro
                35                  40                  45

Pro Pro Pro Gln Leu Pro Gln Pro Pro Gln Ala Gln Pro Leu Leu
50                  55                  60

Pro Gln Pro Gln Pro Pro Pro Pro Pro Pro Pro Pro Gly Pro
65                  70                  75              80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
                100                 105                 110

Val Ala Gln Ser Val Arg Asn Ser Pro Glu Phe Gln Lys Leu Leu Gly
                115                 120                 125

Ile Ala Met Glu Leu Phe Leu Leu Cys Ser Asp Asp Ala Glu Ser Asp
130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
                180                 185                 190

Ala Glu Leu Ala His Leu Val Arg Pro Gln Lys Cys Arg Pro Tyr Leu
                195                 200                 205

Val Asn Leu Leu Pro Cys Leu Thr Arg Thr Ser Lys Arg Pro Glu Glu
                210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Pro Thr Ile Arg Arg Thr Ala
                260                 265                 270

Ala Gly Ser Ala Val Ser Ile Cys Gln His Ser Arg Arg Thr Gln Tyr
                275                 280                 285

Phe Tyr Ser Trp Leu Leu Asn Val Leu Leu Gly Leu Leu Val Pro Val
                290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Gln Val Lys Asp Thr Ser Leu
                325                 330                 335

Lys Gly Ser Phe Gly Val Thr Arg Lys Glu Met Glu Val Ser Pro Ser
                340                 345                 350

Ala Glu Gln Leu Val Gln Val Tyr Glu Leu Thr Leu His His Thr Gln
                355                 360                 365

His Gln Asp His Asn Val Val Thr Gly Ala Leu Glu Leu Leu Gln Gln
                370                 375                 380

Leu Phe Arg Thr Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                405                 410                 415

Ser Arg Ser Gly Ser Ile Val Glu Leu Ile Ala Gly Gly Gly Ser Ser
```

-continued

```
                   420                 425                 430
Cys Ser Pro Val Leu Ser Arg Lys Gln Lys Gly Lys Val Leu Leu Gly
        435                 440                 445

Glu Glu Glu Ala Leu Glu Asp Asp Ser Glu Ser Arg Ser Asp Val Ser
450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
                500                 505                 510

Asp Leu Ala Ser Cys Asp Leu Thr Ser Ser Ala Thr Asp Gly Asp Glu
        515                 520                 525

Glu Asp
    530

(2) INFORMATION FOR SEQ ID NO:30:

(i) SEQUENCE CHARACTERISTICS:
        (A) LENGTH: 552 amino acids
        (B) TYPE: amino acid
        (D) TOPOLOGY: linear (ii) MOLECULE TYPE: peptide (xi) SEQUENCE DESCRIPTION: SEQ ID NO:30:

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro Pro Pro
                35                  40                  45

Pro Pro Pro Gln Leu Pro Gln Pro Pro Gln Ala Gln Pro Leu Leu
    50                  55                  60

Pro Gln Pro Gln Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
                100                 105                 110

Val Ala Gln Ser Val Arg Asn Ser Pro Glu Phe Gln Lys Leu Leu Gly
                115                 120                 125

Ile Ala Met Glu Leu Phe Leu Leu Cys Ser Asp Asp Ala Glu Ser Asp
                130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
                180                 185                 190

Ala Glu Leu Ala His Leu Val Arg Pro Gln Lys Cys Arg Pro Tyr Leu
                195                 200                 205

Val Asn Leu Leu Pro Cys Leu Thr Arg Thr Ser Lys Arg Pro Glu Glu
                210                 215                 220

Ser Val Gln Glu Thr Leu Ala Ala Val Pro Lys Ile Met Ala Ser
225                 230                 235                 240
```

```
Phe Gly Asn Phe Ala Asn Asp Asn Glu Ile Lys Val Leu Leu Lys Ala
                245                 250                 255

Phe Ile Ala Asn Leu Lys Ser Ser Ser Pro Thr Ile Arg Arg Thr Ala
                260                 265                 270

Ala Gly Ser Ala Val Ser Ile Cys Gln His Ser Arg Arg Thr Gln Tyr
                275                 280                 285

Phe Tyr Ser Trp Leu Leu Asn Val Leu Leu Gly Leu Leu Val Pro Val
                290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Val Lys Asp Thr Ser Leu
                325                 330                 335

Lys Gly Ser Phe Gly Val Thr Arg Lys Glu Met Glu Val Ser Pro Ser
                340                 345                 350

Ala Glu Gln Leu Val Gln Val Tyr Glu Leu Thr Leu His His Thr Gln
                355                 360                 365

His Gln Asp His Asn Val Val Thr Gly Ala Leu Glu Leu Leu Gln Gln
                370                 375                 380

Leu Phe Arg Thr Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                405                 410                 415

Ser Arg Ser Gly Ser Ile Val Glu Leu Ile Ala Gly Gly Ser Ser
                420                 425                 430

Cys Ser Pro Val Leu Ser Arg Lys Gln Lys Gly Lys Val Leu Leu Gly
                435                 440                 445

Glu Glu Glu Ala Leu Glu Asp Asp Ser Glu Ser Arg Ser Asp Val Ser
450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
                500                 505                 510

Asp Leu Ala Ser Cys Asp Leu Thr Ser Ser Ala Thr Asp Gly Asp Glu
                515                 520                 525

Glu Asp Ile Leu Ser His Ser Ser Gln Val Ser Ala Val Pro Ser
                530                 535                 540

Asp Pro Ala Met Asp Leu Asn Asp
545                 550

(2) INFORMATION FOR SEQ ID NO:31:

(i) SEQUENCE CHARACTERISTICS:
        (A) LENGTH: 589 amino acids
        (B) TYPE: amino acid
        (D) TOPOLOGY: linear (ii) MOLECULE TYPE: peptide (xi) SEQUENCE DESCRIPTION: SEQ ID NO:31:

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln
                20                  25                  30
```

-continued

```
Gln Gln Gln Gln Gln Gln Gln Gln Pro Pro Pro Pro Pro Pro Pro
        35                  40                  45
Pro Pro Pro Gln Leu Pro Gln Pro Pro Gln Ala Gln Pro Leu Leu
    50                  55                  60
Pro Gln Pro Gln Pro Pro Pro Pro Pro Pro Pro Pro Pro Gly Pro
65                  70                  75                  80
Ala Val Ala Glu Glu Pro Leu His Arg Pro Lys Lys Glu Leu Ser Ala
                85                  90                  95
Thr Lys Lys Asp Arg Val Asn His Cys Leu Thr Ile Cys Glu Asn Ile
            100                 105                 110
Val Ala Gln Ser Val Arg Asn Ser Pro Glu Phe Gln Lys Leu Leu Gly
            115                 120                 125
Ile Ala Met Glu Leu Phe Leu Leu Cys Ser Asp Asp Ala Glu Ser Asp
            130                 135                 140
Val Arg Met Val Ala Asp Glu Cys Leu Asn Lys Val Ile Lys Ala Leu
145                 150                 155                 160
Met Asp Ser Asn Leu Pro Arg Leu Gln Leu Glu Leu Tyr Lys Glu Ile
                165                 170                 175
Lys Lys Asn Gly Ala Pro Arg Ser Leu Arg Ala Ala Leu Trp Arg Phe
            180                 185                 190
Ala Glu Leu Ala His Leu Val Arg Pro Gln Lys Cys Arg Pro Tyr Leu
            195                 200                 205
Val Asn Leu Leu Pro Cys Leu Thr Arg Thr Ser Lys Arg Pro Glu Glu
            210                 215                 220
Ser Val Gln Glu Thr Leu Ala Ala Val Pro Lys Ile Met Ala Ser
225                 230                 235                 240
Phe Gly Asn Phe Ala Asn Asp Asn Glu Ile Lys Val Leu Leu Lys Ala
                245                 250                 255
Phe Ile Ala Asn Leu Lys Ser Ser Pro Thr Ile Arg Arg Thr Ala
            260                 265                 270
Ala Gly Ser Ala Val Ser Ile Cys Gln His Ser Arg Arg Thr Gln Tyr
            275                 280                 285
Phe Tyr Ser Trp Leu Leu Asn Val Leu Leu Gly Leu Leu Val Pro Val
            290                 295                 300
Glu Asp Glu His Ser Thr Leu Leu Ile Leu Gly Val Leu Leu Thr Leu
305                 310                 315                 320
Arg Tyr Leu Val Pro Leu Leu Gln Gln Gln Val Lys Asp Thr Ser Leu
                325                 330                 335
Lys Gly Ser Phe Gly Val Thr Arg Lys Glu Met Glu Val Ser Pro Ser
            340                 345                 350
Ala Glu Gln Leu Val Gln Val Tyr Glu Leu Thr Leu His His Thr Gln
            355                 360                 365
His Gln Asp His Asn Val Val Thr Gly Ala Leu Glu Leu Leu Gln Gln
            370                 375                 380
Leu Phe Arg Thr Pro Pro Pro Glu Leu Leu Gln Thr Leu Thr Ala Val
385                 390                 395                 400
Gly Gly Ile Gly Gln Leu Thr Ala Ala Lys Glu Glu Ser Gly Gly Arg
                405                 410                 415
Ser Arg Ser Gly Ser Ile Val Glu Leu Ile Ala Gly Gly Gly Ser Ser
            420                 425                 430
Cys Ser Pro Val Leu Ser Arg Lys Gln Lys Gly Lys Val Leu Leu Gly
            435                 440                 445
Glu Glu Glu Ala Leu Glu Asp Asp Ser Glu Ser Arg Ser Asp Val Ser
```

```
                450                 455                 460
Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
                500                 505                 510

Asp Leu Ala Ser Cys Asp Leu Thr Ser Ser Ala Thr Asp Gly Asp Glu
                515                 520                 525

Glu Asp Ile Leu Ser His Ser Ser Gln Val Ser Ala Val Pro Ser
                530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp
                580                 585
```

(2) INFORMATION FOR SEQ ID NO:32:

(i) SEQUENCE CHARACTERISTICS:
        (A) LENGTH: 154 amino acids
        (B) TYPE: amino acid
        (D) TOPOLOGY: linear (ii) MOLECULE TYPE: peptide (xi) SEQUENCE DESCRIPTION: SEQ ID NO:32:

```
Met Glu Val Gln Leu Gly Leu Gly Arg Val Tyr Pro Arg Pro Pro Ser
1                   5                  10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala
                35                  40                  45

Pro Pro Gly Ala Ser Leu Leu Leu Gln Gln Gln Gln Gln Gln Gln Gln
                50                  55                  60

Gln Gln Gln Gln Gln Gln Gln Gln Gln Glu Thr Ser Pro Arg Gln
65                  70                  75                  80

Gln Gln Gln Gln Gln Gly Glu Asp Gly Ser Pro Gln Ala His Arg Arg
                85                  90                  95

Gly Pro Thr Gly Tyr Leu Val Leu Asp Glu Glu Gln Pro Ser Gln
                100                 105                 110

Pro Gln Ser Ala Leu Glu Cys His Pro Glu Arg Gly Cys Val Pro Glu
                115                 120                 125

Pro Gly Ala Ala Val Ala Ala Ser Lys Gly Leu Pro Gln Gln Leu Pro
                130                 135                 140

Ala Pro Pro Asp Glu Asp Asp Ser Ala Ala
145                 150
```

(2) INFORMATION FOR SEQ ID NO:33:

(i) SEQUENCE CHARACTERISTICS:
        (A) LENGTH: 325 amino acids
        (B) TYPE: amino acid
        (D) TOPOLOGY: linear (ii) MOLECULE TYPE: peptide (xi) SEQUENCE DESCRIPTION: SEQ ID NO:33:

```
Arg Arg Ser Ser Ala Gln Gln Arg Lys Lys Arg Ala Thr His Ser Ala
 1               5                  10                  15

Gly Lys Arg Lys Gly Ser Gln Lys Asp Leu Arg Pro Pro Asp Leu Trp
            20                  25                  30

Ile His His Glu Glu Met Glu Met Lys Asn Ile Glu Lys Pro Ser Gly
            35                  40                  45

Thr Asp Pro Ala Gly Arg Asp Ser Pro Ile Gln Ser Cys Gln Asp Leu
     50                  55                  60

Thr Pro Val Ser His Ser Gln Ser Glu Thr Gln Leu Gly Ser Lys Ser
 65              70                  75                      80

Thr Ser His Ser Gly Gln Asp Thr Glu Glu Ala Gly Ser Ser Met Ser
                85                  90                  95

Thr Leu Glu Arg Ser Leu Ala Ala Arg Arg Ala Pro Arg Ala Lys Leu
                100                 105                 110

Met Ile Pro Met Asp Ala Gln Ser Asn Asn Pro Ala Val Val Ser Ala
            115                 120                 125

Ile Pro Val Pro Thr Leu Glu Ser Ala Gln Tyr Pro Gly Ile Leu Pro
            130                 135                 140

Ser Pro Thr Cys Gly Tyr Pro His Pro Gln Phe Thr Leu Arg Pro Val
145                 150                 155                 160

Pro Phe Pro Thr Leu Ser Val Asp Arg Gly Phe Gly Ala Gly Arg Ser
                165                 170                 175

Gln Ser Val Ser Glu Gly Pro Thr Thr Gln Gln Pro Pro Met Leu Pro
                180                 185                 190

Pro Ser Gln Pro Glu His Ser Ser Ser Glu Glu Ala Pro Ser Arg Thr
            195                 200                 205

Ile Pro Thr Ala Cys Val Arg Pro Thr His Pro Leu Arg Ser Phe Ala
210                 215                 220

Asn Pro Leu Leu Pro Pro Met Ser Ala Ile Glu Pro Lys Val Pro
225                 230                 235                 240

Tyr Thr Pro Leu Leu Ser Gln Pro Gly Pro Thr Leu Pro Lys Thr His
                245                 250                 255

Val Lys Thr Ala Ser Leu Gly Leu Ala Gly Lys Ala Arg Ser Pro Leu
            260                 265                 270

Leu Pro Val Ser Val Pro Thr Ala Pro Glu Val Ser Glu Glu Ser His
            275                 280                 285

Lys Pro Thr Glu Asp Ser Ala Asn Val Tyr Glu Gln Asp Asp Leu Ser
            290                 295                 300

Glu Gln Met Ala Ser Leu Glu Gly Leu Met Lys Gln Leu Asn Ala Ile
305                 310                 315                 320

Thr Gly Ser Ala Phe
                325

(2) INFORMATION FOR SEQ ID NO:34:

(i) SEQUENCE CHARACTERISTICS:
        (A) LENGTH: 6450 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 361..2146
```

-continued (xi) SEQUENCE DESCRIPTION: SEQ ID NO:34:

```
GAGTTGTGCC TGGAGTGATG TTTAAGCCAA TGTCAGGGCA AGGCAACAGT CCCTGGCCGT         60

CCTCCAGCAC CTTTGTAATG CATATGAGCT CGGGAGACCA GTACTAAAAG TTGGAGGCCC        120

GGGAGCCCAG GAGCTGGCGG AGGGCGTTCG TCCTGGGAGC TGCACTTGCT CCGTCGGGTC        180

GCCGGCTTCA CCGGACCGCA GGCTCCCGGG GCAGGGCCGG GGCCAGAGCT CGCGTGTCGG        240

CGGGACATGC GCTGCGTCGC CTCTAACCTC GGGCTGTGCT CTTTTTCCAG GTGGCCCGCC        300

GGTTTCTGAG CCTTCTGCCC TGCGGGGACA CGGTCTGCAC CCTGCCCGCG GCCACGGACC        360
```

| ATG ACC ATG ACC CTC CAC ACC AAA GCA TCT GGG ATG GCC CTA CTG CAT<br>Met Thr Met Thr Leu His Thr Lys Ala Ser Gly Met Ala Leu Leu His<br>1               5                  10                  15 | 408 |
|---|---|
| CAG ATC CAA GGG AAC GAG CTG GAG CCC CTG AAC CGT CCG CAG CTC AAG<br>Gln Ile Gln Gly Asn Glu Leu Glu Pro Leu Asn Arg Pro Gln Leu Lys<br>                    20                  25                  30 | 456 |
| ATC CCC CTG GAG CGG CCC CTG GGC GAG GTG TAC CTG GAC AGC AGC AAG<br>Ile Pro Leu Glu Arg Pro Leu Gly Glu Val Tyr Leu Asp Ser Ser Lys<br>            35                  40                  45 | 504 |
| CCC GCC GTG TAC AAC TAC CCC GAG GGC GCC GCC TAC GAG TTC AAC GCC<br>Pro Ala Val Tyr Asn Tyr Pro Glu Gly Ala Ala Tyr Glu Phe Asn Ala<br>    50                  55                  60 | 552 |
| GCG GCC GCC GCC AAC GCG CAG GTC TAC GGT CAG ACC GGC CTC CCC TAC<br>Ala Ala Ala Ala Asn Ala Gln Val Tyr Gly Gln Thr Gly Leu Pro Tyr<br>65                  70                  75                  80 | 600 |
| GGC CCC GGG TCT GAG GCT GCG GCG TTC GGC TCC AAC GGC CTG GGG GGT<br>Gly Pro Gly Ser Glu Ala Ala Ala Phe Gly Ser Asn Gly Leu Gly Gly<br>                    85                  90                  95 | 648 |
| TTC CCC CCA CTC AAC AGC GTG TCT CCG AGC CCG CTG ATG CTA CTG CAC<br>Phe Pro Pro Leu Asn Ser Val Ser Pro Ser Pro Leu Met Leu Leu His<br>            100                 105                 110 | 696 |
| CCG CCG CCG CAG CTG TCG CCT TTC CTG CAG CCC CAC GGC CAG CAG GTG<br>Pro Pro Pro Gln Leu Ser Pro Phe Leu Gln Pro His Gly Gln Gln Val<br>    115                 120                 125 | 744 |
| CCC TAC TAC CTG GAG AAC GAG CCC AGC GGC TAC ACG GTG CGC GAG GCC<br>Pro Tyr Tyr Leu Glu Asn Glu Pro Ser Gly Tyr Thr Val Arg Glu Ala<br>            130                 135                 140 | 792 |
| GGC CCG CCG GCA TTC TAC AGG CCA AAT TCA GAT AAT CGA CGC CAG GGT<br>Gly Pro Pro Ala Phe Tyr Arg Pro Asn Ser Asp Asn Arg Arg Gln Gly<br>145                 150                 155                 160 | 840 |
| GGC AGA GAA AGA TTG GCC AGT ACC AAT GAC AAG GGA AGT ATG GCT ATG<br>Gly Arg Glu Arg Leu Ala Ser Thr Asn Asp Lys Gly Ser Met Ala Met<br>                    165                 170                 175 | 888 |
| GAA TCT GCC AAG GAG ACT CGC TAC TGT GCA GTG TGC AAT GAC TAT GCT<br>Glu Ser Ala Lys Glu Thr Arg Tyr Cys Ala Val Cys Asn Asp Tyr Ala<br>            180                 185                 190 | 936 |
| TCA GGC TAC CAT TAT GGA GTC TGG TCC TGT GAG GGC TGC AAG GCC TTC<br>Ser Gly Tyr His Tyr Gly Val Trp Ser Cys Glu Gly Cys Lys Ala Phe<br>            195                 200                 205 | 984 |
| TTC AAG AGA AGT ATT CAA GGA CAT AAC GAC TAT ATG TGT CCA GCC ACC<br>Phe Lys Arg Ser Ile Gln Gly His Asn Asp Tyr Met Cys Pro Ala Thr<br>    210                 215                 220 | 1032 |
| AAC CAG TGC ACC ATT GAT AAA AAC AGG AGG AAG AGC TGC CAG GCC TGC<br>Asn Gln Cys Thr Ile Asp Lys Asn Arg Arg Lys Ser Cys Gln Ala Cys<br>225                 230                 235                 240 | 1080 |
| CGG CTC CGC AAA TGC TAC GAA GTG GGA ATG ATG AAA GGT GGG ATA CGA<br>Arg Leu Arg Lys Cys Tyr Glu Val Gly Met Met Lys Gly Gly Ile Arg<br>                    245                 250                 255 | 1128 |
| AAA GAC CGA AGA GGA GGG AGA ATG TTG AAA CAC AAG CGC CAG AGA GAT | 1176 |

```
Lys Asp Arg Arg Gly Gly Arg Met Leu Lys His Lys Arg Gln Arg Asp
            260                 265                 270

GAT GGG GAG GGC AGG GGT GAA GTG GGG TCT GCT GGA GAC ATG AGA GCT      1224
Asp Gly Glu Gly Arg Gly Glu Val Gly Ser Ala Gly Asp Met Arg Ala
            275                 280                 285

GCC AAC CTT TGG CCA AGC CCG CTC ATG ATC AAA CGC TCT AAG AAG AAC      1272
Ala Asn Leu Trp Pro Ser Pro Leu Met Ile Lys Arg Ser Lys Lys Asn
290                 295                 300

AGC CTG GCC TTG TCC CTG ACG GCC GAC CAG ATG GTC AGT GCC TTG TTG      1320
Ser Leu Ala Leu Ser Leu Thr Ala Asp Gln Met Val Ser Ala Leu Leu
305                 310                 315                 320

GAT GCT GAG CCC CCC ATA CTC TAT TCC GAG TAT GAT CCT ACC AGA CCC      1368
Asp Ala Glu Pro Pro Ile Leu Tyr Ser Glu Tyr Asp Pro Thr Arg Pro
            325                 330                 335

TTC AGT GAA GCT TCG ATG ATG GGC TTA CTG ACC AAC CTG GCA GAC AGG      1416
Phe Ser Glu Ala Ser Met Met Gly Leu Leu Thr Asn Leu Ala Asp Arg
            340                 345                 350

GAG CTG GTT CAC ATG ATC AAC TGG GCG AAG AGG GTG CCA GGC TTT GTG      1464
Glu Leu Val His Met Ile Asn Trp Ala Lys Arg Val Pro Gly Phe Val
            355                 360                 365

GAT TTG ACC CTC CAT GAT CAG GTC CAC CTT CTA GAA TGT GCC TGG CTA      1512
Asp Leu Thr Leu His Asp Gln Val His Leu Leu Glu Cys Ala Trp Leu
            370                 375                 380

GAG ATC CTG ATG ATT GGT CTC GTC TGG CGC TCC ATG GAG CAC CCA GTG      1560
Glu Ile Leu Met Ile Gly Leu Val Trp Arg Ser Met Glu His Pro Val
385                 390                 395                 400

AAG CTA CTG TTT GCT CCT AAC TTG CTC TTG GAC AGG AAC CAG GGA AAA      1608
Lys Leu Leu Phe Ala Pro Asn Leu Leu Leu Asp Arg Asn Gln Gly Lys
                405                 410                 415

TGT GTA GAG GGC ATG GTG GAG ATC TTC GAC ATG CTG CTG GCT ACA TCA      1656
Cys Val Glu Gly Met Val Glu Ile Phe Asp Met Leu Leu Ala Thr Ser
            420                 425                 430

TCT CGG TTC CGC ATG ATG AAT CTG CAG GGA GAG GAG TTT GTG TGC CTC      1704
Ser Arg Phe Arg Met Met Asn Leu Gln Gly Glu Glu Phe Val Cys Leu
            435                 440                 445

AAA TCT ATT ATT TTG CTT AAT TCT GGA GTG TAC ACA TTT CTG TCC AGC      1752
Lys Ser Ile Ile Leu Leu Asn Ser Gly Val Tyr Thr Phe Leu Ser Ser
    450                 455                 460

ACC CTG AAG TCT CTG GAA GAG AAG GAC CAT ATC CAC CGA GTC CTG GAC      1800
Thr Leu Lys Ser Leu Glu Glu Lys Asp His Ile His Arg Val Leu Asp
465                 470                 475                 480

AAG ATC ACA GAC ACT TTG ATC CAC CTG ATG GCC AAG GCA GGC CTG ACC      1848
Lys Ile Thr Asp Thr Leu Ile His Leu Met Ala Lys Ala Gly Leu Thr
                485                 490                 495

CTG CAG CAG CAG CAC CAG CGG CTG GCC CAG CTC CTC CTC ATC CTC TCC      1896
Leu Gln Gln Gln His Gln Arg Leu Ala Gln Leu Leu Leu Ile Leu Ser
            500                 505                 510

CAC ATC AGG CAC ATG AGT AAC AAA GGC ATG GAG CAT CTG TAC AGC ATG      1944
His Ile Arg His Met Ser Asn Lys Gly Met Glu His Leu Tyr Ser Met
            515                 520                 525

AAG TGC AAG AAC GTG GTG CCC CTC TAT GAC CTG CTG CTG GAG ATG CTG      1992
Lys Cys Lys Asn Val Val Pro Leu Tyr Asp Leu Leu Leu Glu Met Leu
            530                 535                 540

GAC GCC CAC CGC CTA CAT GCG CCC ACT AGC CGT GGA GGG GCA TCC GTG      2040
Asp Ala His Arg Leu His Ala Pro Thr Ser Arg Gly Gly Ala Ser Val
545                 550                 555                 560

GAG GAG ACG GAC CAA AGC CAC TTG GCC ACT GCG GGC TCT ACT TCA TCG      2088
Glu Glu Thr Asp Gln Ser His Leu Ala Thr Ala Gly Ser Thr Ser Ser
            565                 570                 575
```

```
CAT TCC TTG CAA AAG TAT TAC ATC ACG GGG GAG GCA GAG GGT TTC CCT       2136
His Ser Leu Gln Lys Tyr Tyr Ile Thr Gly Glu Ala Glu Gly Phe Pro
        580                 585                 590

GCC ACA GTC T GAGAGCTCCC TGGCTCCCAC ACGGTTCAGA TAATCCCTGC              2186
Ala Thr Val
        595

TGCATTTTAC CCTCATCATG CACCACTTTA GCCAAATTCT GTCTCCTGCA TACACTCCGG      2246

CATGCATCCA ACACCAATGG CTTTCTAGAT GAGTGGCCAT TCATTTGCTT GCTCAGTTCT      2306

TAGTGGCACA TCTTCTGTCT TCTGTTGGGA ACAGCCAAAG GGATTCCAAG GCTAAATCTT      2366

TGTAACAGCT CTCTTTCCCC CTTGCTATGT TACTAAGCGT GAGGATTCCC GTAGCTCTTC      2426

ACAGCTGAAC TCAGTCTATG GGTTGGGGCT CAGATAACTC TGTGCATTTA AGCTACTTGT      2486

AGAGACCCAG GCCTGGAGAG TAGACATTTT GCCTCTGATA AGCACTTTTT AAATGGCTCT      2546

AAGAATAAGC CACAGCAAAG AATTTAAAGT GGCTCCTTTA ATTGGTGACT GGAGAAAGC       2606

TAGGTCAAGG GTTTATTATA GCACCCTCTT GTATTCCTAT GGCAATGCAT CCTTTTATGA      2666

AAGTGGTACA CCTAAAGCT TTTATATGAC TGTAGCAGAG TATCTGGTGA TTGTCAATTC       2726

ACTTCCCCCT ATAGGAATAC AAGGGGCCAC ACAGGGAAGG CAGATCCCCT AGTTGGCCAA      2786

GACTTATTTT AACTTGATAC ACTGCAGATT CAGAGTGTCC TGAAGCTCTG CCTCTGGCTT      2846

TCCGGTCATG GGTTCCAGTT AATTCATGCC TCCCATGGAC CTATGGAGAG CAACAAGTTG      2906

ATCTTAGTTA AGTCTCCCTA TATGAGGGAT AAGTTCCTGA TTTTTGTTTT TATTTTTGTG      2966

TTACAAAAGA AAGCCCTCCC TCCCTGAACT TGCAGTAAGG TCAGCTTCAG GACCTGTTCC      3026

AGTGGGCACT GTACTTGGAT CTTCCCGGCG TGTGTGTGCC TTACACAGGG GTGAACTGTT      3086

CACTGTGGTG ATGCATGATG AGGGTAAATG GTAGTTGAAA GGAGCAGGGG CCCTGGTGTT      3146

GCATTTAGCC CTGGGCATG GAGCTGAACA GTACTTGTGC AGGATTGTTG TGGCTACTAG       3206

AGAACAAGAG GGAAAGTAGG GCAGAAACTG GATACAGTTC TGAGCACAGC CAGACTTGCT     3266

CAGGTGGCCC TGCACAGGCT GCAGCTACCT AGGAACATTC CTTGCAGACC CCGCATTGCC     3326

TTTGGGGGTG CCCTGGGATC CCTGGGGTAG TCCAGCTCTT ATTCATTTCC CAGCGTGGCC     3386

CTGGTTGGAA GAAGCAGCTG TCAAGTTGTA GACAGCTGTG TTCCTACAAT TGGCCCAGCA     3446

CCCTGGGGCA CGGGAGAAGG GTGGGGACCG TTGCTGTCAC TACTCAGGCT GACTGGGGCC     3506

TGGTCAGATT ACGTATGCCC TTGGTGGTTT AGAGATAATC CAAAATCAGG GTTTGGTTTG     3566

GGGAAGAAAA TCCTCCCCCT TCCTCCCCCG CCCCGTTCCC TACCGCCTCC ACTCCTGCCA     3626

GCTCATTTCC TTCAATTTCC TTTGACCTAT AGGCTAAAAA AGAAAGGCTC ATTCCAGCCA     3686

CAGGGCAGCC TTCCCTGGGC CTTTGCTTCT CTAGCACAAT TATGGGTTAC TTCCTTTTTC     3746

TTAACAAAAA AGAATGTTTG ATTTCCTCTG GGTGACCTTA TTGTCTGTAA TTGAAACCCT    3806

ATTGAGAGGT GATGTCTGTG TTAGCCAATG ACCCAGGTAG CTGCTCGGGC TTCTCTTGGT    3866

ATGTCTTGTT TGGAAAAGTG GATTTCATTC ATTTCTGATT GTCCAGTTAA GTGATCACCA    3926

AAGGACTGAG AATCTGGGAG GGCAAAAAAA AAAAAAAAG TTTTTATGTG CACTTAAATT     3986

TGGGGACAAT TTTATGTATC TGTGTTAAGG ATATGCTTAA GAACATAATT CTTTTGTTGC    4046

TGTTTGTTTA AGAAGCACCT TAGTTTGTTT AAGAAGCACC TTATATAGTA TAATATATAT    4106

TTTTTTGAAA TTACATTGCT TGTTTATCAG ACAATTGAAT GTAGTAATTC TGTTCTGGAT    4166

TTAATTTGAC TGGGTTAACA TGCAAAAACC AAGGAAAAAT ATTTAGTTTT TTTTTTTTTT    4226

TTTGTATACT TTTCAAGCTA CCTTGTCATG TATACAGTCA TTTATGCCTA AAGCCTGGTG    4286

ATTATTCATT TAAATGAAGA TCACATTTCA TATCAACTTT TGTATCCACA GTAGACAAAA    4346
```

```
TAGCACTAAT CCAGATGCCT ATTGTTGGAT ATTGAATGAC AGACAATCTT ATGTAGCAAA    4406

GATTATGCCT GAAAAGGAAA ATTATTCAGG GCAGCTAATT TTGCTTTTAC CAAAATATCA    4466

GTAGTAATAT TTTTGGACAG TAGCTAATGG GTCAGTGGGT TCTTTTTAAT GTTTATACTT    4526

AGATTTTCTT TTAAAAAAAT TAAAATAAAA CAAAAAAAAT TTCTAGGACT AGACGATGTA    4586

ATACCAGCTA AAGCCAAACA ATTATACAGT GGAAGGTTTT ACATTATTCA TCCAATGTGT    4646

TTCTATTCAT GTTAAGATAC TACTACATTT GAAGTGGGCA GAGAACATCA GATGATTGAA    4706

ATGTTCGCCC AGGGGTCTCC AGCAACTTTG GAAATCTCTT TGTATTTTTA CTTGAAGTGC    4766

CACTAATGGA CAGCAGATAT TTTCTGGCTG ATGTTGGTAT TGGGTGTAGG AACATGATTT    4826

AAAAAAAAAA CTCTTGCCTC TGCTTTCCCC CACTCTGAGG CAAGTTAAAA TGTAAAAGAT    4886

GTGATTTATC TGGGGGCTC AGGTATGGTG GGGAAGTGGA TTCAGGAATC TGGGGAATGG     4946

CAAATATATT AAGAAGAGTA TTGAAAGTAT TTGGAGGAAA ATGGTTAATT CTGGGTGTGC    5006

ACCAAGGTTC AGTAGAGTCC ACTTCTGCCC TGGAGACCAC AAATCAACTA GCTCCATTTA    5066

CAGCCATTTC TAAAATGGCA GCTTCAGTTC TAGAGAAGAA AGAACAACAT CAGCAGTAAA    5126

GTCCATGGAA TAGCTAGTGG TCTGTGTTTC TTTTCGCCAT TGCCTAGCTT GCCGTAATGA    5186

TTCTATAATG CCATCATGCA GCAATTATGA GAGGCTAGGT CATCCAAAGA GAAGACCCTA    5246

TCAATGTAGG TTGCAAAATC TAACCCCTAA GGAAGTGCAG TCTTTGATTT GATTTCCCTA    5306

GTAACCTTGC AGATATGTTT AACCAAGCCA TAGCCCATGC CTTTTGAGGG CTGAACAAAT    5366

AAGGGACTTA CTGATAATTT ACTTTTGATC ACATTAAGGT GTTCTCACCT TGAAATCTTA    5426

TACACTGAAA TGGCCATTGA TTTAGGCCAC TGGCTTAGAG TACTCCTTCC CCTGCATGAC    5486

ACTGATTACA AATACTTTCC TATTCATACT TTCCAATTAT GAGATGGACT GTGGGTACTG    5546

GGAGTGATCA CTAACACCAT AGTAATGTCT AATATTCACA GGCAGATCTG CTTGGGGAAG    5606

CTAGTTATGT GAAAGGCAAA TAAAGTCATA CAGTAGCTCA AAAGGCAACC ATAATTCTCT    5666

TTGGTGCAAG TCTTGGGAGC GTGATCTAGA TTACACTGCA CCATTCCCAA GTTAATCCCC    5726

TGAAAACTTA CTCTCAACTG GAGCAAATGA ACTTTGGTCC CAAATATCCA TCTTTTCAGT    5786

AGCGTTAATT ATGCTCTGTT TCCAACTGCA TTTCCTTTCC AATTGAATTA AAGTGTGGCC    5846

TCGTTTTTAG TCATTTAAAA TTGTTTTCTA AGTAATTGCT GCCTCTATTA TGGCACTTCA    5906

ATTTTGCACT GTCTTTTGAG ATTCAAGAAA AATTTCTATT CATTTTTTTG CATCCAATTG    5966

TGCCTGAACT TTTAAAATAT GTAAATGCTG CCATGTTCCA AACCCATCGT CAGTGTGTGT    6026

GTTTAGAGCT GTGCACCCTA GAAACAACAT ACTTGTCCCA TGAGCAGGTG CCTGAGACAC    6086

AGACCCCTTT GCATTCACAG AGAGGTCATT GGTTATAGAG ACTTGAATTA ATAAGTGACA    6146

TTATGCCAGT TTCTGTTCTC TCACAGGTGA TAAACAATGC TTTTTGTGCA CTACATACTC    6206

TTCAGTGTAG AGCTCTTGTT TTATGGGAAA AGGCTCAAAT GCCAAATTGT GTTTGATGGA    6266

TTAATATGCC CTTTTGCCGA TGCATACTAT TACTGATGTG ACTCGGTTTT GTCGCAGCTT    6326

TGCTTTGTTT AATGAAACAC ACTTGTAAAC CTCTTTTGCA CTTTGAAAAA GAATCCAGCG    6386

GGATGCTCGA GCACCTGTAA ACAATTTTCT CAACCTATTT GATGTTCAAA TAAAGAATTA    6446

AACT                                                                6450
```

(2) INFORMATION FOR SEQ ID NO:35:

(i) SEQUENCE CHARACTERISTICS:
        (A) LENGTH: 595 amino acids
        (B) TYPE: amino acid (D) TOPOLOGY: linear (ii) MOLECULE TYPE: protein (xi) SEQUENCE DESCRIPTION: SEQ ID NO:35:

```
Met Thr Met Thr Leu His Thr Lys Ala Ser Gly Met Ala Leu Leu His
  1               5                  10                  15

Gln Ile Gln Gly Asn Glu Leu Glu Pro Leu Asn Arg Pro Gln Leu Lys
             20                  25                  30

Ile Pro Leu Glu Arg Pro Leu Gly Glu Val Tyr Leu Asp Ser Ser Lys
             35                  40                  45

Pro Ala Val Tyr Asn Tyr Pro Glu Gly Ala Ala Tyr Glu Phe Asn Ala
         50                  55                  60

Ala Ala Ala Asn Ala Gln Val Tyr Gly Gln Thr Gly Leu Pro Tyr
 65                  70                  75                  80

Gly Pro Gly Ser Glu Ala Ala Phe Gly Ser Asn Gly Leu Gly Gly
             85                  90                  95

Phe Pro Pro Leu Asn Ser Val Ser Pro Ser Leu Met Leu Leu His
            100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
            130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
            210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
            290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Val
```

```
                    385                 390                 395                 400
Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
                450                 455                 460

Thr Leu Lys Ser Leu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
                515                 520                 525

Lys Cys Lys Asn Val Val Pro Leu Tyr Asp Leu Leu Leu Glu Met Leu
                530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
        595

(2) INFORMATION FOR SEQ ID NO:36:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:36:

Gly Arg Lys Lys Arg Arg Gln Arg Arg Pro Pro Gly Gly Gln Gln
1               5                   10                  15

Gln Gln Gln Gln Gln Gln Gln Gln Gln Gln Gln
                20                  25

(2) INFORMATION FOR SEQ ID NO:37:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:37:

Gly Arg Lys Lys Arg Arg Gln Arg Arg Pro Pro Gly Gly Ser Ala
1               5                   10                  15

Thr Leu Asp Ala Leu Leu Ala Ala Leu Arg Arg Ile
                20                  25

(2) INFORMATION FOR SEQ ID NO:38:
```

```
    (i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:38:

Gly Arg Lys Lys Arg Arg Gln Arg Arg Arg Pro Pro Gly Gly Ser Ala
1               5                   10                  15

Thr Leu Asp Ala Leu Leu Ala Ala Leu Gly Gly Ile
            20                  25

(2) INFORMATION FOR SEQ ID NO:39:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:39:

Gly Arg Lys Lys Arg Arg Gln Arg Arg Arg Pro Pro Gly Gly Ser Ala
1               5                   10                  15

Thr Leu Asp Ala Leu Leu Ala Ala Leu Arg Gly Ile
            20                  25

(2) INFORMATION FOR SEQ ID NO:40:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:40:

Gly Arg Lys Lys Arg Arg Gln Arg Arg Arg Pro Pro Gly Gly Ser Ala
1               5                   10                  15

Thr Leu Gln Ala Leu Leu Ala Ala Leu Arg Arg Ile
            20                  25

(2) INFORMATION FOR SEQ ID NO:41:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:41:

Ser Ala Thr Leu Asp Ala Lys Leu Ala Ala Leu Arg Arg Ile
1               5                   10

(2) INFORMATION FOR SEQ ID NO:42:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:42:
```

```
Gly Arg Lys Lys Arg Arg Gln Arg Arg Pro Pro Gly Gly Ser Ala
1               5                   10                  15

Thr Leu Asp Ala Lys Leu Ala Ala Leu Arg Arg Ile
            20                  25
```

(2) INFORMATION FOR SEQ ID NO:43:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:43:

```
Ser Ala Thr Leu Asp Ala Leu Leu Ala Ala Leu
1               5                   10
```

(2) INFORMATION FOR SEQ ID NO:44:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:44:

```
Gly Arg Lys Lys Arg Arg Gln Arg Arg Pro Pro Gly Gly Ser Ala
1               5                   10                  15

Thr Leu Asp Ala Leu Leu Ala Ala Leu
            20                  25
```

(2) INFORMATION FOR SEQ ID NO:45:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:45:

```
Ala Leu Leu Ala Ala Leu Arg Arg Ile
1               5
```

(2) INFORMATION FOR SEQ ID NO:46:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:46:

```
Lys Asp Arg Asn Leu Arg Arg Ile Thr Arg Met Val Leu Val
1               5                   10
```

(2) INFORMATION FOR SEQ ID NO:47:

(i) SEQUENCE CHARACTERISTICS:
        (A) LENGTH: 28 amino acids
        (B) TYPE: amino acid
        (D) TOPOLOGY: linear (ii) MOLECULE TYPE: peptide

```
        (xi) SEQUENCE DESCRIPTION: SEQ ID NO:47:

Gly Arg Lys Lys Arg Arg Gln Arg Arg Pro Pro Gly Gly Lys Asp
1               5                  10                  15

Arg Asn Leu Arg Arg Ile Thr Arg Met Val Leu Val
            20                  25

(2) INFORMATION FOR SEQ ID NO:48:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:48:

Leu Asp Glu Asn Phe Lys Arg Cys Phe Arg Glu Phe Cys Ile
1               5                  10

(2) INFORMATION FOR SEQ ID NO:49:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:49:

Asp Leu Ser Leu Ala Arg Leu Ala Thr Ala Arg Leu Ala Ile
1               5                  10

(2) INFORMATION FOR SEQ ID NO:50:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:50:

Gly Arg Lys Lys Arg Arg Gln Arg Arg Pro Pro Gly Gly Asp Leu
1               5                  10                  15

Ser Leu Ala Arg Leu Ala Thr Ala Arg Leu Ala Ile
            20                  25

(2) INFORMATION FOR SEQ ID NO:51:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:51:

Ile Asn Leu Lys Ala Leu Ala Ala Leu Ala Lys Lys Ile Leu
1               5                  10

(2) INFORMATION FOR SEQ ID NO:52:

(i) SEQUENCE CHARACTERISTICS:
        (A) LENGTH: 12 amino acids
        (B) TYPE: amino acid
        (D) TOPOLOGY: linear
```

(ii) MOLECULE TYPE: peptide (xi) SEQUENCE DESCRIPTION: SEQ ID NO:52:

Gly Arg Lys Lys Arg Arg Gln Arg Arg Pro Pro
1               5                   10

(2) INFORMATION FOR SEQ ID NO:53:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:53:

Gly Arg Lys Lys Arg Arg Gln Arg Arg Pro Pro Gly Gly Ser Ala
1               5                   10                  15

Thr Leu Asp Ala Leu Leu Ala Ala Leu Glu Glu Ile
            20                  25

(2) INFORMATION FOR SEQ ID NO:54:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:54:

Gly Arg Lys Lys Arg Arg Gln Arg Arg Pro Pro Gly Gly Ser Ala
1               5                   10                  15

Thr Leu Asp Ala Leu Leu Ala Ala Leu Gln Gln Ile
            20                  25

(2) INFORMATION FOR SEQ ID NO:55:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:55:

Asp Leu Ser Leu Ala Arg Leu Ala Thr Ala Arg Leu Ala Ile
1               5                   10

(2) INFORMATION FOR SEQ ID NO:56:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:56:

Gly Arg Lys Lys Arg Arg Gln Arg Arg Pro Pro Gly Gly Asp Leu
1               5                   10                  15

Ser Leu Ala Arg Leu Ala Thr Ala Arg Leu Ala Ile
            20                  25

(2) INFORMATION FOR SEQ ID NO:57:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:57:

CCTTTACCCA CGCGGCCTGC CCAGT                                             25

(2) INFORMATION FOR SEQ ID NO:58:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

CTGCTGGCCA GCGGGGGTGC CCAG                                              24

(2) INFORMATION FOR SEQ ID NO:59:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

ACGCTTGATG CCAAATTAGC CGCCCTGCGA                                        30

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

ATGGATCCCA AGGTCTACGC C                                                 21

(2) INFORMATION FOR SEQ ID NO:61:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

CGCTGGTCGA CTAGATGCGT CGCAG                                             25

(2) INFORMATION FOR SEQ ID NO:62:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:62:

CGCTGGTCGA CTAGTCCTGG GCACC                                               25

(2) INFORMATION FOR SEQ ID NO:63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

ATCCCTGGTC GATGGATCCC AA                                                  22

(2) INFORMATION FOR SEQ ID NO:64:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

TCTCTGGATC CCTCCCAGGG CG                                                  22

(2) INFORMATION FOR SEQ ID NO:65:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

CTGGATCCGT CGCAGGGCGG CTGGTTTGG                                           29

(2) INFORMATION FOR SEQ ID NO:66:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

CTGCGACGGA TCCAGAGAGC TG                                                  22

(2) INFORMATION FOR SEQ ID NO:67:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

GCTCTAGAAC ATCAGTCGTC GGA                     23

(2) INFORMATION FOR SEQ ID NO:68:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:68:

Asp Xaa Xaa Asp
1

(2) INFORMATION FOR SEQ ID NO:69:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:69:

Asp Ser Val Asp
1

(2) INFORMATION FOR SEQ ID NO:70:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:70:

Asp Glu Glu Asp
1

(2) INFORMATION FOR SEQ ID NO:71:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:71:

Asp Leu Asn Asp
1

(2) INFORMATION FOR SEQ ID NO:72:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:72:

Asp Gly Thr Asp